United States Patent
Brown et al.

(10) Patent No.: US 7,189,712 B2
(45) Date of Patent: Mar. 13, 2007

(54) 1,3-OXAZOLE COMPOUNDS FOR THE TREATMENT OF CANCER

(75) Inventors: Matthew Lee Brown, San Francisco, CA (US); Mui Cheung, Durham, NC (US); Scott Howard Dickerson, Durham, NC (US); Cassandra Gauthier, Longmont, CO (US); Philip Anthony Harris, Durham, NC (US); Robert Neil Hunter, Durham, NC (US); Gregory Pacofsky, Raleigh, NC (US); Michael Robert Peel, Durham, NC (US); Jeffrey Alan Stafford, San Diego, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/530,810

(22) PCT Filed: Oct. 10, 2003

(86) PCT No.: PCT/US03/33317

§ 371 (c)(1), (2), (4) Date: Apr. 8, 2005

(87) PCT Pub. No.: WO2004/032882

PCT Pub. Date: Apr. 22, 2004

(65) Prior Publication Data

US 2005/0288515 A1    Dec. 29, 2005

Related U.S. Application Data

(60) Provisional application No. 60/417,548, filed on Oct. 10, 2002.

(51) Int. Cl.
*A61K 31/541*    (2006.01)
*A61K 31/5355*    (2006.01)
*A61K 31/496*    (2006.01)
*A61K 31/4525*    (2006.01)
*A61K 31/443*    (2006.01)
*A61K 31/421*    (2006.01)
*C07D 417/10*    (2006.01)
*C07D 413/10*    (2006.01)

(52) U.S. Cl. ............................. 514/227.8; 514/236.8; 514/254.02; 514/326; 514/340; 514/377; 544/60; 544/137; 544/369; 546/209; 546/271.4; 548/234

(58) Field of Classification Search ............... 514/377, 514/227.8, 236.8, 254.02, 326, 340; 548/234; 544/60, 137, 369; 546/209, 271.4
See application file for complete search history.

(56) References Cited

U.S. PATENT DOCUMENTS 6,197,975 B1 * 3/2001 Goulet et al. ............... 548/453
6,399,773 B1 * 6/2002 Liu et al. .................... 544/106

OTHER PUBLICATIONS

Manley et al. "Therapies directed at vascular endothelial growth factor" Expert Opin. Investig. Drugs, 2002, pp. 1715-1736.*
Davies et al. "Structure-based design of cyclin-dependent kinase inhibitors" Pharmacology & Therapeutics, 2002, pp. 125-133.*
Toogood, Peter "Cyclin-Dependent Kinase Inhibitors for Treating Cancer" Medicinal Research Reviews, 2001, pp. 487-498.*

* cited by examiner

*Primary Examiner*—Joseph K. McKane
*Assistant Examiner*—Joseph R. Kosack
(74) *Attorney, Agent, or Firm*—John L. Lemanowicz; Jennifer L. Fox

(57) ABSTRACT

Oxazole derivatives, which are useful as VEGFR2, CDK2, and CDK4 inhibitors are described herein. The described invention also includes methods of making such oxazole derivatives as well as methods of using the same in the treatment of hyperproliferative diseases.

5 Claims, No Drawings

1,3-OXAZOLE COMPOUNDS FOR THE TREATMENT OF CANCER

This application is filed pursuant to 35 U.S.C. § 371 as a United States National Phase Application of International Application No. PCT/US2003/033317 filed Oct. 10, 2003, which claims priority from U.S. 60/417,548 tiled Oct. 10, 2002.

BACKGROUND OF THE INVENTION

The present invention relates to oxazole derivatives, compositions and medicaments containing the same, as well as processes for the preparation and use of such compounds, compositions, and medicaments. Such oxazole derivatives are useful in the treatment of diseases associated with inappropriate protein kinase activity.

An important large family of enzymes is the protein kinase enzyme family. Currently, there are about 400 different known protein kinases. While three to four percent of the human genome is a code for the formation of protein kinases, there may be thousands of distinct and separate kinases in the human body. Protein kinases serve to catalyze the phosphorylation of an amino acid side chain in various proteins by the transfer of the γ-phosphate of the ATP-Mg$^{2+}$ complex to said amino acid side chain. It is well established that protein kinase enzymes control a number of signaling processes inside cells, thereby governing cell function, growth, differentiation and destruction (apoptosis) through reversible phosphorylation of the hydroxy groups of serine, theonine, and tyrosine residues in proteins. To this end protein kinases are key regulators of many cell functions, including signal transduction, transcriptional regulation, cell motility, and cell division. Furthermore, several oncogenes have also been shown to encode protein kinases, suggesting that kinases play a role in oncogenesis. The aforementioned cell processes are highly regulated, often by complex intermeshed pathways where each kinase is itself regulated by one or more kinases. Consequently, aberrant or inappropriate protein kinase activity can contribute to the rise of disease states associated with such aberrant kinase activity. Consequently, due to their physiological relevance, variety, and pervasiveness, protein kinases have become one of the most important and widely studied enzyme families in biochemical and medical research.

The protein kinase family of enzymes is typically classified into two main subfamilies: protein tyrosine kinases (PTK(s)) and protein serine/theonine kinases (PSTK(s)), based on the amino acid residue phosphorylated. PSTK(s) catalyze phosphorylation of hydroxy substituents on serine or theonine side chains. PSTK(s) include cyclic AMP and cyclic GMP dependent protein kinases, calcium and phospholipid dependent protein kinase, calcium and calmodulin-dependent protein kinases, casein kinases, cell division cycle protein kinases and others. These kinases are usually cytoplasmic or associated with the particulate fractions of cells, possibly by anchoring proteins. Aberrant PSTK activity has been implicated or is suspected in a number of pathologies such as rheumatoid arthritis, psoriasis, septic shock, bone loss, many cancers and other proliferative diseases. Accordingly, PSTK(s) and the signal transduction pathways which they are part of are important targets for drug design. PTK(s) phosphorylate hydroxy substituents on tyrosine side chains. PTK(s) are present in much smaller quantities but also play an equally important role in cell regulation. These kinases include several receptors for molecules such as growth factors and hormones, including the epidermal growth factor receptor (EGFR), vascular endothelial growth factor receptor (VEGFR), insulin receptor, platelet derived growth factor receptor (PDGFR), and others. Studies have indicated that many tyrosine kinases are transmembrane proteins with their receptor domains located on the outside of the cell and their kinase domains on the inside. Aberrant PTK activity has also been implicated or suspected in a number of pathologies such as osteoarthritis, rheumatoid arthritis, psoriasis, a variety of cancers, and other proliferative diseases. Accordingly, PTK and their signal transduction pathways are also important targets for drug design.

The present invention relates to a series of substituted oxazole compounds, which exhibit PTK and/or PSTK inhibition.

In particular, these compounds exhibit inhibition of the PTK:VEGFR2. VEGFR2 kinase is found in endothelial cells and is involved in angiogenesis—the growth and proliferation of blood vessels from existing capillaries. Angiogenesis plays an important role in development, homeostasis, wound healing, the female reproductive cycle, and in pathological conditions such as rheumatoid arthritis, diabetic retinopathy, mascular degeneration, psoriasis, and cancer. The role of angiogenesis in disease states is discussed, for instance, in Fan et al, Trends in Pharmacol Sci. 16:54–66; Shawver et al, DDT Vol. 2, No. 2 February 1997; Folkmann, 1995, Nature Medicine 1:27–31. Activation of VEGFR2 by Vascular Endothelial Growth Factor (VEGF) is a critical step in the signal transduction pathway that initiates tumor angiogenesis. The VEGF ligand activates VEGFR2 by binding to its extracellular VEGF binding site. This leads to receptor dimerization of VEGFRs and autophosphorylation of tyrosine residues at the intracellular kinase domain of VEGFR2. The kinase domain operates to transfer a phosphate from ATP to the tyrosine residues, thus providing binding sites for signaling proteins downstream of VEGFR2 leading ultimately to angiogenesis. (Ferrara and Davis-Smyth, Endocrine Reviews, 18(1):4–25, 1997; McMahon, G., The Oncologist, Vol. 5, No. 90001, 3–10, April 2000). Solid tumors will not grow beyond 1–2 mm in size without the support of additional vascularization. Most tumor types, if not all, secrete VEGF in order to stimulate angiogenesis. Inhibition of VEGFR2 would therefore interrupt a critical process involved in tumor growth and metastasis, as well as other pathological angiogenic conditions.

In addition, these compounds exhibit inhibition of a family of PSTK(s) called cyclin dependent kinases (CDKs). Progression through the eukaryotic cell cycle is controlled by CDKs and their interaction with a family of proteins termed cyclins (Myerson, et al., EMBO Journal 1992, 11, 2909–17). The coordinate activation and inactivation of different cyclin/CDK complexes is necessary for normal progression through the cell cycle (Pines, Trends in Biochemical Sciences 1993, 18, 195–7; Sherr, Cell 1993, 73, 1059–1065.). Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer. (Pines, Current Opinion in Cell Biology 1992, 4, 144–8; Lees, Current Opinion in Cell Biology 1995, 7, 773–80; Hunter and Pines, Cell 1994, 79, 573–82). Consequently, inhibition of CDKs may prevent progression in the cell cycle in normal cells and limit the toxicity of cytotoxics that act in S-phase, G2, or mitosis. Such disruption of the cell cycle of normal proliferating cells should therefore protect such proliferating cells such as hair follicles and epithelial mucosa from the effects of cytotoxic agents and thereby provide a potent treatment for side effects associated with cancer chemo- and radiotherapies.

The present inventors have discovered novel oxazole derivatives, which inhibit the activity of VEGFR2 and/or the CDKs, specifically CDK2 and CDK4 activity. Such oxazole derivatives are useful in the treatment of disorders associated with inappropriate VEGFR2 and/or CDK activity.

BRIEF SUMMARY OF THE INVENTION

Accordingly, in one aspect of the present invention, there is provided a compound of Formula (I):

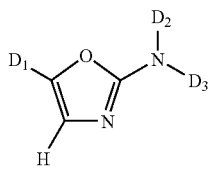

(I)

or a salt, solvate, or physiologically functional derivative thereof;
wherein:
$D_1$ is aryl, heteroaryl, or heterocyclic said aryl, heteroaryl and heterocyclic groups being optionally substituted with at least one group R;
R is independently selected from the group consisting of halo, $C_1$–$C_6$ alkyl, $C_2$–$C_6$ alkynyl, $C_1$–$C_6$ alkoxy, —$NR^1R^2$, $C_1$–$C_4$ haloalkyl, hydroxy, —$C(O)R^1$, —$OC(O)R^1$, —$C(O)NR^1R^2$, —$S(O)_2R^1$, $C_1$–$C_6$ alkylsulfanyl, cyano, $C_1$–$C_2$ halalkoxy, or
the group defined by —$(Y)_o$—$(Y^1)_r$—$(Y^2)$;
   wherein:
      Y is O and o is 0 or 1;
      $Y^1$ is C(H)(R'), and r is 0, 1, 2, 3, or 4; and
      $Y^2$ is aryl, heteroaryl, heterocyclic, $C_3$–$C_7$ cycloalkly, or $C_2$–$C_6$ alkenyl;
$D_2$ is hydrogen or $C_1$–$C_4$ alkyl;
$D_3$ is aryl or heteroaryl said aryl or heteroaryl groups being optionally substituted with at least one group Q;
Q is independently selected from the group consisting of halo, $C_1$–$C_4$ haloalkyl, $C_1$–$C_6$ alkyl, $C_1$–$C_6$ alkoxy, $C_1$–$C_4$ haloalkoxy, hydroxy, aralkoxy, $C_1$–$C_6$ alkenyl, alkynyl, $C_1$–$C_4$ hydroxyalkyl, cyano, aryloxy, $C_1$–$C_2$ halalkoxy, —$NO_2$, or —$C(O)OR^1$, or
the group defined by -$(Z)_q$-$(Z^1)_r$-$(Z^2)$,
   wherein:
      Z is NH and q is 0 or 1; or
      Z is $CH_2$ and q is 0, 1, 2, or 3; or
      Z is $O(CH_2)_n$, where n is 1, 2, 3, or 4 and q is 0 or 1;
      $Z^1$ is $S(O)_2$ or C(O); and r is 0 or 1, and
      $Z^2$ is $C_1$–$C_6$ alkyl, aryl, heteroaryl, heterocyclic, hydroxy, halo, aralkyl, $C_1$–$C_2$ haloalkyl, $C(H)(R')R^3$, $NH(CH_2)_nNR^1R^2$, $NH(CH_2)_nR^3$, $NH(CH_2)_nOR^1$ or $NR^1R^2$ where n is 1, 2, 3, or 4;
$R^1$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;

$R^2$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;
$R^3$ is heteroaryl or heterocyclic, and
R' is hydrogen or $C_1$–$C_3$ alkyl.

In a second aspect of the present invention, there is provided a compound of Formula (I):

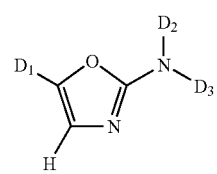

(I)

or a salt, solvate, or physiologically functional derivative thereof;
wherein:
$D_1$ is

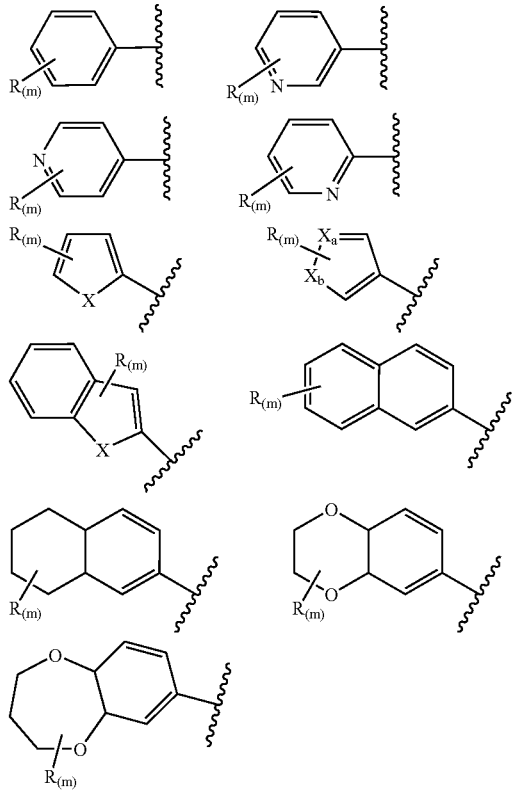

where
X is selected from N, O, or S;
$X_a$ is N and $X_b$ is N, O, or S, or
$X_a$ is O and $X_b$ is N, or
$X_a$ is S and $X_b$ is N;
m is 0, 1, 2, 3, or 4;
R is independently selected from the group consisting of halo, $C_1$–$C_6$ alkyl, $C_2$–$C_6$ alkynyl, $C_1$–$C_6$ alkoxy, —$NR^1R^2$, $C_1$–$C_4$ haloalkyl, hydroxy, —$C(O)R^1$, —$OC(O)R^1$, —$C(O)NR^1R^2$, —$S(O)_2R^1$, $C_1$–$C_6$ alkylsulfanyl, cyano, $C_1$–$C_2$ halalkoxy, or
the group defined by —$(Y)_o$—$(Y^1)_r$—$(Y^2)$;

wherein:
Y is O and o is 0 or 1;
$Y^1$ is C(H)(R'), and r is 0, 1, 2, 3, or 4; and
$Y^2$ is aryl, heteroaryl, heterocyclic, $C_3$–$C_7$cycloalkyl, or $C_2$–$C_6$ alkenyl;
$D_2$ is hydrogen or $C_1$–$C_4$ alkyl;
$D_3$ is selected from the group

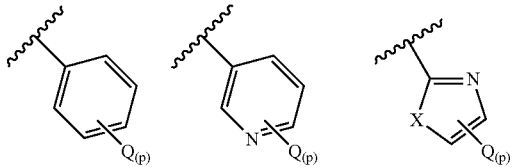

where X is selected from N, O, or S, and
p is 0, 1, 2, 3, 4, or 5;
Q is independently selected from the group consisting of halo, $C_1$–$C_4$ haloalkyl, $C_1$–$C_6$ alkyl, $C_1$–$C_6$ alkoxy, $C_1$–$C_4$ haloalkoxy, hydroxy, aralkoxy, $C_1$–$C_6$ alkenyl, alkynyl, $C_1$–$C_4$ hydroxyalkyl, cyano, aryloxy, $C_1$–$C_2$ halalkoxy, —$NO_2$, or —C(O)OR$^1$, or
the group defined by -(Z)$_q$-(Z$^1$)$_r$-(Z$^2$),
wherein:
Z is NH and q is 0 or 1; or
Z is $CH_2$ and q is 0, 1, 2, or 3; or
Z is O(CH$_2$)$_n$ where n is 1, 2, 3, or 4 and q is 0 or 1;
$Z^1$ is S(O)$_2$ or C(O); and r is 0 or 1, and
$Z^2$ is $C_1$–$C_6$ alkyl, aryl, heteroaryl, heterocyclic, hydroxy, halo, aralkyl, $C_1$–$C_2$ haloalkyl, C(H)(R')R$^3$, NH(CH$_2$)$_n$NR$^1$R$^2$, NTH(CH$_2$)$_n$R$^3$, NH(CH$_2$)$_n$OR$^1$ or NR$^1$R$^2$; where
n is 1, 2, 3, or 4;
$R^1$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl heterocyclic, or aralkyl;
$R^2$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;
$R^3$ is heteroaryl or heterocyclic, and
R' is hydrogen or $C_1$–$C_3$ alkyl.

In a third aspect of the present invention, there is provided a compound of Formula (II):

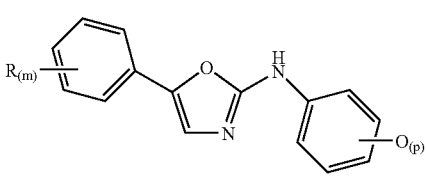

(II)

or a salt, solvate, or physiologically functional derivative thereof;
wherein:
m is 0, 1, 2, 3, or 4;
p is 0, 1, 2, 3, 4, or 5;
R is independently selected from the group consisting of halo, $C_1$–$C_6$ alkyl, $C_2$–$C_6$ alkynyl, $C_1$–$C_6$ alkoxy, —NR$^1$R$^2$, $C_1$–$C_4$ haloalkyl, hydroxy, —C(O)R$^1$, —OC(O)R$^1$, —C(O)NR$^1$R$^2$, —S(O)$_2$R$^1$, $C_1$–$C_6$ alkylsulfanyl, cyano, $C_1$–$C_2$ halalkoxy, or
the group defined by —(Y)$_o$—(Y$^1$)$_r$—(Y$^2$);

wherein:
Y is O and o is 0 or 1;
$Y^1$ is C(H)(R'), and r is 0, 1, 2, 3, or 4; and
$Y^2$ is aryl, heteroaryl, heterocyclic, $C_3$–$C_7$ cycloalkyl, or $C_2$–$C_6$ alkenyl;
Q is independently selected from the group consisting of halo, $C_1$–$C_4$ haloalkyl, $C_1$–$C_6$ alkyl, $C_1$–$C_6$ alkoxy, $C_1$–$C_4$ haloalkoxy, hydroxy, aralkoxy, $C_1$–$C_6$ alkenyl, alkynyl, $C_1$–$C_4$ hydroxyalkyl, cyano, aryloxy, $C_1$–$C_2$ halalkoxy, —$NO_2$, or —C(O)OR$^1$, or
the group defined by -(Z)$_q$-(Z$^1$)$_r$-(Z$^2$),
wherein:
Z is and NH q is 0 or 1; or
Z is $CH_2$ and q is 0, 1, 2, or 3; or
Z is O(CH$_2$)$_n$ where n is 1, 2, 3, or 4 and q is 0 or 1;
$Z^1$ is S(O)$_2$ or C(O); and r is 0 or 1, and
$Z^2$ is $C_1$–$C_6$ alkyl, aryl, heteroaryl, heterocyclic, hydroxy, halo, aralkyl, $C_1$–$C_2$ haloalkyl, C(H)(R')R$^3$, NH(CH$_2$)$_n$NR$^1$R$^2$, NH(CH$_2$)$_n$R$^3$, NH(CH$_2$)$_n$OR$^1$ or NR$^1$R$^2$, where
n is 1, 2, 3, or 4;
$R^1$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;
$R^2$ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl heterocyclic, or aralkyl;
$R^3$ is heteroaryl or heterocyclic, and
R' is hydrogen or $C_1$–$C_3$ alkyl.

In a fourth aspect of the present invention, there is provided a compound of Formula (III):

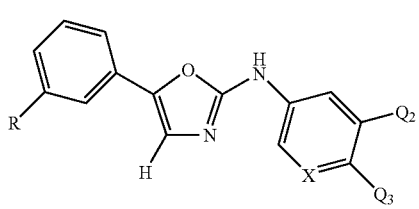

(III)

or a salt, solvate, or physiologically functional derivative thereof;
wherein:
R is independently selected from the group consisting of $C_1$–$C_6$ alkoxy, hydroxy, $C_1$–$C_6$ alkylsulfanyl, $C_1$–$C_2$ haloalkoxy, or
the group defined by —(Y)$_o$—(Y$^1$)$_r$—(Y$^2$);
wherein:
Y is O and o is 0 or 1;
$Y^1$ is C(H)(R'), and r is 0, 1, 2, 3, or 4; and
$Y^2$ is aryl, heteroaryl, heterocyclic, or $C_3$–$C_7$ cycloalkyl;
$Q_2$ is hydrogen, $C_1$–$C_6$ alkyl, $C_2$–$C_6$ alkenyl, $C_2$–$C_6$ alkynyl, halo, cyano, or $C_1$–$C_4$haloalkyl;
$Q_3$ is hydrogen or
the group defined by -(Z)$_q$-(Z$^1$)$_r$-(Z$^2$),
wherein:
Z is $CH_2$ and q is 0, 1, or 2; or
Z is O(CH$_2$)$_n$ where n is 1, 2, 3, or 4 and q is 0 or 1;
$Z^1$ is C(O); and r is 0 or 1, and
$Z^2$ is NH(CH$_2$)$_n$NR$^1$R$^2$ or NR$^1$R$^2$, where n is 1, 2, 3, or 4;

R¹ is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;

R² is hydrogen, $C_1$–$C_4$ alkyl, $C_2$–$C_6$ alkenyl, $C_2$–$C_6$ alkynyl, aryl, heteroaryl, $C_3$–$C_7$ cycloalkyl, heterocyclic, or aralkyl;

R³ is heteroaryl or heterocyclic;

R' is hydrogen or $C_1$–$C_3$ alkyl; and

X is CH or N.

In a fifth aspect of the present invention, there is provided a pharmaceutical composition including a therapeutically effective amount of a compound of Formula (I), (II), or (III) or a salt, solvate, or a physiologically functional derivative thereof and one or more of pharmaceutically acceptable carriers, diluents and excipients.

In a sixth aspect of the present invention, there is provided a method of treating a disorder in a mammal, said disorder being mediated by inappropriate VEGFR2 or CDK activity, including: administering to said mammal a therapeutically effective amount of a compound of Formula (I), (II), or (III) or a salt, solvate or a physiologically functional derivative thereof.

In a seventh aspect of the present invention, there is provided a compound of Formula (I), (II), or (III) or a salt, solvate, or a physiologically functional derivative thereof for use in therapy.

In an eighth aspect of the present invention, there is provided the use of a compound of Formula (I), (II), or (III) or a salt, solvate, or a physiologically functional derivative thereof in the preparation of a medicament for use in the treatment of a disorder mediated by inappropriate VEGFR2 or CDK activity.

In a ninth aspect of the present invention, there is provided a pharmaceutical composition including a therapeutically effective amount of a compound of Formula (I), (II), or (III) or a salt, solvate, or a physiologically functional derivative thereof and one or more of pharmaceutically acceptable carriers, diluents and excipients for preventing or reducing the severity of epithelial cytotoxicity in a subject receiving cytotoxic therapy.

In a tenth aspect of the present invention, there is provided a a method of preventing or reducing the severity of epithelial cytotoxicity in a patient receiving cytotoxic therapy, comprising administering to said patient a therapeutically effective amount of a compound of Formula (I), (II), or (III) or a salt, solvate, or physiologically functional derivative thereof.

In an eleventh aspect of the present invention, there is provided a method of treating a disorder in a mammal, said disorder being mediated by inappropriate VEGFR2 activity, including: administering to said mammal therapeutically effective amounts of (i) a compound of Formula (I), (II), or (III) or a salt, solvate or physiologically functional derivative thereof and (ii) an agent to inhibit growth factor receptor function.

In a twelfth aspect of the present invention, there is provided a method of treating a disorder in a mammal, said disorder being characterized by inappropriate angiogenesis, including: administering to said mammal a therapeutically effective amount of a compound of Formula (I), (II), or (III) or a salt, solvate or physiologically functional derivative thereof.

In a thirteenth aspect of the present invention, there is provided a method of treating cancer in a mammal, including administering to said mammal a therapeutically effective amount of a compound of Formula (I), (II), or (III) or salt, solvate or physiologically functional derivative thereof.

In a fourteenth aspect of the present invention, there is provided a method of treating cancer in a mammal, including administering to said mammal therapeutically effective amounts of (i) a compound of Formula (I), (II), or (III) or salt, solvate or physiologically functional derivative thereof and (ii) at least one additional anti-cancer therapy.

DETAILED DESCRIPTION OF THE INVENTION

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower haloalkyl, lower alkoxy, lower alkylsulfanyl, lower alkylsulfenyl, lower alkylsulfonyl, oxo, mercapto, amino optionally substituted by alkyl, carboxy, carboxamide optionally substituted by alkyl, aminosulfonyl optionally substituted by alkyl, nitro, or lower perfluoroalkyl, multiple degrees of substitution being allowed. Examples of "alkyl" as used herein include, but are not limited to, methyl, ethyl, propyl, n-butyl, n-pentyl, isobutyl, isopropyl, t-butyl and the like.

As used herein, the term "$C_1$–$C_6$alkyl" refers to an alkyl group, as defined above, which contains at least 1, and at most 6, carbon atoms. Examples of "$C_1$–$C_6$ alkyl" groups useful in the present invention include, but are not limited to, methyl, ethyl, propyl, isopropyl, isobutyl and n-butyl.

In a like manner, the terms "$C_1$–$C_3$ alkyl" and "$C_1$–$C_4$alkyl" refer to an alkyl group, as defined above, which contains at least 1, and at most 3 or 4, carbon atoms respectively. Examples of "$C_1$–$C_3$ alkyl" and "$C_1$–$C_4$ alkyl" groups useful in the present invention include methyl, ethyl, n-propyl, isopropyl, and t-butyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the terms "$C_1$–$C_3$ alkylene" and "$C_1$–$C_4$ alkylene" refer to an alkylene group, as defined above, which contains at least 1, and at most 3 or 4, carbon atoms respectively. Examples of "$C_1$–$C_3$ alkylene" groups useful in the present invention include, but are not limited to, methylene, ethylene, and n-propylene.

As used herein, the term "alkenyl" refers to a hydrocarbon radical having from two to ten carbons and at least one carbon-carbon double bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkenyl" as used herein include, but are not limited to ethenyl, propenyl, 1-butenyl, 2-butenyl, and isobutenyl.

As used herein, the term "$C_2$–$C_6$ alkenyl" refers to an alkenyl group as defined above containing at least 2 and at most 6 carbon atoms. Examples of "$C_2$–$C_6$ alkenyl" groups useful in the present invention include, but are not limited to, ethenyl, propenyl, 1-butenyl, 2-butenyl, and isobutenyl.

As used herein, the term "alkenylene" refers to an straight or branched chain divalent hydrocarbon radical having from two to ten carbon atoms and one or more carbon-carbon double bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "$C_1$–$C_3$ alkenylene" refers to an alkenylene group as defined above containing at least 1, and at most 3, carbon atoms. Examples of "$C_1$–$C_3$ alkenylene" groups useful in the present invention include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group which includes lower alkyl, lower alkoxy, lower alkylsulfanyl, lower alkylsulfenyl, lower alkylsulfonyl, oxo, aryl, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkynyl" as used herein, include but are not limited to acetylenyl, 1-propynyl, 1-butynyl, 2-butynyl, 1-pentynyl, and 1-hexynyl.

As used herein, the term "$C_2$–$C_6$ alkynyl" refers to an alkynyl group as defined above containing at least 2 and at most 6 carbon atoms. Examples of "$C_2$–$C_6$ alkynyl" groups useful in the present invention include, but are not limited to, acetylenyl, 1-propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon-carbon triple bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkynylene" as used herein include, but are not limited to, ethyne-1,2-diyl, propyne-1,3-diyl, and the like.

As used herein, the term "$C_2$–$C_3$ alkynylene" refers to an alkynylene group as defined above containing at least 2 and at most 3 carbon atoms. Examples of "$C_2$–$C_3$ alkynylene" groups useful in the present invention include, but are not limited to, ethyne-1,2-diyl, propyne-1,3-diyl, and the like.

As used herein, the term "halogen" or "halo" refers to fluoro (—F), chloro (—Cl), bromo (—Br), or iodo (—I).

As used herein, the terms "$C_1$–$C_2$ haloalkyl" and "$C_1$–$C_4$ haloalkyl" refers to a straight or branched chain hydrocarbon containing at least 1, and at most 2 or 4, carbon atoms substituted with at least one halogen, halogen being as defined herein. Examples of branched or straight chained "$C_1$–$C_2$ haloalkyl" and "$C_1$–$C_6$ haloalkyl" groups useful in the present invention include, but are not limited to, methyl, ethyl, propyl, isopropyl, isobutyl and n-butyl substituted independently with one or two halogens, e.g., fluoro, chloro, bromo and iodo.

As used herein, the term "$C_3$–$C_7$ cycloalkyl" refers to a non-aromatic cyclic hydrocarbon ring having from three to seven carbon atoms, which optionally includes a $C_1$–$C_4$ alkylene linker through which it may be attached. Exemplary "$C_3$–$C_7$ cycloalkyl" groups include, but are not limited to, cyclopropyl, cyclobutyl, cyclopentyl, cyclohexyl and cycloheptyl.

As used herein, the term "$C_3$–$C_7$ cycloalkylene" refers to a non-aromatic alicyclic divalent hydrocarbon radical having from three to seven carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "$C_3$–$C_7$ cycloalkenyl" refers to a non-aromatic cyclic hydrocarbon ring having from three to seven carbon atoms, and one or more carbon-carbon double bonds, which optionally includes a $C_1$–$C_4$ alkylene linker through which it may be attached. Exemplary "$C_3$–$C_7$ cycloalkenyl" groups include, but are not limited to, cyclobutenyl, cyclopentenyl, cyclohexenyl and cycloheptenyl.

As used herein, the term "heterocyclic" or the term "heterocyclyl" refers to a three to twelve-member non-aromatic ring being saturated or having one or more degrees of unsaturation containing one or more heteroatomic substitutions selected from S, SO, $SO_2$, O, or N, optionally substituted with substituents selected from the group consisting of lower alkyl; lower alkoxy; lower alkylsulfanyl; lower alkylsulfenyl; lower alkylsulfonyl; oxo; hydroxy; mercapto; amino optionally substituted by alkyl, aralkyl, or heterocyclyl; carboxy; carboxamide optionally substituted by alkyl; aminosulfonyl optionally substituted by alkyl; aryl; heteroaryl; heterocyclyl; nitro; cyano; halo; or lower perfluoroalkyl; multiple degrees of substitution being allowed. Such a ring may optionally include a $C_1$–$C_4$ alkylene linker through which it may be attached and may also be optionally fused to one or more of another "heterocyclic" ring(s), cycloalkyl ring(s), aryl ring(s), or heteroaryl ring(s). Examples of "heterocyclic" groups include, but are not limited to, tetrahydrofuranyl including tetrahydrofuran-2-yl; pyranyl; dioxanyl including 1,4-dioxanyl and 1,3-dioxanyl;

piperidinyl including 4-piperdin-1-yl, 6-piperdin-1-yl, and 1-propylpiperdin-4-yl; piperazinyl including 4-methylpiperazin-1-yl, 4-ethylpiperazin-1-yl, and 3,5-dimethylpiperazin-1-yl; pyrrolidinyl including 4-pyrrolidin-1-yl; morpholinyl including morpholin-4-yl and 4-thiomorpholin-4-yl; tetrahydrothiopyranyl; tetrahydrothiophenyl; benzofuranyl including 2,3-dihydro-1-benzofuran-5-yl; benzodioxepinyl including 3,4dihydro-2H-1,5-benzodioxepin-7-yl; benzodioxinyl including 2,3-dihydro-1,4-benzodioxin-6-yl and the like.

As used herein, the term "aryl" refers to an optionally substituted benzene ring or to an optionally substituted benzene ring system fused to one or more optionally substituted benzene rings to form, for example, anthracene, phenanthene, or napthalene ring systems. Such a ring may also be optionally fused to one or more of another "heterocyclic" ring(s), heteroaryl ring(s), or cycloalkyl ring(s). Exemplary optional substituents include lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carboxamide optionally substituted by alkyl or heterocyclic, aminosulfonyl optionally substituted by alkyl, acyl, aroyl, heteroaroyl, acyloxy, aroyloxy, heteroaroyloxy, alkoxycarbonyl, nitro, cyano, halo, lower perfluoroalkyl, heteroaryl, or aryl, multiple degrees of substitution being allowed. Examples of "aryl" groups include, but are not limited to, phenyl, 2-naphthyl, 1-naphthyl, 5,5,8,8-tetramethyl-5,6,7,8-tetrahydronaphthalen-2-yl, biphenyl, as well as substituted derivatives thereof.

As used herein, the term "aralkyl" refers to an aryl or heteroaryl group, as defined herein including both unsubstituted and substituted versions thereof, attached through a lower alkylene linker, wherein lower alkylene is as defined herein. Examples of "aralkyl" include, but are not limited to, benzyl, phenylpropyl, 2-pyridinylmethyl, 4pyridinylmethyl, 3-isoxazolylmethyl, 5-methyl-3-isoxazolylmethyl, and 2-imidazoyly ethyl.

As used herein, the term "heteroaryl" refers to a monocyclic five to seven membered aromatic ring, or to a bicyclic aromatic ring system comprising a heteroaryl fused to another heteraryl or aryl ring. Such heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of lower alkyl, lower alkoxy, lower alkylsulfanyl, lower alkylsulfenyl, lower alkylsulfonyl, oxo, hydroxy, mercapto, amino (optionally substituted by alkyl, aralkyl, aminoalkylene, heterocyclyl, or heterocyclylcarboxamide), carboxy, tetrazolyl, carboxamide optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, lower perfluoroalkyl, heteroaryl, or aryl, multiple degrees of substitution being allowed. Examples of "heteroaryl" groups used herein include, but are not limited to, furanyl, thiophenyl, pyrrolyl, imidazolyl, pyrazolyl, triazolyl, tetrazolyl, thiazolyl, oxazolyl, isoxazolyl including 3-methylisoxazol-3-yl, oxadiazolyl, thiadiazolyl, isothiazolyl, pyridinyl, pyridazinyl, pyrazinyl, pyrimidinyl, quinolinyl, isoquinolinyl, benzofuranyl benzothiophenyl, indolyl, indolinyl, indazolyl, and substituted versions thereof.

As used herein, the term "amino" refers to the group —NH$_2$.

As used herein the term "alkylamino" refers to the group —NHR$_a$ wherein R$_a$ is alkyl as defined above.

As used herein the term "aminoalkylene" refers to the group —(CH$^2$)$_x$NR$_a$R$_b$ wherein x is 1, 2, 3, or 4, R$_a$ is hydrogen or alkyl and R$_b$ is hydrogen or alkyl.

As used herein the term "arylamino" refers to the group —NHR$_a$ wherein R$_a$ is aryl as defined above.

As used herein the term "aralkylamino" refers to the group —NHR$_a$ wherein R$_a$ is an aralkyl group as defined above.

As used herein, the term "alkoxy" refers to the group R$_a$O—, where R$_a$ is alkyl as defined above.

As used herein, the term "C$_3$–C$_7$ cycloalkoxy" refers to the group R$_a$O—, where R$_a$ is C$_3$–C$_7$ cycloalkyl as defined above.

As used herein, the term "alkenyloxy" refers to the group R$_a$O—, where R$_a$ is alkenyl as defined above.

As used herein the term "aralkoxy" refers to the group R$_b$R$_a$O—, where R$_a$ is alkylene and R$_b$ is aryl or heteroaryl, as defined above.

As used herein the term "heterocyclalkoxy" refers to the group R$_b$R$_a$O—, where R$_a$ is alkylene and R$_b$ is heterocyclic, as defined above.

As used herein the term "halalkoxy" refers to the group R$_a$O—, where R$_a$ is C$_1$–C$_2$ haloalkyl as defined above.

As used herein, the term "alkylsulfanyl" refers to the group R$_a$S—, where R$_a$ is alkyl as defined above.

As used herein, the term "alkylsulfenyl" refers to the group R$_a$S(O)—, where R$_a$ is alkyl as defined above.

As used herein, the term "alkylsulfonyl" refers to the group R$_a$SO$_2$—, where R$_a$ is alkyl as defined above.

As used herein, the term "oxo" refers to the group =O.

As used herein, the term "hydroxy" refers to the group —OH.

As used herein, the term "mercapto" refers to the group —SH.

As used herein, the term "carboxy" refers to the group —COOR$_a$, wherein R$_a$ is hydrogen or C$_1$–C$_4$alkyl.

As used herein, the term "cyano" refers to the group —CN.

As used herein, the term "nitro" refers to the group —NO$_2$.

As used herein the term "cyanoalkyl" refers to the group —R$_a$CN wherein R$_a$ is C$_1$–C$_3$ alkylene as defined above. Exemplary "cyanoalkyl" groups useful in the present invention include, but are not limited to, cyanomethyl, cyanoethyl, and cyanopropyl.

As used herein, the term "aminosulfonyl" refers to the group —SO$_2$NH$_2$.

As used herein, the term "carboxamide" refers to the group —C(O)NH$_2$.

As used herein, the term "heterocyclylcarboxamide" refers to the group —C(O)NHR$_a$, wherein R$_a$ is heterocyclyl as defined above.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$— or S(O)$_2$.

As used herein, the term "acyl" refers to the group R$_a$C(O)—, where R$_a$ is alkyl, cycloalkyl, or heterocyclyl as defined herein.

As used herein, the term "aroyl" refers to the group R$_a$C(O)—, where R$_a$ is aryl as defined herein.

As used herein, the term "heteroaroyl" refers to the group R$_a$C(O)—, where R$_a$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of Formula (I), (II), or (III), or a salt or physiologically functional derivative thereof and a solvent. Such solvents for the purpose of the invention may not interfere with the biological activity of the solute. Examples of suitable solvents include, but are not limited to, water, methanol, ethanol and acetic acid. Preferably, the solvent used is a pharmaceutically acceptable solvent. Examples of suitable pharmaceutically acceptable solvents include water, ethanol and acetic acid. Most preferably the solvent used is water.

The compounds of Formulae (I), (II), or (III) have the ability to crystallize in more than one form, a characteristic, which is known as polymorphism, and it is understood that such polymorphic forms ("polymorphs") are within the scope of Formulae (I) and (II). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention may include mixtures of enantiomers as well as purified enantiomers or enantiomerically enriched mixtures. Also included within the scope of the invention are the individual isomers of the compounds represented by Formula (I), (II), or (III) above as well as any wholly or partially equilibrated mixtures thereof. The present invention also covers the individual isomers of the compounds represented by the formulas above as mixtures with isomers thereof in which one or more chiral centers are inverted.

It is to be understood that the following embodiments refer to compounds within the scope of all of Formula (I), (II), or (III) as defined above unless specifically limited by the definition of each Formula or specifically limited otherwise. It is also understood that the embodiments of the present invention described herein, including uses and compositions, are applicable to all of Formula (I), (II), or (III).

In one embodiment, $D_1$ is selected from

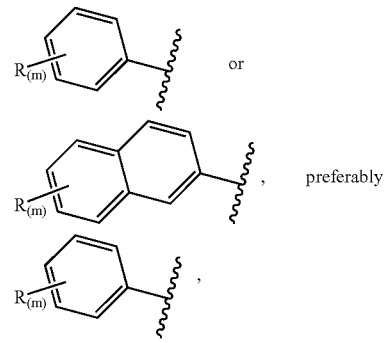

preferably wherein R is as defined above and m is 0, 1, 2, 3, or 4.

In one embodiment $D_1$ is:

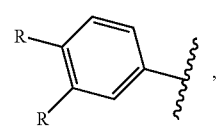

wherein R is as defined above.

In another embodiment, $D_1$ is:

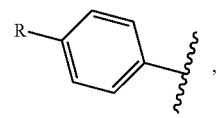

wherein R is as defined above.

In another embodiment, $D_1$ is:

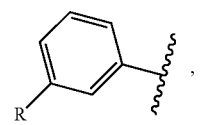

wherein R is as defined above.

In another embodiment, $D_1$ is:

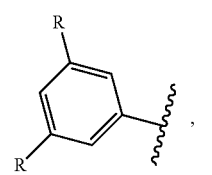

wherein R is as defined above.

In another embodiment, $D_1$ is a heteroaryl ring optionally substituted with one or more R groups; preferably, D1 is furanyl, benzofuranyl, thiophenyl, benzothiophenyl, pyridinyl, isoxazolyl, or thiazolyl, each optionally substituted with one or more R groups, wherein R is as defined above.

In one embodiment, $D_1$ is selected from

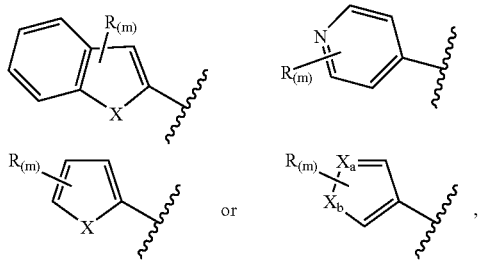

wherein $X$, $X_a$, $X_b$, R, and m are as defined above.

In another embodiment, $D_1$ is selected from

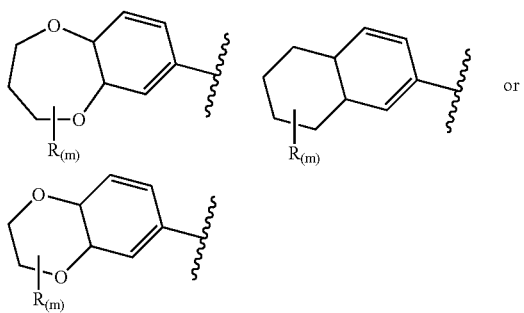

wherein R and m are as defined above.

In a one embodiment, $D_1$ is phenyl substituted with $R_{(m)}$ wherein m is 0, 1, or 2 and R is $C_1$–$C_6$ alkoxy, halo, or the group defined by —$(Y)_o$—$(Y^1)_r$—$(Y^2)$; wherein Y is O and o is 0 or 1; $Y^1$ is C(H)(R'), and r is 0, 1, 2, 3, or 4 and $Y^2$ is aryl, heteroaryl, heterocyclic, or $C_3$–$C_7$ cycloalkyl.

In a preferred embodiment, $D_1$ is phenyl substituted with $R_{(m)}$ wherein m is 0 or 1 and R is $C_1$–$C_8$ alkoxy or halo, more preferably $D_1$ is phenyl substituted with $R_{(m)}$ wherein m is 0 or 1 and R is methoxy, —F, or —Br, most preferably, $D_1$ is phenyl substituted with $R_{(m)}$ wherein m is 1 and R is methoxy or —F.

In another preferred embodiment, $D_1$ is phenyl substituted with $R_{(m)}$ wherein m is 1 and R is the group defined by —$(Y)_o$—$(Y^1)_r$—$(Y^2)$; wherein Y is O and o is 0 or 1; $Y^1$ is C(H)(R'), and r is 0, 1, 2, 3, or 4 and $Y^2$ is aryl, heteroaryl, heterocyclic, or $C_3$–$C_7$ cycloalkyl, more preferably $D_1$ is phenyl substituted with $R_{(m)}$ wherein m is 1 and R is the group defined by —$(Y)_o$—$(Y^1)_r$—$(Y^2)$; wherein Y is O and o is 0 or 1; r is 0, and $Y^2$ is aryl, heteroaryl, or $C_3$–$C_7$ cycloalkyl, most preferably $D_1$ is phenyl substituted with $R_{(m)}$ wherein m is 1 and R is unsubstituted or substituted cyclopentyloxy, phenyl, pyrimidinyl, or pyridinyl, suitable substituents being recited in the definition of cycloalkyl, aryl, and heteroaryl recited above.

In one embodiment, $D_2$ is hydrogen or $C_1$–$C_4$ alkyl. In a preferred embodiment, $D_2$ is hydrogen or methyl. In a more preferred embodiment, $D_2$ is hydrogen.

In one embodiment, $D_3$ is:

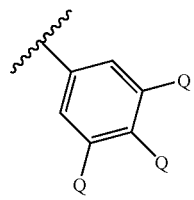

wherein Q is as defined above.
In another embodiment, $D_3$ is:

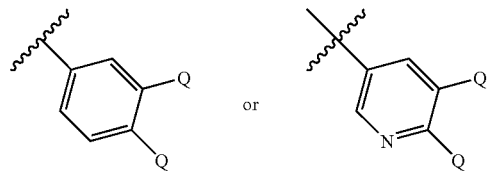

wherein Q is as defined above.
In another embodiment, $D_3$ is:

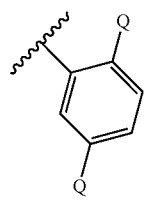

wherein Q is as defined above.
In another embodiment, $D_3$ is:

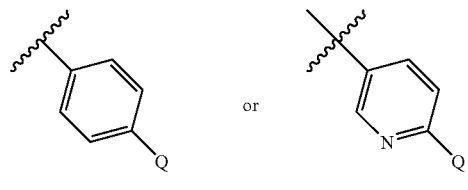

wherein Q is as defined above.

In one embodiment, $D_3$ is phenyl substituted with $Q_{(p)}$ wherein p is 0, 1, 2, or 3 and Q is independently selected from the group consisting of halo, $C_1$–$C_4$ haloalkyl, $C_1$–$C_6$ alkoxy, hydroxy, —C(O)OR$^1$, or —NR$^1$R$^2$, or the group defined by -$(Z)_q$-$(Z^1)_r$-$(Z^2)$, wherein Z is NH and q is 0 or 1; or Z is CH$_2$ and q is 0, 1, 2, or 3; or Z is O(CH$_2$)$_n$where n is 1, 2, 3, or 4 and q is 0 or 1; $Z^1$ is S(O)$_2$ or C(O); and r is 0 or 1, and $Z^2$ is $C_1$–$C_6$ alkyl, aryl, heteroaryl, heterocyclic, hydroxy, halo, aralkyl, $C_1$–$C_2$ haloalkyl, C(H)(R')R$^3$, NH(CH$_2$)$_n$NR$^1$R$^2$, NH(CH$_2$)$_n$R$_3$, NH(CH$_2$)$_n$OR$^1$ or NR$^1$R$^2$; where n is 1, 2, 3, or 4.

In a preferred embodiment, $D_3$ is phenyl substituted with $Q_{(p)}$ wherein p is 0 or 1 and Q is independently selected from the group consisting of $C_1$–$C_6$ alkoxy, or or the group defined by -$(Z)_q$-$(Z^1)_r$-$(Z^2)$, wherein Z is CH$_2$ and q is 1, 2, or 3; $Z^1$ is $S(O)_2$ or $C(O)$; and r is 1, and $Z^2$ is $C_1$–$C_6$ alkyl, aryl, heteroaryl, heterocyclic, halo, aralkyl, $C_1$–$C_2$ haloalkyl, $C(H)(R')R^3$, $NH(CH_2)_nNR^1R^2$, $NH(CH_2)_nR^3$, $NH(CH_2)_nOR^1$ or $NR^1R^2$; where n is 1, 2, 3, or 4 and $R^1$, $R^2$, $R^3$ are as defined herein; preferably $D_3$ is phenyl substituted with $Q_{(p)}$ wherein p is 1 and Q is the group defined by $-(Z)_q$-$(Z^1)_r$-$(Z^2)$, wherein q is 0; r is 0; and $Z^2$ is aryl, heteroaryl, heterocyclic; most preferably $D_3$ is phenyl substituted with $Q_{(p)}$ wherein p is 1 and Q is the group defined by 4-methylpiperizinyl, dimethylpiperizinyl, 4-ethylpiperizinyl, morpholinyl, piperidinyl, and thiomorpholinyl.

In a preferred embodiment, $D_3$ is phenyl substituted with $Q_{(p)}$ wherein p is 2 and Q is independently selected from the group consisting of halo, $C_1$–$C_4$ haloalkyl, $C_1$–$C_6$ alkoxy, hydroxy, —$C(O)OR^1$, or —$NR^1R^2$, or the group defined by $-(Z)_q$-$(Z^1)_r$-$(Z^2)$, wherein or Z is $CH_2$ and q is 0, 1, 2, or 3; or Z is $O(CH_2)_n$ where n is 1, 2, 3, or 4 and q is 0 or 1; and $Z^1$ is $S(O)_2$ or $C(O)$; and r is 0 or 1, and $Z^2$ is $C_1$–$C_6$ alkyl, aryl, heteroaryl, heterocyclic, hydroxy, halo, aralkyl, $C_1$–$C_2$ haloalkyl, $C(H)(R')R^3$, $NH(CH_2)_nNR^1R^2$, $NH(CH_2)_nR^3$, $NH(CH_2)_nOR^1$ or $NR^1R^2$; where n is 1, 2, 3, or 4; more preferably $D_3$ is phenyl substituted with $Q_{(p)}$ wherein p is 2 and Q is independently selected from the group consisting of $C_1$–$C_6$ alkoxy, hydroxy, or the group defined by $(Z)_q$-$(Z^1)_r$-$(Z^2)$, wherein Z is $CH_2$ and q is 0, 1, 2, or 3; or Z is $O(CH_2)_n$ where n is 1, 2, 3, or 4 and q is 0 or 1; and $Z^1$ is $S(O)_2$; and r is 1, and $Z^2$ is $C_1$–$C_6$ alkyl, aryl, heteroaryl, heterocyclic, halo, aralkyl, $C_1$–$C_2$ haloalkyl, $C(H)(R')R^3$, $NH(CH_2)_nNR^1R^2$, $NH(CH_2)_nR^3$, $NH(CH_2)_nOR^1$ or $NR^1R^2$; where n is 1, 2, 3, or 4; most preferably $D_3$ is phenyl substituted with $Q_{(p)}$ wherein p is 2 and Q is methoxy and the group defined by $-(Z)_q$-$(Z^1)_r$-$(Z^2)$, wherein q is 0; and $Z^1$ is $S(O)_2$; and r is 1, and $Z^2$ is $C_1$–$C_6$ alkyl, aryl, heteroaryl, heterocyclic, halo, aralkyl, $C_1$–$C_2$ haloalkyl, $C(H)(R')R^3$, $NH(CH_2)_nNR^1R^2$, $NH(CH_2)_nR^3$, $NH(CH_2)_nOR^1$ or $NR^1R^2$; where n is 1, 2, 3, or 4.

Specific examples of compounds of the present invention include the following:

5-(3-Methoxyphenyl)-N-phenyl-1,3-oxazol-2-amine;
3-(2-Anilino-1,3-oxazol-5-yl)phenol;
N-[4-(4-Methylpiperazin-1-yl)phenyl]-5-phenyl-1,3-oxazol-2-amine;
5-(3-Methoxyphenyl)-N-[4-(4-methylpiperazin-1-yl)phenyl-]1,3-oxazol-2-amine;
N-[4-(4-Ethylpiperazin-1-yl)phenyl]-5-(3-methoxyphenyl)-1,3-oxazol-2-amine;
N-[4-(4-Ethylpiperazin-1-yl)phenyl]-5-phenyl-1,3-oxazol-2-amine;
N-[4-(Morpholin-4-ylmethyl)phenyl]-5-phenyl-1,3-oxazol-2-amine;
5-(3-Methoxyphenyl)-N-(4-morpholin-4-ylphenyl)-1,3-oxazol-2-amine;
5-(3-Methoxyphenyl)-N-(4-piperidin-1-ylphenyl)-1,3-oxazol-2-amine;
5-(3-Methoxyphenyl)-N-[4-(morpholin-4-ylmethyl)phenyl]-1,3-oxazol-2-amine;
5-(3-Ethoxyphenyl)-N-[4-(4-methylpiperazin-1-yl)phenyl]-1,3-oxazol-2-amine;
5-(3-Isopropoxyphenyl)-N-[4-(4-methylpiperazin-1-yl)phenyl]-1,3-oxazol-2-amine;
5-[3-(Cyclopentyloxy)phenyl]-N-[4-(4-methylpiperazin-1-yl)phenyl]-1,3-oxazol-2-amine;
5-(3-Isobutoxyphenyl)-N-[4-(4-methylpiperazin-1-yl)phenyl]-1,3-oxazol-2-amine;
5-[3-(Benzyloxy)phenyl]-N-[4-(4-methylpiperazin-1-yl)phenyl]-1,3-oxazol-2-amine;
N-[(4-Methylpiperazin-1-yl)phenyl]-5-{3-[(2-methylprop-2-enyl)oxy]phenyl}-1,3-oxazol-2-amine;
N-[4-(4-Methylpiperazin-1-yl)phenyl]-5-(3-propoxyphenyl)-1,3-oxazol-2-amine;
5-[3-(Cyclohexyloxy)phenyl]-N-[4-(4-methylpiperazin-1-yl)phenyl]-1,3-oxazol-2-amine;
N-[3-Chloro-4-(4-methylpiperazin-1-yl)phenyl]-5-(3-methoxyphenyl)-1,3-oxazol-2-amine;
N-[3-Fluoro-4-(4-methylpiperazin-1-yl)phenyl]-5-(3-methoxyphenyl)-1,3-oxazol-2-amine;
5-(3-Methoxyphenyl)-N-[4-(4-methylpiperazin-1-yl)-3-(trifluoromethyl)phenyl]-1,3-oxazol-2-amine;
5-(3-Methoxyphenyl)-N-[3-methyl-4-(4-methylpiperazin-1-yl)phenyl]-1,3-oxazol-2-amine;
N-[4-(3,5-Dimethylpiperazin-1-yl)phenyl]-5-(3-methoxyphenyl)-1,3-oxazol-2-amine;
5-(3-Methoxyphenyl)-N-[2-methyl-4-(4-methylpiperazin-1-yl)phenyl]-1,3-oxazol-2-amine;
5-[3-(Cyclopentyloxy)phenyl]-N-[4-(4-methylpiperazin-1-yl)-3-(trifluoromethyl)phenyl]-1,3-oxazol-2-amine;
N-[3-Chloro-4-(4-methylpiperazin-1-yl)phenyl]-5-[3-(cyclopentyloxy)phenyl]-1,3-oxazol-2-amine;
5-[3-(Cyclopentyloxy)phenyl]-N-[3-methyl-4-(4-methylpiperazin-1-yl)phenyl]-1,3-oxazol-2-amine;
5-[3-(Cyclopentyloxy)phenyl]-N-[3-fluoro-4-(4-methylpiperazin-1-yl)phenyl]-1,3-oxazol-2-amine;
3-(2-{[4-(4-Methylpiperazin-1-yl)phenyl]amino}-1,3-oxazol-5-yl)phenol;
5-[3-(Cyclopentyloxy)phenyl]-N-(4-thiomorpholin-4-ylphenyl)-1,3-oxazol-2-amine;
N-[5-(3-Methoxyphenyl)-1,3-oxazol-2-yl]-6-(4-methylpiperazin-1-yl)pyridin-3-amine;
6-(1H-Imidazol-1-yl)-N-[5-(3-methoxyphenyl)-1,3-oxazol-2-yl]pyridin-3-amine;
N-[5-(3-Methoxyphenyl)-1,3-oxazol-2-yl]-6-piperidin-1-yl)pyridin-3-amine;
N-{5-[3-(Cyclopentyloxy)phenyl]-1,3-oxazol-2-yl}-6-(4-methylpiperazin-1-yl)pyridin-3-amine;
$N^2$, $N_2$-Diethyl-$N^5$-[5-(3-methoxyphenyl)-1,3-oxazol-2-yl]pyridine-2,5-diamine;
$N^5$-{5-[3-(Cyclopentyloxy)phenyl]-1,3-oxazol-2-yl}-$N^2$, $N^2$-diethylpyridine-2,5-diamine;
N-{5-[3-(Cyclopentyloxy)phenyl]-1,3-oxazol-2-yl}-5-methyl-6-(4-methylpiperazin-1-yl)pyridin-3-amine;
5-(3-Methoxyphenyl)-N-{4-[(4-methylpiperazin-1-yl)methyl]phenyl}-1,3-oxazol-2-amine;
N-{4-[(4-Methylpiperazin-1-yl)methyl]phenyl}-5-phenyl-1,3-oxazol-2-amine;
N-{4-[(Dimethylamino)methyl]phenyl}-5-(3-methoxyphenyl)-1,3-oxazol-2-amine;
5-[3-(Cyclopentyloxy)phenyl]-N-{4-[(dimethylamino)methyl]phenyl}-1,3-oxazol-2-amine;
N-{4-[2-(Dimethylamino)ethyl]phenyl}-5-(3-methoxyphenyl)-1,3-oxazol-2-amine;
5-(3-Methoxyphenyl)-N-[4-(piperidin-1-ylmethyl)phenyl]-1,3-oxazol-2-amine;
5-(3-Methoxyphenyl)-N-[4-(pyrrolidin-1-ylmethyl) phenyl]-1,3-oxazol-2-amine;
N-{4-[(Diethylamino)methyl]phenyl}-5-(3-methoxyphenyl)-1,3-oxazol-2-amine;
N-[2-(Diethylamino)ethyl]-4-{[5-(3-methoxyphenyl)-1,3-oxazol-2-yl]amino}benzamide;
5-(3-Methoxyphenyl)-N-{4-[(4-methylpiperazin-1-yl)carbonyl]phenyl}-1,3-oxazol-2-amine;
4-({5-[3-(Cyclopentyloxy)phenyl]-1,3-oxazol-2-yl}amino)-N-[2-(diethylamino)ethyl]benzamide;

5-(3-Methoxyphenyl)-N-[4-(1-propylpiperidin-4-yl)-1,3-thiazol-2-yl]-1,3-oxazol-2-amine;
N,5-diphenyl-1,3-oxazol-2-amine;
N-methyl-1-{4-[(5-phenyl-1,3-oxazol-2-yl)amino]phenyl}methanesulfonamide;
N-{4-[(methylsulfonyl)methyl]phenyl}-5-phenyl-1,3-oxazol-2-amine;
N,N-diethyl-4-methoxy-3-[(5-phenyl-1,3-oxazol-2-yl)amino]benzenesulfonamide;
N-butyl-4-methoxy-3-[(5-phenyl-1,3-oxazol-2-yl)amino]benzenesulfonamide;
N-(3,4-dimethoxyphenyl)-5-phenyl-1,3-oxazol-2-amine;
N-[5-(ethylsulfonyl)-2-methoxyphenyl]-5-phenyl-1,3-oxazol-2-amine;
5-phenyl-N-[3-(phenylsulfonyl)phenyl]-1,3-oxazol-2-amine;
N,N-diethyl-4-[(5-phenyl-1,3-oxazol-2-yl)amino]benzamide;
4-(ethylsulfonyl)-2-[(5-phenyl-1,3-oxazol-2-yl)amino]phenol;
N-(2-methoxyphenyl)-5-phenyl-1,3-oxazol-2-amine;
N-butyl-3-[(5-phenyl-1,3-oxazol-2-yl)amino]benzenesulfonamide;
N,N-dimethyl-4-[(5-phenyl-1,3-oxazol-2-yl)amino]benzenesulfonamide;
2,5-dimethoxy-4-[(5-phenyl-1,3-oxazol-2-yl)amino]benzenesulfonamide;
N-(2-methoxy-5-nitrophenyl)-5-phenyl-1,3-oxazol-2-amine;
2-{4-[(5-phenyl-1,3-oxazol-2-yl)amino]phenyl}ethanol;
1-{4-methoxy-3-[(5-phenyl-1,3-oxazol-2-yl)amino]phenyl}ethanone;
{3-[(5-phenyl-1,3-oxazol-2-yl)amino]phenyl}methanol;
N-[5-(ethylsulfonyl)-2-methoxyphenyl]-5-(3-methoxyphenyl)-1,3-oxazol-2-amine;
4-(2-{[5-(ethylsulfonyl)-2-methoxyphenyl]amino}-1,3-oxazol-5-yl)phenol;
3-{[5-(4-fluorophenyl)-1,3-oxazol-2-yl]amino}-4-methoxy-N,N-dimethylbenzenesulfonamide;
N-{5-(ethylsulfonyl)-2-[2-(1H-imidazol-1-yl)ethoxy]phenyl}-5-(4-fluorophenyl)-1,3-oxazol-2-amine;
N-[5-(ethylsulfonyl)-2-(2-pyridin-2-ylethoxy)phenyl]-5-phenyl-1,3-oxazol-2-amine;
N-{5-(ethylsulfonyl)-2-[2-(1-H1,2,3-triazol-1-yl)ethoxy]phenyl}-5-phenyl-1,3-oxazol-2-amine;
5-phenyl-N-(3,4,5-trimethoxyphenyl)-1,3-oxazol-2-amine;
N-(2,5-dimethoxyphenyl)-5-phenyl-1,3-oxazol-2-amine;
3-methyl-5-[(5-phenyl-1,3-oxazol-2-yl)amino]benzene-1,2-diol;
N-(3,5-dimethoxyphenyl)-5-phenyl-1,3-oxazol-2-amine;
N-(3-methylphenyl)-5-phenyl-1,3-oxazol-2-amine;
N-{3-[2-(1-H-imidazol-1-yl)ethoxy]-4-methoxyphenyl}-5-phenyl-1,3-oxazol-2-amine;
N-{4-[2-(1-H-imidazol-1-yl)ethoxy]-3-methoxyphenyl}-5-phenyl-1,3-oxazol-2-amine;
N-[5-(ethylsulfonyl)-2-methoxyphenyl]-5-(4-fluorophenyl)-1,3-oxazol-2-amine;
5-(4-fluorophenyl)-N-{2-methoxy-5-[(methylsulfonyl)methyl]phenyl}-1,3-oxazol-2-amine;
N-(5-{[5-(3-iodophenyl)-1,3-oxazol-2-yl]amino}-2-methylphenyl)methanesulfonamide;
3-{[5-(4-fluorophenyl)-1,3-oxazol-2-yl]amino}-N,N-dimethylbenzenesulfonamide;
N-[3-(ethylsulfonyl)phenyl]-5-(4-fluorophenyl)-1,3-oxazol-2-amine;
3-{[5-(4-fluorophenyl)-1,3-oxazol-2-yl]amino}-4-methoxy-N-(pyridin-2-ylmethyl)benzenesulfonamide;
5-(4-fluorophenyl)-N-[2-methoxy-5-(methylsulfonyl)phenyl]-1,3-oxazol-2-amine;
N-{2-methoxy-5-[(2-pyridin-2-ylethyl)sulfonyl]phenyl}-5-phenyl-1,3-oxazol-2-amine;
3-{[5-(4-fluorophenyl)-1,3-oxazol-2-yl]amino}-4-methoxybenzenesulfonamide;
N-{5-[(1-ethylpropyl)sulfonyl]-2-methoxyphenyl}-5-(4-fluorophenyl)-1,3-oxazol-2-amine;
5-(4-fluorophenyl)-N-(2-methoxy-5-{[(5-methylisoxazol-3-yl)methyl]sulfonyl}phenyl)-1,3-oxazol-2-amine;
3-{[5-(3-bromophenyl)-1,3-oxazol-2-yl]amino}-4-methoxybenzenesulfonamide;
5-(4-fluorophenyl)-N-[5-(isobutylsulfonyl)-2-methoxyphenyl]-1,3-oxazol-2-amine;
5-(4-fluorophenyl)-N-{2-methoxy-5-[(tetrahydrofuran-2-ylmethyl)sulfonyl]phenyl}-1,3-oxazol-2-amine;
5-(4-fluorophenyl)-N-[2-methoxy-5-(tetrahydrofuran-3-ylsulfonyl)phenyl]-1,3-oxazol-2-amine;
5-(4-fluorophenyl)-N-(2-methoxy-5-{[2-(4-methyl-1,3-thiazol-5-yl)ethyl]sulfonyl}phenyl)-1,3-oxazol-2-amine;
5-(4-fluorophenyl)-N-[5-(isopropylsulfonyl)-2-methoxyphenyl]-1,3-oxazol-2-amine;
5-(3-bromophenyl)-N-[5-(isopropylsulfonyl)-2-methoxyphenyl]-1,3-oxazol-2-amine;
5-(4-fluorophenyl)-N-(5-{[2-(1-H-imidazol-1-yl)ethyl]sulfonyl}-2-methoxyphenyl)-1,3-oxazol-2-amine;
5-(3-bromophenyl)-N-(2-methoxy-5-{[2-(4-methyl-1,3-thiazol-5-yl)ethyl]sulfonyl}phenyl)-1,3-oxazol-2-amine;
N-(2-ethoxyphenyl)-5-(3-methoxyphenyl)-1,3-oxazol-2-amine;
N-(3,4-dimethoxyphenyl)-5-(3-methoxyphenyl)-1,3-oxazol-2-amine;
N-(3,4-dimethoxyphenyl)-5-(4-fluorophenyl)-1,3-oxazol-2-amine;
N-(3,4-dimethoxyphenyl)-5-(4-methylphenyl)-1,3-oxazol-2-amine;
5-(3,4-dichlorophenyl)-N-(3,4-dimethoxyphenyl)-1,3-oxazol-2-amine;
5-[4-(diethylamino)phenyl]-N-(3,4-dimethoxyphenyl)-1,3-oxazol-2-amine;
5-(4-chloro-3-methylphenyl)-N-(3,4-dimethoxyphenyl)-1,3-oxazol-2-amine;
N-[5-(ethylsulfonyl)-2-methoxyphenyl]-5-(4-fluorophenyl)-1,3-oxazol-2-amine;
5-(3,4-difluorophenyl)-N-[5-(ethylsulfonyl)-2-methoxyphenyl]-1,3-oxazol-2-amine;
4-chloro-3-{[5-(4-fluorophenyl)-1,3-oxazol-2-yl]amino}-N,N-dimethylbenzenesulfonamide;
4-chloro-N,N-diethyl-3-{[5-(4-fluorophenyl)-1,3-oxazol-2-yl]amino}benzenesulfonamide;
5-(4-fluorophenyl)-N-[3-(methylsulfonyl)phenyl]-1,3-oxazol-2-amine;
N-[2-chloro-5-(methylsulfonyl)phenyl]-5-(4-fluorophenyl)-1,3-oxazol-2-amine;
N-[2-chloro-5-(ethylsulfonyl)phenyl]-5-(4-fluorophenyl)-1,3-oxazol-2-amine;
5-(4-fluorophenyl)-N-(3,4,5-trimethoxyphenyl)-1,3-oxazol-2-amine;
5-(3-bromophenyl)-N-(3,4,5-trimethoxyphenyl)-1,3-oxazol-2-amine;
5-(1,1'-biphenyl-3-yl)-N-(3,4,5-trimethoxyphenyl)-1,3-oxazol-2-amine;
4-methoxy-N-(2-morpholin-4-ylethyl)-3-[(5-phenyl-1,3-oxazol-2-yl)amino]benzenesulfonamide;
3-{[5-(4-fluorophenyl)-1,3-oxazol-2-yl]amino}-4-methoxy-N-(3-pyrrolidin-1-ylpropyl)benzenesulfonamide;

3-{[5-(4-fluorophenyl)-1,3-oxazol-2-yl]amino}-N-[3-(1-H-imidazol-1-yl)propyl]-4-methoxybenzenesulfonamide;
3-{[5-(4-fluorophenyl)-1,3-oxazol-2-yl]amino}-4-methoxy-N-(pyridin-3-ylmethyl)benzenesulfonamide;
3-{[5-(4-fluorophenyl)-1,3-oxazol-2-yl]amino}-4-methoxy-N-(pyridin-4-ylmethyl)benzenesulfonamide;
3-{[5-(4-fluorophenyl)-1,3-oxazol-2-yl]amino}-N-isopropyl-4-methoxybenzenesulfonamide;
3-{[5-(4-fluorophenyl)-1,3-oxazol-2-yl]amino}-4-methoxy-N-(tetrahydrofuran-2-ylmethyl)benzenesulfonamide;
5-(4-fluorophenyl)-N-[2-methoxy-5-(morpholin-4-ylsulfonyl)phenyl]-1,3-oxazol-2-amine;
5-(4-fluorophenyl)-N-{2-methoxy-5-[(4-methylpiperazin-1-yl)sulfonyl]phenyl}-1,3-oxazol-2-amine;
5-(4-fluorophenyl)-N-[2-methoxy-5-(thiomorpholin-4-ylsulfonyl)phenyl]-1,3-oxazol-2-amine;
N-(cyclopropylmethyl)-3-{[5-(4-fluorophenyl)-1,3-oxazol-2-yl]amino}-4-methoxybenzenesulfonamide;
3-{[5-(4-fluorophenyl)-1,3-oxazol-2-yl]amino}-4-methoxy-N-(3-methoxypropyl)benzenesulfonamide;
3-{[5-(4-fluorophenyl)-1,3-oxazol-2-yl]amino}-4-methoxy-N-methylbenzenesulfonamide;
N-(2-ethoxyethyl)-3-{[5-(4-fluorophenyl)-1,3-oxazol-2-yl]amino}-4-methoxybenzenesulfonamide;
N-[5-(isopropylsulfonyl)-2-methoxyphenyl]-5-(3-pyridin-2-ylphenyl)-1,3-oxazol-2-amine;
N-[2-methoxy-5-(tetrahydrofuran-3-ylsulfonyl)phenyl]-5-(3-pyridin-2-ylphenyl)-1,3-oxazol-2-amine;
N-[5-(isobutylsulfonyl)-2-methoxyphenyl]-5-(3-pyridin-2-ylphenyl)-1,3-oxazol-2-amine;
5-(1,1'-biphenyl-3-yl)-N-{2-methoxy-5-[(1-pyridin-4-ylethyl)sulfonyl]phenyl}-1,3-oxazol-2-amine;
N-{2-methoxy-5-[(tetrahydrofuran-2-ylmethyl)sulfonyl]phenyl}-5-(3-pyridin-2-ylphenyl)-1,3-oxazol-2-amine;
N-(2-methoxy-5-{[2-(4-methyl-1,3-thiazol-5-yl)ethyl]sulfonyl}phenyl)-5-(3-pyridin-2-ylphenyl)-1,3-oxazol-2-amine;
5-(4-chlorophenyl)-N-[5-(ethylsulfonyl)-2-methoxyphenyl]-1,3-oxazol-2-amine;
4-(2-{[5-(ethylsulfonyl)-2-methoxyphenyl]amino}-1,3-oxazol-5-yl)benzonitrile;
4-(2-{[5-(ethylsulfonyl)-2-methoxyphenyl]amino}-1,3-oxazol-5-yl)benzamide;
5-(4-bromophenyl)-N-[5-(ethylsulfonyl)-2-methoxyphenyl]-1,3-oxazol-2-amine;
N-[5-(ethylsulfonyl)-2-methoxyphenyl]-5-(3-methyl-1-benzothien-2-yl)-1,3-oxazol-2-amine;
5-(3-bromophenyl)-N-[5-(ethylsulfonyl)-2-methoxyphenyl]-1,3-oxazol-2-amine;
5-(3-chlorophenyl)-N-[5-(ethylsulfonyl)-2-methoxyphenyl]-1,3-oxazol-2-amine;
N-[5-(ethylsulfonyl)-2-methoxyphenyl]-5-pyridin-3-yl-1,3-oxazol-2-amine;
3-(2-{[5-(ethylsulfonyl)-2-methoxyphenyl]amino}-1,3-oxazol-5-yl)benzonitrile;
3-(2-{[5-(ethylsulfonyl)-2-methoxyphenyl]amino}-1,3-oxazol-5-yl)benzamide;
N-[5-(ethylsulfonyl)-2-methoxyphenyl]-5-(3-fluorophenyl)-1,3-oxazol-2-amine;
N-[5-(ethylsulfonyl)-2-methoxyphenyl]-5-[4-(trifluoromethyl)phenyl]-1,3-oxazol-2-amine;
5-(3,4-dichlorophenyl)-N-[5-(ethylsulfonyl)-2-methoxyphenyl]-1,3-oxazol-2-amine;
5-(4-chloro-3-methylphenyl)-N-[5-(ethylsulfonyl)-2-methoxyphenyl]-1,3-oxazol-2-amine;
5-[5-(2,4-dichlorophenyl)-2-furyl]-N-[5-(ethylsulfonyl)-2-methoxyphenyl]-1,3-oxazol-2-amine;
N-[5-(ethylsulfonyl)-2-methoxyphenyl]-5-(2-naphthyl)-1,3-oxazol-2-amine;
N-[5-(ethylsulfonyl)-2-methoxyphenyl]-5-(5,5,8,8-tetramethyl-5,6,7,8-tetrahydronaphthalen-2-yl)-1,3-oxazol-2-amine;
5-(2,3-dihydro-1,4-benzodioxin-6-yl)-N-[5-(ethylsulfonyl)-2-methoxyphenyl]-1,3-oxazol-2-amine;
5-(3,5-difluorophenyl)-N-[5-(ethylsulfonyl)-2-methoxyphenyl]-1,3-oxazol-2-amine;
N-[5-(ethylsulfonyl)-2-methoxyphenyl]-5-(3-trifluoromethylphenyl)-1,3-oxazol-2-amine;
N-[5-(ethylsulfonyl)-2-methoxyphenyl]-5-[4-(methylsulfonyl)phenyl]-1,3-oxazol-2-amine;
5-(3,4-dimethoxyphenyl)-N-[5-(ethylsulfonyl)-2-methoxyphenyl]-1,3-oxazol-2-amine;
5-(3,4-dihydro-2H-1,5-benzodioxepin-7-yl)-N-[5-(ethylsulfonyl)-2-methoxyphenyl]-1,3-oxazol-2-amine;
5-(5-chlorothien-2-yl)-N-[5-(ethylsulfonyl)-2-methoxyphenyl]-1,3-oxazol-2-amine;
methyl 3-{[5-(3-bromophenyl)-1,3-oxazol-2-yl]amino}-4-methoxybenzoate;
3-{[5-(3-bromophenyl)-1,3-oxazol-2-yl]amino}-4-methoxybenzenesulfonyl fluoride;
3-(2-{[5-(ethylsulfonyl)-2-methoxyphenyl]amino}-1,3-oxazol-5-yl)phenyl benzoate;
3-(2-{[5-(ethylsulfonyl)-2-methylphenyl]amino}-1,3-oxazol-5-yl)phenol;
5-[3-(cyclopropylmethoxy)phenyl]-N-[5-(ethylsulfonyl)-2-methoxyphenyl]-1,3-oxazol-2-amine;
5-(3-butoxyphenyl)-N-[5-(ethylsulfonyl)-2-methoxyphenyl]-1,3-oxazol-2-amine;
N-[5-(ethylsulfonyl)-2-methoxyphenyl]-5-[3-(pyridin-2-ylmethoxy)phenyl]-1,3-oxazol-2-amine;
5-(3-benzyloxyphenyl)-N-[5-(ethylsulfonyl)-2-methoxyphenyl]-1,3-oxazol-2-amine;
N-[5-(ethylsulfonyl)-2-methoxyphenyl]-5-[3-(tetrahydro-2H-pyran-4-yloxy)phenyl]-1,3-oxazol-2-amine;
N-[5-(ethylsulfonyl)-2-methoxyphenyl]-5-[3-(2-pyridin-2-ylethoxy)phenyl]-1,3-oxazol-2-amine;
5-{3-[(2,3-dimethoxybenzyl)oxy]phenyl}-N-[5-(ethylsulfonyl)-2-methoxyphenyl]-1,3-oxazol-2-amine;
N-[5-(ethylsulfonyl)-2-methoxyphenyl]-5-[3-(1-pyridin-4-ylethoxy)phenyl]-1,3-oxazol-2-amine;
N-[5-(ethylsulfonyl)-2-methoxyphenyl]-5-[3-(tetrahydrofuran-3-yloxy)phenyl]-1,3-oxazol-2-amine;
5-{3-[(2-chloropyrimidin-4-yl)oxy]phenyl}-N-[5-(ethylsulfonyl)-2-methoxyphenyl]-1,3-oxazol-2-amine;
4-[3-(2-{[5-(ethylsulfonyl)-2-methoxyphenyl]amino}-1,3-oxazol-5-yl)phenoxy]-N-isopropylpyrimidin-2-amine;
N-[5-(ethylsulfonyl)-2-methoxyphenyl]-5-(3-phenoxyphenyl)-1,3-oxazol-2-amine;
5-(3',5'-difluoro-1,1'-biphenyl-3-yl)-N-[5-(ethylsulfonyl)-2-methoxyphenyl]-1,3-oxazol-2-amine;
N-[5-(ethylsulfonyl)-2-methoxyphenyl]-5-(3-thien-2-ylphenyl)-1,3-oxazol-2-amine;
N-[5-(ethylsulfonyl)-2-methoxyphenyl]-5-(3-thien-3-ylphenyl)-1,3-oxazol-2-amine;
N-[5-(ethylsulfonyl)-2-methoxyphenyl]-5-(3-pyridin-3-ylphenyl)-1,3-oxazol-2-amine;
N-[5-(ethylsulfonyl)-2-methoxyphenyl]-5-(3-vinylphenyl)-1,3-oxazol-2-amine;
5-(3-ethylphenyl)-N-[5-(ethylsulfonyl)-2-methoxyphenyl]-1,3-oxazol-2-amine;
N-[5-(ethylsulfonyl)-2-methoxyphenyl]-5-(3-pyridin-4-ylphenyl)-1,3-oxazol-2-amine;
N-[5-(ethylsulfonyl)-2-methoxyphenyl]-5-(3-pyridin-2-ylphenyl)-1,3-oxazol-2-amine;

N-[5-(ethylsulfonyl)-2-methoxyphenyl]-5-[3-(1-methyl-1H-imidazol-5-yl)phenyl]-1,3-oxazol-2-amine;
5-(1,1'-biphenyl-3-yl)-N-[5-(ethylsulfonyl)-2-methoxyphenyl]-1,3-oxazol-2-amine;
N-[5-(ethylsulfonyl)-2-methoxyphenyl]-5-[3-(2-furyl)phenyl]-1,3-oxazol-2-amine;
N-[5-(ethylsulfonyl)-2-methoxyphenyl]-5-(3-pyridin-2-ylphenyl)-1,3-oxazol-2-amine;
N-[5-(ethylsulfonyl)-2-methoxyphenyl]-5-(4'-fluoro-1,1-biphenyl-3-yl)-1,3-oxazol-2-amine;
5-[3-(2,3-dihydro-1-benzofuran-5-yl)phenyl]-N-[5-(ethylsulfonyl)-2-methoxyphenyl]-1,3-oxazol-2-amine;
N-[5-(ethylsulfonyl)-2-methoxyphenyl]-5-[3-(1,3-thiazol-2-yl)phenyl]-1,3-oxazol-2-amine;
4-methoxy-3-{[5-(3-pyridin-3-ylphenyl)-1,3-oxazol-2-yl]amino}benzenesulfonamide;
3-{[5-(1,1'-biphenyl-3-yl)-1,3-oxazol-2-yl]amino}-4-methoxybenzenesulfonamide;
4-methoxy-3-({5-[3-(1-methyl-1-H-imidazol-5-yl)phenyl]-1,3-oxazol-2-yl}amino)benzenesulfonamide;
-3-{[5-(4'-fluoro-1,1'-biphenyl-3-yl)-1,3-oxazol-2-yl]amino}-4-methoxy-N-methylbenzenesulfonamide;
methyl 4-methoxy-3-{[5-(3-pyridin-2-ylphenyl)-1,3-oxazol-2-yl]amino}benzoate;
3-{[5-(4'-fluoro-1,1'-biphenyl-3-yl)-1,3-oxazol-2-yl]amino}-4-methoxybenzenesulfonamide;
N-{5-[(1-ethylpropyl)sulfonyl]-2-methoxyphenyl}-5-(3-pyridin-2-ylphenyl)-1,3-oxazol-2-amine;
1-[3-(2-{[5-(ethylsulfonyl)-2-methoxyphenyl]amino}-1,3-oxazol-5-yl)phenyl]ethanone;
1-[4-(2-{[5-(ethylsulfonyl)-2-methoxyphenyl]amino}-1,3-oxazol-5-yl)phenyl]ethanone;
4-methoxy-3-{[5-(3-pyridin-3-ylphenyl)-1,3-oxazol-2-yl]amino}benzenesulfonyl fluoride;
4-methoxy-3-{[5-(3-pyridin-2-ylphenyl)-1,3-oxazol-2-yl]amino}benzenesulfonyl fluoride;
3'-(2-{[5-(ethylsulfonyl)-2-methoxyphenyl]amino}-1,3-oxazol-5-yl)-1,1'-biphenyl-4-carbonitrile;
3'-(2-{[5-(ethylsulfonyl)-2-methoxyphenyl]amino}-1,3-oxazol-5-yl)-1,1'-biphenyl-3-carboxylic acid;
3'-(2-{[5-(ethylsulfonyl)-2-methoxyphenyl]amino}-1,3-oxazol-5-yl)-1,1'-biphenyl-3-carbonitrile;
N-[5-(ethylsulfonyl)-2-methoxyphenyl]-5-(3'-fluoro-1,1'-biphenyl-3-yl)-1,3-oxazol-2-amine;
N-[5-(ethylsulfonyl)-2-methoxyphenyl]-5-(3-quinolin-3-ylphenyl)-1,3-oxazol-2-amine;
N-[5-(ethylsulfonyl)-2-methoxyphenyl]-5-[3-(5-methylthien-2-yl)phenyl]-1,3-oxazol-2-amine;
N-[5-(ethylsulfonyl)-2-methoxyphenyl]-5-[3-(1-H-indol-5-yl)phenyl]-1,3-oxazol-2-amine;
Methyl 3'-(2-{[5-(ethylsulfonyl)-2-methoxyphenyl]amino}-1,3-oxazol-5-yl)-1,1'-biphenyl-4-carboxylate;
3-{[5-(3'-fluoro-1,1'-biphenyl-3-yl)-1,3-oxazol-2-yl]amino}-4-methoxy-N-methylbenzenesulfonamide;
3-{[5-(1,1'-biphenyl-3-yl)-1,3-oxazol-2-yl]amino}-4-methoxybenzenesulfonyl fluoride;
3-{[5-(3'-fluoro-1,1'-biphenyl-3-yl)-1,3-oxazol-2-yl]amino}-4-methoxybenzenesulfonamide;
N-[5-(ethylsulfonyl)-2-methoxyphenyl]-5-(2'-fluoro-1,1'-biphenyl-3-yl)-1,3-oxazol-2-amine;
5-(2'-chloro-1,1'-biphenyl-3-yl)-N-[5-(ethylsulfonyl)-2-methoxyphenyl]-1,3-oxazol-2-amine;
4-methoxy-N-methyl-3-{[5-(3-pyridin-2-ylphenyl)-1,3-oxazol-2-yl]amino}benzenesulfonamide;
N-ethyl-4-methoxy-3-{[5-(3-pyridin-2-ylphenyl)-1,3-oxazol-2-yl]amino}benzenesulfonamide;
4-methoxy-3-{[5-(3-pyridin-2-ylphenyl)-1,3-oxazol-2-yl]amino}benzenesulfonamide;
N-isopropyl-4-methoxy-3-{[5-(3-pyridin-2-ylphenyl)-1,3-oxazol-2-yl]amino}benzenesulfonamide;
N-(cyclopropylmethyl)-4-methoxy-3-{[5-(3-pyridin-2-ylphenyl)-1,3-oxazol-2-yl]amino}benzenesulfonamide;
N,N-diethyl-4-methoxy-3-{[5-(3-pyridin-2-ylphenyl)-1,3-oxazol-2-yl]amino}benzenesulfonamide;
N-isopropyl-4-methoxy-3-{[5-(3-pyridin-3-ylphenyl)-1,3-oxazol-2-yl]amino}benzenesulfonamide;
3-{[5-(1,1'-biphenyl-3-yl)-1,3-oxazol-2-yl]amino}-N-isopropyl-4-methoxybenzenesulfonamide;
3-{[5-(1,1'-biphenyl-3-yl)-1,3-oxazol-2-yl]amino}-4-methoxy-N,N-dimethylbenzenesulfonamide;
3-{[5-(1,1'-biphenyl-3-yl)-1,3-oxazol-2-yl]amino}-N-cyclopropyl-4-methoxybenzenesulfonamide;
3-{[5-(1,1'-biphenyl-3-yl)-1,3-oxazol-2-yl]amino}-N-butyl-4-methoxybenzenesulfonamide;
3-{[5-(1,1'-biphenyl-3-yl)-1,3-oxazol-2-yl]amino}-N,N-diethyl-4-methoxybenzenesulfonamide;
3-{[5-(1,1'-biphenyl-3-yl)-1,3-oxazol-2-yl]amino}-4-methoxy-N-(tetrahydrofuran-2-ylmethyl)benzenesulfonamide;
4-[3-(2-{[5-(ethylsulfonyl)-2-methoxyphenyl]amino}-1,3-oxazol-5-yl)phenyl]-N-isopropylpyrimidin-2-amine;
N-benzyl-4-[3-(2-{[5-(ethylsulfonyl)-2-methoxyphenyl]amino}-1,3-oxazol-5-yl)phenyl]pyrimidin-2-amine;
$N^1$-{4-[3-(2-{[5-(ethylsulfonyl)-2-methoxyphenyl]amino}-1,3-oxazol-5-yl)phenyl]pyrimidin-2-yl}-$N^3$,$N^3$-dimethylpropane-1,3-diamine;
N-[5-(ethylsulfonyl)-2-methoxyphenyl]-5-[3-(2-phenylpyrimidin-4-yl)phenyl]-1,3-oxazol-2-amine;
N-[5-(ethylsulfonyl)-2-methoxyphenyl]-5-[3-(2-isopropylpyrimidin-4-yl)phenyl]-1,3-oxazol-2-amine;
5-[3-(2-tert-butylpyrimidin-4-yl)phenyl]-N-[5-(ethylsulfonyl)-2-methoxyphenyl]-1,3-oxazol-2-amine;
3'-(2-{[5-(ethylsulfonyl)-2-methoxyphenyl]amino}-1,3-oxazol-5-yl)-1,1'-biphenyl-4-carboxylic acid;
3'-(2-{[5-(ethylsulfonyl)-2-methoxyphenyl]amino}-1,3-oxazol-5-yl)-N-(2-morpholin-4-ylethyl)-1,1'-biphenyl-4-carboxamide;
3'-(2-{[5-(ethylsulfonyl)-2-methoxyphenyl]amino}-1,3-oxazol-5-yl)-N-[3-(4-methylpiperazin-1-yl)propyl]-1,1'-biphenyl-4-carboxamide;
or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of Formula (I), (II), or (III). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of Formula (I), (II), or (III), as well as salts, solvates and physiological functional derivatives thereof, may be administered as the raw chemical, it is possible to present the active ingredient as a pharmaceutical composition. Accordingly, the invention further provides pharmaceutical compositions that include therapeutically effective amounts of compounds of the Formula (I), (II), or (III) and salts, solvates and physiological functional derivatives thereof, and one or more pharmaceutically acceptable carriers, diluents, or excipients. The compounds of the Formula (I), (II), or (III) and salts, solvates and physiological functional derivatives thereof, are as described above. The carrier(s), diluent(s) or excipient(s) must be acceptable in the sense of being compatible with the other ingredients of the Formulation and not deleterious to the recipient thereof. In accordance with another aspect of the invention there is also provided a process for the preparation of a pharmaceutical formulation including admixing a compound of the Formula (I) or (II), or or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, of a compound of the Formula (I), (II), or (III) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in he pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar—agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are Formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared using a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of Formula (I), (II), or (III) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I), (II), or (III) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouthwashes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) or (II) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of Formula (I), (II), or (III) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of Formula (I), (II), or (III) or a pharmaceutically acceptable salt or solvate thereof, or a physiologically functional derivative thereof, and the use of at least one other cancer treatment method. Preferably, combination therapies according to the present invention comprise the administration of at least one compound of Formula (I), (II), or (III) or a pharmaceutically acceptable salt or solvate thereof, or a physiologically functional derivative thereof, and at least one other pharmaceutically active agent, preferably an anti-neoplastic agent. The compound(s) of Formula (I), (II), or (III) and the other pharmaceutically active agent(s) may be administered together or separately and, when administered separately this may occur simultaneously or sequentially in any order. The amounts of the compound(s) of Formula (I) or (II) and the other pharmaceutically active agent(s) and the relative timings of administration will be selected in order to achieve the desired combined therapeutic effect The compounds of the Formula (I), (II), or (III) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of Formula (I), (II), or (III) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of Formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithamycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; cyclooxygenase type 2 (COX-2) inhibitors such as celecoxib; other angiogenic inhibiting agents such as VEGFR inhibitors other than those described herein and TIE-2 inhibitors; growth factor function inhibitors such as inhibitors of the functions of hepatocyte growth factor; erb-B2, erb-B4, epidermal growth factor receptor (EGFr), platelet derived growth factor receptor (PDGFr), vascular endothelial growth factor receptor (VEGFR) other than those described in the present invention, and TIE-2; and other tyrosine kinase inhibitors such as cyclin dependent inhibitors such as CDK2 and CDK4 inhibitors.

In one aspect of the present invention, there is provided a method of preventing or reducing the severity of epithelial cytotoxicity in a patient receiving cytotoxic therapy, comprising administering to said patient a therapeutically effective amount of a compound of Formula (I), (II), or (III) or a salt, solvate, or physiologically functional derivative thereof.

In one aspect of the present invention, there is provided a method of treating cancer in a mammal, including administering to said mammal therapeutically effective amounts of (i) a compound of Formula (I), (II), or (III), or salt, solvate or physiologically functional derivative thereof and (ii) at least one additional anti-cancer therapy. In one embodiment, the anti-cancer therapy is cytotoxic.

The compounds of Formula (I), (II), or (III) and salts, solvates and physiological functional derivatives thereof, are believed to have anticancer activity as a result of inhibition of the protein kinase CDK2, CDK4, or VEGFR2 and its effect on selected cell lines whose growth is dependent on CDK2, CDK4, or VEGFR2 kinase activity.

The present invention thus also provides compounds of Formula (I), (II), or (III) and pharmaceutically acceptable salts or solvates thereof, or physiologically functional derivatives thereof, for use in medical therapy, and particularly in the treatment of disorders mediated by inappropriate VEGFR2 or CDK activity.

The inappropriate CDK activity referred to herein be any CDK activity that deviates from the normal CDK activity expected in a particular mammalian subject Inappropriate CDK activity may take the form of, for instance, an abnormal increase in activity, or an aberration in the timing-and or control of CDK activity. Such inappropriate activity may result then, for example, from overexpression or mutation of the protein kinase or ligand leading to inappropriate or uncontrolled activation of the receptor. Furthermore, it is also understood that unwanted CDK activity may reside in an abnormal source, such as a malignancy. That is, the level of CDK activity does not have to be abnormal to be considered inappropriate, rather the activity derives from an abnormal source.

The inappropriate VEGFR2 activity referred to herein be any VEGFR2 activity that deviates from the normal VEGFR2 activity expected in a particular mammalian subject Inappropriate VEGFR2 activity may take the form of, for instance, an abnormal increase in activity, or an aberration in the timing and or control of VEGFR2 activity. Such inappropriate activity may result then, for example, from overexpression or mutation of the protein kinase or ligand leading to inappropriate or uncontrolled activation of the receptor. Furthermore, it is also understood that unwanted VEGFR2 activity may reside in an abnormal source, such as a malignancy. That is, the level of VEGFR2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase or ligand leading to inappropriate or uncontrolled activation of angiogenesis. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting CDK2 and/or CDK4 for the prevention and/or treatment of disorders related to unregulated CDK activity, and/or inhibiting VEGFR2 for the prevention and/or treatment of disorders related to unregulated VEGFR2 activity. In particular, the compounds of the present invention can also be used in the treatment of certain forms of cancer. Furthermore, the compounds of the present invention can be used to provide additive or synergistic effects with certain existing cancer chemotherapies and radiation, and/or be used to provide protection from the epithelial cytotoxic effects of certain existing cancer chemotherapies and radiation.

A further aspect of the invention provides a method of treatment of a mammal suffering from a disorder mediated by inappropriate CDK activity, including susceptible malignancies, which includes administering to said subject an effective amount of a compound of Formula (I), (II), or (III) or a pharmaceutically acceptable salt, solvate, or a physiologically functional derivative thereof. In a preferred embodiment, the disorder is cancer. In one embodiment the CDK is CDK2. In another embodiment, the CDK is CDK4.

A further aspect of the invention provides a method of treatment of a mammal suffering from a disorder mediated by inappropriate VEGFR2 activity, including susceptible malignancies, which includes administering to said subject an effective amount of a compound of Formula (I), (II), or (III) or a pharmaceutically acceptable salt, solvate, or a physiologically functional derivative thereof. In a preferred embodiment, the disorder is cancer.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephosclerosis, thombotic microangiopathy syndromes, proliferative retinopathies, organ transplant rejection and glomerulopathies; and metabolic disorders include psoriasis, diabetes mellitus, chonic wound healing, inflammation and neurodegenerative diseases.

A further aspect of the invention provides a method of treatment of a mammal suffering from cancer, which includes administering to said subject an effective amount of a compound of Formula (I), (II), or (III) or a pharmaceutically acceptable salt or solvate thereof, or a physiologically functional derivative thereof.

A further aspect of the present invention provides the use of a compound of Formula (I), (II), or (III) or a pharmaceutically acceptable salt or solvate thereof, or a physiologically functional derivative thereof, in the preparation of a medicament for the treatment of a disorder characterized by inappropriate CDK or VEGFR2 activity. In a preferred embodiment, the disorder is cancer. In one embodiment, the CDK is CDK2. In another embodiment, the CDK is CDK4.

A further aspect of the present invention provides the use of a compound of Formula (I), (II), or (III) or a pharmaceutically acceptable salt or solvate thereof, or a physiologically functional derivative thereof, in the preparation of a medicament for the treatment of cancer and malignant tumors.

The mammal requiring treatment with a compound of the present invention is typically a human being.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of general Formula (I), (II), or (III) may be prepared by methods known in the art of organic synthesis as set forth in part by the following synthesis schemes. In all of the schemes described below,; it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley Et Sons). These groups are removed at a convenient stage of the compound synthesis using methods that are readily apparent to those skilled in the art. The selection of processes as well as the reaction conditions and order of their execution shall be consistent with the preparation of compounds of Formula (I), (II), or (III). Those skilled in the art will recognize if a stereocenter exists in compounds of Formula (I), (II), or (III). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (II), wherein $R_{(m)}$ and $Q_{(p)}$ are as described above, can be prepared according to the condensation shown in Scheme 1 and further detailed in the Examples section following. Typically, a general method for the preparation of compounds of general Formula (II) involves the treatment of chloro-oxazole A with an appropriate aniline B. The reaction may optionally be treated with base and heated to temperatures between 25° C. and 200° C. R, Q, m, and p are as described above for Formula (II).

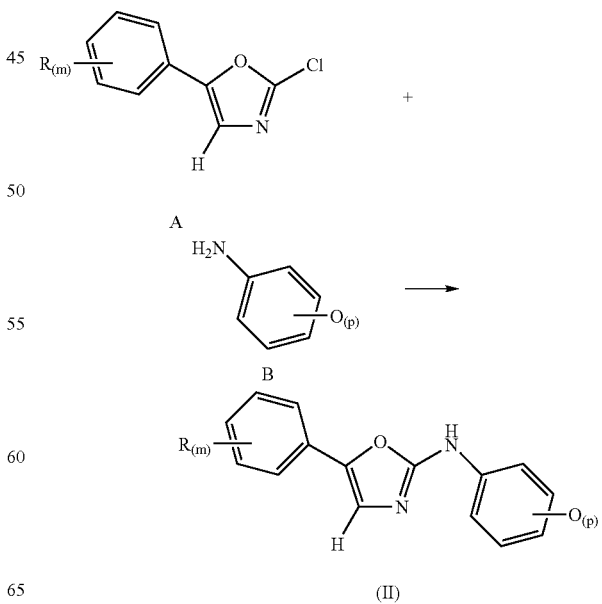

SCHEME 1

(II)

Compounds of general formula A can be obtained using a variety of procedures known in the literature. For example in Scheme 2, compounds of general Formula A can be prepared from oxazolinones of general formula C by treatment of said oxazolinone with a chlorinating agent, optionally in the presence of a base, a phase transfer catalyst, and heat, typically at about 100° C. Preferably, the chlorinating agent is thionyl chloride or phosphorus oxychloride and the like. The base is, preferably, a dialkylaniline such as diethylaniline. A phase transfer catalyst is, preferably, a tetra-alkylammonium chloride such as tetra-ethylammonium chloride. R and m are as described above for Formula (II).

SCHEME 2

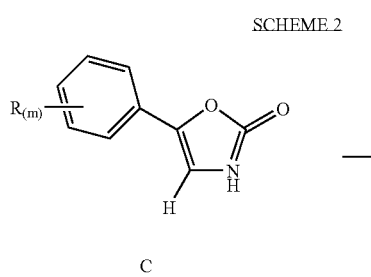

Compounds of general formula C can be obtained using a variety of procedures known in the literature. As shown in Scheme 3, treatment of an α-bromoacetophenone of general formula D with potassium cyanate gives isocyanates of general formula E that cyclize to give oxazolones of general formula C. R and m are as described above for Formula (II).

SCHEME 3

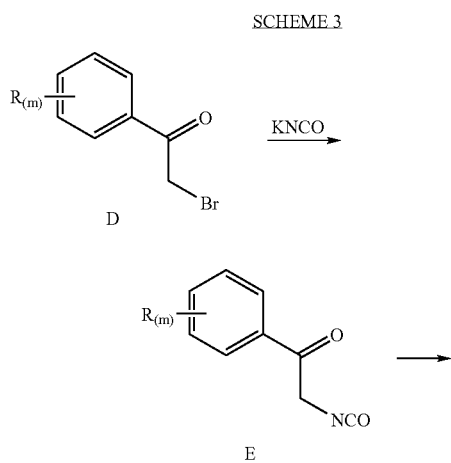

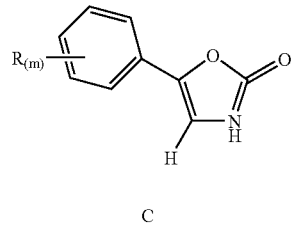

C

Alternatively as shown in Scheme 4, α-bromoacetophenones of general formula D can be treated with thiazolidinedione in the presence of a base such as potassium carbonate in dimethylformamide to give a substituted thiazolidinedione of general formula F. Said substituted thiazolidinedione F, upon treatment with lithium hydroxide, undergo a rearrangement to afford oxazolones of general formula C. R and m are as described above for Formula (II).

SCHEME 4

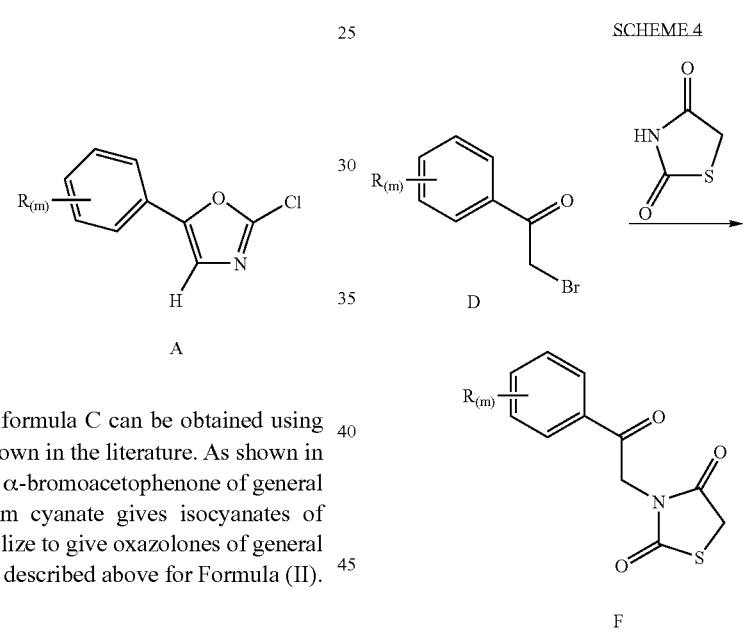

Alternatively as shown in Scheme 5, α-bromoacetophenones of general formula D can be treated with sodium azide in a suitable solvent, such as a lower alcohol, to afford α-azido ketones of general formula G. Said azido ketones can be treated with an appropriate aryl isothiocyanate in the presence of triphenylphosphine to give compounds of general Formula (II) directly. R, Q, m, and p are as described above for Formula (II).

SCHEME 5

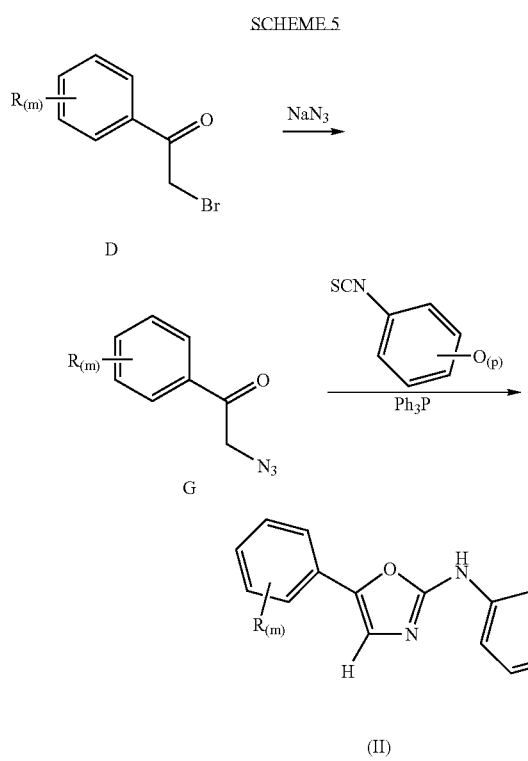

Aniline moieties of Formula (II) or anilines depicted in structure B are available through multi-step organic synthesis familiar to one skilled in the art. The following schemes illustrate methods that can be used to derive anilines of structure B, which are incorporated into compounds of Formula (II) of the present invention.

As shown in Scheme 6, an appropriately substituted meta- or para-nitro benzylamine can be condensed with an alkyl- or aryl-sulfonyl chloride under suitable conditions (e.g., triethylamine, dichloromethane) to provide sulfonamide I. The nitro moiety of I can be reduced using either $SnCl_2$/conc. HCl or $H_2$ 10% Pd/C to provide the desired aniline B. Other embodiments of the present invention can be derived from anilines by the method shown in Scheme 6. $Z^2$ is as described above for Formula (I) and (II).

SCHEME 6

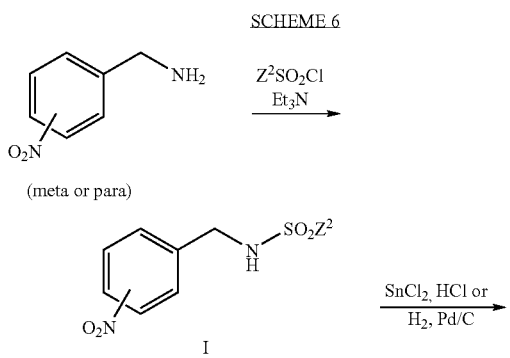

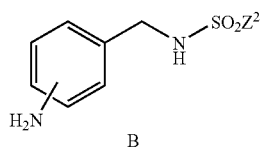

As shown in Scheme 7, nitro-substituted benzyl chloride H can be converted to a sodium benzylsulfonate salt I by a reaction at elevated temperature with $Na_2SO_3$ in a $H_2O$/dioxane mixture. Treatment of I with $SOCl_2$ (cat. DMF/$CH_2Cl_2$) provides the corresponding sulfonyl-chloride J, which can be treated with an amine to provide sulfonamide K. Reduction of the nitro group in K can be accomplished in similar fashion as described in Scheme 6. $R^1$ and $R^2$ are as described above for Formula (I) and (II).

SCHEME 7

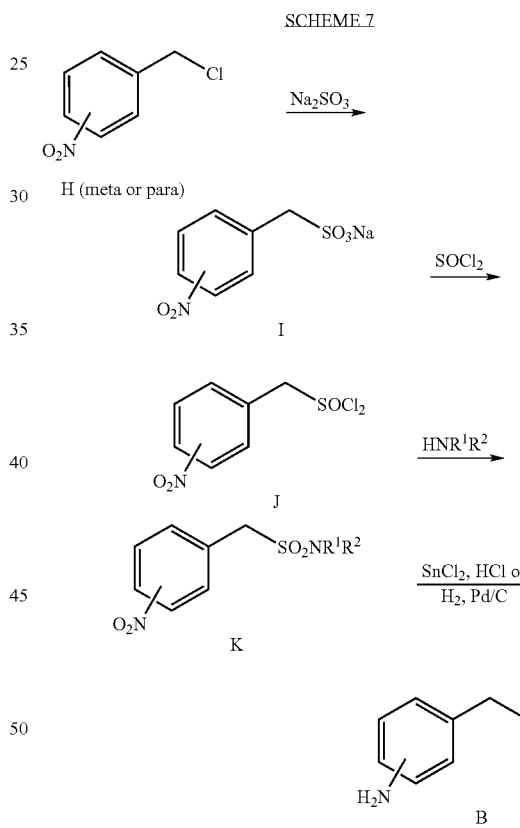

Scheme 8 depicts the synthesis of other anilines of structure B that are useful in the preparation of compounds of Formula (II). An appropriate thiolate anion undergoes a displacement reaction with H to provide a benzylic sulfide L. Oxidation of the sulfide, for example with mCPBA, provides the corresponding sulfone, which can then be reduced to the desired aniline B. Alternately, treatment of alkyl halide H with an appropriate sulfinic acid provided the corresponding sulfone, which can then be reduced to the desired aniline B. $Z^2$ is as described above for Formula (I) and (II).

SCHEME 8

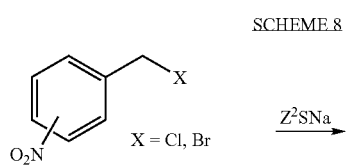
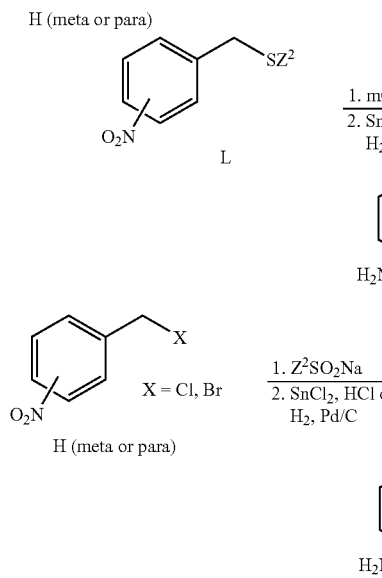

Scheme 9 depicts the synthesis of other anilines of structure B that are useful in the preparation of compounds of Formula (I) and (II). The 2-methoxyacetanilide undergoes chlorosulfonylation under standard conditions to provide the expected arylsulfonyl chloride M. Amination of M with an amine affords a sulfonamide, which can be hydrolyzed under appropriate conditions to provide the desired aniline B.

SCHEME 9

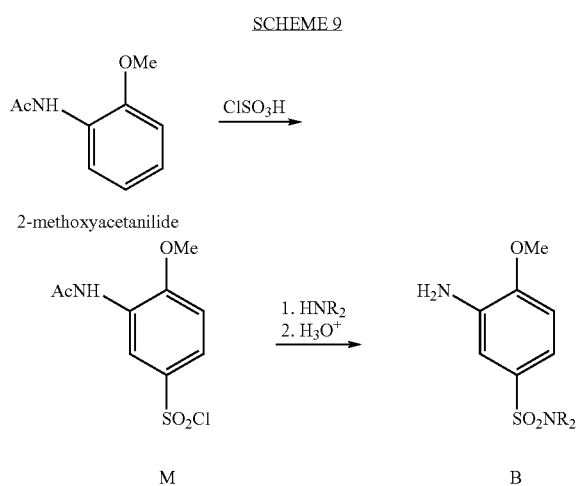

Scheme 10 depicts the synthesis of other anilines of structure B that are useful in the preparation of compounds of Formula (I) and (II). Para-methoxy sulfenimide N can be prepared as described in the prior art A Mitsunobu-type substitution with an alcohol provides phenyl sulfide O. (In certain cases, one who is skilled in the art will recognize that the same phenylsulfide O can be derived by alkylation of the paramethoxy thiophenoxide anion with an alkyl halide.) Oxidation of sulfide O affords sulfone P, which undergoes nitration to provide methoxynitrosulfone Q. Q can be reduced to aniline B, as described above. $Z^2$ is as described above for Formula (I) and (II).

SCHEME 10

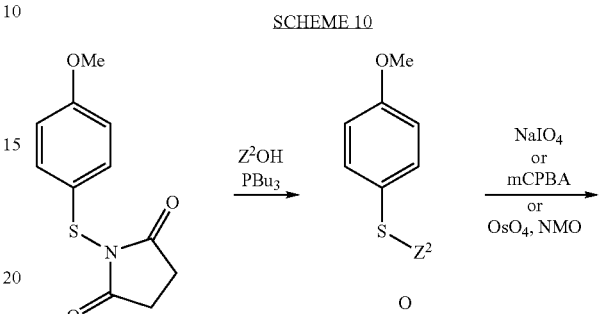
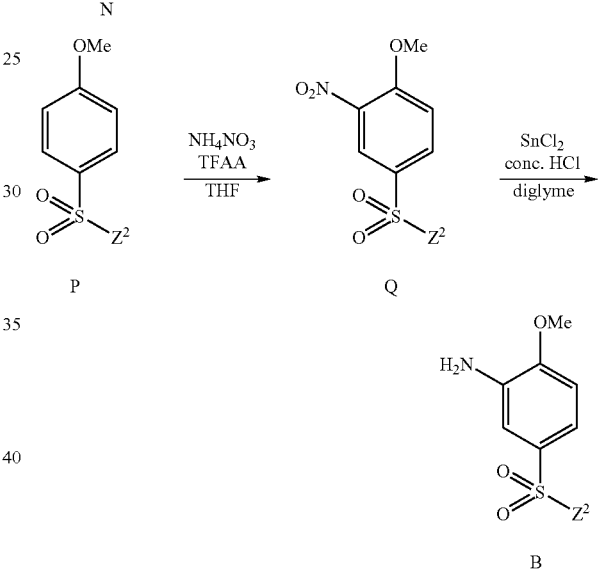

In Scheme 11, the R substituent of compounds of structure S may be obtained by Suzuki or Stille palladium coupling reactions with compounds of structure R. Compounds of structure R can be prepared according to synthetic sequences shown in Schemes 1–5 and further detailed in the Examples section below. R, Q, and p are as described above for Formula (III)

SCHEME 11

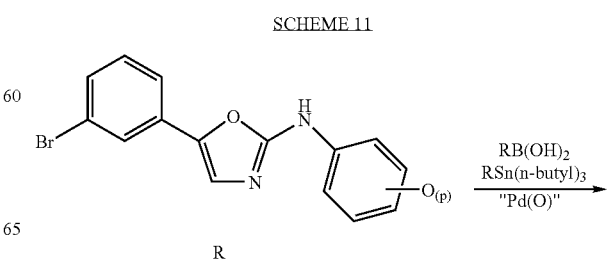

-continued

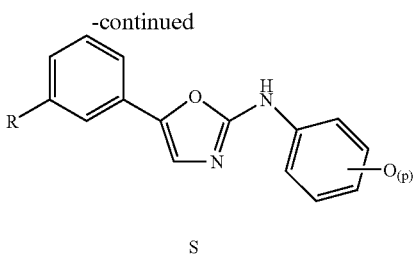

S

Scheme 12 depicts the synthesis of substituted pyrimidine derivatives of structure V. The oxazole derivative T was condensed with dimethylformamide di-tert-butyl acetal in DMF to afford the β-dimethylamino enone U, which can be treated with an appropriate alkyl guanidine sulfate under basic conditions to afford the substituted pyrimidine derivative V illustrated below.

SCHEME 12

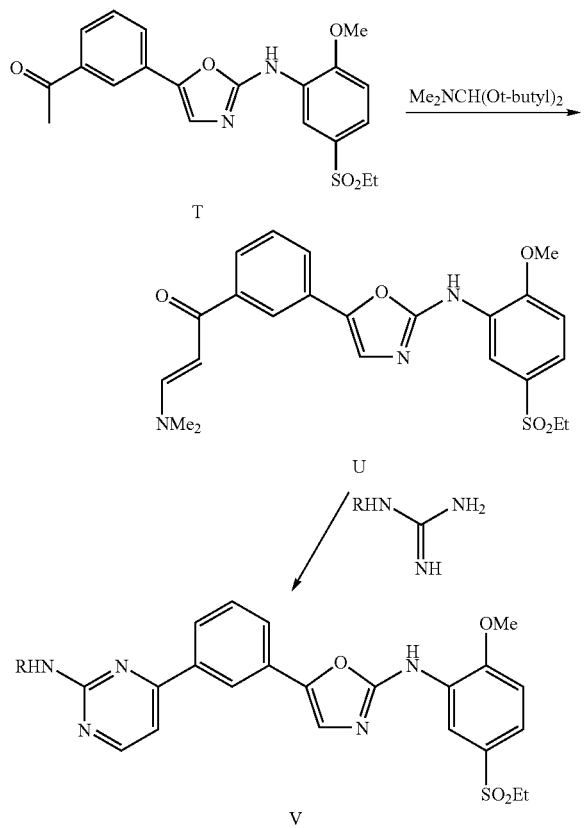

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

--- g (grams);
L (liters);
μL (microliters);
M (molar);
i.v. (intravenous);
MHz (megahertz);
mmol (millimoles);
min (minutes);
mp (melting point);
Tr (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
IBCF (isobutyl chloroformate);
HOSu (N-hydroxysuccinimide);
Et$_2$O (diethyl ether);
BOC (tert-butyloxycarbonyl);
DCC (dicyclohexylcarbodiimide);
Ac (acetyl);
TMSE (2-(trimethylsilyl)ethyl);
TIPS (triisopropylsilyl);
DMAP (4-dimethylaminopyridine);
OMe (methoxy);
Et (ethyl);
HPLC (high pressure liquid chomatography);
BOP (bis(2-oxo-3-oxazolidinyl)phosphinic chloride);
TBAF (tetra-n-butylammonium fluoride);
mCPBA (meta-chloroperbenzoic acid.
mg (milligrams);
mL (milliliters);
psi (pounds per square inch);
mM (millimolar);
Hz (Hertz);
mol (moles);
RT (ambient temperature);
h (hours);
TLC (thin layer chromatography);
RP (reverse phase);
i-PrOH (isopropanol);
TFA (trifluoroacetic acid);
THF (tetrahydrofuran);
EtOAc (ethyl acetate);
DCM (dichloromethane);
DMF (N,N-dimethylformamide);
CDI (1,1-carbonyldiimidazole);
HOAc (acetic acid);
HOBT (1-hydroxybenzotriazole);
EDC (ethylcarbodiimide hydrochloride);
FMOC (9-fluorenylmethoxycarbonyl);
CBZ (benzyloxycarbonyl);
atm (atmosphere);
TMS (trimethylsilyl);
TBS (t-butyldimethylsilyl);
Me (methyl);
Et (ethyl);
tBu (tert-butyl);

---

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR (H NMR or +$^1$H NMR below) spectra were recorded on a Varian VXR-300, a Varian Unity-300, a Varian Unity-400 instrument, or a General Electric QE-300. Chemical shifts are expressed in parts per million (ppm, δ units).

Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), atmospheric pressure chemical ionization (APCI), electron impact (EI), or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

Intermediate 1a

Preparation of
2-amino-1-(3-methoxyphenyl)ethanone-HCl

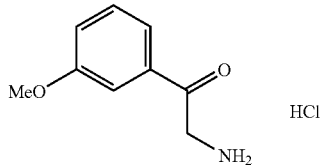

A suspension of 2-bromo-1-(3-methoxyphenyl)ethanone (5 g, 0.022 mol) and sodium diformylamide (2.5 g, 0.026 mol) was stirred at RT in acetonitrile (12.5 mL) for 18 h. Subsequently, the reaction was warmed to 70° C., filtered, and rinsed with warm acetonitrile. The filtrate was concentrated under reduced pressure to afford 5.28 g of an amber oil that solidified upon standing at RT. The resulting solid was suspended in 1M HCl (50 mL) and stirred at RT for 18 h. The mixture was diluted with diethyl ether (50 mL) and stirred at RT for 1 h. The solids were collected by vacuum filtration and dried in a vacuum oven at 70° C. to afford the title compound (3.0 g, 68%) as a white powder. $^1$H NMR (400 MHz, d$_6$-DMSO): δ 3.84 (s, 3H), 4.59 (s, 2H), 7.30 (dd, J$_1$=8.15, J$_2$=2.65, 1H), 7.50 (m, 2H), 7.60 (dr J=8.06, 1H), 8.34 (s, 3H). MS (ES+, m/z)=166 (m+H)$^+$.

Intermediate 1b

Preparation of
5-(3-methoxyphenyl)-1,3-oxazole-2-thiol

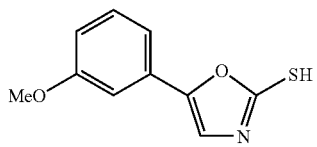

A solution of sodium carbonate (1.98g, 0.016 mol) in water (5 mL) was added slowly to a mixture of Intermediate 1a (3.01 g, 0.015 mol) and carbon disulfide (2.3 g, 0.030 mol) in ethanol (20 mL). After stirring at 80° C. for 18 h, the reaction was cooled, treated with glacial acetic acid (5 mL), and stirred for an additional 15 min. The solids were collected by vacuum filtration, rinsed with ethanol, and air-dried to afford the title compound (1.75 g, 56%). $^1$H NMR (300 MHz, d$_6$-DMSO): δ 3.79 (s, 3H), 6.92 (dd, J$_1$=7.90, J$_2$=2.13, 1H), 7.16 (m, 2H), 7.36 (t, J=7.97, 1H), 7.90 (s, 1H), 13.33 (s, 1H). MS (ES-, m/z)=206 (m-H)$^-$.

Intermediate 1c

Preparation of
5-(3-methoxyphenyl)-2-(methylthio)-1,3-oxazole

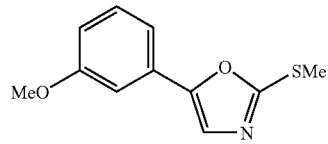

Methyl iodide (0.82 g, 5.8 mmol) was added slowly to a mixture of Intermediate 1b (1.01 g, 4.8 mmol) and K$_2$CO$_3$ (0.66 g, 4.8 mmol) in THF (5.0 mL) and DMF (2.5 mL). After stirring at RT for 1.5 h, the reaction was diluted with H$_2$O (50 mL) and washed with EtOAc (3×25 mL). The combined organic layers were washed with H$_2$O (2×25 mL) and brine (25 mL), dried with anhydrous magnesium sulfate, filtered, and concentrated under reduced pressure to afford the title compound (0.97 g, 91%) as a solid. $^1$H NMR (400 MHz, d$_6$-DMSO): δ 2.68 (s, 3H) 3.79 (s, 3H), 6.91 (dd, J$_1$=7.87, J$_2$=2.93, 1H), 7.19 (m, 1H), 7.22 (d, J=7.69, 1H), 7.35 (t, J=7.97, 1H), 7.72 (s, 1H). MS (ES+, m/z)=222 (m+H)$^+$.

Intermediate 1d

Preparation of
5-(3-methoxyphenyl)-2-(methylsulfonyl)-1,3-oxazole

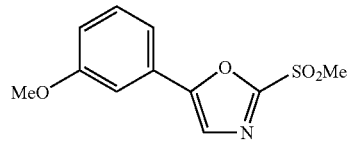

A solution of the Intermediate 1c (1.40 g, 6.3 mmol) in dichloromethane (15 mL) was slowly treated with solid mCPBA (75%) (3.35 g, 14.6 mmol). After the reaction stirred at RT for 1 h, it was filtered and rinsed with dichloromethane. The filtrate was-diluted with EtOAc (100 mL) and washed with saturated aqueous sodium bicarbonate solution and brine. The organic layer was dried with anhydrous magnesium sulfate, filtered, and concentrated under reduced pressure. The residue was chromatographed on silica gel with hexanes/EtOAc 1:1 to afford the title compound (1.21 g, 76%) as a white solid. $^1$H NMR (400 MHz, d$_6$-DMSO): δ 3.58 (s, 3H), 3.83 (s, 3H), 7.06 (d, J=8.06, 1H), 7.41 (m, 3H), 8.09 (s, 1H). MS (ES+, m/z)=254 (m+H)$^+$.

Example 1

5-(3-methoxyphenyl)-N-phenyl-1,3-oxazol-2-amine

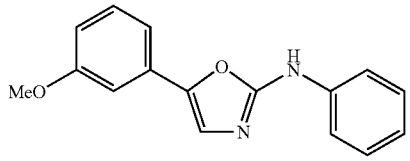

A mixture of Intermediate 1d (0.82 g, 3.23 mmol) and aniline (0.60 g, 6.47 mmol) was heated to 100° C. for 1.5 h. Upon cooling, the mixture was diluted with isopropanol. The title compound was collected by vacuum filtration to afford a white solid (0.20 g, 23%). $^1$H NMR (400 MHz, $d_6$-DMSO): δ 3.79 (s, 3H), 6.84 (dd, $J_1$=8.15, $J_2$=1.74, 1H), 6.94 (t, J=7.32, 1H), 7.11 (m, 1 H), 7.16 (d, J=8.06, 1H), 7.32 (m, 3H), 7.48 (s, 1H), 7.63 (dd, $J_1$=8.61, $J_2$=1.10, 2H), 10.30 (s, 1H). MS (ES+, m/z)=267 (m+H)$^+$.

Example 2

3-(2-anilino-1,3-oxazol-5-yl)phenol

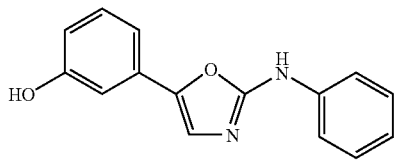

A solution of the title compound of Example 1 (0.110 g, 0.41 mmol) in dichloromethane (5 mL) was carefully treated with boron tribromide (0.516 g, 2.06 mmol). After stirring for 1 h, the reaction was carefully poured over ice. After the ice melted, the mixture was extracted with ethyl acetate (2×250 mL). The combined organic layers were dried over anhydrous magnesium sulfate, filtered, and concentrated under reduced pressure. The title compound was dried under vacuum at RT to afford a light brown solid (1.13 g, 47%). $^1$H NMR (400 MHz, $d_6$-DMSO): δ 6.74 (dd, $J_1$=8.1, $J_2$=2.2 1H), 6.99 (d, J=2, 1H), 7.05 (d, J=7.9, 1H), 7.21 (t, J=7.9, 1H), 7.64 (s, 1H), 9.48 (bs, 1H).

Example 3

N-[4-(4-methylpiperazin-1-yl)phenyl]-5-phenyl-1,3-oxazol-2-amine

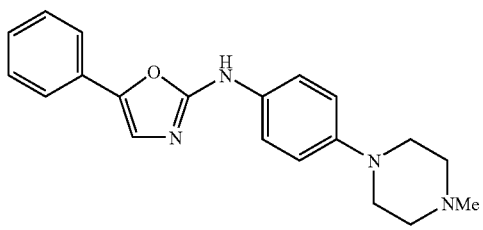

Sodium hydride (60% in mineral oil, 0.51 g, 0.013 mol) was suspended in dry THF (8 mL) under an atmosphere of nitrogen. The suspension was treated with 4-(4-methylpiperazin-1-yl)-aniline (0.23 g9 1.0 mmol) and 2-chloro-5-phenyl-1,3-oxazole (0.19 g, 1.0 mmol) and heated to 60° C. and stirred for 18 h. The reaction was cooled to RT and quenched with methanol (10 drops). Silica gel was added and the solvent was evaporated under reduced pressure to dryness and purified by silica gel chromatography using 10% methanol in dichloromethane to elute the title compound (0.10 g, 31%). $^1$H NMR (400 MHz, $d_6$-DMSO): δ 2.21 (s, 3H), 2.45 (m, 4H), 3.04 (m, 4H), 6.91 (d, J=8.97, 2H), 7.24 (t, J=7.32, 1H), 7.41 (m, 3H), 7.47 (d, J=8.97, 2H), 7.55 (d, J=7.51, 2H), 9.99 (s, 1H). MS (ES+, m/z)=335 (m+H)$^+$.

Intermediate 4a

Preparation of 5-(3-methoxyphenyl)-1,3-oxazol-2-(3H)-one

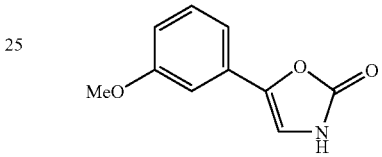

A solution of 2-bromo-3'-methoxyacetophenone (40.0 g, 0.18 mol) and thiazolidinedione (24.5 g, 0.21 mol) in dry DMF (175 mL) was treated with $K_2CO_3$ (36.2 g, 0.26 mol) and stirred at RT for 1.5 h. The reaction mixture was slowly poured into ice water (1.7 L). The resulting pink solid, was collected by filtration and washed with water (200 mL). (Excess water was removed by suction) The filter cake was stirred at RT for 30 min in an aqueous solution (350 mL),of lithium hydroxide-hydrate (29.3 g, 0.7 mol) and THF (350 mL). After ice water (700 mL) was added, the suspension was slowly poured into a stirred solution of acetic acid (40 mL, 0.70 mol) in water (1.7 L). The resulting tan solid was collected by filtration, washed with water (500 mL), and dried under vacuum to afford the title compound (23.8 g, 72%). $^1$H NMR (300 MHz, $d_6$-DMSO): δ 3.80 (s, 3H), 6.86 (dd, 1H, $J_1$=8.1, $J_2$=2.4 Hz), 7.05 (bs, 1H), 7.09 (d, 1H, J=7.8), 7.33 (t, 1H, J=8.1), 7.54 (s, 1H).

Intermediate 4b

Preparation of 2-chloro-5-(3-methoxyphenyl)-1,3-oxazole

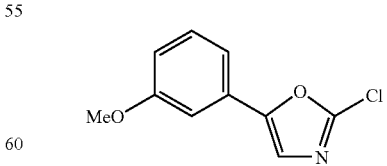

A combination of Intermediate 4a (10.0 g, 0.05 mol) and dry tetraethylammonium chloride (20 g, 0.12 mol) was dissolved in dry acetonitrile (100 mL) at RT under nitrogen. The solution was treated with diethyl aniline (8.4 mL, 7.8 g, 0.05 mol), followed by a dropwise addition of phosphorus oxychloride (29 mL, 48.0 g, 0.31 mol). The mixture was heated at reflux for 4 days. The reaction mixture was cooled to RT and evaporated under reduced pressure. The residue was dissolved in CHCl₃ (200 mL) and stirred with ice (50 g) for 15 min. After separating the organic layer, the aqueous layer was washed with additional CHCl₃ (3×30 mL). The combined organic layers were back washed with water (3×50 mL), saturated sodium bicarbonate, and brine. The organic layer was dried over anhydrous magnesium sulfate, filtered through a pad of sica gel,and evaporated to leave an orange oil. The oil was purified by bulb-to-bulb distillation to afford the title compound (9.77 g, 90%) as a clear oil that solidified at RT. $^1$H NMR (400 MHz, d$_6$-DMSO): δ 3.76 (s, 3H), 6.92 (dd, J$_1$=8.3, J$_2$=2.5, 1H), 7.17 (s, 1H), 7.19 (d, J=6.8, 1H), 7.34 (t, J=8.3), 7.76 (s, 1H). MS (APCI, m/z) =209 (m+1).

Example 4

5-(3-Methoxyphenyl)-N-[4-(4-methylpiperazin-1-yl) phenyl]-1,3-oxazol-2-amine

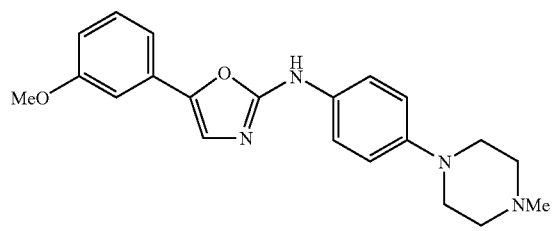

Sodium hydride (60% in mineral oil, 0.25 g, 6.3 mmol) was suspended in dry THF (4 mL) under nitrogen. To the suspension was added 4-(4-methylpiperazin-1-yl)-aniline (0.096 g, 0.5 mmol) and Intermediate 4b (0.105 g, 0.5 mmol). The resulting mixture was stirred at 60° C. for 18 h. After the reaction was cooled to RT, methanol (10 drops) was carefully added to destroy any residual sodium hydride. Silica gel was added and the solvent was evaporated under reduced pressure. The residue was purified by silica gel chromatography using 10% methanol in dichloromethane to elute the title compound (0.06 g, 31%) as a tan solid. $^1$H NMR (400 MHz, d$_6$-DMSO): δ 9.96 (s, 1H), 7.42 (d, J=9.0, 2H), 7.38 (s, 1H), 7.27 (t, J=8.0, 1H), 7.09 (d, J=7.9, 1H), 7.04 (s, 1H), 6.86 (d, J=8.9, 2H), 6.77 (dd, J$_1$=8.2, J$_2$=2.3 Hz, 1H), 3.74 (s, 3H), 2.99 (m, 4H), 2.40 (m, 4H), 2.16 (s, 3H). MS (APCI, m/z)=365 (m+1).

Intermediate 5a

Preparation of
2-bromo-5-(3-hydroxyphenyl)-1,3-oxazole

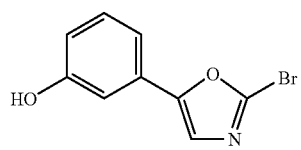

Boron tribromide (5.0 mL, 13.25 g, 53 mmol) was added dropwise to a stirred solution of 2-bromo-5-(3-methoxyphenyl)-1,3-oxazole (2.1 g, 10 mmol) in dry dichloromethane (50 mL) at RT under Nitrogen. The reaction mixture was stirred for about 1 h and then carefully poured over ice. After the ice melted, the mixture was extracted with ethyl acetate (2×250 mL). The combined organic extracts were dried over anhydrous magnesium sulfate, filtered, and concentrated under reduced pressure. The resulting solid was collected by filtration and dried under vacuum to afford a light brown solid (1.13 g, 47%). $^1$H NMR (400 MHz, d$_6$-DMSO): δ 6.74 (dd, J$_1$=8.1, J$_2$=2.2, 1H), 6.99 (d, J=2, 1H), 7.05 (d, J=7.9, 1H), 7.21 (t, J=7.9, 1H), 7.64 (s, 1H), 9.48 (bs, 1H).

Intermediate 5b

Preparation of
2-Bromo-5-(3-ethoxyphenyl)-1,3-oxazole

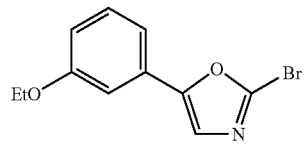

A mixture of Intermediate 5a (0.25 g, 1.0 mmol), iodoethane (0.2 mL, 0.39 g, 2.5 mmol), and K$_2$CO$_3$ (0.37 g, 2.7 mmol) in dry DMSO (2 mL) was stirred at RT for about 24 h. After adding water (25 mL), the resulting mixture was extracted with ethyl acetate. The organic layer was dried over anhydrous magnesium sulfate, filtered, and evaporated under reduced pressure to leave an oil. Purification by silica gel column chromatography using 5% ethyl acetate in hexanes as an eluent afforded the title compound (0.14 g, 52%). $^1$H NMR (400 MHz, d$_6$-DMSO): δ 1.28 (t, J=7, 3H), 4.02 (q, J=7, 2H), 6.90 (dd, J=8, 1H), 7.17 (m, 2H), 7.33 (t, J=8, 1H), 7.73 (s, 1H). MS (APCI, m/z)=267, 269.

Example 5

5-(3-Ethoxyphenyl)-N-[4-(4-methylpiperazin-1-yl) phenyl]-1,3-oxazol-2-amine

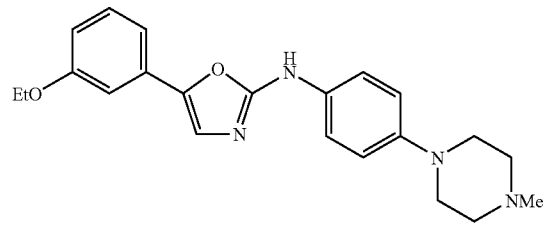

$^1$H NMR (400 MHz, d$_6$-DMSO): δ 9.94 (s, 1H), 7.42 (d, J=8.9, 2H), 7.37 (s, 1H), 7.25 (t, J=8.0, 1H), 7.06 (d, J=7.7, 1H), 7.03 (s, 1H), 6.86 (d, J=9.0, 2H), 6.75 (dd, J$_1$=8.1, J$_2$=2.2, 1H), 4.00-(q, J=7.0, 2H), 2.99 (m, 4H), 2.40 (m, 4H), 2.16 (s, 3H), 1.29 (t, J=7.0, 3H). MS (APCI, m/z)=379 (m+1).

Unless otherwise indicated, the compounds of Examples 6–99 were prepared according to the general procedures set forth towards the syntheses of the title compounds of Examples 3–5. It will be readily apparent to those skilled in the art that the syntheses of these examples are illustrated in Schemes 1–4 described above. The NMR data characterizing these examples describe either the salt or the free base form.

Example 6

N-[4-(4-Ethylpiperazin-1-yl)phenyl]-5-(3-methoxyphenyl)-1,3-oxazol-2-amine

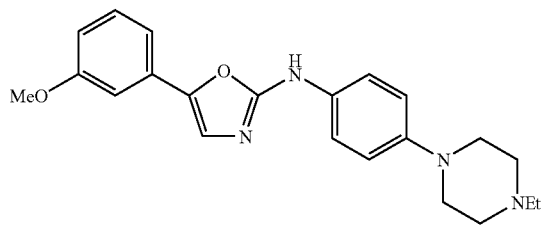

$^1$H NMR (400 MHz, d$_6$-DMSO): δ 1.02 (t, J=7.05, 2H), 2.36 (d, J=7.5, 1H), 2.99 (s, 3H), 3.74 (s, 2H), 6.76 (s, 1H), 6.86 (d, J=8.97, 2H), 7.04 (s, 1H), 7.09 (m, 1H), 7.27 (t, J=7.79, 1H), 7.38 (s, 1H), 7.42 (d, J=8.97, 2H), 9.95 (s, 1H).

Example 7

N-[4-(4-Ethylpiperazin-1-yl)phenyl]-5-phenyl-1,3-oxazol-2-amine

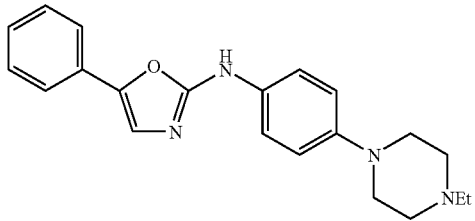

$^1$H NMR (400 MHz, d$_6$-DMSO): δ 1.03 (t, J=7.05, 1H), 3.00 (s, 2H), 6.86 (d, J=8.97, 1H), 7.19 (t, J=7.14, 1H), 7.36 (m, 1H), 7.43 (d, J=8.97, 1H), 7.50 (d, J=7.51, 1H), 9.95 (s, 1H).

Example 8

N-[4-(Morpholin-4-ylmethyl)phenyl]-5-phenyl-1,3-oxazol-2-amine

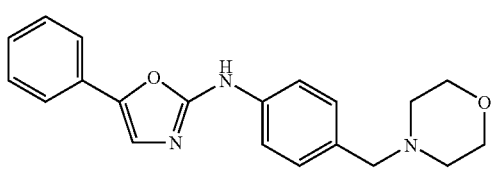

$^1$H NMR (400 MHz, d$_6$-DMSO): δ 2.32 (s, 2H), 3.38 (s, 1H), 3.55 (s, 3H), 7.25 (m, 2H), 7.42 (t, J=7.78, 1H), 7.45 (s, 1H), 7.57 (d, J=8.24, 3H), 10.28 (s, 1H).

Example 9

5-(3-Methoxyphenyl)-N-(4-morpholin-4-ylphenyl)-1,3-oxazol-2-amine

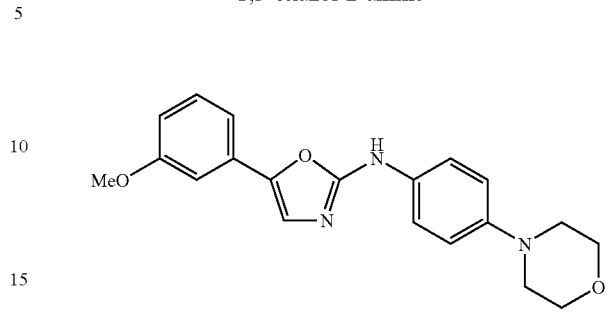

$^1$H NMR (400 MHz, d$_6$-DMSO): δ 2.97 (m, 2H), 3.68 (m, 2H), 3.74 (s, 1H), 6.77 (d, J=10.62, 1H), 6.87 (d, J=8.97, 1H), 7.04 (s, 1H), 7.09 (d, J=7.51, 1H), 7.27 (t, J=7.97, 1H), 7.38 (s, 1H), 7.44 (d, J=8.97, 1H), 9.98 (s, 1H).

Example 10

5-(3-Methoxyphenyl)-N-(4-piperidin-1-ylphenyl)-1,3-oxazol-2-amine

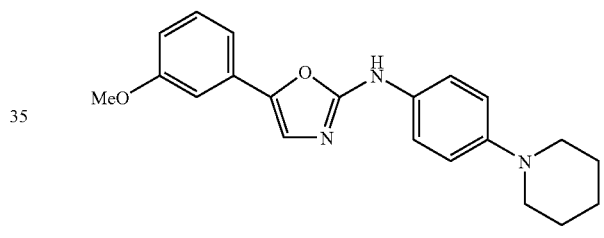

$^1$H NMR (400 MHz, d$_6$-DMSO): δ 1.44 (s, 1H), 1.56 (s, 2H), 2.97 (d, J=5.31, 2H), 3.74 (s, 1H), 6.76 (dd, J$_1$=8.06, J$_2$=2.20, 1H), 6.85 (d, J=8.42, 1H), 7.03 (s, 1H), 7.08 (d, J=7.51, 1H), 7.27 (t, J=8.15, 1H), 7.38 (s, 1H), 7.41 (d, J=8.79, 1H), 9.93 (s, 1H).

Example 11

5-(3-Methoxyphenyl)-N-[4-(morpholin-4-ylmethyl)phenyl]-1,3-oxazol-2-amine

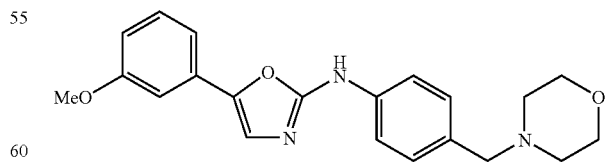

$^1$H NMR (400 MHz, d$_6$-DMSO): δ 2.27 (s, 3H), 3.33 (s, 2H), 3.50 (s, 3H), 3.74 (s, 2H), 6.79 (d, J=8.79, 1H), 7.06 (s, 1H), 7.11 (d, J=7.87, 1H), 7.18 (d, J=7.87, 2H), 7.28 (t, J=7.87, 1H), 7.43 (s, 1H), 7.52 (d, J=7.87, 2H), 10.24 (s, 1H).

Intermediate 12a

Preparation of
2-Bromo-5-(3-isopropoxyphenyl)-1,3-oxazole

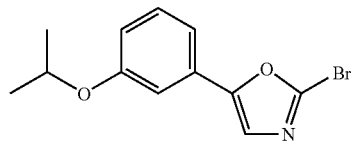

In a similar manner as described in Intermediate 5b, from Intermediate 5a (0.25 g, 1 mmol) and 2-iodopropane (0.25 g, 1.5 mmol) afforded the title compound as an oil (0.16 g, 56%). $^1$H NMR (400 MHz, $d_6$-DMSO): δ 1.22 (d, J=5.8, 6H), 4.64 (hept, J=5.8, 1H), 6.90 (dd, $J_1$=9.5, $J_2$=2.3, 1H), 7.16 (m, 2H), 7.32 (t, J=7.9, 1H), 7.74 (s, 1H). MS (APCI, m/z)=281, 283 (m+1).

Example 12

5-(3-isopropoxyphenyl)-N-[4-(4-methylpiperazin-1-yl)phenyl]-1,3-oxazol-2-amine

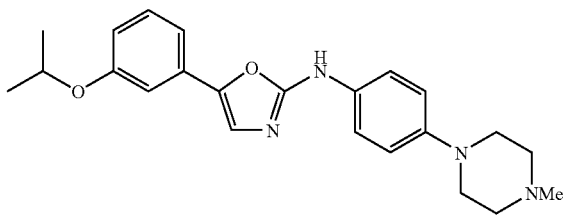

$^1$H NMR (400 MHz, $d_6$-DMSO): δ 9.93 (s, 1H), 7.42 (d, J=9.2, 2H), 7.37 (s, 1H), 7.25 (t, J=7.9, 1H), 7.04 (d, J=7.9, 1H), 7.02 (s, 1H), 6.86 (d, J=9.2, 2H), 6.74 (dd, $J_1$=8.2, $J_2$=2.2, 1H), 4.60 (m, 1H), 2.99 (m, 4H), 2.40 (m, 4H), 2.17 (s, 3H), 1.22 (d, J=6.0, 6H). MS (APCI, m/z)=393 (m+1).

Intermediate 13a

Preparation of
2-bromo-5-(3-cyclopentyloxyphenyl)-1,3-oxazole

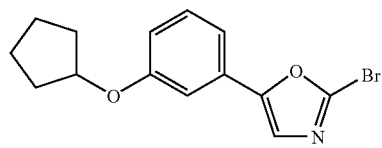

In a similar manner as described in Intermediate 5b, from Intermediate 5a (0.25 g, 1 mmol) and iodocyclopentane (0.29 g, 1.5 mmol) afforded the title compound as an oil (0.17 g, 54%). $^1$H NMR (400 MHz, $d_6$-DMSO): δ 1.5–2.0 (m, 8H), 4.84 (m, 1H), 6.88 (dd, $J_1$=8.2, $J_2$=2.3, 1H), 7.13 (d, J=2, 1H), 7.16 (d, J=7.9, 1H), 7.32 (t, J=7.8, 1H), 7.74 (s, 1H). MS (APCI, m/z)=307, 309 (m+1).

Example 13

5-[3-(cyclopentyloxy)phenyl]-N-[4-(4-methylpiperazin-1-yl)phenyl]-1,3-oxazol-2-amine

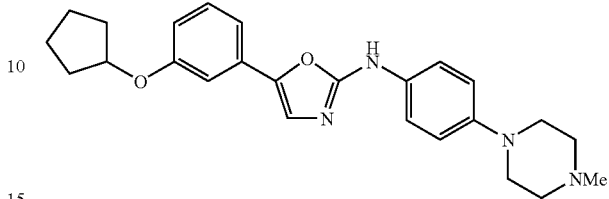

$^1$H NMR (400 MHz, $d_6$-DMSO): δ 9.92 (s, 1H), 7.42 (d, J=8.9, 2H), 7.37 (s, 1H), 7.24 (t, J=7.9, 1H), 7.04 (d, J=7.7, 1H), 7.00 (t, J=2.0, 1H), 6.86 (d, J=9.0, 2H), 6.73 (dd, $J_1$=8.3, $J_2$=2.4, 1H), 4.80 (m, 1H), 2.99 (m, 4H), 2.40 (m, 4H), 2.16 (s, 3H), 1.82–1.95 (m, 2H), 1.48–1.74 (m, 6H). MS (APCI, m/z)=419 (m+1).

Intermediate 14a

Preparation of
2-Bromo-5-(3-isobutoxyphenyl)-1,3-oxazole

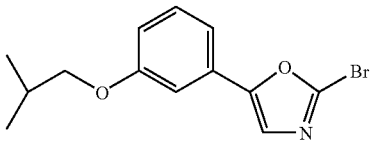

In a similar manner as described in Intermediate 5b, from Intermediate 5a (0.25 g, 1 mmol) and iodoisobutane (0.29 g, 1.5 mmol) afforded the title compound as a solid, (65.0 mg, 19%). $^1$H NMR (400 MHz, $d_6$-DMSO): δ 0.94 (d, J=7.8, 6H), 1.97 (m, 1H), 3.75 (d, J=6.6, 1H), 6.92 (dd; $J_1$=8.1, $J_2$=2.2, 1H), 7.18 (m, 2H), 7.33 (t, J=7.9, 1H), 7.75 (s, 1H). MS (APCI, m/z)=296, 298 (m+1).

Example 14

5-(3-Isobutoxyphenyl)-N-[4-(4-methylpiperazin-1-yl)phenyl]-1,3-oxazol-2-amine

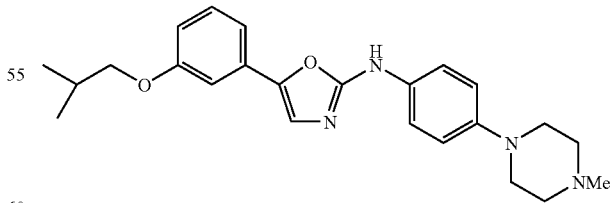

$^1$H NMR (400 MHz, $d_6$-DMSO): δ 9.94 (s, 1H), 7.42 (d, J=8.9, 2H), 7.38 (s, 1H), 7.25 (t, J=8.0, 1H), 7.07 (d, J=8.0, 1H), 7.03 (t, J=2.0, 1H), 6.86 (d, J=9.0, 2H), 6.76 (dd, $J_1$=8.1, $J_2$=2.0, 1H), 3.72 (d, J=6.6, 2H), 2.99 (m, 4H), 2.41 (m, 4H), 2.17 (s, 3H), 1.97 (m, 1H), 0.94 (d, J=6.6, 6H). MS (APCI, m/z)=407 (m+1).

Intermediate 15a

Preparation of
2-Bromo-5-(3-benzyloxyphenyl)-1,3-oxazole

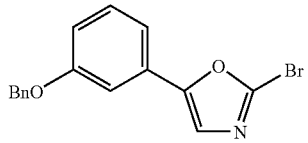

In a similar manner as described in Intermediate 5b, from Intermediate 5a (0.25 g, 1 mmol) and benzyl bromide (0.25 g, 1.5 mmol) afforded the title compound (90.0 mg, 27%) as a solid. $^1$H NMR (400 MHz, d$_6$-DMSO): δ 5.11, (s, 2H), 7.0 (dd, J$_1$=8.2, J$_2$=2.4, 1H), 7.22 (d, J=7.8, 1H), 7.3–7.5 (m, 7H), 7.77 (s, 1H). MS (APCI, m/z)=330, 332 (m+1).

Example 15

5-[3-(Benzyloxy)phenyl]-N-[4-(4-methylpiperazin-1-yl)phenyl]-1,3-oxazol-2-amine

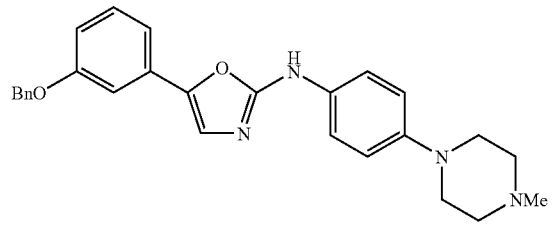

$^1$H NMR (400 MHz, d$_6$-DMSO): δ 9.95 (s, 1H), 7.26–7.45 (m, 9H), 7.15 (s, 1H), 7.09 (d, J=7.9, 1H), 6.82–6.88 (m, 3H), 5.09 (s, 2H), 3.00 (m, 4H), 2.42 (m 4H), 2.18 (s, 3H). MS (APCI, m/z)=441 (m+1).

Intermediate 16a

Preparation of 2-bromo-5-(3-(2-methylprop-2-enyl)oxyphenyl)-1,3-oxazole

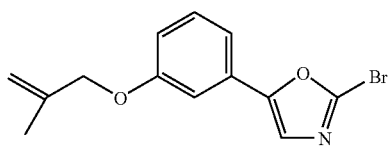

In a similar manner as described in Intermediate 5b, from Intermediate 5a (0.2 g, 1 mmol) and 3-bromo-2-methylpropene (0.2 mL, 2 mmol) afforded the title compound (0.24 g, 95%) as an oil. $^1$H NMR (400 MHz, d$_6$-DMSO): δ 1.73 (s, 3H), 4.48 (s, 2H), 4.92 (s, 1H), 5.03 (s, 1H), 6.94 (dd, J$_1$=8.1, J$_2$=2.2, 1H), 7.2 (m, 2H), 7.34 (t, J=8.2, 1H), 7.76 (s, 1H). MS (APCI, m/z)=250, 252 (m+1).

Example 16

N-[4-(4-methylpiperazin-1-yl)phenyl]-5-{3-[(2-methylprop-2-enyl)oxy]phenyl}-1,3-oxazol-2-amine

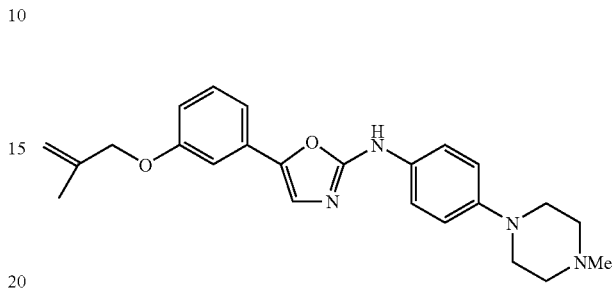

$^1$H NMR (400 MHz, d$_6$-DMSO): δ 9.94 (s, 1H), 7.42 (d, J=9.1, 2H), 7.38 (s, 1H), 7.26 (t, J=7.9, 1H), 7.08 (m, 2H), 6.86 (d, J=9.1, 2H), 6.79 (d, J=7.6, 1H), 5.03 (s, 1H), 4.92 (s, 1H), 4.45 (s, 2H), 2.99 (m, 4H), 2.40 (m, 4H), 2.16 (s, 3H), 1.73 (s, 3H). MS (APCI, m/z)=405 (m+1).

Intermediate 17a

Preparation of
2-chloro-5-(3-hydroxyphenyl)-1,3-oxazole

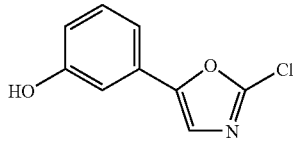

Under an atmosphere of nitrogen, a solution of Intermediate 4b (7.7 g, 37 mmol) in dry dichloromethane (180 mL) was treated with boron tribromide (18 mL 47.7 g, 0.19 mol) at 0° C. over 5 min by syringe, by permitting the boron tribromide to contact the inner side of the flask during addition. After stirring for 30 min, the reaction was warmed to RT and stirred for an additional 2 h. The mixture was poured into ice water (ca. 700 mL) and stirred. After the ice melted, K$_2$CO$_3$ (56 g, 0.400 mol) was slowly added, followed by ethyl acetate (300 mL). After being stirred at RT for 30 min, the organic layer was separated and the aqueous layer was extracted with additional ethyl acetate (3×50 mL). The combined organic layers were dried over anhydrous magnesium sulfate, filtered, and concentrated under reduced pressure. Purification by silica gel chromatography using 30% ethyl acetate in hexanes afforded the title compound (5.45 g, 75%) as a pale yellow solid. $^1$H NMR (400 MHz, d$_6$-DMSO): δ 6.75 (dd, J$_1$=8.1, J$_2$=2.2, 1H), 6.99 (d, J=2.1, 1H), 7.06 (d, J=7.7, 1H), 7.22 (t, J=8.1, 1H), 7.67 (s, 1H), 9.7 (s, 1H). MS (APCI, m/z)=196 (m+1).

Intermediate 17b

Preparation of
2-chloro-5-(3-propoxyphenyl)-1,3-oxazole

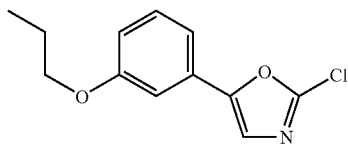

In a similar manner as described in Intermediate 5b, from Intermediate 17b (0.2 g, 1 mmol) and 1-iodopropane (0.2 mL, 2 mmol) afforded the title compound (0.2 g, 86%) as an oil. $^1$H NMR (400 MHz, d$_6$-DMSO): δ 0.94 (t, J=7.4, 3H), 1.7 (hex, J=7.2, 2H), 3.93 t, J=6.5, 2H), 6.93 (dd, J$_1$=9.9, J$_2$=2.4, 1H), 7.2 (m, 2H), 7.33 (t, J=7.9, 1H), 7.77 (s, 1H). MS (APCI, m/z)=238 (m+1).

Example 17

N-[4-(4-methylpiperazin-1-yl)phenyl]-5-(3-propoxyphenyl)-1,3-oxazol-2-amine

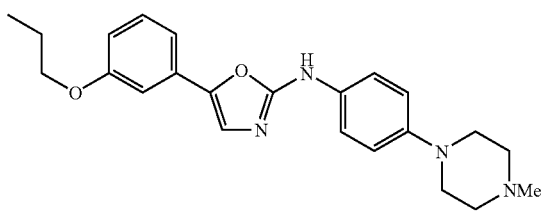

$^1$H NMR (400 MHz, d$_6$-DMSO): δ 0.94 (t, J=7.32, 2H) 1.69 (m, 1H), 2.17 (s, 2H), 2.99 (s, 2H), 3.91 (t, J=6.41, 1H), 6.76 (d, J=8.42, 1H), 6.86 (d, J=8.97, 1H), 7.05 (m, 1H), 7.25 (t, J=7.96, 1H), 7.38 (s, 1H), 7.42 (d, J=8.97, 1H), 9.94 (s, 1H).

Intermediate 18a

Preparation of
2-chloro-5-(3-cyclohexyloxyphenyl)-1,3-oxazole

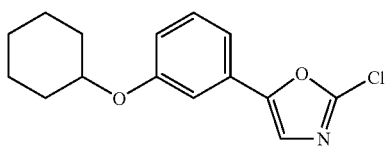

A stirred solution of Intermediate 17a (0.2 g, 1 mmol) in dry THF (2 mL) under nitrogen was treated with cyclohexanol (0.15 g, 1.5 mmol), triphenylphosphine (0.39 g, 1.5 mmol), and diethyl azodicarboxylate (0.24 mL, 0.26 g, 1.5 mmol). After the mixture was stirred at RT for 30 min, an additional amount of cyclohexanol (0.15 g, 1.5 mmol), triphenylphosphine (0.39 g, 1.5 mmol), and diethyl azodicarboxylate (0.24 mL, 0.26 g, 1.5 mmol) was added and stirred for 1 h. Silica gel was added to the reaction and the solvent was evaporated under reduced pressure. Purification by silica gel chromatography with 5% ethyl acetate in hexanes afforded the title compound (0.249 g, 90%) as a colorless oil.

Example 18

5-[3-(cyclohexyloxy)phenyl]-N-[4-(4-methylpiperazin-1-yl)phenyl]-1,3-oxazol-2-amine

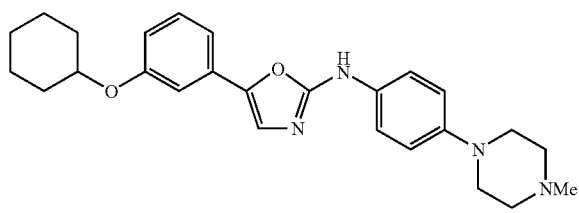

$^1$H NMR (400 MHz, d$_6$-DMSO): δ 1.19 (m, 6H), 1.71 (m, 2H), 1.92 (m, 2H), 2.20 (s, 3H), 2.44 (m, J$_1$=4.85, J$_2$=4.85, 4H), 3.03 (m, 4H), 4.37 (m, 1H), 6.82 (dd, J$_1$=8.33, J$_2$=2.65, 1H), 6.90 (d, J=9.16, 2H), 7.09 (m, 2H), 7.29 (t, J=7.97, 1H), 7.41 (s, 1H), 7.46 (d, J=8.97, 2H), 9.96 (s, 1H). MS (ES+, m/z)=433 (m+H)$^+$.

Intermediate 19a

Preparation of
1-(2-Chloro-4-nitrophenyl)-4-methylpiperazine

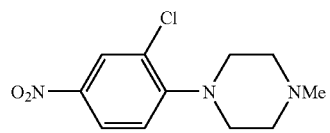

3-Chloro-4-fluoronitrobenzene (2.0 g, 11.4 mmol) was added to a stirred suspension of K$_2$CO$_3$ (1.6 g, 11.4 mmol) and N-methylpiperazine (1.3 mL, 1.17 g, 11.4 mmol) in dry DMSO (8 mL) and was heated at 100° C. for 1 h. The reaction was cooled to about 50° C. and poured into ice water (300 mL). The solid was collected by filtration, washed with water, and dried under vacuum to afford the title compound (2.43 g, 84%).

Intermediate 19b

Preparation of
3–Chloro-4-(4-methylpiperazin-1-yl)aniline

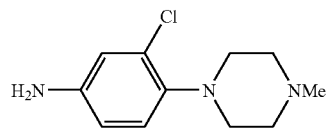

To a stirred solution of 1-(2-chloro-4-nitrophenyl)-4-methylpiperazine (2.43 g, 9.5 mmol) in 2N HCl (35 mL) at RT was added tin (II) chloride (7.2 g, 38 mmol). After 1 h, the solids were collected by filtration and dissolved in aqueous 1 N NaOH (300 mL). The aqueous solution was extracted with ethyl acetate (3×50 mL). The combined organic layers were washed with brine, dried over anhydrous magnesium sulfate, filtered, and evaporated to afford the title compound (2.02 g, 95%).

Example 19

N-[3-chloro-4-(4-methylpiperazin-1-yl)phenyl]-5-(3-methoxyphenyl)-1,3-oxazol-2-amine

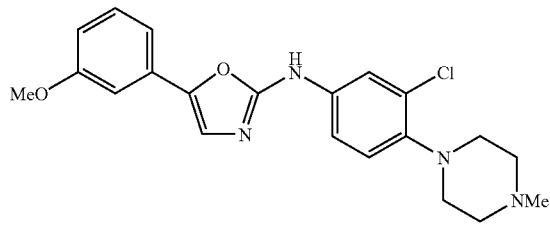

$^1$H NMR (400 MHz, d$_6$-DMSO): δ 2.23 (s, 2H), 2.90 (s, 2H), 3.79 (s, 2H), 6.84 (dd, J$_1$=8.51, J$_2$=2.29, 1H), 7.10 (d, J=2.20, 1H), 7.14 (m, 1H), 7.33 (t, J=7.97, 1H), 7.45 (dd, J$_1$=8.79, J$_2$=2.56, 1H), 7.48 (s, 1H), 7.81 (d, J=2.56, 1H), 10.37 (s, 1H).

Intermediate 20a

Preparation of 1-(2-Fluoro-4-nitrophenyl)-4-methylpiperazine

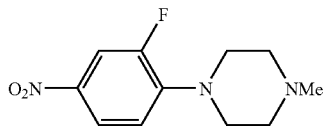

In a similar manner as described in Example 19a, from 3,4-difluoronitrobenzene (1.4 mL, 2.01 g, 12.5 mmol) afforded the title compound (2.0 g, 67%).

Intermediate 20b

Preparation of 3-Fluoro-4-(4-methylpiperazin-1-yl)aniline

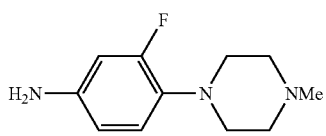

In a similar manner as described in Example 19b, from Intermediate 20a (2 g, 8.4 mmol) afforded the title compound (1.48 g, 84%). $^1$H NMR (400 MHz, d$_6$-DMSO): δ 2.14 (s, 3H), 2.40 (bs, 4H), 2.70 (bs, 4H), 4.90 (bs, 2H), 6.24 (m, 2H), 6.69 (t, J=8.6, 1H).

Example 20

N-[3-fluoro-4-(4-methylpiperazin-1-yl)phenyl]-(3-methoxyphenyl)-1,3-oxazol-2-amine

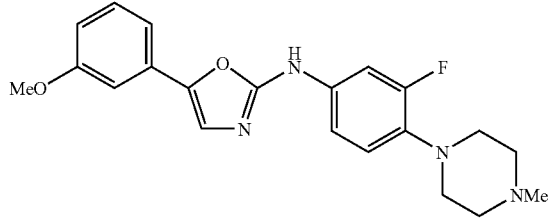

$^1$H NMR (400 MHz, d$_6$-DMSO): δ 2.23 (s, 1H), 2.93 (s, 2H), 3.79 (s, 2H), 6.84 (d, J=8.06, 1H), 7.01 (m, 1H), 7.10 (d, J=2.56, 1H), 7.15 (d, J=8.06, 1H), 7.25 (dd, J$_1$=8.51, J$_2$=1.74, 1H), 7.33 (t, J=7.97, 1H), 7.47 (s, 1H), 7.55 (dd, J$_1$=15.01, J$_2$=2.56, 1H), 10.34 (s, 1H).

Intermediate 21a

Preparation of 1-methyl-4-[4-nitro-2(trifluoromethyl)phenyl]piperazine

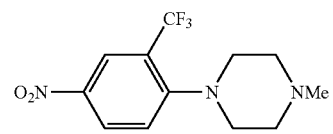

In a similar manner as described in Example 19a, from 4-fluoro-3-trifluoromethylnitrobenzene (1.3 mL, 1.98 g, 9.6 mmol) afforded the title compound (2.2 g, 90%).

Intermediate 21b

Preparation of 4-(4-methylpiperazin-1-yl)-3-(trifluoromethyl)phenylamine

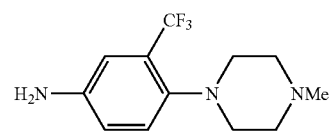

In a similar manner as described in Example 19b, from Intermediate 21a (2.22 g, 8.6 mmol) afforded the title compound (1.82 g, 82%). $^1$H NMR (400 MHz, d$_6$-DMSO): δ 2.13 (s, 3H), 2.4 (bs, 4H), 2.6 (bs, 4H), 5.27 (bs, 2H), 6.70 (dd, J$_1$=8.6, J$_2$=2.7, 1H), 6.74 (d, J=2.7, 1H), 7.16 (d, J=8.6, 1H).

Example 21

5-(3-Methoxyphenyl)-N-[4-(4-methylpiperazin-1-yl)-3(trifluoromethyl)phenyl-]1,3-oxazol-2-amine

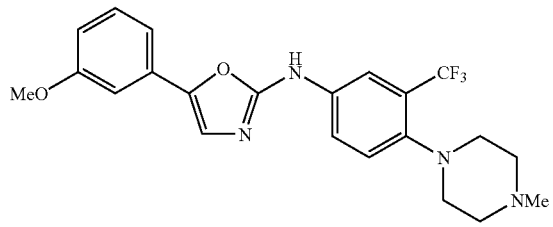

¹H NMR (400 MHz, d₆-DMSO): δ 2.22 (s, 2H), 2.80 (t, J=4.58, 3H), 3.79 (s, 2H), 6.85 (m, 1H), 7.11 (dd, J₁=2.29, J₂=1.56, 1H), 7.16 (dd, J₁=7.78, J₂=1.19, 1H), 7.34 (t, J=8.06, 1H), 7.52 (s, 1H), 7.55 (d, J=8.79, 1H), 7.79 (m, 1H), 8.06 (d, J=2.56, 1H), 10.59 (s, 1H).

Intermediate 22a

Preparation of 1-methyl-4-[4-nitro-2-methylphenyl]piperazine

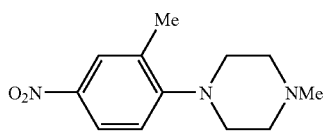

In a similar manner as described in Example 19a, from 2-fluoro-5-nitrotoluene (2.0 g, 12.9 mmol) was obtained the title compound, 1.44 g (47%).

Intermediate 22b

Preparation of 4-(4-Methylpiperazin-1-yl)-3-methylphenylamine

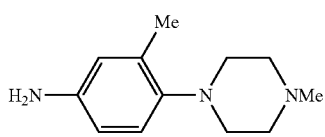

In a similar manner as described in Example 19b, from 1-methyl-4-[4-nitro-2-methylphenyl]piperazine (1.44 g, 6.1 mmol) was obtained the title compound, 1.19 g (95%). ¹H NMR (400 MHz, d₆-DMSO): δ 2.19 (s, 3H), 2.27 (s, 3H), 2.4 (bs, 4H), 2.9 (bs, 4H), 7.06 (d, J=8.4, 1H), 7.95 (m, 2H).

Example 22

5-(3-Methoxyphenyl)-N-[3-methyl-4-(4-methylpiperazin-1-yl)phenyl]-1,3-oxazol-2-amine

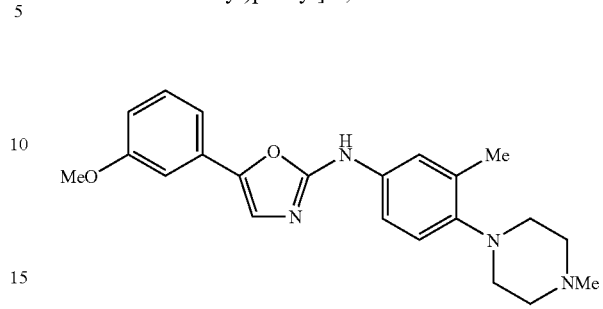

¹H NMR (400 MHz, d₆-DMSO): δ 2.22 (d, J=1.65, 4H), 2.78 (t, J=4.49, 3H), 3.79 (s, 2H), 6.82 (dd, J₁=7.87, J₂=2.38, 1H), 6.99 (d, J=8.42, 1H), 7.09 (d, J=3.85, 1H), 7.14 (d, J=7.87, 1H), 7.32 (t, J=7.96, 1H), 7.40 (m, 2H), 7.44 (s, 1H), 10.07 (s, 1H).

Intermediate 23a

Preparation of 3,5-dimethyl-1-(4-nitrophenyl)piperazine

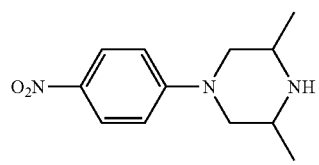

In a similar manner as described in Example 19a, from 4-fluoronitrobenzene (1.9 mL, 2.53 g, 18 mmol) and 2,6-dimethylpiperazine (2.0 g, 17.5 mmol) was obtained the title compound, 3.4 g (83%).

Intermediate 23b

Preparation of 4-(3,5-dimethylpiperazin-1-yl)aniline

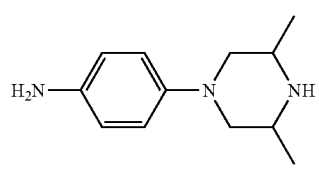

A solution of Intermediate 23a (3.4 g, 14 mmol) in MeOH (20 mL) and THF (20 mL) was treated with palladium on carbon (10%, 0.34 g) and hydrogenated at 45 psi for 1 h. The catalyst was removed by filtration through a pad of celite. The filtrate was evaporated under reduced pressure to afford the title compound (2.9 g, 99%). ¹H NMR (400 MHz, d₆-DMSO): δ 0.92 (d, J=6.4, 6H), 1.91 (t, J=10.6, 2H), 2.78 (bs, 2H), 3.14 (d, J=10.2, 2H), 4.4 (bs, 2H), 6.42 (d, J=8.6, 2H), 6.60 (d, J=8.7, 2H).

Example 23

N-[4-(3,5-dimethylpiperazin-1-yl)phenyl]-5-(3-methoxyphenyl)-1,3-oxazol-2-amine

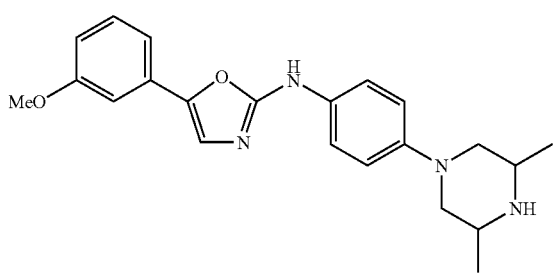

$^1$H NMR (400 MHz, d$_6$-DMSO): δ 1.01 (d, J=6.23, 3H), 2.05 (m, 1H), 2.85 (s, 1H), 3.16 (d, J=5.13, 1H), 3.40 (d, J=12.82, 1H), 3.79 (s, 2H), 6.81 (dd, J$_1$=8.24, J$_2$=2.38, 1H), 6.89 (d, J=8.97, 1H), 7.08 (s, 1H), 7.13 (d, J=7.51, 1H), 7.32 (t, J=7.87, 1H), 7.42 (s, 1H), 7.45 (d, J=8.97, 1H), 9.98 (s, 1H)

Intermediate 24a

Preparation of 1-methyl-4-(3-methyl-4-nitrophenyl)piperazine

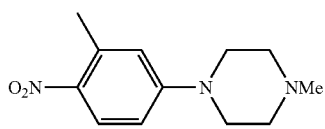

In a similar manner as described in Example 19a, from 3-fluoro-5-nitrotoluene (2.0 g, 13 mmol) afforded the title compound (2.44 g, 80%).

Intermediate 24b

Preparation of 2-methyl-4-(4-methylpiperazin-1-yl)aniline

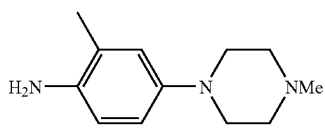

In a similar manner as described in Example 19b, from Intermediate 24a (2.44 g, 10.4 mmol) afforded the title compound (0.667 g, 31%). $^1$H NMR (400 MHz, d$_6$-DMSO): δ 2.00 (s, 3H), 2.18 (s, 3H), 2.40 (m, 4H), 2.86 (m, 4H), 4.30 (bs, 2H), 6.40–6.70 (m, 3H).

Example 24

5-(3-methoxyphenyl)-N-[2-methyl-4-(4-methylpiperazin-1-yl)phenyl]-1,3-oxazol-2-amine

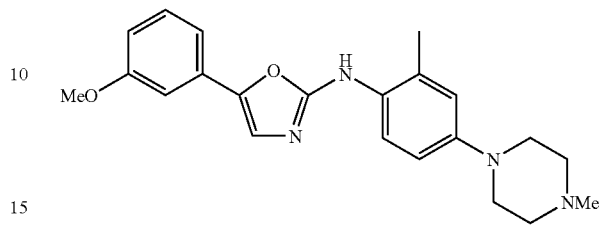

$^1$H NMR (400 MHz, d$_6$-DMSO): δ 2.21 (s, 3H), 2.43 (m, 2H), 3.07 (m, 2H), 3.29 (s, 1H), 3.77 (s, 2H), 6.77 (m, 1H), 7.05 (s, 1H), 7.09 (d, J=7.51, 1H), 7.29 (t, J=7.97, 1H), 7.33 (s, 1H), 7.45 (d, J=8.79, 1H), 9.03 (s, 1H).

Example 25

5-[3-(Cyclopentyloxy)phenyl]-N-[4-(4-methylpiperazin-1-yl)-3-(trifluoromethyl)phenyl]-1,3-oxazol-2-amine

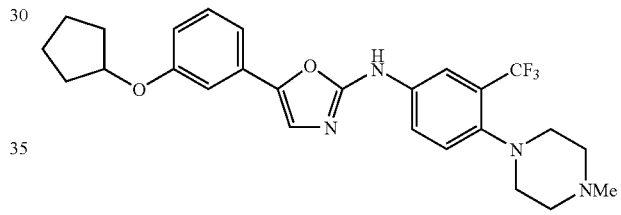

$^1$H NMR (400 MHz, d$_6$-DMSO): δ 1.59 (s, 1H), 1.72 (m, 3H), 1.92 (s, 1H), 2.21 (s, 2H), 2.42 (s, 2H), 2.80 (s, 3H), 3.29 (s, 1H), 6.81 (d, J=10.07, 1H), 7.10 (m, 1H), 7.31 (t, J=8.06, 1H), 7.51 (s, 1H), 7.54 (d, J=8.42, 1H), 7.78 (d, J=7.32, 1H), 8.05 (s, 1H), 10.55 (s, 1H).

Example 26

N-[3-Chloro-4-(4-methylpiperazin-1-yl)phenyl]-5-[3-(cyclopentyloxy)phenyl]-1,3-oxazol-2-amine

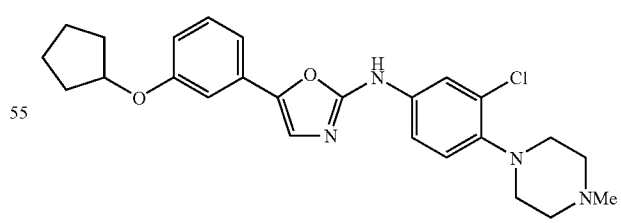

$^1$H NMR (400 MHz, d$_6$-DMSO): δ 1.59 (m, 2H), 1.71 (m, J=3.11, 4H), 1.92 (m, 2H), 2.22 (s, 3H), 2.46 (s, 4H), 2.90 (m, 4H), 4.85 (m, $_1$H), 6.80 (dd, J$_1$=8.33, J$_2$=2.11, 1H), 7.07 (m, 1H), 7.10 (d, J=7.69, 1H), 7.14 (d, J=8.79, 1H), 7.30 (t, J=7.97, 1H), 7.45 (dd, J$_1$=8.61, J$_2$=2.56, 1H), 7.47 (s, 1H), 7.81 (d, J=2.56, 1H), 10.33 (s, 1H). MS (APCI, m/z)=453 (m+1).

Example 27

5-[3-(cyclopentyloxy)phenyl]-N-[3-methyl-4-(4-methylpiperazin-1-yl)phenyl]-1,3-oxazol-2-amine

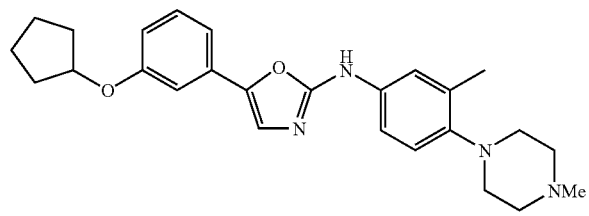

¹H NMR (400 MHz, d₆-DMSO): δ 1.59 (m, 2H), 1.71 (m, 4H), 1.91 (m, 2H), 2.22 (s, 6H), 2.45 (m, 4H), 2.77 (m, $J_1$=4.49, $J_2$=4.49, 4H), 4.85 (m, 1H), 6.78 (dd, $J_1$=8.42, $J_2$=2.38, 1H), 6.98 (d, J=8.61, 1H), 7.05 (s, 1H), 7.09 (d, J=7.69, 1H), 7.30 (t, J=8.06, 1H), 7.39 (m, 2H), 7.43 (s, 1H), 10.03 (s, 1H). MS (APCI, m/z)=433 (m+1).

Example 28

5-[3-(Cyclopentyloxy)phenyl]-N-[3-fluoro-4-(4-methylpiperazin-1-yl)phenyl]-1,3-oxazol-2-amine

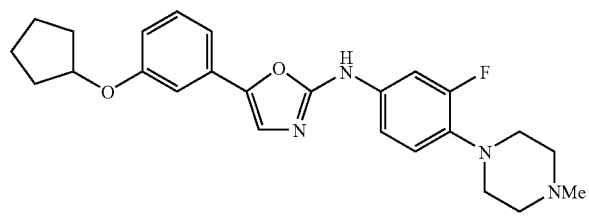

¹H NMR (400 MHz, d₆-DMSO): δ 1.59 (s, 1H), 1.71 (m, 2H), 1.93 (d, J=4.21, 1H), 2.22 (s, 2H), 2.93 (s, 2H), 3.28 (d, J=10.25, 2H), 4.85 (s, 1H), 6.80 (dd, $J_1$=8.42, $J_2$=2.20, 1H), 7.00 (m, 1H), 7.06 (d, J=2.01, 1H), 7.10 (d, J=8.24, 1H), 7.24 (dd, $J_1$=9.06, $J_2$=1.74, 1H), 7.30 (t, J=8.06, 1H), 7.46 (s, 1H), 7.55 (dd, $J_1$=14.83, $J_2$=2.56, 1H), 10.31 (s, 1H).

Example 29

3-(2-{[4-(4-methylpiperazin-1-yl)phenyl]amino}-1,3-oxazol-5-yl)phenol

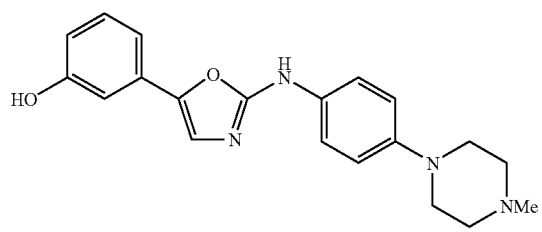

To a stirred solution of the title compound of Example 4 (0.20 g, 0.45 mmol) in methanol (50 mL) was added palladium on carbon (10% w/w, 0.1 g) and was hydrogenated at 50 psi for 12 h. The catalyst was removed by filtration and the solvent was evaporated from the filtrate to leave a tan solid. Trituration with diethyl ether afforded a solid that was collected by filtration and dried under vacuum to leave the title compound (0.16 g, 96%). ¹H NMR (400 MHz, d₆-DMSO): δ 2.20 (s, 3H), 2.43 (m, 4H), 3.03 (m, 4H), 6.62 (d, J=9.16, 1H), 6.90 (m, 3H), 6.95 (d, J=7.69, 1H), 7.17 (t, J=7.87, 1H), 7.29 (s, 1H), 7.46 (d, J=8.61, 2H), 9.95 (s, 1H). MS (APCI, m/z)=336 (m+1).

Example 30

5-[3-(Cyclopentyloxy)phenyl]-N-(4-thiomorpholin-4-ylphenyl)-1,3-oxazol-2-amine

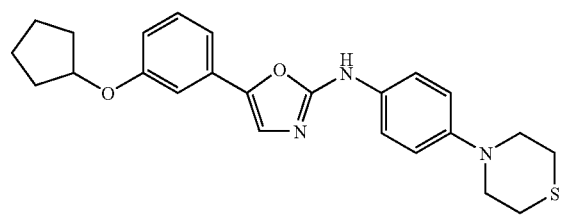

¹H NMR (400 MHz, d₆-DMSO): δ 1.59 (m, 2H), 1.71 (m, 4H), 1.92 (m, 2H), 2.68 (m, 4H), 3.37 (m, 4H), 4.85 (m, 1H), 6.78 (dd, $J_1$=8.15, $J_2$=2.47, 1H), 6.91 (d, J=9.16, 2H), 7.05 (s, 1H), 7.09 (d, J=7.87, 1H), 7.29 (t, J=7.97, 1H), 7.42 (s, 1H), 7.48 (d, J=8.97, 2H), 10.00 (s, 1H). MS (APCI, m/z)=422 (m+H)⁺.

Intermediate 31a

Preparation of 1-methyl-4-(5-nitropyridin-2-yl)piperazine

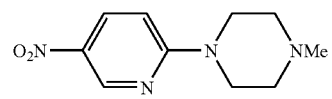

In a similar manner as described in Example 19a, from 2-chloro-5-nitropyridine (2.0 g, 12.6 mmol) and N-methylpiperazine (1.4 mL, 1.26 g, 12.6 mmol) was obtained the title compound (1.66 g, 60%).

Intermediate 31b

Preparation of 6-(4-methylpiperazin-1-yl)pyridin-3-amine

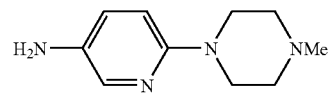

In a similar manner as described in Example 19b, from Intermediate 31a (1.66 g, 7.5 mmol) was obtained the title compound. ¹H NMR (400 MHz, d₆DMSO): δ 2.14 (s, 3H), 2.32 (m, 4H), 3.16 (m, 4H), 4.5 (bs, 2H), 6.55 (d, J=8.8, 1H), 6.84 (dd, $J_1$=8.8, $J_2$=2.9, 1H), 8.90 (d, J=2.9, 1H).

Example 31

N-[5-(3-methoxyphenyl)-1,3-oxazol-2-yl]-6-(4-methylpiperazin-1-yl)pyridin-3-amine

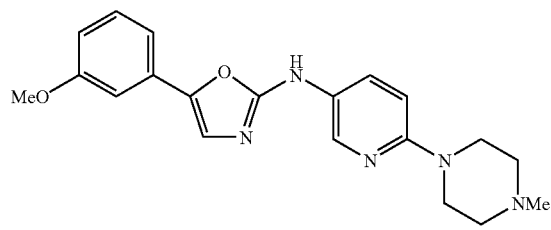

$^1$H NMR (400 MHz, d$_6$-DMSO): δ 2.21 (s, 2H), 2.39 (s, 2H), 3.38 (s, 2H), 3.78 (s, 2H), 6.84 (m, 1H), 7.08 (s, 1H), 7.13 (d, J=8.24, 1H), 7.32 (t, J=7.97, 1H), 7.43 (s, 1H), 7.86 (dd, J$_1$=9.80, J$_2$=2.84, 1H), 8.35 (s, 1H), 10.04 (s, 1H).

Intermediate 32a

Preparation of 2-(1H-imidazol-1-yl)-5-nitropyridine

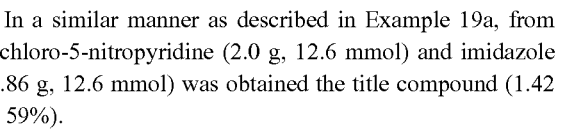

In a similar manner as described in Example 19a, from 2-chloro-5-nitropyridine (2.0 g, 12.6 mmol) and imidazole (0.86 g, 12.6 mmol) was obtained the title compound (1.42 g, 59%).

Intermediate 32b

Preparation of 6-(1H-imidazol-1-yl)pyridin-3-amine

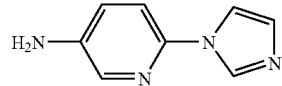

In a similar manner as described in Example 19b, from Intermediate 32a (1.42 g, 7.5 mmol) was obtained the title compound (0.359 g, 30%). $^1$H NMR (400 MHz, d$_6$-DMSO): δ 5.45 (bs, 2H), 7.02 (s, 1H), 7.10 (dd, J$_1$=8.8, J$_2$=2.9, 1H), 7.42 (d, J=8.6, 1H), 7.71 (s, 1H), 7.80 (d, J=2.8, 1H), 8.25 (s, 1H).

Example 32

6-(1H-imidazol-1-yl)-N-[5-(3-methoxyphenyl)-1,3-oxazol-2-yl]pyridin-3-amine

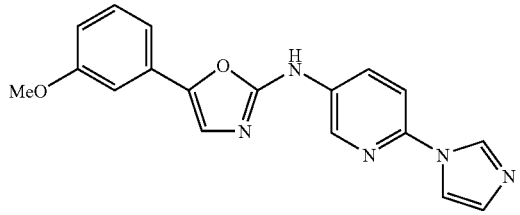

$^1$H NMR (400 MHz, d$_6$-DMSO): δ 3.80 (s, 2H), 6.86 (d, J=10.25, 1H), 7.10 (s, 1H), 7.13 (s, 1H), 7.18 (d, J=8.06, 1H), 7.35 (t, J=7.87, 1H), 7.55 (s, 1H), 7.79 (d, J=8.97, 1H), 7.78 (s, 1H), 8.29 (dd, J$_1$=8.97, J$_2$=2.56, 1H), 8.43 (s, 1H), 8.69 (d, J=2.56, 1H), 10.76 (s, 1H).

Intermediate 33a

Preparation of 5-nitro-2-piperidin-1-ylpyridine

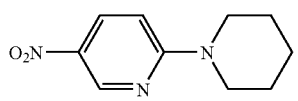

In a similar manner as described in Example 19, from 2-chloro-5-nitropyridine (2.0 g, 12.6 mmol) and piperidine (1.2 mL 1.03 g, 12.6 mmol) was obtained the title compound (1.42 g, 62%).

Intermediate 33b

Preparation of 6-piperidin-1-ylpyridine-3-amine

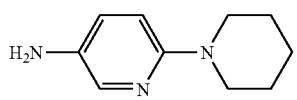

In a similar manner as described in Example 19, from Intermediate 33a (1.63 g, 7.9 mmol) was obtained the title compound. $^1$H NMR (400 MHz, d$_6$-DMSO): δ 1.51 (bs, 6H), 3.21 (bs, 4H), 4.49 (bs, 2H), 6.58 (d, J=8.7, 1H), 6.87 (dd, J$_1$=8.7, J$_2$=2.9, 1H), 7.57 (d, J=2.7, 1H).

Example 33

N-[5-(3-methoxyphenyl)-1,3-oxazol-2-yl]-6-piperidin-1-ylpyridin-3-amine

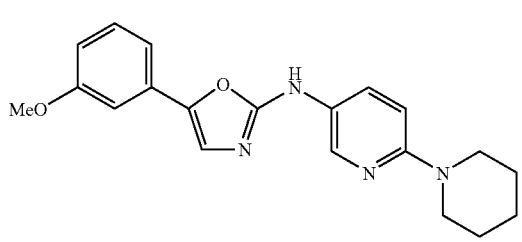

¹H NMR (400 MHz, d₆-DMSO): δ 1.55 (s, 5H), 3.40 (s, 3H), 3.78 (s, 2H), 6.82 (d, J=8.79, 2H), 7.08 (s, 1H), 7.12 (d, J=7.69, 1H), 7.32 (t, J=7.97, 1H), 7.42 (s, 1H), 7.82 (dd, J₁=9.16, J₂=2.75, 1H), 8.32 (d, J=2.75, 1H), 9.99 (s, 1H).

Example 34

N-{5-[3-(cyclopentyloxy)phenyl]-1,3-oxazol-2-yl}-6-(4-methylpiperazin-1-yl)pyridin-3-amine

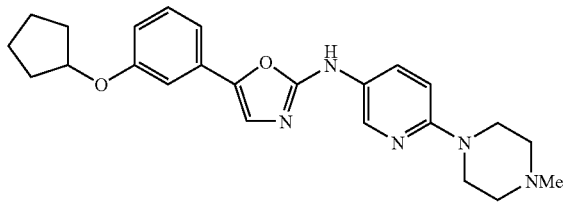

¹H NMR (400 MHz, d₆-DMSO): δ 1.58 (m, 2H), 1.70 (m, 4H), 1.92 (m, 2H), 2.20 (s, 3H) 2.39 (m, 4H), 3.37 (m, 4H), 4.84 (m, 1H), 6.78 (dd, J₁=8.06, J₂=1.83, 1H) 6.84 (d, J=9.15, 1H), 7.04 (s, 1H), 7.08 (d, J=7.69, 1H), 7.29 (t, J=7.97, 1H), 7.42 (s, 1H), 7.85 (dd, J₁=9.16, J₂=2.75, 1H), 8.35 (d, J=2.75, 1H), 10.00 (s, 1H). MS (APCI, m/z)=420 (m+1).

Intermediate 35a

Preparation of N,N-diethyl-5-nitropyridin-2-amine

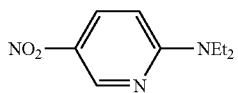

In a similar manner as described in Example 19a, from 2-chloro-5-nitropyridine (2.0 g, 12.6 mmol) and diethylamine (1.3 mL, 0.92 g, 12.6 mmol) was obtained the title compound (1.86 g, 77%).

Intermediate 35b

Preparation of N²,N²-diethylpyridine-2,5-diamine

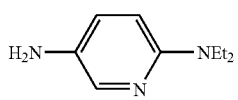

In a similar manner as described in Example 19b, from Intermediate 35a (1.86 g, 9.5 mmol) was obtained the title compound. ¹H NMR (400 MHz, d₆-DMSO): δ 0.95 (t, J=7.0, 6H), 3.29 (q, J=7.0, 4H), 4.25 (bs, 2H), 6.33 (d, J=8.8, 1H), 6.82 (dd, J₁=8.8, J₂=2.9, 1H), 7.49 (d, J=2.9, 1H).

Example 35

N²,N²-diethyl-N⁵-[5-(3-methoxyphenyl)-1,3-oxazol-2-yl]pyridine-2,5-diamine

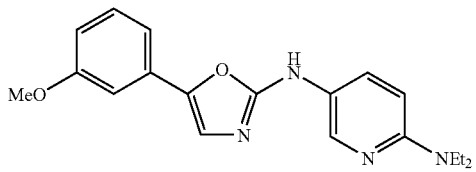

¹HNMR (400 MHz, d₆-DMSO): δ 1.08 (t, J=6.87, 5H), 3.44 (q, J=7.08, 3H), 3.78 (s, 2H), 6.58 (d, J=9.15, 1H), 6.81 (dd, J₁=8.15, J₂=2.29, 1H), 7.07 (s, 1H), 7.11 (d, J=7.51, 1H), 7.31 (t, J=8.06, 1H), 7.40 (s, 1H), 7.75 (dd, J₁=9.06, J₂=2.65, 1H), 8.26 (d, J=2.75, 1H), 9.84 (s, 1H).

Example 36

N⁵-{5-[3-(cyclopentyloxy)phenyl]-1,3-oxazol-2-yl}-N²,N²-diethylpyridine-2,5-diamine

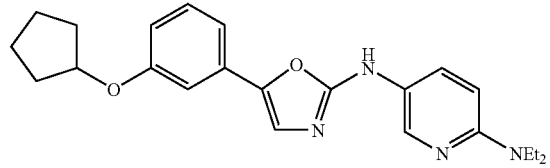

¹H NMR (400 MHz, d₆-DMSO): δ 1.08 (t, J=6.87, 6H), 1.58 (m, 2H), 1.70 (m, 4H), 1.91 (m, 2H), 3.44 (q, J=6.59, 4H), 4.84 (m, 1H), 6.58 (d, J=9.52, 1H), 6.77 (d, J=9.52, 1H), 7.03 (s, 1H), 7.07 (d, J=7.87, 1H), 7.28 (t, J=7.69, 1H), 7.39 (s, 1H), 7.74 (d, J=11.90, 1H), 8.25 (s, 1H), 9.80 (s, 1H). MS (APCI, m/z)=393 (m+1).

Example 37

N-{5-[3-(cyclopentyloxy)phenyl]-1,3-oxazol-2-yl}-5-methyl-6-(4-methylpiperazin-1-yl)pyridin-3-amine

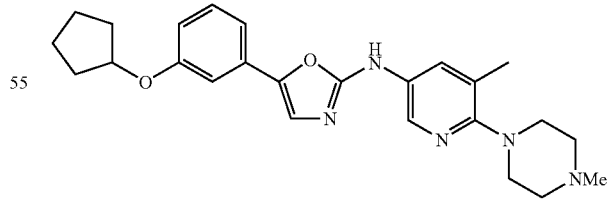

¹H NMR (400 MHz, d₆-DMSO): δ 1.59 (m, 2H), 1.71 (m, 4H), 1.92 (m, 2H), 2.22 (s, 3H), 2.23 (s, 3H), 2.45 (m, 4H), 2.96 (m, 4H), 4.85 (m, 1H), 6.80 (dd, J₁=7.87, J₂=2.38, 1H), 7.06 (s, 1H), 7.10 (d, J=7.51, 1H), 7.30 (t, J=7.87, 1H), 7.45 (s, 1H), 7.83 (d, J=2.20, 1H), 8.31 (d, J=2.56, 1H), 10.20 (s, 1H). MS (APCI, m/z)=434 (m+1).

Example 38

5-(3-methoxyphenyl)-N-{4-[(4-methylpiperazin-1-yl)methyl]phenyl}-1,3-oxazol-2-amine

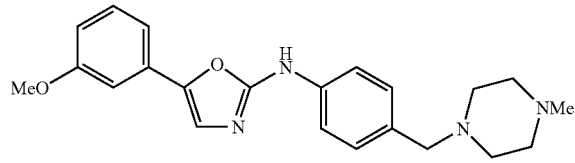

¹H NMR (400 MHz, d₆-DMSO): δ 1.18 (s, 1H), 2.12 (s, 2H), 2.30 (s, 3H), 3.33 (s, 1H), 3.74 (s, 2H), 6.79 (d, J=10.80, 1H), 7.06 (s, 1H), 7.11 (d, J=7.51, 1H), 7.16 (d, J=8.24, 1H), 7.28 (t, J=7.96, 1H), 7.43 (s, 1H), 7.52 (d, J=8.42, 1H), 10.23 (s, 1H).

Example 39

N-{4-[(4-methylpiperazin-1-yl)methyl]phenyl}-5-phenyl-1,3-oxazol-2-amine

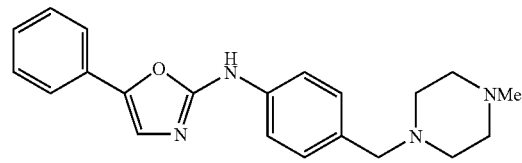

¹H NMR (400 MHz, d₆-DMSO): δ 2.12 (s, 2H), 2.30 (s, 4H), 3.33 (s, 1H), 7.19 (m, 2H), 7.36 (d, J=7.69, 1H), 7.40 (d, J=2.38, 1H), 7.52 (dd, J₁=7.96, J₂=3.57, 3H), 10.23 (s, 1H).

Example 40

N-{4-[(dimethylamino)methyl]phenyl}-5-(3-methoxyphenyl)-1,3-oxazol-2-amine

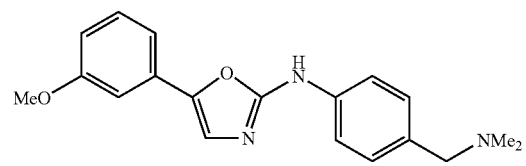

¹H NMR (400 MHz, d₆-DMSO): δ 2.16 (s, 4H), 3.38 (s, 1H), 3.79 (s, 2H), 6.84 (d, J=7.69, 1H), 7.11 (s, 1H), 7.16 (d, J=7.87, 1H), 7.22 (d, J=8.61, 1H), 7.33 (t, J=7.87, 1H), 7.48 (s, 1H), 7.58 (d, J=8.42, 1H), 10.30 (s, 1H).

Example 41

5-[3-(cyclopentyloxy)phenyl]-N-{4-[(dimethylamino)methyl]phenyl}-1,3-oxazol-2-amine

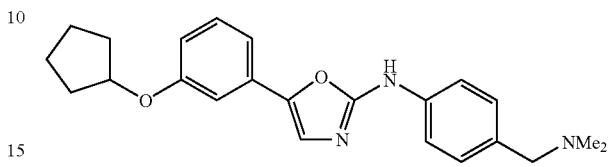

¹H NMR (400 MHz, d₆-DMSO): δ 10.20 (s, 1H), 7.52 (d, J=8.6, 2H), 7.42 (s, 1H), 7.26 (t, J=8.0, 1H), 7.16 (d, J=8.6, 2H), 7.06 (d, J=7.9, 1H), 7.02 (t, J=2.0, 1H), 6.75 (dd, J₁=8.2, J₂=2.4, 1H), 4.81 (m, 1H), 3.28 (s, 2H), 2.08 (s, 6H), 1.82–1.95 (m, 2H), 1.48–1.72 (m, 6H). MS (APCI, m/z)=333 (M-44).

Example 42

N-{4-[2-(dimethylamino)ethyl]phenyl}-5-(3-methoxyphenyl)-1,3-oxazol-2-amine

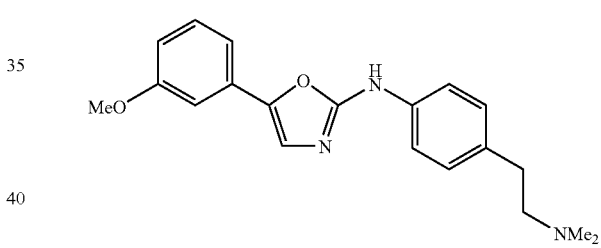

¹H NMR (400 MHz, d₆-DMSO): δ 2.16 (s, 3H), 2.60 (m, 1H), 3.74 (s, 1H), 6.78 (d, J=9.34, 1H), 7.05 (s, 1H), 7.10 (d, J=7.69, 1H), 7.28 (t, J=8.33, 1H), 7.41 (s, 1H), 7.47 (d, J=8.06, 1H), 10.16 (s, 1H).

Example 43

5-(3-methoxyphenyl)-N-[4-(piperidin-1-ylmethyl)phenyl]-1,3-oxazol-2-amine

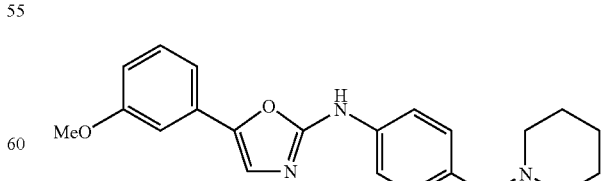

¹H NMR (400 MHz, d₆-DMSO): δ 1.36 (s, 1H), 1.47 (s, 3H), 2.28 (s, 2H), 3.22 (s, 1H), 3.75 (s, 2H), 6.78 (d, J=8.24, 1H), 7.06 (s, 1H), 7.13 (m, 2H), 7.28 (t, J=8.15, 1H), 7.43 (s, 1H), 7.51 (d, J=8.24, 1H), 10.22 (s, 1H).

Example 44

5-(3-methoxyphenyl)-N-[4-(pyrrolidin-1-ylmethyl)phenyl]-1,3-oxazol-2-amine

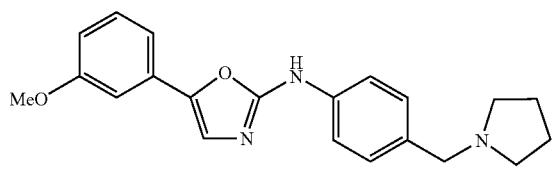

¹H NMR (400 MHz, d₆-DMSO): δ 2.36 (s, 2H), 3.46 (s, 1H), 3.75 (s, 2H), 6.79 (dd, J₁=8.51, J₂=3.02, 1H), 7.06 (m, 1H), 7.11 (d, J=7.87, 1H), 7.18 (d, J=8.61, 1H), 7.28 (t, J=7.97, 1H), 7.43 (s, 1H), 7.51 (d, J=8.42, 1H), 10.22 (s, 1H).

Example 45

N-{4-[(diethylamino)methyl]phenyl}-5-(3-methoxyphenyl)-1,3-oxazol-2-amine

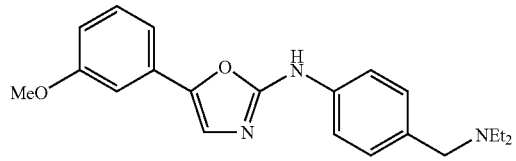

¹H NMR (400 MHz, d₆-DMSO): δ 0.96 (t, J=6.87, 4H), 3.40 (s, 1H), 3.75 (s, 2H), 6.79 (d, J=8.06, 1H), 7.06 (m, 1H), 7.11 (d, J=8.24, 1H), 7.18 (d, J=8.61, 1H), 7.29 (t, J=7.87, 1H), 7.43 (s, 1H), 7.51 (d, J=8.24, 1H), 10.21 (s, 1H).

Example 46

N-[2-(diethylamino)ethyl]-4-{[5-(3-methoxyphenyl)-1,3-oxazol-2-yl]amino}benzamide

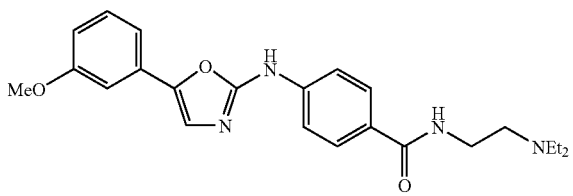

¹H NMR (400 MHz, d₆-DMSO): δ 0.96 (t, J=7.14, 6H), 2.50 (m, 4H), 3.32 (m, 4H), 3.80 (s, 3H), 6.85 (d, J=7.87, 1H), 7.13 (s, 1H), 7.18 (d, J=8.42, 1H), 7.35 (t, J=7.97, 1H), 7.53 (s, 1H), 7.67 (d, J=8.42, 2H), 7.80 (d, J=8.24, 2H), 8.21 (s, 1H), 10.63 (s, 1H). MS (APCI, m/z)=409 (m+1).

Example 47

5-(3-methoxyphenyl)-N-{4-[(4-methylpiperazin-1-yl)carbonyl]phenyl}-1,3-oxazol-2-amine

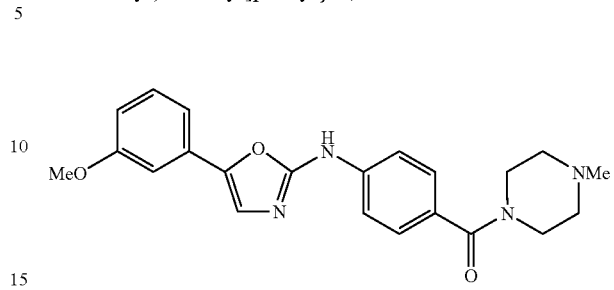

¹H NMR (400 MHz, d₆-DMSO): δ 2.18 (s, 3H), 2.30 (m, 4H), 3.50 (m, 4H), 3.80 (s, 3H), 6.85 (dd, J₁=8.61, J₂=2.38, 1H), 7.13 (s, 1H), 7.18 (d, J=7.32, 1H), 7.33 (d, J=8.06, 1H), 7.37 (d, J=8.61, 2H), 7.52 (s, 1H), 7.68 (d, J=8.61, 2H), 10.58 (s, 1H). MS (APCI, m/z)=393 (m+1).

Example 48

4-({5-[3-(cyclopentyloxy)phenyl]-1,3-oxazol-2-yl}amino)-N-[2-(diethylamino)ethyl]benzamide

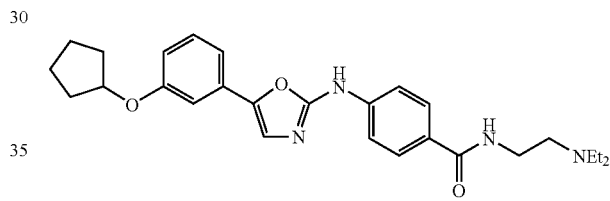

¹H NMR (400 MHz, d₆-DMSO): δ 1.00 (m, 6H), 1.59 (m, 2H), 1.71 (m, 4H), 1.92 (m, 2H), 2.58 (m, 4H), 3.32 (s, 4H), 4.86 (m, 1H), 6.82 (dd, J₁=8.33, J₂=2.29, 1H), 7.09 (s, 1H), 7.13 (d, J=8.06, 1H), 7.32 (t, J=8.06, 1H), 7.52 (s, 1H), 7.67 (d, J=8.61, 2H), 7.81 (d, J=8.61, 2H), 8.28 (s, 1H), 10.62 (s, 1H). MS (APCI, m/z)=463 (m+H)⁺.

Example 49

5-(3-methoxyphenyl)-N-[4-(1-propylpiperidin-4-yl)-1,3-thiazol-2-yl]-1,3-oxazol-2-amine

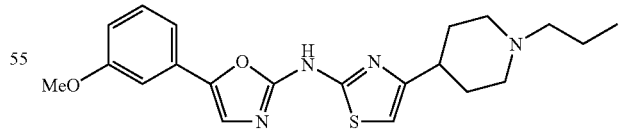

In a similar manner as described in Example 4, from Intermediate 4b (0.19 g, 0.9 mmol) and 4-(1-propylpiperidin-4-yl)-1,3-thiazol-2-amine (0.20 g, 0.9 mmol) was obtained the title compound (0.11 g, 31%). ¹H NMR (400 MHz, d₆-DMSO): δ 0.84 (t, J=7.42, 2H), 1.45 (m, 1H), 1.58 (m, J=10.99, 1H), 1.91 (m, J=14.28, 2H), 3.78 (s, 2H), 6.43 (s, 1H), 6.81 (dd, J₁=7.87, J₂=2.20, 1H), 7.10 (m, 1H), 7.14 (d, J=7.87, 1H), 7.31 (t, J=7.97, 1H), 7.55 (s, 1H).

Example 50

N,5-diphenyl-1,3-oxazol-2-amine

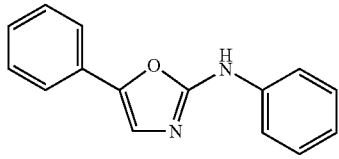

$^1$H NMR (400 MHz, d$_6$-DMSO): δ 10.28 (s, 1H), 7.61 (d, J=7.9, 2H), 7.55 (d, J=7.5, 2H), 7.45–7.37 (m, 3H), 7.31–7.21 (m, 3H), 6.92 (t, J=7.3, 1H). MS (ES+, m/z)=237 (m+H)$^+$.

Example 51

N-methyl-1-{4-[(5-phenyl-1,3-oxazol-2-yl)amino]phenyl}methanesulfonamide

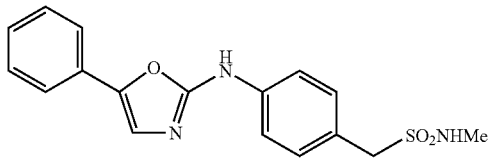

$^1$H NMR (400 MHz, d$_6$-DMSO): δ 10.39 (s, 1H), 7.59 (d, J=8.6, 2H), 7.56 (d, J=7.5, 2H), 7.45 (s, 1H), 7.40 (t, J=7.8, 2H), 7.30–7.21 (m, 3H), 6.83 (d, J=4.9, 1H), 4.22 (s, 2H), 2.52 (d, J=4.4, 3H). MS (ES+, m/z)=344 (m+H)$^+$.

Example 52

N-{4-[(methylsulfonyl)methyl]phenyl}-5-phenyl-1,3-oxazol-2-amine

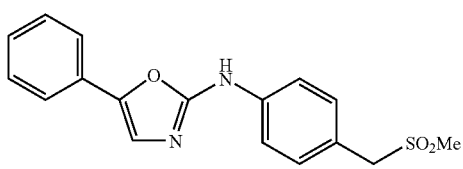

$^1$H NMR (400 MHz, d$_6$-DMSO): δ 10.46 (s, 1H), 7.62 (d, J=8.6, 2H), 7.56 (d, J=7.5, 2H), 7.46 (s, 1H), 7.41 (t, J=7.8, 2H), 7.32 (d, J=8.6, 2H), 7.25 (t, J=7.4, 1H), 4.37 (s, 2H), 2.84 (s, 3H). MS (ES+, m/z)=329 (m+H)$^+$.

Example 53

N,N-diethyl-4-methoxy-3-[(5-phenyl-1,3-oxazol-2-yl)amino]benzenesulfonamide

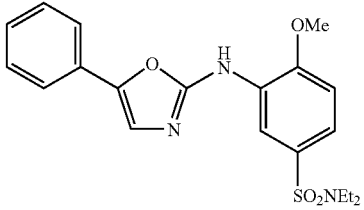

$^1$H NMR (400 MHz, d$_6$-DMSO): δ 9.46 (s, 1H), 8.69 (d, J=2.2, 1H), 7.58 (d, J=7.3, 2H), 7.50 (s, 1H), 7.44–7.35 (m, 3H), 7.25 (t, J=7.4, 1H), 7.16 (d, J=8.6, 1H), 3.92 (s, 3H), 3.12 (q, J=7.1, 4H), 1.02 (t, J=7.1, 6H). MS (ES+, m/z)=402 (m+H)$^+$.

Example 54

N-butyl-4-methoxy-3-[(5-phenyl-1,3-oxazol-2-yl)amino]benzenesulfonamide

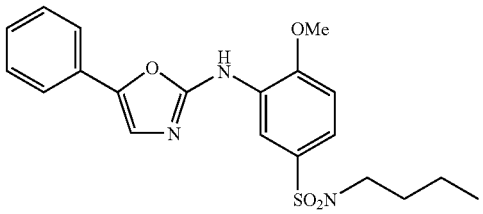

$^1$H NMR (400 MHz, d$_6$-DMSO): δ 9.67 (bs, 1H), 8.65 (d, J=2.2, 1H), 7.59 (d, J=7.5, 2H), 7.51 (s, 1H), 7.44–7.37 (m, 4H), 7.26 (t, J=7.4, 1H), 7.17 (d, J=8.6, 1H), 3.91 (s, 3H), 2.73–2.66 (m, 2H), 1.35–1.26 (m, 2H), 1.24–1.14 (m, 2H), 0.75 (t, J=7.2, 3H). MS (ES+, m/z)=402 (m+H)$^+$.

Example 55

N-(3,4-dimethoxyphenyl)-5-phenyl-1,3-oxazol-2-amine

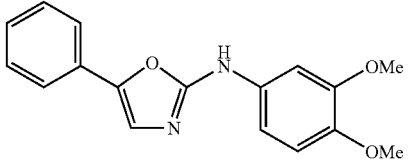

$^1$H NMR (400 MHz, d$_6$-DMSO): δ 10.55 (s, 1H), 7.57–7.53 (m, 3H), 7.41 (t, J=7.8, 2H), 7.31–7.23 (m, 2H), 7.07 (dd, J$_1$=8.6, J$_2$=2.4, 1H), 6.91 (d, J=8.8, 1H), 3.73 (s, 3H), 3.69 (s, 3H). MS (ES+, m/z)=297 (m+H)$^+$.

Example 56

N-[5-(ethylsulfonyl)-2-methoxyphenyl]-5-phenyl-1,3-oxazol-2-amine

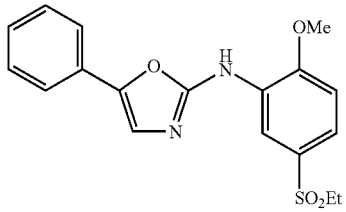

$^1$H NMR (400 MHz, d$_6$-DMSO): δ 9.72 (s, 1H), 8.75 (d, J=2.2, 1H), 7.59 (d, J=7.5, 2H), 7.51 (s, 1H), 7.46 (dd, J$_1$=8.4, J$_2$=2.2, 1H), 7.41 (t, J=7.8, 2H), 7.29–7.22 (m, 2H), 3.94 (s, 3H), 3.17 (q, J=7.4, 2H), 1.08 (t, J=7.4, 3H). MS (ES+, m/z)=359 (m+H)$^+$.

Example 57

5-phenyl-N-[3-(phenylsulfonyl)phenyl]-1,3-oxazol-2-amine

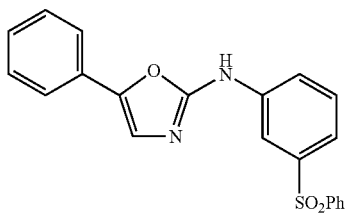

$^1$H NMR (400 MHz, d$_6$-DMSO): δ 10.81 (s, 1H), 8.36 (s, 1H), 7.90 (d, J=8.6, 2H), 7.77 (d, J=8.4, 1H), 7.70–7.46 (m, 8H), 7.42 (t, J=7.8, 2H), 7.26 (t, J=7.4, 1H). MS (ES+, m/z)=377 (m+H)$^+$.

Example 58

N,N-diethyl-4-[(5-phenyl-1,3-oxazol-2-yl)amino]benzamide

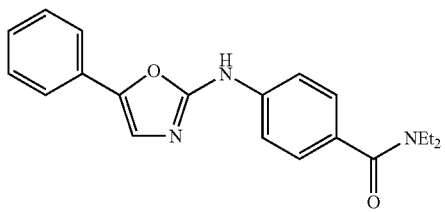

$^1$H NMR (400 MHz, d$_6$-DMSO): δ 10.52 (s, 1H), 7.67 (s, 1H), 7.61–7.54 (m, 2H), 7.47 (s, 1H), 7.40 (t, J=7.8, 2H), 7.34 (t, J=7.8, 2H), 7.42 (t, J=7.5, 1H), 6.88 (d, J=7.5, 1H), 3.39 (bs, 2H), 3.17 (bs, 2H), 1.11 (bs, 3H), 1.05 (bs, 3H). MS (ES+, m/z)=336 (m+H)$^+$.

Example 59

4-(ethylsulfonyl)-2-[(5-phenyl-1,3-oxazol-2-yl)amino]phenol

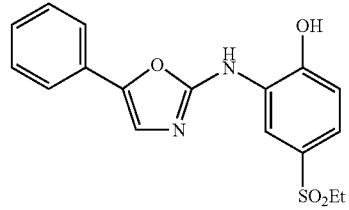

$^1$H NMR (400 MHz, d$_6$-DMSO): δ 11.29 (bs, 1H), 9.84 (bs, 1H), 8.56 (d, J=2.2, 1H), 7.60–7.56 (m, 3H), 7.44–7.35 (m, 3H), 7.27 (t, J=7.3, 1H), 7.08 (d, J=8.4, 1H), 3.14 (q, J=7.3, 2H), 1.08 (t, J=7.3, 3H). MS (ES+, m/z)=345 (m+H)$^+$.

Example 60

N-(2-methoxyphenyl)-5-phenyl-1,3-oxazol-2-amine

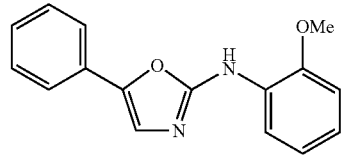

$^1$H NMR (400 MHz, d$_6$-DMSO): δ 9.94 (bs, 1H), 7.92 (bs, 1H), 7.60–7.55 (m, 3H), 7.42 (t, J=7.7, 2H), 7.27 (t, J=7.4, 1H), 7.06 (s, 2H), 6.99–6.92 (m, 1H), 3.82 (s, 3H). MS (ES+, m/z)=267 (m+H)$^+$.

Example 61

N-butyl-3-[(5-phenyl-1,3-oxazol-2-yl)amino]benzenesulfonamide

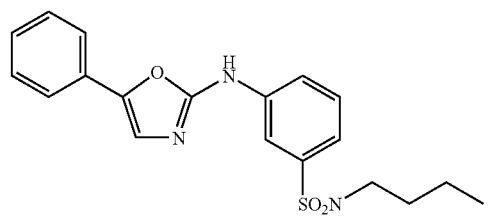

$^1$H NMR (400 MHz, d$_6$-DMSO): δ 10.71 (s, 1H), 8.19 (t, J=1.8, 1H), 7.75 (dd, J$_1$=8.2, J$_2$=1.8, 1H), 7.60–7.47 (m, 4H), 7.41 (t, J=7.7, 2H), 7.32 (d, J=7.9, 1H), 7.26 (t, J=7.4, 2H), 2.73 (q, J=6.5, 2H), 1.36–1.27 (m, 2H), 1.25–1.15 (m, 2H), 0.76 (t, J=7.3, 3H). MS (ES+, m/z)=372 (m+H)$^+$.

Example 62

N,N-dimethyl-4-[(5-phenyl-1,3-oxazol-2-yl)amino]benzenesulfonamide

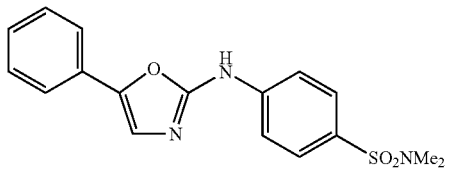

¹H NMR (400 MHz, d₆-DMSO): δ 10.91 (s, 1H), 7.83 (d, J=8.8, 2H), 7.67 (d, J=8.8, 2H), 7.67 (d, J=8.8, 2H), 7.59 (d, J=7.3, 2H), 7.52 (s, 1H), 7.42 (t, J=7.7, 2H), 7.27 (t, J=7.3, 1H), 2.54 (s, 6H). MS (ES+, m/z)=344 (m+H)⁺.

Example 63

2,5-dimethoxy-4-[(5-phenyl-1,3-oxazol-2-yl)amino]benzenesulfonamide

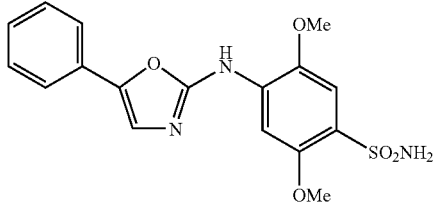

¹H NMR (400 MHz, d₆-DMSO): δ 9.75 (s, 1H), 8.22 (s, 1H), 7.60 (d, J=7.7, 2H), 7.52 (s, 1H), 7.42 (t, J=7.6, 2H), 7.27 (s, 2H), 6.94 (s, 2H), 3.84 (s, 3H), 3.82 (s, 3H). MS (ES+, m/z)=376 (m+H)⁺.

Example 64

N-(2-methoxy-5-nitrophenyl)-5-phenyl-1,3-oxazol-2-amine

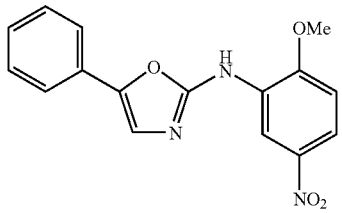

¹H NMR (400 MHz, d₆-DMSO): δ 9.95 (bs, 1H), 9.21 (d, J=2.9, 1H), 7.92 (dd, J₁=9.0, J₂=2.9, 1H), 7.60 (d, J=7.5, 2H), 7.56 (s, 1H), 7.42 (t, J=7.8, 2H), 7.27 (t, J=7.4, 1H), 7.22 (d, J=9.0, 1H), 3.99 (s, 3H). MS (ES+, m/z)=312 (m+H)⁺.

Example 65

2-{4-[(5-phenyl-1,3-oxazol-2-yl)amino]phenyl}ethanol

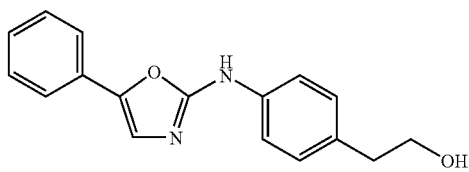

¹H NMR (400 MHz, d₆-DMSO): δ 10.35 (s, 1H), 7.55 (d, J=7.5, 2H), 7.49 (d, J=8.4, 2H), 7.46 (s, 1H), 7.40 (t, J=7.8, 2H), 7.24 (t, J=7.3, 1H), 7.13 (d, J=8.4, 2H), 3.53 (t, J=7.1, 2H), 2.64 (t, J=7.1, 2H). MS (ES+, m/z)=281 (m+H)⁺.

Example 66

1-{4-methoxy-3-[(5-phenyl-1,3-oxazol-2-yl)amino]phenyl}ethanone

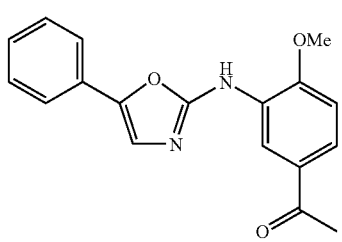

¹H NMR (400 MHz, d₆-DMSO): δ 9.74 (s, 1H), 8.70 (d, J=2.0, 1H), 7.69 (dd, J₁=8.4, J₂=2.0, 1H), 7.58 (d, J=7.5, 2H), 7.55 (s, 1H), 7.41 (t, J=7.7, 2H), 7.26 (t, J=7.5, 1H), 7.13 (d, J=8.4, 1H), 3.92 (s, 3H), 2.51 (s, 3H). MS (ES+, m/z)=309 (m+H)⁺.

Example 67

{3-[(5-phenyl-1,3-oxazol-2-yl)amino]phenyl}methanol

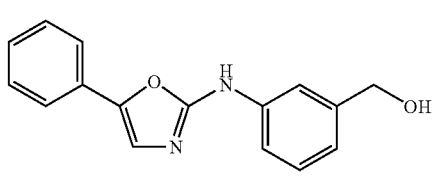

¹H NMR (400 MHz, d₆-DMSO): δ 10.44 (s, 1H), 7.58 (d, J=6.6, 2H), 7.55 (s, 1H), 7.49–7.44 (m, 2H), 7.40 (t, J=7.8, 2H), 7.28–7.20 (m, 2H), 6.89 (d, J=7.5, 1H), 4.45 (s, 3H). MS (ES+, m/z)=267 (m+H)⁺.

Example 68

N-[5-(ethylsulfonyl)-2-methoxyphenyl]-5-(3-methoxyphenyl)-1,3-oxazol-2-amine

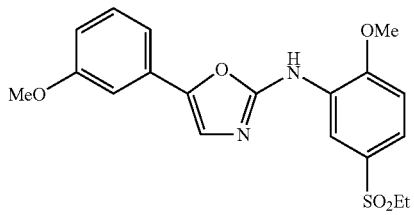

$^1$H NMR (400 MHz, d$_6$-DMSO): δ 9.71 (s, 1H), 8.74 (d, J=2.2, 1H), 7.53 (s, 1H), 7.46 (dd, J$_1$=8.6, J$_2$=2.2, 1H), 7.32 (t, J=8.0, 1H), 7.24 (d, J=8.6, 1H), 7.17 (d, J=7.7, 1H), 7.13 (s, 1H), 6.83 (dd, J$_1$=8.2, J$_2$=2.4, 1H), 3.94 (s, 3H), 3.78 (s, 3H), 3.17 (q, J=7.3, 2H), 1.08 (t, J=7.3, 3H). MS (ES+, m/z)=389 (m+H)$^+$.

Example 69

4-(2-{[5-(ethylsulfonyl)-2-methoxyphenyl]amino}-1,3-oxazol-5-yl)phenol

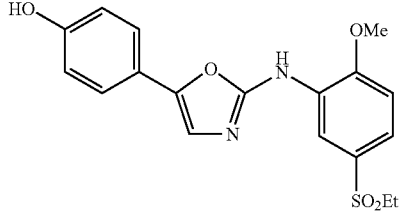

$^1$H NMR (400 MHz, d$_6$-DMSO): δ 9.73 (s, 1H), 8.69 (d, J=1.8, 1H), 7.47 (dd, J$_1$=8.4, J$_2$=2.2, 1H), 7.40 (d, J=8.6, 2H), 7.28 (s, 1H), 7.23 (d, J=8.4, 1H), 6.80 (d, J=8.6, 2H), 3.94 (s, 3H), 3.17 (q, J=7.3, 2H), 1.08 (t, J=7.3, 3H). MS (ES+, m/z)=375 (m+H)$^+$.

Example 70

3-{[5-(4-fluorophenyl)-1,3-oxazol-2-yl]amino}-4-methoxy-N,N-dimethylbenzenesulfonamide

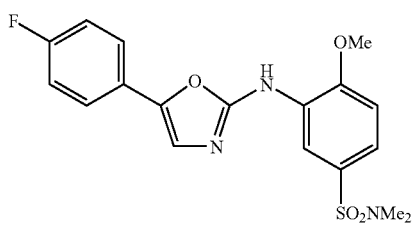

$^1$H NMR (400 MHz, d$_6$-DMSO): δ 9.77 (s, 1H), 8.74 (d, J=2.2, 1H), 7.70 (dd, J$_1$=8.8, J$_2$=5.3, 2H), 7.56 (s, 1H), 7.43 (dd, J$_1$=8.5, J$_2$=2.2, 1H), 7.37 (t, J=8.8, 2H), 7.31 (d, J=8.5, 2H), 4.03 (s, 3H), 2.66 (s, 6H). MS (ES+, m/z)=392 (m+H)$^+$.

Example 71

N-{5-(ethylsulfonyl)-2-[2-(1H-imidazol-1-yl)ethoxy]phenyl}-5-(4-fluorophenyl)-1,3-oxazol-2-amine

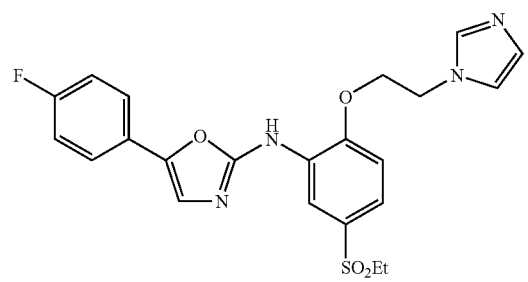

$^1$H NMR (400 MHz, d$_6$-DMSO): δ 10.35 (s, 1H), 8.48 (t, J=1.8, 1H), 8.21 (s, 1H), 7.90 (s, 1H), 7.86 (dd, J$_1$=8.8, J$_2$=5.3, 2H), 7.39 (t, J=8.8, 2H), 7.02 (s, 1H), 6.94 (s, 2H), 5.43 (s, 2H), 4.73 (t, J=4.5, 2H), 4.44 (t, J=4.5, 2H), 3.04 (q, J=7.3, 2H), 0.99 (t, J=7.3, 3H). MS (ES+, m/z)=457 (m+H)$^+$.

Example 72

N-[5-(ethylsulfonyl)-2-(2-pyridin-2-ylethoxy)phenyl]-5-phenyl-1,3-oxazol-2-amine

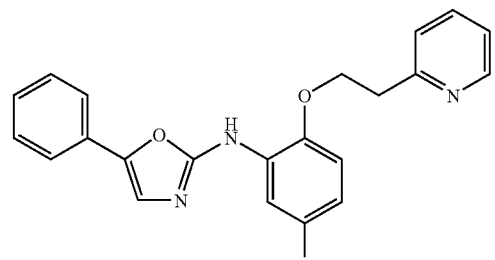

$^1$H NMR (400 MHz, d$_6$-DMSO): δ 9.66 (s, 1H), 8.70 (d, J=2.2, 1H), 8.53 (d, J=4.4, 1H), 7.75–7.67 (m, 1H), 7.59 (d, J=7.5, 2H), 7.50 (s, 1H), 7.43–7.38 (m, 4H), 7.31–7.20 (m, 3H), 4.49 (t, J=6.6, 2H), 3.35–3.20 (m, 2H), 3.15 (q, J=7.4, 2H), 1.06 (t, J=7.4, 3H). MS (ES+, m/z)=450 (m+H)$^+$.

Example 73

N-{5-(ethylsulfonyl)-2-[2-(1H-1,2,3-triazol-1-yl)ethoxy]phenyl}-5-phenyl-1,3-oxazol-2-amine

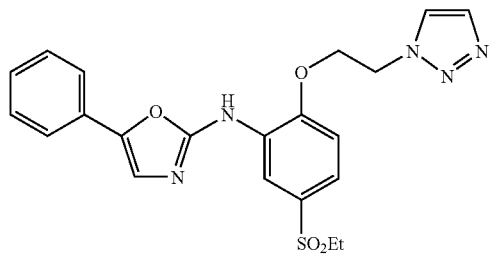

$^1$H NMR (400 MHz, d$_6$-DMSO): δ 9.59 (s, 1H), 8.74 (d, J=2.2, 1H), 8.30 (s, 1H), 7.69 (s, 1H), 7.61 (d, J=7.3, 2H), 7.52 (s, 1H), 7.43–7.37 (m, 3H), 7.28–7.20 (m, 2H), 4.91 (t, J=4.9, 2H), 4.52 (t, J=4.9, 2H), 3.14 (q, J=7.8, 2H), 1.05 (t, J=7.3, 3H). MS (ES+, m/z)=440 (m+H)$^+$.

Example 74

5-phenyl-N-(3,4,5-trimethoxyphenyl)-1,3-oxazol-2-amine

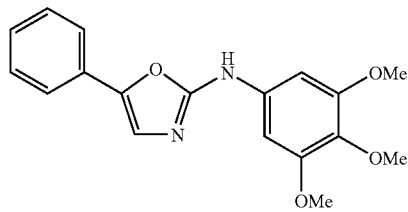

$^1$H NMR (400 MHz, d$_6$-DMSO): δ 10.23 (s, 1H), 7.52 (d, J=7.5, 2H), 7.43 (s, 1H), 7.38 (t, J=7.8, 2H), 7.22 (t, J=7.4, 1H), 6.96 (s, 2H), 3.71 (s, 6H), 3.56 (s, 3H). MS (ES+, m/z)=327 (m+H)$^+$.

Example 75

N-(2,5-dimethoxyphenyl)-5-phenyl-1,3-oxazol-2-amine

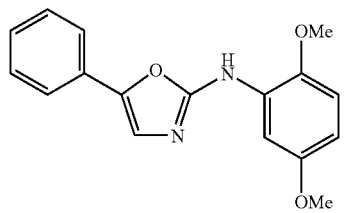

$^1$H NMR (400 MHz, d$_6$-DMSO): δ 9.46 (bs, 1H), 7.75 (d, J=3.0, 1H), 7.55 (d, J=7.5, 2H), 7.48 (s, 1H), 7.38 (t, J=7.8, 2H), 7.23 (t, J=7.4, 1H), 6.91 (d, J=8.9, 1H), 6.51 (dd, J$_1$=8.9, J$_2$=3.0, 1H), 3.75 (s, 3H), 3.66 (s, 3H). MS (ES+, m/z)=297 (m+H)$^+$.

Example 76

3-methyl-5-[(5-phenyl-1,3-oxazol-2-yl)amino]benzene-1,2-diol

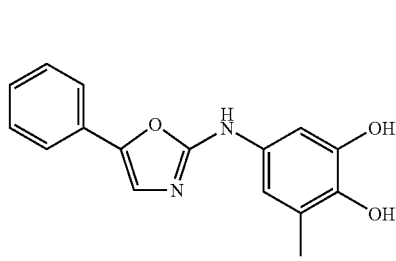

$^1$H NMR (400 MHz, d$_6$-DMSO): δ 10.23 (s, 1H), 8.70 (bs, 1H), 7.55 (d, J=2.5, 2H), 7.51 (d, J=7.5, 2H), 7.42 (s, 1H), 7.38 (t, J=7.7, 2H), 7.22 (t, J=7.3, 1H), 7.18 (d, J=2.5, 1H), 2.15 (s, 3H). MS (ES+, m/z)=301 (m+H)$^+$.

Example 77

N-(3,5-dimethoxyphenyl)-5-phenyl-1,3-oxazol-2-amine

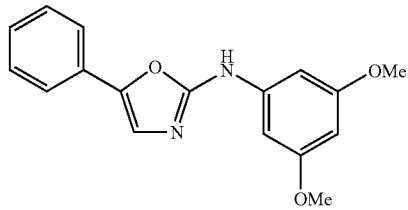

$^1$H NMR (400 MHz, d$_6$-DMSO): δ 10.27 (s, 1H), 7.52 (d, J=7.5, 2H), 7.42 (s, 1H), 7.38 (t, J=7.7, 2H), 7.22 (t, J=7.4, 1H), 6.83 (d, J=2.0, 2H), 6.08 (t, J=2.0, 1H), 3.68 (s, 6H). MS (ES+, m/z)=297 (m+H)$^+$.

Example 78

N-(3-methylphenyl)-5-phenyl-1,3-oxazol-2-amine

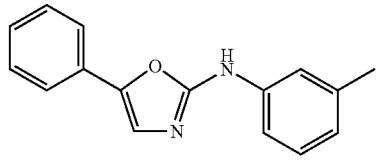

$^1$H NMR (400 MHz, d$_6$-DMSO): δ 10.18 (s, 1H), 7.53 (d, J=7.5, 2H), 7.43–7.34 (m, 4H), 7.21 (t, J=7.4, 1H), 7.13 (t, J=7.8, 1H), 6.92 (d, J=7.5, 1H), 2.24 (s, 3H). MS (ES+, m/z)=251 (m+H)$^+$.

Example 79

N-{3-[2-(1H-imidazol-1-yl)ethoxy]-4-methoxyphenyl}-5-phenyl-1,3-oxazol-2-amine

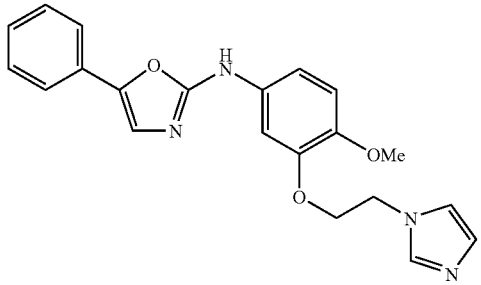

$^1$H NMR (400 MHz, d$_6$-DMSO): δ 10.20 (s, 1H), 9.13 (s, 1H), 7.78 (s, 1H), 7.66 (s, 1H), 7.51 (d, J=7.5, 2H), 7.42–7.35 (m, 4H), 7.22 (t, J=7.4, 1H), 7.06 (dd, J$_1$=8.8, J$_2$=2.4, 1H), 6.90 (d, J=8.8, 1H), 4.58 (t, J=4.7, 2H), 4.30 (t, J=4.7, 2H), 3.63 (s, 3H). MS (ES+, m/z)=377 (m+H)$^+$.

Example 80

N-{4-[2-(1H-imidazol-1-yl)ethoxy]-3-methoxyphenyl}-5-phenyl-1,3-oxazol-2-amine

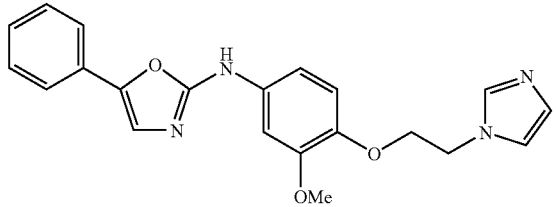

$^1$H NMR (400 MHz, d$_6$-DMSO): δ 10.33 (s, 1H), 9.21 (s, 1H), 7.85 (s, 1H), 7.24 (s, 1H), 7.59 (d, J=7.5, 2H), 7.51–7.41 (m, 4H), 7.30 (t, J=7.4, 1H), 7.12 (dd, J$_1$=8.7, J$_2$=2.3, 1H), 6.96 (d, J=8.7, 1H), 4.59 (t, J=4.8, 2H), 4.33 (t, J=4.8, 2H), 3.76 (s, 3H). MS (ES+, m/z)=377 (m+H)$^+$.

Example 81

N-[5-(ethylsulfonyl)-2-methoxyphenyl]-5-(4-fluorophenyl)-1,3-oxazol-2-amine

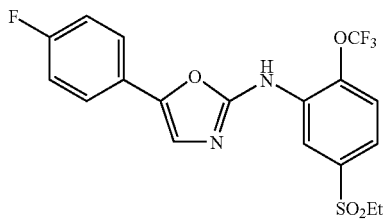

$^1$H NMR (400 MHz, d$_6$-DMSO): δ 10.63 (s, 1H), 9.00 (d, J=1.8, 1H), 7.70–7.63 (m, 3H), 7.50 (d, J=2.2, 1H), 7.55 (s,1H), 7.30 (t, J=8.8, 2H), 3.30 (m, 2H), 1.13 (t, J=7.3, 3H). MS (ES+, m/z)=431 (m+H)$^+$.

Example 82

5-(4-fluorophenyl)-N-{2-methoxy-5-[(methylsulfonyl)methyl]phenyl}-1,3-oxazol-2-amine

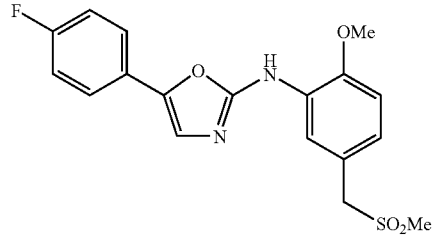

$^1$H NMR (400 MHz, d$_6$-DMSO): δ 9.22 (s, 1H), 8.10 (d, J=1.6, 1H), 7.58 (dd, J$_1$=8.8, J$_2$=5.4, 2H), 7.38 (s, 1H), 7.23 (t, J=8.8, 2H), 7.03–6.95 (m, 2H), 4.36 (s, 2H), 3.82 (s, 3H), 2.86 (s, 3H). MS (ES+, m/z)=377 (m+H)$^+$.

Example 83

N-(5-{[5-(3-iodophenyl)-1,3-oxazol-2-yl]amino}-2-methylphenyl)methanesulfonamide

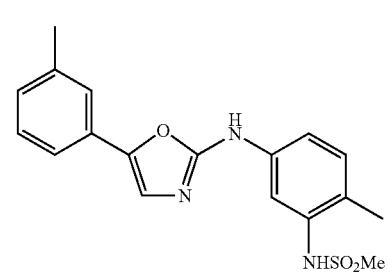

$^1$H NMR (400 MHz, d$_6$-DMSO): δ 10.23 (s, 1H), 9.01 (s, 1H), 7.90 (s, 2H), 7.56 (d, J=8.8, 2H), 7.51 (s, 1H), 7.35 (dd, J$_1$=8.3, J$_2$=2.2, 1H), 7.40–7.20 (m, 2H), 2.95 (s, 3H), 2.18 s, 3H). MS (ES+, m/z)=470 (m+H)$^+$.

Example 84

3-{[5-(4-fluorophenyl)-1,3-oxazol-2-yl]amino}-N,N-dimethylbenzenesulfonamide

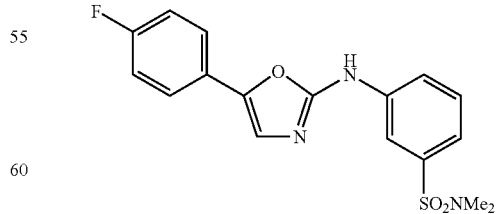

$^1$H NMR (400 MHz, d$_6$-DMSO): δ 10.74 (s, 1H), 8.12 (s, 1H), 7.81 (dd, J$_1$=8.1, J$_2$=2.0, 1H), 7.61–7.50 (m, 3H), 7.46 (s, 1H), 7.28–7.22 (m, 3H), 2.58 (s, 6H). MS (ES+, m/z)=362 (m+H)$^+$.

Example 85

N-[3-(ethylsulfonyl)phenyl]-5-(4-fluorophenyl)-1,3-oxazol-2-amine

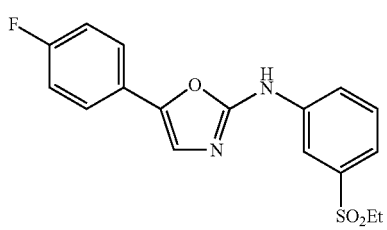

$^1$H NMR (300 MHz, d$_6$-DMSO): δ 10.84 (s, 1H), 8.32 (s, 1H), 7.91 (d, J=8.1, 1H), 7.71–7.60 (m, 3H), 7.54 (s, 1 H), 7.48 (d, J=7.8, 1H), 7.33 (t, J=8.8, 2H), 3.29 (q, J=7.3, 2H), 1.15 (t, J=7.3, 3H). MS (ES+, m/z)=347 (m+H)$^+$.

Example 86

3-{[5-(4-fluorophenyl)-1,3-oxazol-2-yl]amino}-4-methoxy-N-(pyridin-2-ylmethyl)benzenesulfonamide

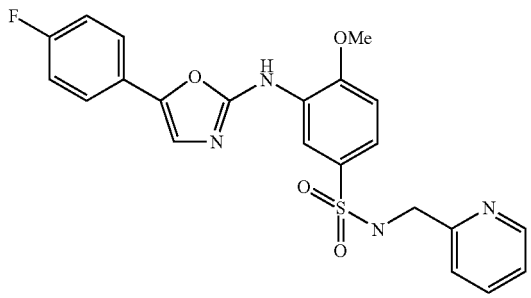

$^1$H NMR (400 MHz, d$_6$-DMSO): δ 9.55 (s, 1H), 8.67 (d, J=2.0, 1H), 8.36 (d, J=4.4, 1H), 7.68–7.58 (m, 4H), 7.45 (s, 1H), 7.39–7.11 (m, 6H), 4.01 (s, 3H), 3.89 (s, 2H). MS (ES+, m/z)=455 (m+H)$^+$.

Example 87

5-(4-fluorophenyl)-N-[2-methoxy-5-(methylsulfonyl)phenyl]-1,3-oxazol-2-amine

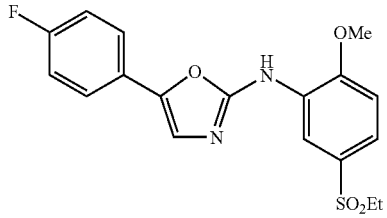

$^1$H NMR (400 MHz, d$_6$-DMSO): δ 9.77 (s, 1H), 8.84 (d, J=2.1, 1H), 7.63 (dd, J$_1$=8.6, J$_2$=5.4, 2H), 7.59–7.54 (m, 2H), 7.32 (q, J=8.6, 3H), 4.00 (s, 3H), 3.17 (s, 3H). MS (ES+, m/z)=363 (m+H)$^+$.

Example 88

N-{2-methoxy-5-[(2-pyridin-2-ylethyl)sulfonyl]phenyl}-5-phenyl-1,3-oxazol-2-amine

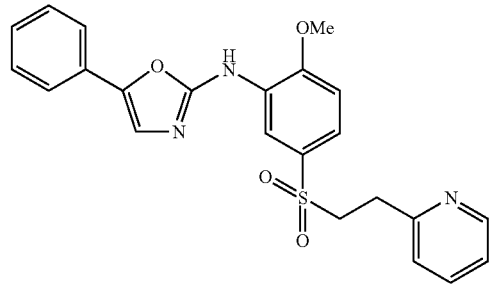

$^1$H NMR (400 MHz, d$_6$-DMSO): δ 9.69 (s, 1H), 8.74 (d, J=2.3, 1H), 8.36–8.34 (m, 1H), 7.62–7.56 (m, 3H), 7.50 (s, 1H), 7.47 (dd, J$_1$=8.6, J$_2$=2.3, 1H), 7.39 (t, J=7.8, 2H), 7.25–7.11 (m, 4H), 3.92 (s, 3H), 3.62–3.58 (m, 2H), 3.02–2.98 (m, 2H). MS (ES+, m/z)=436 (m+H)$^+$.

Example 89

3-{[5-(4-fluorophenyl)-1,3-oxazol-2-yl]amino}-4-methoxybenzenesulfonamide

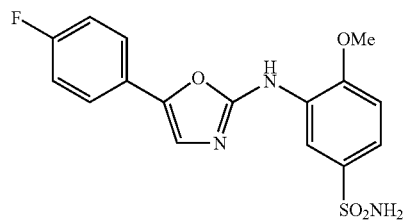

$^1$H NMR (400 MHz, d$_6$-DMSO): δ 9.51 (s, 1H), 8.67 (s, 1H), 7.62–7.58 (m, 2H), 7.44–7.40 (m, 2H), 7.27–7.23 (m, 2H), 7.17–7.12 (m, 3H), 3.88 (s, 3H). MS (ES+, m/z)=354 (m+H)$^+$.

Example 90

N-{5-[(1-ethylpropyl)sulfonyl]-2-methoxyphenyl}-5-(4-fluorophenyl)-1,3-oxazol-2-amine

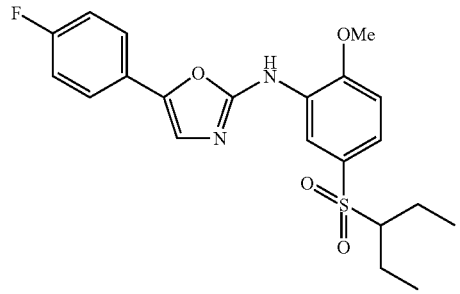

$^1$H NMR (400 MHz, d$_6$-DMSO): δ 9.76 (s, 1H), 8.78 (d, J=2.2, 1H), 7.70–7.65 (m, 2H), 7.54 (s, 1H), 7.50 (dd, J$_1$=8.5, J$_2$=2.2, 1H), 7.36–7.27 (m, 3H), 4.00 (s, 3H) 2.98 (m, 1H), 1.84–1.70 (m, 2H), 1.68–1.53 (m, 2H), 0.95 (t, J=7.4, 6H). MS (ES+, m/z)=419 (m+H)$^+$.

Example 91

5-(4-fluorophenyl)-N-(2-methoxy-5-{[(5-methyl-isoxazol-3-yl)methyl]sulfonyl}phenyl)-1,3-oxazol-2-amine

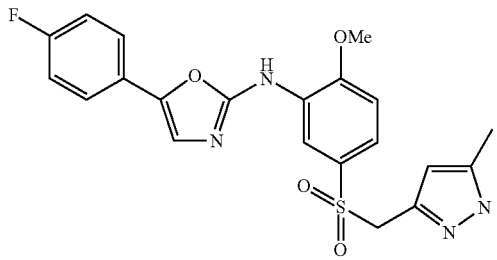

$^1$H NMR (400 MHz, d$_6$-DMSO): δ 9.66 (s, 1H), 8.62 (s, 1H), 7.62–7.58 (m, 2H), 7.45 (s, 1H), 7.37 (d, J=8.4, 1H), 7.27–7.23 (m, 2H), 7.18 (d, J=8.4, 1H), 6.16 (s, 1H) 4.65 (s, 2H), 3.92 (s, 3H), 2.31 (s, 3H). MS (ES+, m/z)=444 (m+H)$^+$.

Example 92

3-{[5-(3-bromophenyl)-1,3-oxazol-2-yl]amino}-4-methoxybenzenesulfonamide

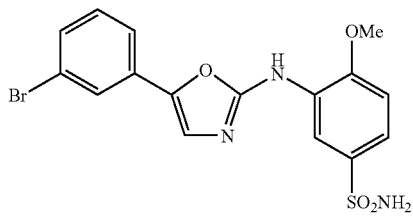

$^1$H NMR (400 MHz, d$_6$-DMSO): δ 9.80 (s, 1H), 8.73 (d, J=2.3, 1H), 7.85 (t, J=1.8, 1H), 7.70 (s, 1H), 7.63 (d, J=7.6, 1H), 7.53–7.40 (m, 4H), 7.22 (d, J=8.5, 2H), 3.96 (s, 3H). MS (ES+, m/z)=426 (m+H)$^+$, 424 (m+H)$^+$.

Example 93

5-(4-fluorophenyl)-N-[5-(isobutylsulfonyl)-2-methoxyphenyl]-1,3-oxazol-2-amine

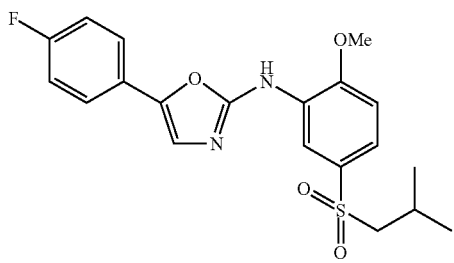

$^1$H NMR (400 MHz, d$_6$-DMSO): δ 8.81 (d, J=2.2, 1H), 7.70–7.65 (m, 2H), 7.56–7.52 (m, 2H), 7.32 (q, J=8.6, 3H), 4.00 (s, 3H), 3.13 (d, J=6.3, 2H), 2.08–2.00 (m, 1H), 0.99 (d, J=6.7, 6H). MS (ES+, m/z)=405 (m+H)$^+$.

Example 94

5-(4-fluorophenyl)-N-{2-methoxy-5-[(tetrahydrofuran-2-ylmethyl)sulfonyl]phenyl}-1,3-oxazol-2-amine

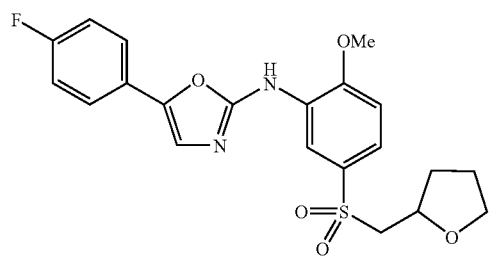

$^1$H NMR (400 MHz, d$_6$-DMSO): δ 9.66 (s, 1H), 8.72 (dd, J$_1$=8.6, J$_2$=5.3, 2H), 7.48–7.46 (m, 2H), 7.27–7.19 (m, 3H), 4.05–3.99 (m, 1H), 3.92 (s, 3H), 3.61–3.55 (m, 1H), 3.38 (d, J=6.0, 2H), 1.95–1.87 (m, 1H), 1.78–1.65 (m, 2H), 1.56–1.47 (m, 1H). MS (ES+, m/z)=433 (m+H)$^+$.

Example 95

5-(4-fluorophenyl)-N-[2-methoxy-5-(tetrahydrofuran-3-ylsulfonyl)phenyl]-1,3-oxazol-2-amine

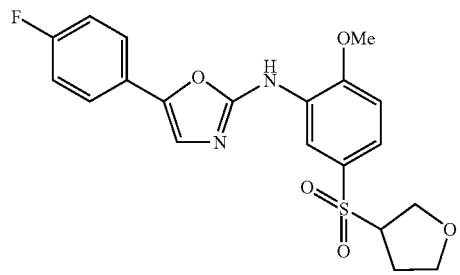

$^1$H NMR (400 MHz, d$_6$-DMSO): δ 9.72 (s, 1H), 8.75 (d, J=2.2, 1H), 7.62–7.58 (m, 2H), 7.49–7.46 (m, 2H), 7.26–7.21 (m, 3H), 4.06–3.95 (m, 1H), 3.94–3.91 (m, 4H), 3.80–3.76 (m, 1H), 3.71–3.65 (m, 1H), 3.60–3.55 (m, 1H), 2.10–2.08 (m, 2H). MS (ES+, m/z)=419 (m+H)$^+$.

Example 96

5-(4-fluorophenyl)-N-(2-methoxy-5-{[2-(4-methyl-1,3-thiazol-5-yl)ethyl]sulfonyl}phenyl)-1,3-oxazol-2-amine

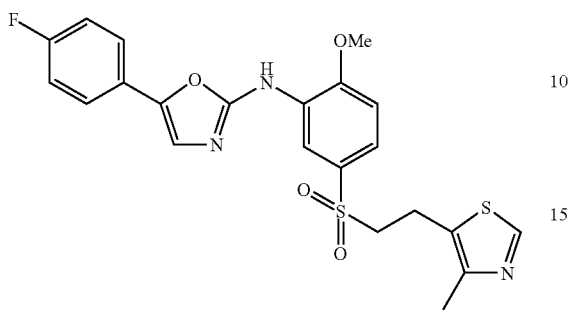

$^1$H NMR (400 MHz, d$_6$-DMSO): δ 9.77 (s, 1H), 8.83–8.80 (m, 2H), 7.70–7.66 (m, 2H), 7.58–7.54 (m, 2H), 7.36–7.27 (m, 3H), 4.00 (s, 3H), 3.57–3.52 (m, 2H), 3.14–3.09 (m, 2H), 2.25 (m, 3H). MS (ES+, m/z)=474 (m+H)$^+$.

Example 97

5-(4-fluorophenyl)-N-[5-(isopropylsulfonyl)-2-methoxyphenyl]-1,3-oxazol-2-amine

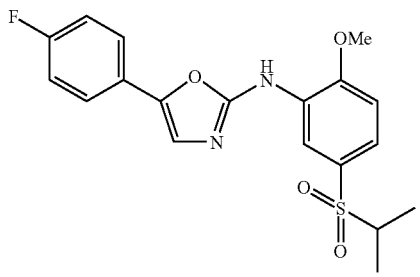

$^1$H NMR (400 MHz, d$_6$-DMSO): δ 9.76 (s, 1H), J=2.3, 1H), 7.70–7.65 (m, 2H), 7.54 (s, 1H), 7.49 (dd, J$_1$=8.5, J$_2$=2.3, 1H), 7.36–7.28 (m, 3H), 4.01 (s, 3H), 3.44–3.27 (m, 1H), 1.19 (d, J=6.9, 6H). MS (ES+, m/z)=391 (m+H)$^+$.

Example 98

5-(3-bromophenyl)-N-[5-(isopropylsulfonyl)-2-methoxyphenyl]-1,3-oxazol-2-amine

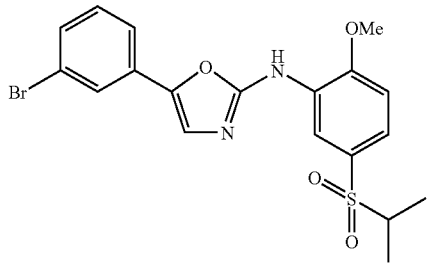

$^1$H NMR (400 MHz, d$_6$-DMSO): δ 9.84 (s, 1H), 8.76 (d, J=2.3, 1H), 7.84 (t, J=1.7, 1H), 7.69 (s, 1H), 7.65–7.62 (m, 1H), 7.52–7.40 (m, 3H), 7.30 (d, J=8.5, 1H), 4.01 (s, 3H), 3.36–3.28 (m, 1H), 1.19 (d, J=6.7, 6H). MS (ES+, m/z)=453 (m+H)$^+$.

Example 99

5-(4-fluorophenyl)-N-(5-{[2-(1H-imidazol-1-yl)ethyl]sulfonyl}-2-methoxyphenyl)-1,3-oxazol-2-amine

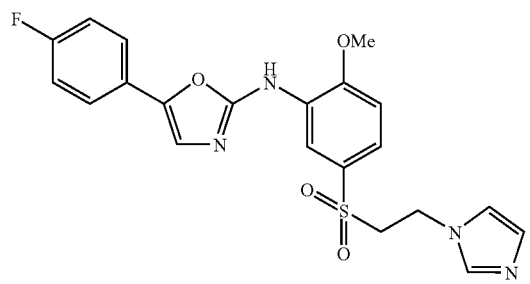

$^1$H NMR (400 MHz, d$_6$-DMSO): δ 9.71 (s, 1H), 8.73 (s, 1H), 7.62–7.56 (m, 3H), 7.47–7.42 (m, 2H), 7.27–7.12 (m, 4H), 6.75 (s, 1H), 4.23 (t, J=7.0, 2H), 3.92 (s, 3H), 3.75 (t, J=7.0, 2H). MS (ES+, m/z)=443 (m+H)$^+$.

Intermediate 100a

Preparation of 3-bromophenacyl azide

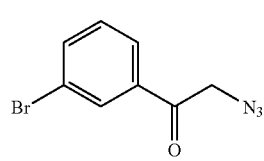

A solution of 20.2 g (73 mmol) of 3-bromophenacyl bromide and 5.42 g (83 mmol) of sodium azide was stirred at RT for 90 min in methanol. The solvent was removed under reduced pressure and the crude product was partitioned between ethyl acetate (200 ml) and water (100 mL). The organic layer was separated, dried over anhydrous magnesium sulfate, and concentrated under reduced pressure to afford the title compound (17.4 g, 99%) as a light yellow solid. $^1$H NMR (400 MHz, d$_6$-DMSO): δ 8.10 (d, J=1.0, 1H), 7.90–7.97 (m, 2H), 7.22 (t, J=7.9, 1H), 4.93 (s, 2H).

Intermediate 100b

Preparation of 4-(ethylsulfonyl)-2-isothiocyanato-1-methoxybenzene

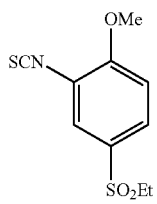

A solution of 5-(ethylsulfonyl)-2-methoxyaniline (15.6 g, 72.5 mmol) in dichloromethane (100 mL) was added dropwise over 1 h to a stirred solution of thiophosgene (9 g, 78.0 mmol) in dichloromethane (300 mL) at RT. After the addition was complete, the reaction was stirred for 2 h. Subsequently, saturated aqueous sodium bicarbonate (200 mL) was added, and the reaction was stirred for an additional 1 h. The organic layer was separated, and the aqueous layer was extracted with dichloromethane (2×100 mL). The combined organic layers were dried over anhydrous magnesium sulfate, filtered, and concentrated under reduced pressure to afford the title compound (18.6 g, 72.4 mmol) as a tan solid. $^1$H NMR (400 MHz, $d_6$-DMSO): δ 7.78 (dd, $J_1$=2.2, $J_2$=8.8, 1H), 7.71 (d, J=2.2, 1H), 7.35 (d, J=8.8, 1H), 3.95 (s, 3H), 3.22 (q, J=7.4, 2H), 1.02 (t, J=7.3, 3H).

Example 100

5-(3-bromophenyl)-N-[5-(ethylsulfonyl)-2-methoxyphenyl]-1,3-oxazol-2-amine

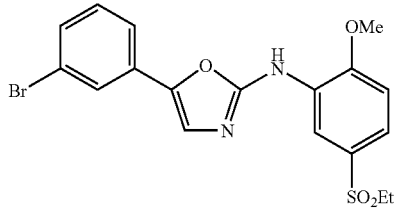

A solution of Intermediate 100a (17.4 g, 72.5 mmol) in dichloromethane (50 mL) was added dropwise over 2 h to a stirred solution of Intermediate 100b (18.6 g, 72.4 mmol) and triphenylphosphine (18.8 g, 73 mmol) in dichloromethane (100 mL). The reaction was kept cool (ca. RT) during the addition by periodically placing the flask in an ice water bath. After the addition was complete, the reaction was stirred at RT for additional 2 h. Subsequently, oxalic acid (6.5 g, 72.0 mmol) was added, and the reaction was briefly warmed with a heat gun until the appearance of precipitate forms. After briefly cooling the flask in ice water, the precipitate was filtered, washed with dichloromethane and diethyl ether, and partitioned between dichloromethane (200 mL) and 1M aqueous sodium hydroxide (100 mL). The organic layer was separated, and the aqueous layer was extracted with additional dichloromethane (2×100 mL). The combined organic layers were dried over anhydrous magnesium sulfate, filtered, and concentrated under reduced pressure to afford the title compound (13.8 g, 31.6 mmol) as a yellow solid. $^1$H NMR (400 MHz, $d_6$-DMSO): δ 9.77 (s, 1H), 8.72 (d, J=2.2, 1H), 7.77 (s, 1H), 7.62 (s, 1H), 7.56 (d, J=7.9, 1H), 7.47–7.33 (m, 3H), 7.22 (d, J=8.6, 1H), 3.93 (s, 3H), 3.17 (q, J=7.3, 2H), 1.06 (t, J=7.3, 3H). MS (ES+, m/z)=439 (m+H)$^+$.

Unless otherwise indicated, the compounds of Examples 101–157 were prepared according to the general procedures set forth in the synthesis of the title compound of Example 100. It will be readily apparent to those skilled in the art that the syntheses of these examples is illustrated in Scheme 5 described above. The NMR data characterizing these examples describe either the salt form or the free base form.

Example 101

5-(3-bromophenyl)-N-(2-methoxy-5-{[2-(4-methyl-1,3-thiazol-5-yl)ethyl]sulfonyl}phenyl)-1,3-oxazol-2-amine

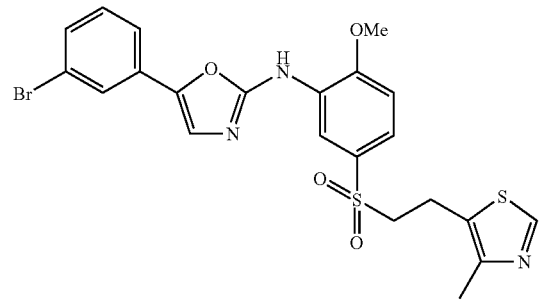

$^1$H NMR (400 MHz, $d_6$-DMSO): δ 9.78 (s, 1H), 8.74–8.72 (m, 2H), 7.77 (s, 1H), 7.62 (s, 1H), 7.56 (d, J=7.7, 1H), 7.49 (dd, $J_1$=8.6, $J_2$=2.2, 1H), 7.42–7.40 (m, 1H), 7.36–7.32 (m, 1H), 7.21 (d, J=8.6, 1H), 3.92 (s, 3H), 3.49–3.45 (m, 2H), 3.06–3.02 (m, 2H), 2.17 (s, 3H). MS (ES+, m/z)=534 (m+H)$^+$.

Example 102

N-(2-ethoxyphenyl)-5-(3-methoxyphenyl)-1,3-oxazol-2-amine

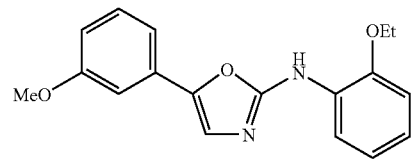

$^1$H NMR (400 MHz, $d_6$-DMSO): δ 9.02 (s, 1H), 8.08 (dd, $J_1$=7.4, $J_2$=2.0, 1H), 7.44 (s, 1H), 7.30 (t, J=8.9, 1H), 7.15 (d, J=7.8, 1H), 7.15 (d, J=2.0, 1H), 7.00–6.83 (m, 3H), 6.80 (dd, $J_1$=8.3, $J_2$=2.4, 1H), 4.08 (q, J=7.0, 2H), 3.77 (s, 1H), 1.36 (t, J=7.0, 3H). MS (ES+, m/z)=311 (m+H)$^+$.

Example 103

N-(3,4-dimethoxyphenyl)-5-(3-methoxyphenyl)-1,3-oxazol-2-amine

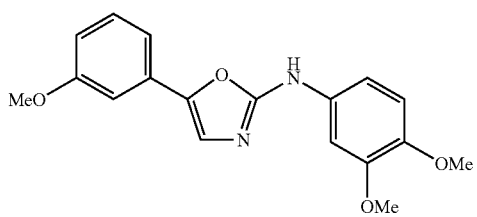

$^1$H NMR (400 MHz, d$_6$-DMSO): δ 10.07 (s, 1H), 7.43 (s, 1H), 7.34–7.27 (m, 2H), 7.14–7.05 (m, 3H), 6.88 (d, J=8.8, 1H), 6.80 (dd, J$_1$=8.2, J$_2$=2.4, 1H), 3.76 (s, 3H), 3.72 (s, 3H), 3.68 (s, 3H). MS (ES+, m/z)=327 (m+H)$^+$.

Example 104

N-(3,4-dimethoxyphenyl)-5-(4-fluorophenyl)-1,3-oxazol-2-amine

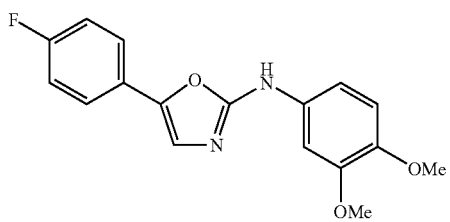

$^1$H NMR (400 MHz, d$_6$-DMSO): δ 10.39 (s, 1H), 7.58 (dd, J$_1$=8.7, J$_2$=5.4, 2H), 7.47 (s, 1H), 7.30–7.23 (m, 4H), 7.07 (dd, J$_1$=8.7, J$_2$=2.5, 1H), 6.90 (d, J=8.8, 1H), 3.72 (s, 3H), 3.69 (s, 3H). MS (ES+, m/z)=315 (m+H)$^+$.

Example 105

N-(3,4-dimethoxyphenyl)-5-(4-methylphenyl)-1,3-oxazol-2-amine

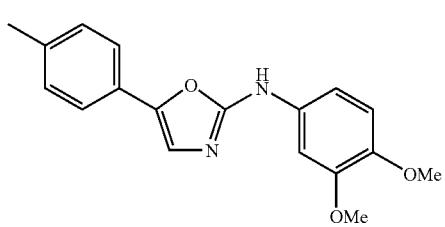

$^1$H NMR (400 MHz, d$_6$-DMSO): δ 10.01 (s, 1H), 7.42 (d, J=8.2, 2H), 7.32 (s, 2H), 7.20 (d, J=8.0, 2H), 7.07 (dd, J$_1$=8.7, J$_2$=2.5, 1H), 6.89 (d, J=8.8, 1H), 3.72 (s, 3H), 3.68 (s, 3H). MS (ES+, m/z)=311 (m+H)$^+$.

Example 106

5-(3,4-dichlorophenyl)-N-(3,4-dimethoxyphenyl)-1,3-oxazol-2-amine

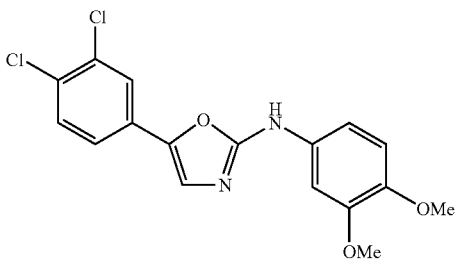

$^1$H NMR (400 MHz, d$_6$-DMSO): δ 10.25 (s, 1H), 7.77 (d, J=2.0, 1H), 7.66 (d, J=8.6, 1H), 7.61 (s, 1H), 7.48 (dd, J$_1$=8.4, J$_2$=2.0, 1H), 6.89 (d, J=8.8, 1H), 3.72 (s, 3H), 3.68 (s, 3H). MS (ES+, m/z)=365 (m+H)$^+$.

Example 107

5-[4-(diethylamino)phenyl]-N-(3,4-dimethoxyphenyl)-1,3-oxazol-2-amine

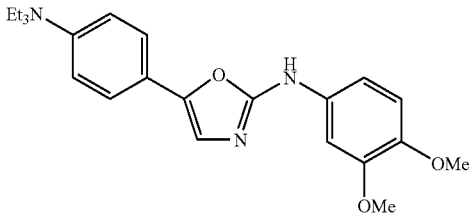

$^1$H NMR (400 MHz, d$_6$-DMSO): δ 12.82 (bs, 1H), 10.37 (bs, 1H), 7.90–7.40 (m, 4H), 7.30 (s, 1H), 7.09 (dd, J$_1$=8.7, J$_2$=2.1, 1H), 6.90 (d, J=8.8, 1H), 3.73 (s, 3H), 3.69 (s, 3H), 1.03 (t, J=7.0, 3H). MS (ES+, m/z)=368 (m+H)$^+$.

Example 108

5-(4-chloro-3-methylphenyl)-N-(3,4-dimethoxyphenyl)-1,3-oxazol-2-amine

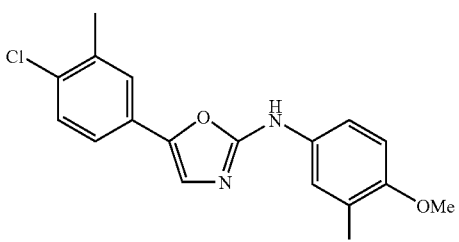

$^1$H NMR (400 MHz, d$_6$-DMSO): δ 10.15 (s, 1H), 7.57 (s, 1H), 7.51–7.46 (m, 2H), 7.44–7.35 (m, 2H), 7.13 (dd, J$_1$=8.7, J$_2$=2.3, 1H), 6.93 (d, J=8.8, 1H), 3.78 (s, 3H), 3.74 (s, 3H), 2.38 (s, 3H). MS (ES+, m/z)=345 (m+H)$^+$.

Example 109

N-[5-(ethylsulfonyl)-2-methoxyphenyl]-5-(4-fluorophenyl)-1,3-oxazol-2-amine

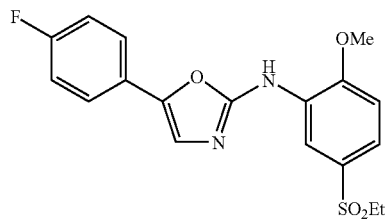

$^1$H NMR (400 MHz, d$_6$-DMSO): δ 9.81 (bs, 1H), 8.71 (d, J=2.2, 1H), 7.62 (dd, J$_1$=8.7, J$_2$=5.4, 2H), 7.51 (s, 1H), 7.48 (dd, J$_1$=8.5, J$_2$=2.3, 1H), 7.30–7.23 (m, 3H), 3.94 (s, 3H), 3.17 (q, J=7.4, 2H), 1.08 (t, J=7.3, 3H). MS (ES+, m/z)=377 (m+H)$^+$.

Example 110

5-(3,4-difluorophenyl)-N-[5-(ethylsulfonyl)-2-methoxyphenyl]-1,3-oxazol-2-amine

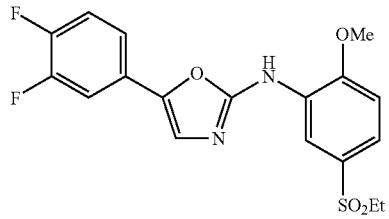

$^1$H NMR (400 MHz, d$_6$-DMSO): δ 9.84 (bs, 1H), 8.77 (d, J=2.2, 1H), 7.75–7.40 (m, 5H), 7.30 (d, J=8.7, 1H), 4.00 (s, 3H), 3.23 (q, J=7.3, 2H), 1.14 (t, J=7.3, 3H). MS (ES+, m/z)=394 (m+H)$^+$.

Example 111

4-chloro-3-{[5-(4-fluorophenyl)-1,3-oxazol-2-yl]amino}-N,N-dimethylbenzenesulfonamide

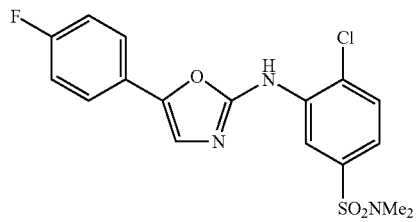

$^1$H NMR (400 MHz, d$_6$-DMSO): δ 9.98 (s, 1H), 8.67 (s, 1H), 7.70 (d, J=8.2, 1H), 7.61 (dd, J$_1$=8.7, J$_2$=5.4, 2H), 7.48 (s, 1H), 7.32 (dd, J$_1$=8.2, J$_2$=2.2, 1H), 7.29–7.23 (m, 2H), 2.60 (s, 6H). MS (ES+, m/z)=396 (m+H)$^+$.

Example 112

4-chloro-N,N-diethyl-3-{[5-(4-fluorophenyl)-1,3-oxazol-2-yl]amino}benzenesulfonamide

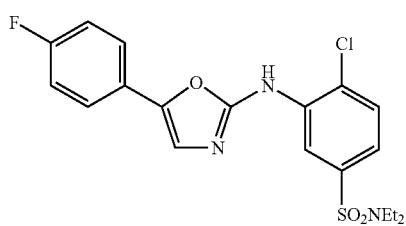

$^1$H NMR (400 MHz, d$_6$-DMSO): δ 10.02 (bs, 1H), 8.79 (d, J=2.0, 1H), 7.75–7.66 (m, 3H), 7.56 (s, 1H), 7.44 (dd, J$_1$=8.4, J$_2$=2.2, 1H), 7.38–7.30 (m, 2H), 3.22 (q, J=7.1, 4H), 1.09 (t, J=7.1, 6H). MS (ES+, m/z)=424 (m+H)$^+$.

Example 113

5-(4-fluorophenyl)-N-[3-(methylsulfonyl)phenyl]-1,3-oxazol-2-amine

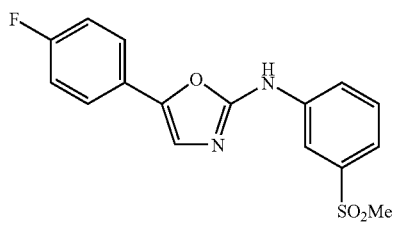

$^1$H NMR (400 MHz, d$_6$-DMSO): δ 10.75 (s, 1H), 8.27 (t, J=1.9, 1H), 7.81 (dd, J$_1$=8.0, J$_2$=1.7, 1H), 7.59 (dd, J$_1$=8.8, J$_2$=5.3, 2H), 7.55 (t, J=8.0, 1H), 7.47–7.43 (m, 2H), 7.25 (t, J=8.8, 2H), 3.15 (s, 3H). MS (ES+, m/z)=333 (m+H)$^+$.

Example 114

N-[2-chloro-5-(methylsulfonyl)phenyl]-5-(4-fluorophenyl)-1,3-oxazol-2-amine

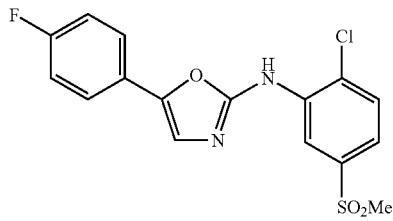

$^1$H NMR (400 MHz, d$_6$-DMSO): δ 10.00 (s, 1H), 8.82 (s, 1H), 7.72 (d, J=8.4, 1H), 7.62 (dd, J$_1$=8.6, J$_2$=5.5, 2H), 7.52 (dd, J$_1$=8.4, J$_2$=2.0, 1H), 7.49 (s, 1H), 7.26 (t, J=8.9, 2H), 3.18 (s, 3H). MS (ES+, m/z)=367 (m+H)$^+$.

Example 115

N-[2-chloro-5-(ethylsulfonyl)phenyl]-5-(4-fluorophenyl)-1,3-oxazol-2-amine

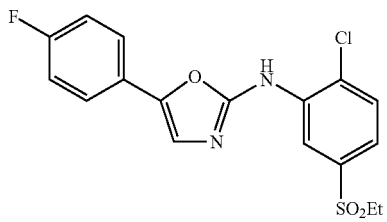

$^1$H NMR (400 MHz, d$_6$-DMSO): δ 10.00 (s, 1H), 8.77 (s, 1H), 7.73 (d, J=8.2, 1H), 7.62 (dd, J$_1$=8.7, J$_2$=5.4, 2H), 7.49 (s, 1H), 7.46 (dd, J$_1$=8.3, J$_2$=2.1, 1H), 7.26 (t, J=8.9, 2H), 3.25 (q, J=7.3, 2H), 1.08 (t, J=7.3, 3H). MS (ES+, m/z)=381 (m+H)$^+$.

Example 116

5-(4fluorophenyl)-N-(3,4,5-trimethoxyphenyl)-1,3-oxazol-2-amine

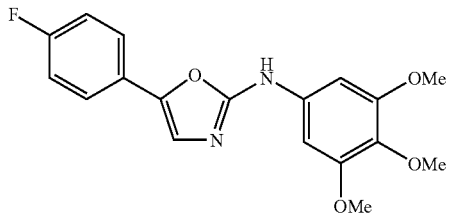

$^1$H NMR (400 MHz, d$_6$-DMSO): δ 10.19 (s, 1H), 7.59 (dd, J$_1$=8.8, J$_2$=5.3, 2H), 7.42 (s, 1H), 7.27 (t, J=8.9, 2H), 7.00 (s, 2H), 3.75 (s, 6H), 3.60 (s, 3H). MS (ES+, m/z)=345 (m+H)$^+$.

Example 117

5-(3-bromophenyl)-N-(3,4,5-trimethoxyphenyl)-1,3-oxazol-2-amine

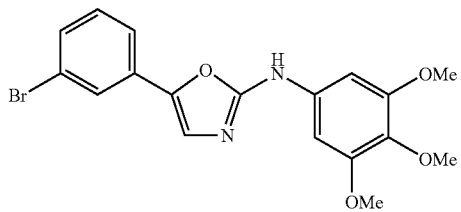

$^1$H NMR (400 MHz, d$_6$-DMSO): δ 10.14 (s, 1H), 7.72 (s, 1H), 7.55 (s, 1H), 7.50 (d, J=7.5, 1H), 7.39 (d, J=8.2, 1H), 7.34 (t, J=7.8, 1H), 6.95 (s, 2H), 3.72 (s, 6H), 3.56 (s, 3H). MS (ES+, m/z)=407 (m+H)$^+$.

Example 118

4-methoxy-N-(2-morpholin-4-ylethyl)-3-[(5-phenyl-1,3-oxazol-2-yl)amino]benzenesulfonamide

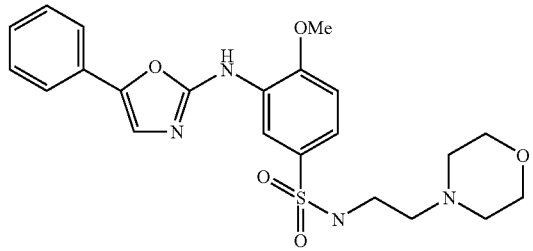

$^1$H NMR (400 MHz, d$_6$-DMSO): δ 9.62 (s, 1H), 8.71 (d, J=2.2, 1H), 7.61 (d, J=7.4, 2H), 7.51 (s, 1H), 7.45–7.41 (m, 3H), 7.35 (t, J=5.8, 1H), 7.28 (t, J=7.4, 1H), 7.19 (d, J=8.6, 1H), 3.94 (s, 3H), 3.49–3.45 (m, 4H), 2.85 (q, J=6.5, 2H), 2.31–2.23 (m, 6H). MS (ES+, m/z)=459 (m+H)$^+$.

Example 119

3-{[5-(4-fluorophenyl)-1,3-oxazol-2-yl]amino}-4-methoxy-N-(3-pyrrolidin-1-ylpropyl)benzenesulfonamide

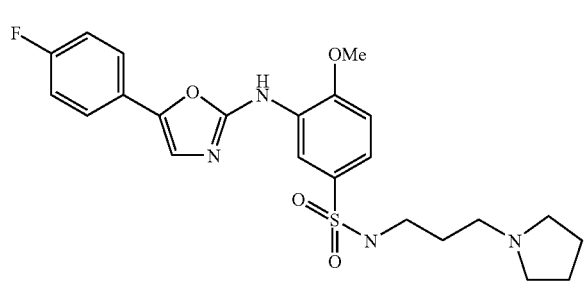

$^1$H NMR (300 MHz, d$_6$-DMSO): δ 9.64 (s, 1H), 8.73 (s, 1H), 7.68 (dd, J$_1$=8.7, J$_2$=5.4, 2H), 7.52 (s, 2H), 7.43 (dd, J$_1$=8.7, J$_2$=2.2, 1H), 7.32 (t, J=8.7, 2H), 7.23 (d, J=8.7, 2H), 7.23 (d, J=8.7, 1H), 3.97 (s, 3H), 2.84–2.76 (m, 2H), 2.36–2.29 (m, 6H), 1.62–1.48 (m, 6H). MS (ES+, m/z)=475 (m+H)$^+$.

Example 120

3-{[5-(4-fluorophenyl)-1,3-oxazol-2-yl]amino}-N-[3-(1H-imidazol-1-yl)propyl]-4-methoxybenzenesulfonamide

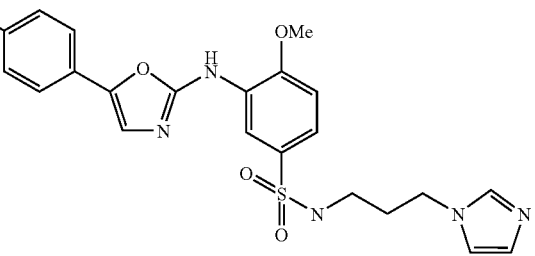

$^1$H NMR (400 MHz, d$_6$-DMSO): δ 9.59 (s, 1H), 8.66 (d, J=2.0, 1H), 7.61–7.52 (m, 4H), 7.44 (s, 1H), 7.34 (dd, $J_1$=8.6, $J_2$=2.1, 1H), 7.25 (t, J=8.7, 2H), 7.14 (d, J=8.6, 1H), 7.03 (s, 1H), 6.80 (s, 1H), 3.92–3.89 (m, 5H), 2.64 (q, J=6.3, 2H), 1.74 (m, 2H). MS (ES+, m/z)=472 (m+H)$^+$.

Example 121

3-{[5-(4-fluorophenyl)-1,3-oxazol-2-yl]amino}-4-methoxy-N-(pyridin-3-ylmethyl)benzenesulfonamide

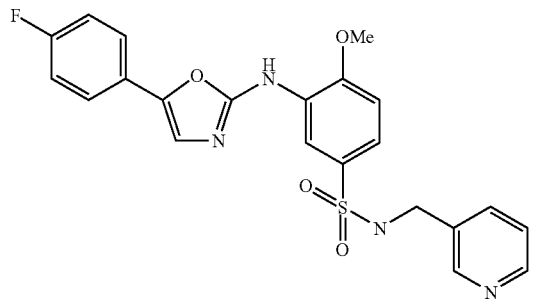

$^1$H NMR (300 MHz, d$_6$-DMSO): δ 9.65 (s, 1H), 8.76 (d, J=2.0, 1H), 8.44 (s, 2H), 8.14 (t, J=5.9, 1H), 7.70–7.65 (m, 3H), 7.53 (s, 1H), 7.45 (dd, $J_1$=8.5, $J_2$=2.0, 1H), 7.35–7.29 (m, 3H), 7.20 (d, J=8.5, 1H), 4.04 (d, J=5.5, 2H), 3.97 (s, 3H). MS (ES+, m/z)=455 (m+H)$^+$.

Example 122

3-{[5-(4-fluorophenyl)-1,3-oxazol-2-yl]amino}-4-methoxy-N-(pyridin-4-ylmethyl)benzenesulfonamide

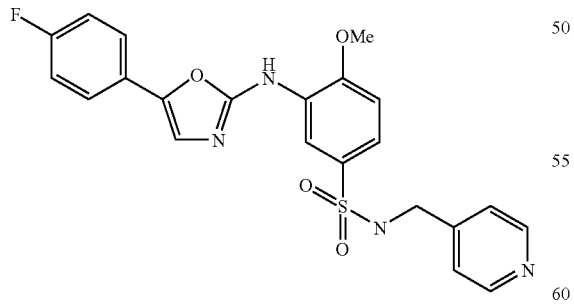

$^1$H NMR (400 MHz, d$_6$-DMSO): δ 9.57 (s, 1H), 8.68 (d, J=2.2, 1H), 8.38–8.35 (m, 2H), 8.06 (t, J=6.1, 1H), 7.62–7.58 (m, 3H), 7.45 (s, 1H), 7.37 (dd, $J_1$=8.6, $J_2$=2.2, 1H), 7.27–7.22 (m, 3H), 7.12 (d, J=8.6, 1H), 3.96 (d, J=6.1, 2H), 3.89 (s, 3H). MS (ES+, m/z)=455 (m+H)$^+$.

Example 123

3-{[5-(4-fluorophenyl)-1,3-oxazol-2-yl]amino}-N-isopropyl-4-methoxybenzenesulfonamide

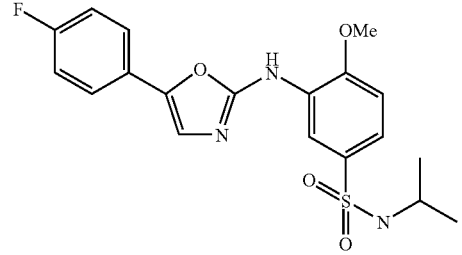

$^1$H NMR (300 MHz, d$_6$-DMSO): δ 9.62 (s, 1H), 8.74 (d, J=2.2, 1H), 7.70–7.65 (m, 2H), 7.52 (s, 1H), 7.48–7.44 (m, 2H), 7.32 (t, J=8.9, 2H), 7.22 (d, J=8.7, 1H), 3.97 (s, 3H), 3.31–3.18 (m, 1H), 0.98 (d, J=6.5, 6H). MS (ES+, m/z)=406 (m+H)$^+$.

Example 124

3-{[5-(4-fluorophenyl)-1,3-oxazol-2-yl]amino}-4-methoxy-N-(tetrahydrofuran-2-ylmethyl)benzenesulfonamide

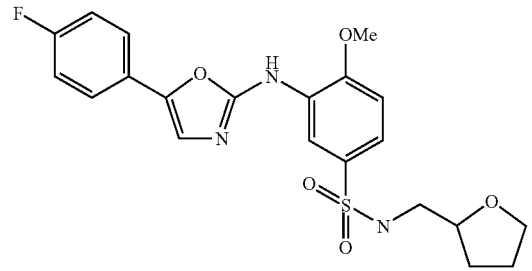

$^1$H NMR (300 MHz, d$_6$-DMSO): δ 9.64 (s, 1H), 8.72 (s, 1H), 7.70–7.59 (m, 3H), 7.52 (s, 1H), 7.45 (d, J=8.4, 1H), 7.32 (t, J=8.8, 2H), 7.22 (d, J=8.4, 1H), 3.97 (s, 3H), 3.85–3.79 (m, 1H), 3.73–3.66 (m, 1H), 3.62–3.54 (m, 1H), 2.82–2.73 (m, 2H), 1.90–1.75 (m, 3H), 1.60–1.52 (m, 1H). MS (ES+, m/z)=448 (m+H)$^+$.

Example 125

5-(4-fluorophenyl)-N-[2-methoxy-5-(morpholin-4-ylsulfonyl)phenyl]-1,3-oxazol-2-amine

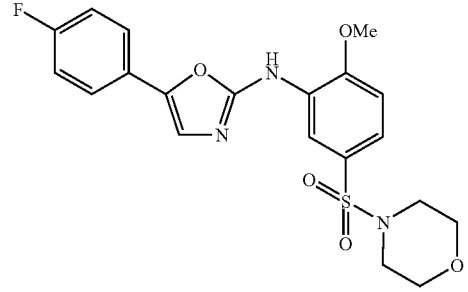

¹H NMR (400 MHz, d₆-DMSO): δ 9.69 (s, 1H), 8.62 (s, 1H), 7.69–7.57 (m, 2H), 7.45 (s, 1H), 7.32–7.20 (m, 4H), 3.92 (s, 3H), 3.57 (bs, 4H), 2.81 (bs, 4H). MS (ES+, m/z)=434 (m+H)⁺.

Example 126

5-(4-fluorophenyl)-N-{2-methoxy-5-[(4-methylpiperazin-1-yl)sulfonyl]phenyl}-1,3-oxazol-2-amine

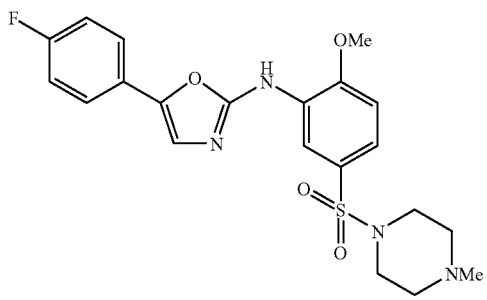

¹H NMR (400 MHz, d₆-DMSO): δ 9.67 (s, 1H), 8.61 (d, J=2.0, 1H), 7.61–7.57 (m, 2H), 7.45 (s, 1H), 7.31–7.18 (m, 4H), 3.92 (s, 3H), 2.83 (bs, 4H), 2.31 (bs, 4H), 2.07 (s, 3H). MS (ES+, m/z)=447 (m+H)⁺.

Example 127

5-(4-fluorophenyl)-N-[2-methoxy-5-(thiomorpholin-4-ylsulfonyl)phenyl]-1,3-oxazol-2-amine

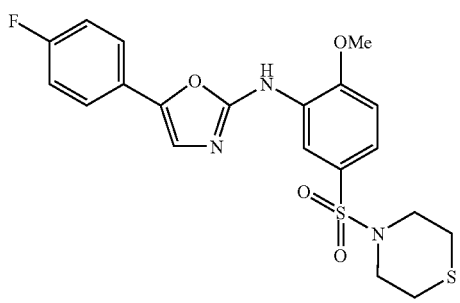

¹H NMR (400 MHz, d₆-DMSO): δ 9.69 (s, 1H), 8.62 (d, J=2.2, 1H), 7.61–7.57 (m, 2H), 7.45 (s, 1H), 7.31 (dd, J₁=8.6, J₂=2.2, 1H), 7.25 (t, J=8.9, 2H), 7.19 (d, J=8.6, 1H), 3.92 (s, 3H), 3.16–3.13 (m, 4H), 3.96–2.60 (m, 4H). MS (ES+, m/z)=450 (m+H)⁺.

Example 128

N-(cyclopropylmethyl)-3-{[5-(4-fluorophenyl)-1,3-oxazol-2-yl]amino}-4-methoxybenzenesulfonamide

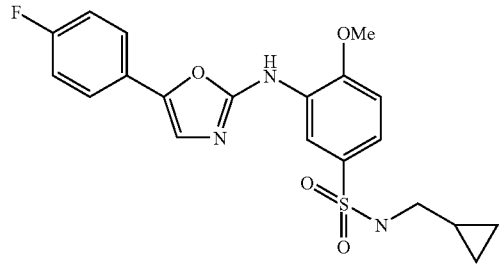

¹H NMR (400 MHz, d₆-DMSO): δ 9.54 (s, 1H), 8.64 (s, 1H), 7.61–7.58 (m, 2H), 7.53 (t, J=5.7, 1H), 7.44 (s, 1H), 7.36 (d, J=7.1, 1H), 7.24 (t, J=8.7, 2H), 7.13 (d, J=8.7, 1H), 3.89 (s, 3H), 2.59 (t, J=7.0, 2H), 0.77–0.72 (m, 1H), 0.31–0.26 (m, 2H), 0.04–0.01 (m, 2H). MS (ES+, m/z)=418 (m+H)⁺.

Example 129

3-{[5-(4-fluorophenyl)-1,3-oxazol-2-yl]amino}-4-methoxy-N-(3-methoxypropyl)benzenesulfonamide

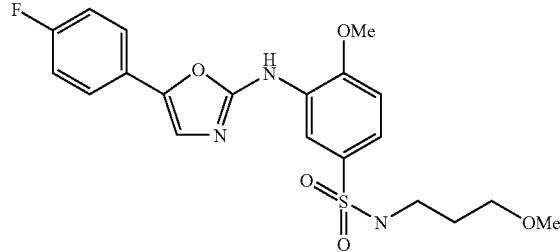

¹H NMR (300 MHz, d₆-DMSO): δ 9.56 (s, 1H), 8.65 (d, J=2.2, 1H), 7.62–7.58 (m, 2H), 7.44 (s, 1H), 7.40–7.34 (m, 2H), 7.25 (t, J=9.0, 2H), 7.15 (d, J=8.6, 1H), 3.89 (s, 3H), 3.21 (t J=6.1, 2H), 3.09 (s, 3H), 2.75–2.70 (m, 2H), 1.56–1.50 (m, 2H). MS (ES+, m/z)=436 (m+H)⁺.

Example 130

3-{[5-(4-fluorophenyl)-1,3-oxazol-2-yl]amino}-4-methoxy-N-methylbenzenesulfonamide

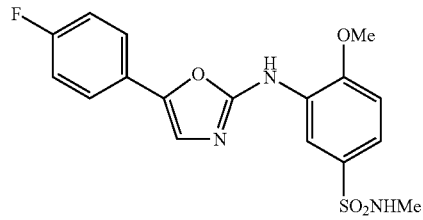

¹H NMR (300 MHz, d₆-DMSO): δ 9.63 (s, 1H), 8.72 (d, J=2.2, 1H), 7.68–7.64 (m, 2H), 7.51 (s, 1H), 7.42 (dd, $J_1$=8.5, $J_2$=2.2, 1H), 7.34–7.29 (m, 3H), 7.23 (d, J=8.5, 1H), 3.97 (s, 3H), 2.43–2.41 (m, 3H). MS (ES+, m/z)=378 (m+H)$^+$.

Example 131

N-(2-ethoxyethyl)-3-{[5-(4-fluorophenyl)-1,3-oxazol-2-yl]amino}-4-methoxybenzenesulfonamide

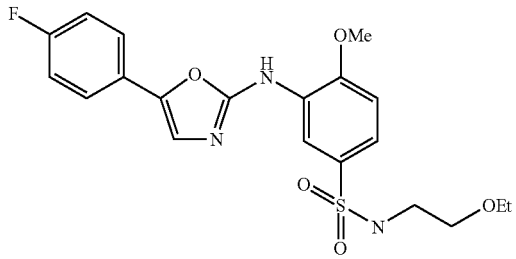

$^1$H NMR (300 MHz, d$_6$-DMSO): δ 9.77 (s, 1H), 8.69 (d, J=2.3, 1H), 7.70–7.65 (m, 3H), 7.55 (s, 1H), 7.47 (dd, $J_1$=8.6, $J_2$=2.2, 1H), 7.33 (t, J=8.9, 2H), 7.23 (d, J=8.6, 1H), 3.97 (s, 3H), 3.40–3.33 (m, 4H), 2.94–2.88 (m, 2H), 1.06 (t, J=7.0, 3H). MS (ES+, m/z)=436 (m+H)$^+$.

Example 132

5-(4-chlorophenyl)-N-[5-(ethylsulfonyl)-2-methoxyphenyl]-1,3-oxazol-2-amine

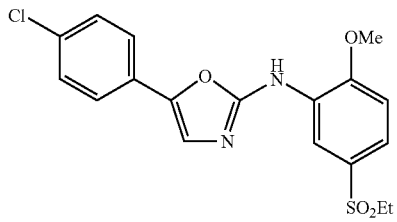

$^1$H NMR (400 MHz, d$_6$-DMSO): δ 9.91 (bs, 1H), 8.69 (d, J=2.2, 1H), 7.85 (d, J=8.3 Hz, 2H), 7.77 (s, 1H), 7.70 (d, J=8.3, 2H), 7.47 (dd, $J_1$=8.7, $J_2$=2.2, 1H), 7.23 (d, J=8.7, 1H), 3.92 (s, 3H), 3.16 (q, J=7.3, 2H), 1.06 (t, J=7.3, 3H). MS (ES+, m/z)=393 (m+H)$^+$.

Example 133

4-(2-{[5-(ethylsulfonyl)-2-methoxyphenyl]amino}-1,3-oxazol-5-yl)benzonitrile

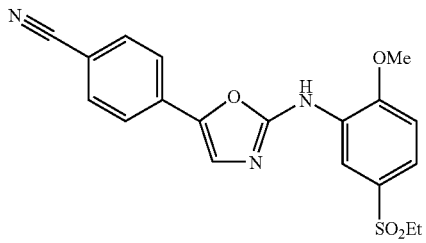

$^1$H NMR (400 MHz, d$_6$-DMSO): δ 9.91 (bs, 1H), 8.69 (d, J=2.2, 1H), 7.85 (d, J=8.3, 2H), 7.77 (s, 1H), 7.70 (d, J=8.3, 2H), 7.47 (dd, $J_1$=8.7, $J_2$=2.2, 1H), 7.23 (d, J=8.7, 1H), 3.92 (s, 3H), 3.16 (q, J=7.3, 2H), 1.06 (t, J=7.3, 3H). MS (ES+, m/z)=384 (m+H)$^+$.

Example 134

4-(2-{[5-(ethylsulfonyl)-2-methoxyphenyl]amino}-1,3-oxazol-5-yl)benzamide

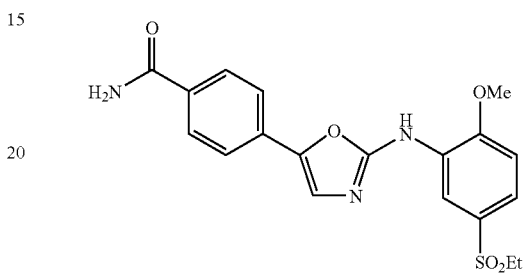

The title compound from Example 133 (84 mg, 0.22 mmol) was treated with conc. HCl (4 mL) and stirred at RT overnight. The reaction mixture was diluted with ethyl acetate and made basic with 5N NaOH. The aqueous layer was extracted with ethyl acetate (3×10 mL). The combined organic layers were dried over anhydrous magnesium sulfate, filtered, and evaporated under reduced pressure to afford the title compound (85 mg, 97% yield) as a yellow solid. $^1$H NMR (400 MHz, d$_6$-DMSO): δ 9.78 (bs, 1H), 8.72 (d, J=2.1, 1H), 7.94 (s, 1H), 7.89 (d, J=8.2, 2H), 7.63–7.61 (m, 3H), 7.46 (dd, $J_1$=8.6, $J_2$=2.1, 1H), 7.32 (s, 1H), 7.22 (d, J=8.6, 1H), 3.93 (s, 3H), 3.15 (q, J=7.3, 2H), 1.07 (t, J=7.3, 3H). MS (ES+, m/z)=402 (m+H)$^+$.

Example 135

5-(4-bromophenyl)-N-[5-(ethylsulfonyl)-2-methoxyphenyl]-1,3-oxazol-2-amine

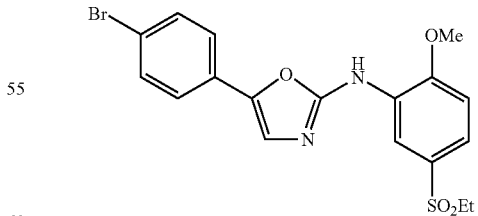

$^1$H NMR (400 MHz, d$_6$-DMSO): δ 9.76 (s, 1H), 8.73 (d, J=2.0, 1H), 7.61 (d, J=8.5, 2H), 7.57 (s, 1H), 7.52 (d, J=8.5, 2H), 7.47 (dd, $J_1$=8.5, $J_2$=2.0, 1H), 7.23 (d, J=8.5, 1H), 3.92 (s, 3H), 3.16 (q, J=7.3, 2H), 1.08 (t, J=7.3, 3H). MS (ES+, m/z)=437 (m+H)$^+$.

Example 136

N-[5-(ethylsulfonyl)-2-methoxyphenyl]-5-(3-methyl-1-benzothien-2-yl)-1,3-oxazol-2-amine

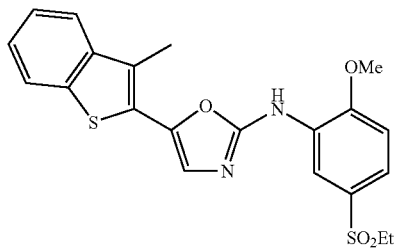

¹H NMR (400 MHz, d₆-DMSO): δ 9.90 (s, 1H), 8.73 (d, J=2.0, 1H), 7.91 (d, J=7.8, 1H), 7.77 (d, J=7.8, 1H), 7.47 (dd, J₁=8.5, J₂=2.0, 1H), 7.40–7.31 (m, 3H), 7.23 (d, J=8.5, 1H), 3.93 (s, 3H), 3.16 (q, J=7.3, 2H), 2.49 (s, 3H), 1.07 (t, J=7.3, 3H). MS (ES+) m/z 429 (m+H)⁺.

Example 137

5-(3-chlorophenyl)-N-[5-(ethylsulfonyl)-2-methoxyphenyl]-1,3-oxazol-2-amine

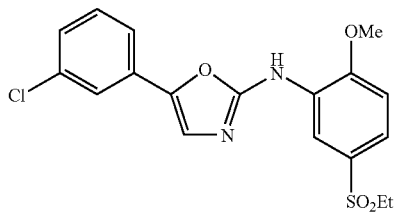

¹H NMR (400 MHz, d₆-DMSO): δ 9.77 (s, 1H), 8.72 (d, J=2.1, 1H), 7.63 (m, 2H), 7.51 (d, J=7.9, 1H), 7.45 (dd, J₁=8.6, J₂=2.2, 1H), 7.41 (d, J=7.9, 1H), 7.28 (d, J=8.2, 1H), 7.22 (d, J=8.6, 1H), 3.93 (s, 3H), 3.15 (q, J=7.3, 2H), 1.06 (t, J=7.3, 3H). MS (ES+, m/z)=393 (m+H)⁺.

Example 138

N-[5-(ethylsulfonyl)-2-methoxyphenyl]-5-pyridin-3-yl-1,3-oxazol-2-amine

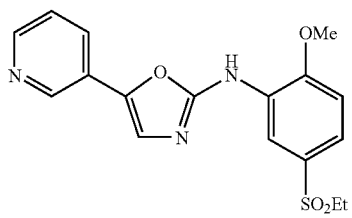

¹H NMR (400 MHz, d₆-DMSO): δ 9.88 (s, 1H), 8.89 (s, 1H), 8.80 (d, J=2.2, 1H), 8.50 (m, 1H), 7.99 (d, J=7.9, 1H), 7.72 (s, 1H), 7.55–7.48 (m, 2H), 7.30 (d, J=8.6, 1H), 4.01 (s, 3H), 3.22 (q, J=7.4, 2H), 1.14 (t, J=7.4, 3H). MS (ES+, m/z)=360 (m+H)⁺.

Example 139

3-(2-{[5-(ethylsulfonyl)-2-methoxyphenyl]amino}-1,3-oxazol-5-yl)benzonitrile

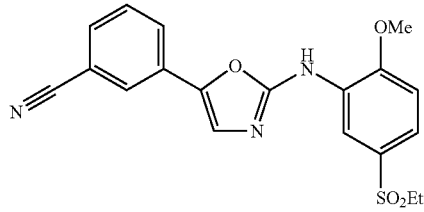

¹H NMR (400 MHz, d₆-DMSO): δ 9.80 (s, 1H), 8.71 (d, J=2.2, 1H), 8.01 (s, 1H), 7.84 (d, J=7.9, 1H), 7.69–7.63 (m, 2H), 7.61 (t, J=7.9, 1H), 7.46 (dd, J₁=8.5, J₂=2.2, 1H), 7.23 (d, J=8.5, 1H), 3.93 (s, 3H), 3.16 (q, J=7.3, 2H), 1.06 (t, J=7.3, 3H). MS (ES+, m/z)=384 (m+H)⁺.

Example 140

3-(2-{[5-(ethylsulfonyl)-2-methoxyphenyl]amino}-1,3-oxazol-5-yl)benzamide

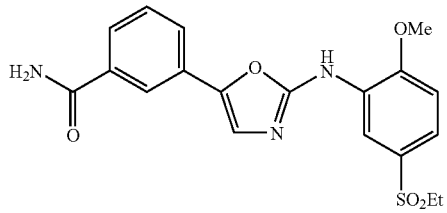

The title compound of Example 139 (20 mg, 0.05 μmol) was treated with conc. HCl (4 mL); the resulting mixture was stirred at RT overnight. The mixture was diluted with ethyl acetate and made neutral with careful addition of 5N NaOH. The aqueous layer was extracted with ethyl acetate (3×10 mL). The combined organic layers were dried over anhydrous magnesium sulfate, filtered, and evaporated under reduced pressure to yield the title compound (19 mg, 91% yield) as a yellow solid. ¹H NMR (400 MHz, d₆-DMSO): δ 9.84 (s, 1H), 8.82 (d, J=2.1, 1H), 8.16 (s, 1H), 8.07 (s, 1H), 7.80–7.76 (m, 2H), 7.62 (s, 1H), 7.57–7.49 (m, 3H), 7.30 (d, J=8.5, 1H), 4.0 (s, 3H), 3.24 (q, J=7.3, 2H), 1.14 (t, J=7.3, 3H). MS (ES+, m/z)=402 (m+H)⁺.

Example 141

N-[5-(ethylsulfonyl)-2-methoxyphenyl]-5-(3-fluorophenyl)-1,3-oxazol-2-amine

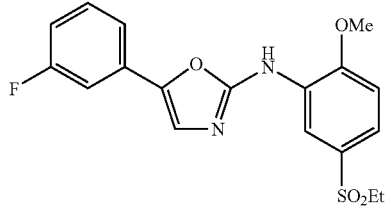

¹H NMR (400 MHz, d₆-DMSO): δ 9.75 (bs, 1H), 8.71 (d, J=2.2, 1H), 7.59 (s, 1H), 7.47–7.36 (m, 4H), 7.22 (d, J=8.6, 1H), 7.08–7.04 (m, 1H), 3.92 (s, 3H), 3.15 (q, J=7.3, 2H), 1.06 (t, J=7.3, 3H). MS (ES+, m/z)=377 (m+H)⁺.

Example 142

N-[5-(ethylsulfonyl)-2-methoxyphenyl]-5-[4-(trifluoromethyl)phenyl]-1,3-oxazol-2-amine

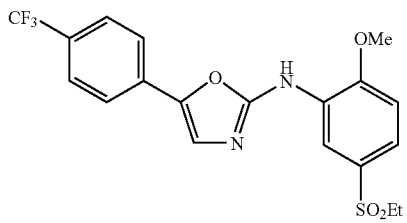

¹H NMR (400 MHz, d₆-DMSO): δ 9.88 (s, 1H), 8.73 (s, 1H), 7.77 (s, 4H), 7.73 (s, 1H), 7.48 (d, J=8.5, 1H), 7.25 (d, J=8.5, 1H), 3.94 (s, 3H), 3.17 (q, J=7.3, 2H), 1.08 (t, J=7.3, 3H). MS (ES+, m/z)=427 (m+H)⁺.

Example 143

5-(3,4-dichlorophenyl)-N-[5-(ethylsulfonyl)-2-methoxyphenyl]-1,3-oxazol-2-amine

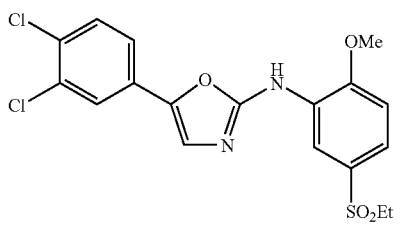

¹H NMR (400 MHz, d₆-DMSO): δ 9.81 (s, 1H), 8.72 (d, J=2.1, 1H), 7.82 (d, J=1.8, 1H), 7.69–7.67 (m, 2H), 7.54 (dd, J₁=8.4, J₂=1.8, 1H), 7.47 (dd, J₁=8.4, J₂=2.1, 1H), 7.24 (d, J=8.4, 1H), 3.94 (s, 3H), 3.23 (q, J=7.3, 2H), 1.14 (t, J=7.3, 3H). MS (ES+, m/z)=429 (m+H)⁺, 427 (m+H)⁺.

Example 144

5-(4-chloro-3-methylphenyl)-N-[5-(ethylsulfonyl)-2-methoxyphenyl]-1,3-oxazol-2-amine

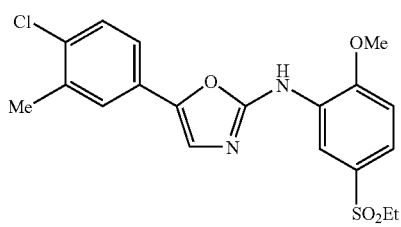

¹H NMR (300 MHz, d₆-DMSO): δ 9.80 (s, 1H), 8.79 (d, J=1.8, 1H), 7.69–7.44 (m, 5H), 7.30 (d, J=8.6, 1H), 4.00 (s, 3H), 3.23 (q, J=7.3, 2H), 2.40 (s, 3H), 1.14 (t, J=7.3, 3H). MS (ES+, m/z)=407, 409 (m+H)⁺.

Example 145

5-[5-(2,4-dichlorophenyl)-2-furyl]-N-[5-(ethylsulfonyl)-2-methoxyphenyl]-1,3-oxazol-2-amine

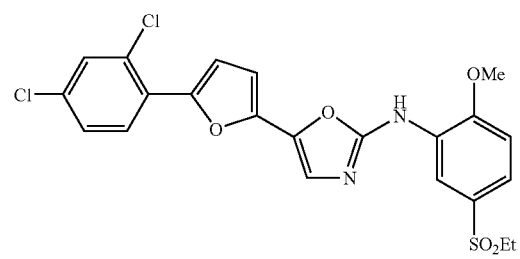

¹H NMR (300 MHz, d₆-DMSO): δ 9.96 (s, 1H), 8.77 (d, J=1.9, 1H), 7.97 (d, J=8.5, 1H), 7.78 (d, J=1.9, 1H), 7.59–7.52 (m, 3H), 7.35 (d, J=3.7, 1H), 7.30 (d, J=8.5, 1H), 6.82 (d, J=3.7, 1H), 3.99 (s, 3H), 3.24 (q, J=7.3, 2H), 1.14 (t, J=7.3, 3H). MS (ES+, m/z)=493, 495 (m+H)⁺.

Example 146

N-[5-(ethylsulfonyl)-2-methoxyphenyl]-5-(2-naphthyl)-1,3-oxazol-2-amine

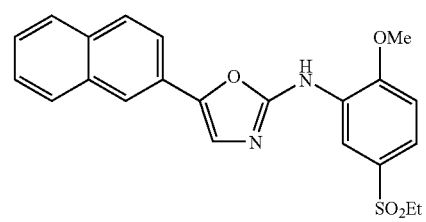

¹H NMR (400 MHz, d₆-DMSO): δ 9.77 (s, 1H), 8.76 (d, J=2.0, 1H), 8.01 (s, 1H), 7.93 (d, J=8.8, 1H), 7.86 (m, 2H), 7.75 (d, J=8.6, 1H), 7.62 (s, 1H), 7.52–43 (m, 3H), 7.23 (d, J=8.6, 1H), 3.94 (s, 3H), 3.17 (q, J=7.3, 2H), 1.08 (t, J=7.3, 3H). MS (ES+, m/z)=409 (m+H)⁺.

Example 147

N-[5-(ethylsulfonyl)-2-methoxyphenyl]-5-(5,5,8,8-tetramethyl-5,6,7,8-tetrahydronaphthalen-2-yl)-1,3-oxazol-2-amine

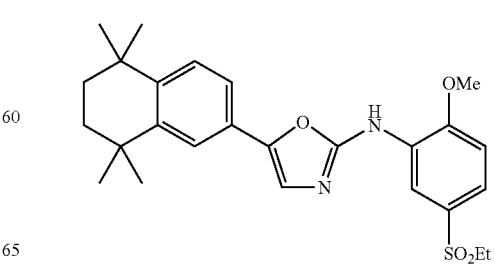

¹H NMR (300 MHz, d₆-DMSO): δ 9.71 (bs, 1H), 8.81 (d, J=2.0, 1H), 7.57 (s, 1H), 7.53–7.49 (m, 2H), 7.40 (bs, 2H), 7.28 (d, J=8.7, 1H), 4.00 (s, 3H), 3.23 (q, J=7.3, 2H), 1.68 (bs, 4H), 1.32 (s, 6H), 1.27 (s, 6H), 1.14 (t, J=7.3, 3H). MS (ES+, m/z)=469 (m+H)⁺.

Example 148

5-(2,3-dihydro-1,4-benzodioxin-6-yl)-N-[5-(ethylsulfonyl)-2-methoxyphenyl]-1,3-oxazol-2-amine

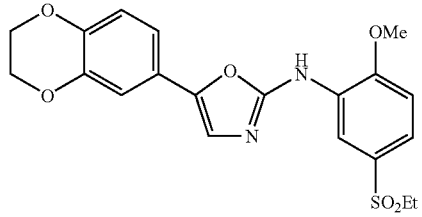

¹H NMR (300 MHz, d₆-DMSO): δ 9.68 (bs, 1H), 8.80 (d, J=2.2, 1H), 7.50 (dd, J₁=8.5, J₂=2.2, 1H), 7.41 (s, 1H), 7.29 (d, J=8.7, 1H), 7.13–7.10 (m, 2H), 6.95 (d, J=8.5, 1H), 4.30 (s, 4H), 4.00 (s, 3H), 3.22 (q, J=7.3, 2H), 1.14 (t, J=7.3, 3H). MS (ES+, m/z)=417 (m+H)⁺.

Example 149

5-(3,5-difluorophenyl)-N-[5-(ethylsulfonyl)-2-methoxyphenyl]-1,3-oxazol-2-amine

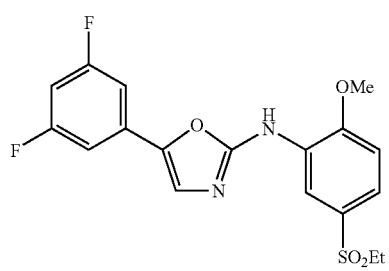

¹H NMR (400 MHz, d₆-DMSO): δ 9.81 (s, 1H), 8.69 (d, J=2.2, 1H), 7.69 (s, 1H), 7.46 (dd, J₁=8.5, J₂=2.2, 1H), 7.27–7.22 (m, 3H), 7.13–7.08 (m, 1H), 3.93 (s, 3H), 3.16 (q, J=7.3, 2H), 1.06 (t, J=7.3, 3H). MS (ES+, m/z)=395 (m+H)⁺.

Example 150

N-[5-(ethylsulfonyl)-2-methoxyphenyl]-5-(3-trifluoromethylphenyl)-1,3-oxazol-2-amine

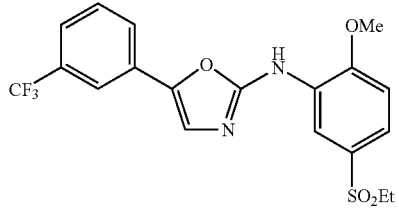

¹H NMR (400 MHz, d₆-DMSO): δ 9.83 (bs, 1H), 8.73 (s, 1H), 7.87–7.85 (m, 2H), 7.71 (s, 1H), 7.65–7.57 (m, 2H), 7.45 (d, J=8.6, 1H), 7.23 (d, J=8.6, 1H), 3.93 (s, 3H), 3.15 (q, J=7.3, 2H), 1.06 (t, J=7.3, 3H). MS (ES+, m/z)=427 (m+H)⁺.

Example 151

N-[5-(ethylsulfonyl)-2-methoxyphenyl]-5-[4-(methylsulfonyl)phenyl]-1,3-oxazol-2-amine

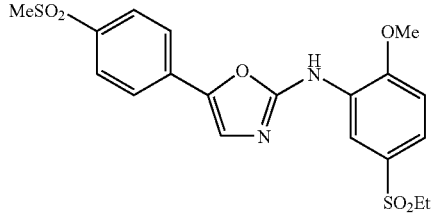

¹H NMR (300 MHz, d₆-DMSO): δ 10.01 (s, 1H), 8.79 (d, J=2.1, 1H), 8.02 (d, J=8.4, 2H), 7.87 (d, J=8.4, 2H), 7.85 (s, 1H), 7.56 (dd, J₁=8.5, J₂=2.1, 1H), 7.32 (d, J=8.5, 1H), 4.01 (s, 3H), 3.27 (s, 3H), 3.23 (q, J=7.3, 2H), 1.15 (t, J=7.3, 3H). MS (ES+, m/z)=437 (m+H)⁺.

Example 152

5-(3,4-dimethoxyphenyl)-N-[5-(ethylsulfonyl)-2-methoxyphenyl]-1,3-oxazol-2-amine

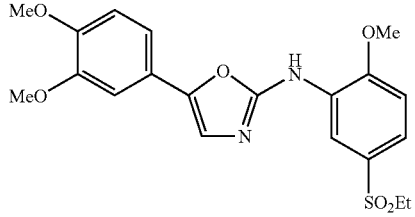

¹H NMR (400 MHz, d₆-DMSO): δ 9.58 (bs, 1H), 8.72 (d, J=2.2, 1H), 7.43 (dd, J₁=8.5, J₂=2.2, 1H), 7.35 (s, 1H), 7.20 (d, J=8.7, 1H), 7.14–7.10 (m, 2H), 6.98 (d, J=8.5, 1H), 3.92 (s, 3H), 3.77 (s, 3H), 3.73 (s, 3H), 3.15 (q, J=7.3, 2H), 1.06 (t, J=7.3, 3H). MS (ES+, m/z)=419 (m+H)⁺.

Example 153

5-(3,4dihydro-2H-1,5-benzodioxepin-7-yl)-N-[5-(ethylsulfonyl)-2-methoxyphenyl]-1,3-oxazol-2-amine

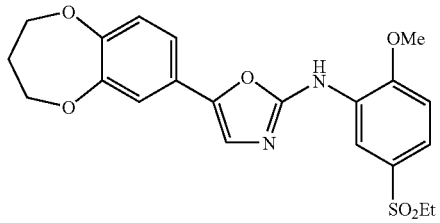

$^1$H NMR (400 MHz, $d_6$-DMSO): δ 9.62 (s, 1H), 8.72 (d, J=2.0, 1H), 7.43 (dd, $J_1$=8.4, $J_2$=2.0, 1H), 7.38 (s, 1H), 7.21–7.18 (m, 2H), 7.13 (dd, $J_1$=8.4, $J_2$=2.0, 1H), 6.98 (d, J=8.3, 1H), 4.12–4.08 (m, 4H), 3.92 (s, 3H), 3.14 (q, J=7.3, 2H), 2.06 (m, 2H), 1.06 (t, J=7.3, 3H). MS (ES+, m/z)=431 (m+H)$^+$.

Example 154

5-(5-chlorothien-2-yl)-N-[5-(ethylsulfonyl)-2-methoxyphenyl]-1,3-oxazol-2-amine

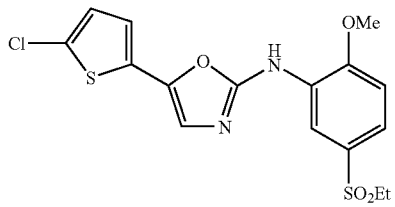

$^1$H NMR (400 MHz, $d_6$-DMSO): δ 9.81 (bs, 1H), 8.66 (s, 1H), 7.45 (d, J=8.4, 1H), 7.34 (s, 1H), 7.21 (d, J=8.4, 1H), 7.11 (m, 2H), 3.90 (s, 3H), 3.14 (q, J=7.3, 2H), 1.05 (t, J=7.3, 3H). MS (ES+, m/z)=399, 401 (m+H)$^+$.

Example 155 methyl 3-{[5-(3-bromophenyl)-1,3-oxazol-2-yl]amino}-4-methoxybenzoate

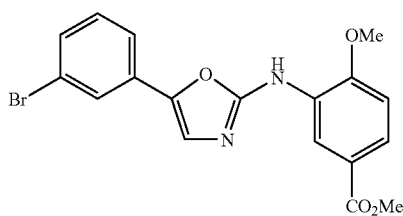

$^1$H NMR (400 MHz, $d_6$-DMSO): δ 9.55 (s, 1H), 8.83 (d, J=2.0, 1H), 7.79 (s, 1H), 7.66–7.57 (m, 3H), 7.45–7.35 (m, 2H), 7.14 (d, J=8.6, 1H), 3.93(s, 3H), 3.82 (s, 3H). MS (ES+, m/z)=403, 405 (m+H)$^+$.

Example 156

3-{[5-(3-bromophenyl)-1,3-oxazol-2-yl]amino}-4-methoxybenzenesulfonyl fluoride

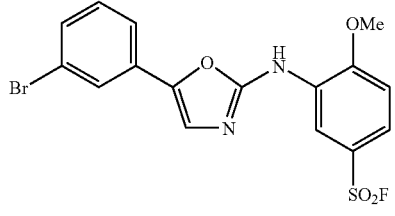

$^1$H NMR (400 MHz, $d_6$-DMSO): δ 10.07 (bs, 1H), 9.00 (d, J=2.1, 1H), 7.78 (s, 1H), 7.72 (dd, $J_1$=8.7, $J_2$=2.1, 1H), 7.65 (s, 1H), 7.56 (d, J=7.7, 1H), 7.43–7.32 (m, 3H), 3.89 (s, 3H). MS (ES+, m/z)=427, 429 (m+H)$^+$.

Example 157

3-(2-{[5-(ethylsulfonyl)-2-methoxyphenyl]amino}-1,3-oxazol-5-yl)phenyl benzoate

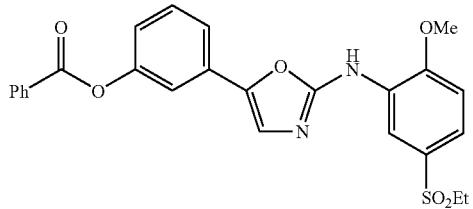

$^1$H NMR (400 MHz, $d_6$-DMSO): δ 9.73 (s, 1H), 8.73 (d, J=2.2, 1H), 8.11 (d, J=7.5, 2H), 7.72 (t, J=7.5, 1H), 7.60–7.56 (m, 3H), 7.51–7.50 (m, 3H), 7.45 (dd, $J_1$=8.4, $J_2$=2.2, 1H), 7.22 (d, J=8.6, 1H), 7.19–7.16 (m, 1H), 3.92 (s, 3H), 3.14 (q, J=7.3, 2H), 1.05 (t, J=7.3, 3H). MS (ES+, m/z)=479 (m+H)$^+$.

Example 158

3-(2-{[5-(ethylsulfonyl)-2-methylphenyl]amino}-1,3-oxazol-5-yl)phenol

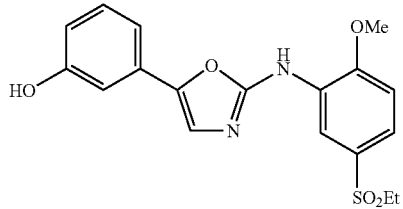

The title compound of Example 157 (1.9 g, 3.30 mmol) was treated with MeOH (20 mL) and 5N NaOH (20 mL); the resulting mixture was stirred at reflux (85° C.) for 3 h. After cooling to RT, 6N HCl (20 mL) was slowly added to the reaction, followed by saturated aqueous solution of NaHCO$_3$. The resulting precipitate was collected by filtra tion. The isolated solid was washed sequentially with water, MeOH, and diethyl ether to yield the title compound (1.2 g, 97%) as a yellow solid. $^1$H NMR (400 MHz, $d_6$-DMSO): δ 9.67 (s, 1H), 9.55 (s, 1H), 8.73 (d, J=2.2, 1H), 7.44 (dd, $J_1$=8.6, $J_2$=2.2, 1H), 7.41 (s, 1H), 7.22–7.15 (m, 2H), 7.00 (d, J=7.8, 1H), 6.94 (s, 1H), 6.64 (d, J=7.8, 1H), 3.92 (s, 3H), 3.14 (q, J=7.3, 2H), 1.06 (t, J=7.3, 3H). MS (ES+, m/z)=375 (m+H)$^+$.

Example 159

5-[3-(cyclopropylmethoxy)phenyl]-N-[5-(ethylsulfonyl)-2-methoxyphenyl]-1,3-oxazol-2-amine

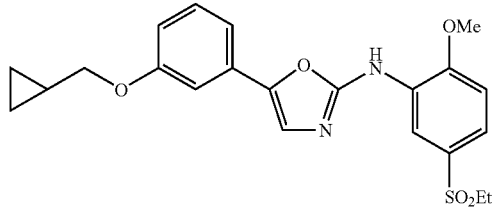

To a solution of the title compound of Example 158 (100 mg, 0.27 μmol, 1 eq.), cyclopropylmethanol (2 eq.) and triphenylphosphine (2 eq.) in dichloromethane (5 mL) was added diethyl azodicarboxylate (2 eq.) drop wise under nitrogen. The mixture stirred at RT overnight, and was subsequently evaporated to a smaller volume (≅1 mL). Product was purified by prep thin layer chromatography. $^1$H NMR (300 MHz, $d_6$-DMSO): δ 9.75 (s, 1H), 8.79 (s, 1H), 7.58 (s, 1H), 7.52 (d, J=8.6, 1H), 7.38–7.28 (m, 2H), 7.22–7.19 (m, 2H), 6.67 (d, J=7.2, 1H), 4.00 (s, 3H), 3.90 (d, J=6.8, 2H), 3.23 (q, J=7.3, 2H), 1.27 (m, 1H), 1.14 (t, J=7.3, 3H), 0.61 (d, J=7.8, 2H), 0.37 (d, J=4.7, 2H). MS (ES+, m/z)=429 (m+H)$^+$.

Unless otherwise indicated, the compounds of Examples 160–167 were prepared according to the general procedure set forth in the synthesis of the title compound of Example 159. The NMR data characterizing these examples describe either the salt form or the free base form.

Example 160

5-(3-butoxyphenyl)-N-[5-(ethylsulfonyl)-2-methoxyphenyl]-1,3-oxazol-2-amine

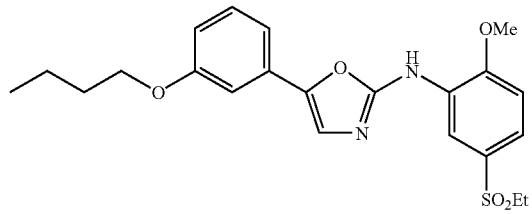

$^1$H NMR (400 MHz, $d_6$-DMSO): δ 9.67 (s, 1H), 8.73 (d, J=2.2, 1H), 7.51 (s, 1H), 7.44 (d, J=8.4, 1H), 7.30–7.26 (m, 1H), 7.22 (d, J=8.4, 1H), 7.14–7.12 (m, 2H), 6.80 (m, 1H), 3.97 (t, J=6.4, 2H), 3.93 (s, 3H), 3.14 (q, J=7.3, 2H), 1.69–1.65 (m, 2H), 1.44–1.38 (m, 2H), 1.07 (t, J=7.3, 3H), 0.90 (t, J=7.3, 3H). MS (ES+, m/z)=431 (m+H)$^+$.

Example 161

N-[5-(ethylsulfonyl)-2-methoxyphenyl]-5-[3-(pyridin-2-ylmethoxy)phenyl]-1,3-oxazol-2-amine

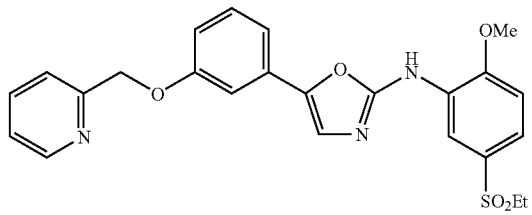

$^1$H NMR (400 MHz, $d_6$-DMSO): δ 9.69 (s, 1H), 8.72 (d, J=2.0, 1H), 8.54 (d, J=4.6, 1H), 7.82–7.78 (m, 1H), 7.52–7.49 (m, 2H), 7.45 (dd, $J_1$=8.3, $J_2$=2.2, 1H), 7.33–7.16 (m, 5H), 6.91 (dd, $J_1$=8.3, $J_2$=2.2, 1H), 5.18 (s, 2H), 3.92 (s, 3H), 3.15 (q, J=7.3, 2H), 1.06 (t, J=7.3, 3H). MS (ES+, m/z)=466 (m+H)$^+$.

Example 162

5-(3-benzyloxyphenyl)-N-[5-(ethylsulfonyl)-2-methoxyphenyl]-1,3-oxazol-2-amine

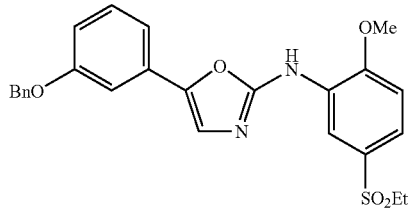

$^1$H NMR (400 MHz, $d_6$-DMSO): δ 9.76 (s, 1H), 8.80 (d, J=1.9, 1H), 7.59 (s, 1H), 7.52–7.50 (m, 3H), 7.46–7.36 (m, 4H), 7.31–7.22 (m, 3H), 6.97 (d, J=6.8, 1H), 5.18 (s, 2H), 4.00 (s, 3H), 3.23 (q, J=7.3, 2H), 1.14 (t, J=7.3, 3H). MS (ES+, m/z)=465 (m+H)$^+$.

Example 163

N-[5-(ethylsulfonyl)-2-methoxyphenyl]-5-[3-(tetrahydro-2H-pyran-4yloxy)phenyl]-1,3-oxazol-2-amine

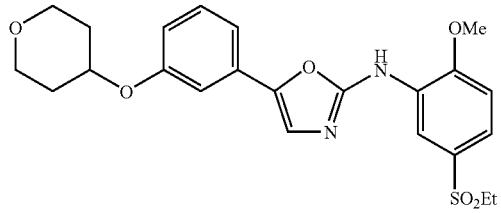

$^1$H NMR (300 MHz, $d_6$-DMSO): δ 9.75 (s, 1H), 8.81 (d, J=2.1, 1H), 7.60 (s, 1H), 7.54–7.52 (m, 1H), 7.41–7.29 (m, 2H), 7.24–7.21 (m, 2H), 6.96 (d, J=7.1, 1H), 4.67 (m, 1H), 4.02 (s, 3H), 3.92–3.88 (m, 2H), 3.57–3.51 (m, 2H), 3.24 (q, J=7.3, 2H), 2.04–2.01 (m, 2H), 1.65–1.62 (m, 2H), 1.14 (t, J=7.3, 3H). MS (ES+, m/z)=459 (m+H)⁺.

Example 164

N-[5-(ethylsulfonyl)-2-methoxyphenyl]-5-[3-(2-pyridin-2-ylethoxy)phenyl]-1,3-oxazol-2-amine

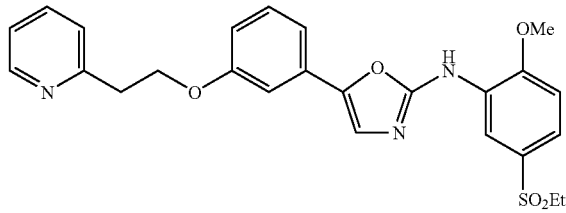

¹H NMR (400 MHz, d₆-DMSO): δ 9.68 (s, 1H), 8.72 (d, J=2.2, 1H), 8.47 (d, J=4.5, 1H), 7.71–7.67 (m, 1H), 7.50 (s, 1H), 7.44 (dd, J₁=8.6, J₂=2.2, 1H), 7.34 (d, J=7.7, 1H), 7.30–7.26 (m, 1H), 7.22–7.10 (m, 4H), 6.80 (dd, J₁=8.3, J₂=2.2, 1H), 4.35 (t, J=6.5, 2H), 3.72 (s, 3H), 3.18–3.13 (m, 4H), 1.06 (t, J=7.3, 3H). MS (ES+, m/z)=480 (m+H)⁺.

Example 165

5-{3-[(2,3-dimethoxybenzyl)oxy]phenyl}-N-[5-(ethylsulfonyl)-2-methoxyphenyl]-1,3-oxazol-2-amine

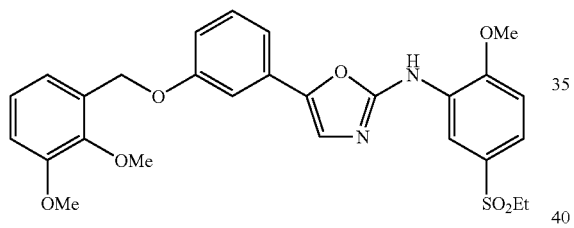

¹H NMR (400 MHz, d₆-DMSO): δ 9.77 (bs, 1H), 8.69 (s, 1H), 7.53 (s, 1H), 7.45 (dd J₁=8.6, J₂=2.2, 1H), 7.33–7.29 (m, 1H), 7.27–7.21 (m, 2H), 7.16 (d, J=7.7, 1H), 7.02–6.99 (m, 3H), 6.89–6.86 (m, 1H), 5.05 (s, 2H), 3.92 (s, 3H), 3.77 (s, 3H), 3.72 (s, 3H), 3.15 (q, J=7.3, 2H), 1.06 (t, J=7.3, 3H). MS (ES+, m/z)=525 (m+H)⁺.

Example 166

N-[5-(ethylsulfonyl)-2-methoxyphenyl]-5-[3-(1-pyridin-4-ylethoxy)phenyl]-1,3-oxazol-2-amine

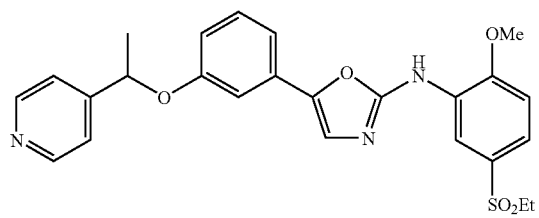

¹H NMR (400 MHz, d₆-DMSO): δ 9.65 (s, 1H), 8.70 (s, 1H), 8.50 (d, J=5.2, 2H), 7.47 (s, 1H), 7.45 (d, J=8.4, 1H), 7.38 (d, J=5.2, 2H), 7.25–7.21 (m, 2H), 7.16 (s, 1H), 7.09 (d, J=7.5, 1H), 6.75(d, J=8.2, 1H), 5.56 (q, J=6.3, 1H), 3.92 (s, 3H), 3.15 (q, J=7.3, 2H), 1.52 (d, J=6.3, 3H), 1.06 (t, J=7.3, 3H). MS (ES+, m/z)=480 (m+H)⁺.

Example 167

N-[5-(ethylsulfonyl)-2-methoxyphenyl]-5-[3-(tetrahydrofuran-3-yloxy)phenyl]-1,3-oxazol-2-amine

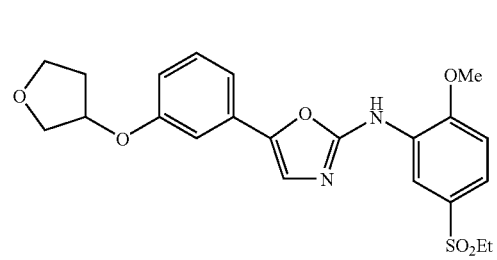

¹H NMR (400 MHz, d₆-DMSO): δ 9.66 (s, 1H), 8.72 (d, J=2.2, 1H), 7.52 (s, 1H), 7.45 (dd, J₁=8.4, J₂=2.2, 1H), 7.32–7.28 (m, 1H), 7.22 (d, J=8.6, 1H), 7.15 (d, J=7.6, 1H), 7.10 (s, 1H), 6.80 (dd, J₁=8.2, J₂=2.2, 1H), 5.02 (m, 1H), 3.93 (s, 3H), 3.89–3.70 (m, 4H), 3.15 (q, J=7.3, 2H), 2.22–2.17 (m, 1H), 1.95–1.91 (m, 1H), 1.06 (t, J=7.3, 3H). MS (ES+, m/z)=445 (m+H)⁺.

Example 168

5-{3-[(2-chloropyrimidin-4-yl)oxy]phenyl}-N-[5-(ethylsulfonyl)-2-methoxyphenyl]-1,3-oxazol-2-amine

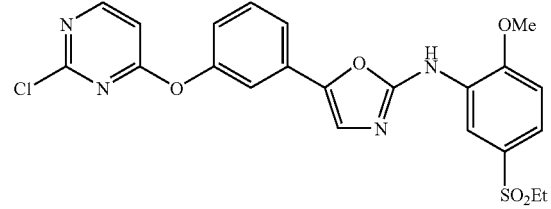

To a mixture of the title compound of Example 158 (100 mg, 0.27 μmol) in THF (3 mL) was added a solution of 1M potassium t-butoxide in THF (320 mL, 0.32 μmol 1.2 eq.), followed by a solution of 2,4-dichloropyrimidine (40 mg, 0.27 μmol) in DMF (1 mL). The mixture was stirred at 50° C. for 30 min. After cooling to RT, the mixture was diluted with diethyl ether and washed with 6N HCl. The aqueous layer was made basic with 5N NaOH and extracted with ethyl acetate (3×10 mL). The combined organic layers were dried over anhydrous magnesium sulfate, filtered, and evaporated under reduced pressure. Purification by silica gel chromatography yielded the title compound (55 mg, 42%) as an off-white solid. ¹H NMR (300 MHz, d₆-DMSO): 9.81 (s, 1H), 8.79 (d, J=2.2, 1H), 7.69 (d, J=5.7, 1H), 7.66 (s, 1H), 7.60 (d, J=4.9, 2H), 7.54–7.51 (m, 2H), 7.28–7.22 (m, 3H), 4.00 (s, 3H), 3.22 (q, J=7.3, 2H), 1.13 (t, J=7.3, 3H). MS (ES+, m/z)=487,489 (m+H)⁺.

Example 169

4-[3-(2-{[5-(ethylsulfonyl)-2-methoxyphenyl]amino}-1,3-oxazol-5-yl)phenoxy]-N-isopropylpyrimidin-2-amine

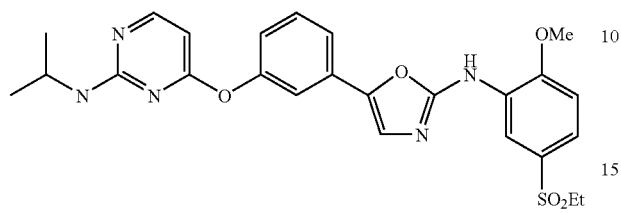

The title compound of Example 168 (40 mg) was treated with isopropylamine (2 mL) and stirred at 100° C. overnight in a sealed tube. The mixture was evaporated to dryness and purified by thin layer chromatography to afford the title compound (28 mg, 67% yield) as a yellow solid, which was isolated as the HCl salt $^1$H NMR (400 MHz, $d_6$-DMSO): δ 9.77 (bs, 1H), 8.68 (s, 1H), 8.26 (d, J=6.4, 1H), 7.58 7.45 (m, 5H), 7.23 (d, J=8.4, 1H), 7.14 (m, 1H), 6.61–6.64 (m, 2H), 3.92 (s, 3H), 3.32 (m, 1H), 3.15 (q, J=7.3, 2H), 1.05 (m, 9H). MS (ES+, m/z)=510 (m+H)$^+$.

Example 170

N-[5-(ethylsulfonyl)-2-methoxyphenyl]-5-(3-phenoxyphenyl)-1,3-oxazol-2-amine

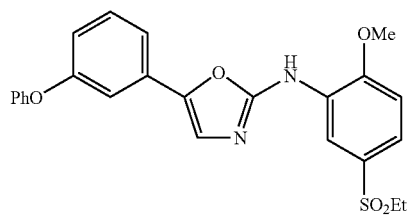

Pyridine (5 eq.) was added to a mixture of the title compound of Example 158 (100 mg, 0.27 mmol, 1 eq.), Cu(OAc)$_2$ (1 eq.), phenylboronic acid (2 eq.), powered 4A molecular sieves, and dichloromethane (5 mL). After stirring at RT overnight, the reaction was diluted with diethyl ether and washed with 6N HCl solution. The aqueous layer was separated, made basic with 5N NaOH solution, and extracted with ethyl acetate (3×20 mL). The combined organic layers were dried over anhydrous magnesium sulfate, filtered, and evaporated under reduced pressure. Purification by thin layer chromatography gave the title compound (22 mg, 18%) as an off-white solid. $^1$H NMR (400 MHz, $d_6$-DMSO): δ 9.82 (s, 1H), 8.80 (d, J=2.1, 1H), 7.62 (s, 1H), 7.62 (s, 1H), 7.53–7.42 (m, 5H), 7.30–7.27 (m, 2H), 7.22–7.17 (m, 1H), 7.09 (d, J=8.0, 2H), 6.95 (d, J=7.6, 1H), 3.98 (s, 3H), 3.22 (q, J=7.3, 2H), 1.13 (t, J=7.3, 3H). MS (ES+, m/z)=451 (m+H)$^+$.

Example 171

5-(3',5'-difluoro-1,1'-biphenyl-3-yl)-N-[5-(ethylsulfonyl)-2-methoxyphenyl]-1,3-oxazol-2-amine

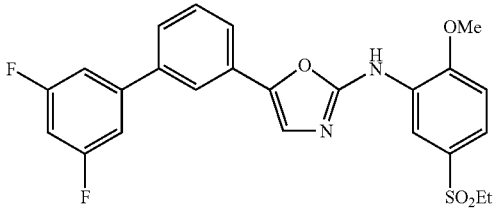

In a pyrex sealed tube, a mixture of the title compound of Example 100 (123 mg, 0.28 mmol), 3,5-difluoro(tributylstannyl)benzene (400 mg, 1 mmol), tetrabutylammonium chloride (170 mg, 0.61 mmol), and tetrakistriphenylphosphine palladium(0) (20 mg, 0.017 mmol) was suspended in dry acetonitrile (10 mL) and stirred at 100° C. After the reaction was determine to be complete by TLC analysis, the reaction was cooled and diluted with ethyl acetate (50 mL), quenched with 1M aqueous potassium fluoride solution (20 mL), and stirred for 3 h. The organic layer was separated, dried over anhydrous magnesium sulfate, filtered, and concentrated under reduced pressure. The crude product was purified by column chromatography on silica gel eluting with hexane:ethyl acetate (1:1) to afford the title compound (83 mg, 63%) as a solid white powder. $^1$H NMR (400 MHz, $d_6$-DMSO): δ 9.72 (s, 1H), 8.74 (d, J=2.2, 1H), 7.91 (s, 1H), 7.60–7.64 (m, 3H), 7.42–7.53 (m, 4H), 7.23 (d, J=8.6, 1H), 3.94 (s, 3H), 3.16 (q, J=7.3, 2H), 1.07 (t, J=7.3, 3H). MS (ES+, m/z)=471 (m+H)$^+$.

Unless otherwise indicated, the compounds of Examples 172–203 were prepared according to the general procedures set forth in the synthesis of the title compound of Example 171. It will be readily apparent to those skilled in the art that the syntheses of these examples is illustrated in Scheme 11 described above. The NMR data characterizing these examples describe either the salt form or the free base form.

Example 172

N-[5-(ethylsulfonyl)-2-methoxyphenyl]-5-(3-thien-2-ylphenyl)-1,3-oxazol-2-amine

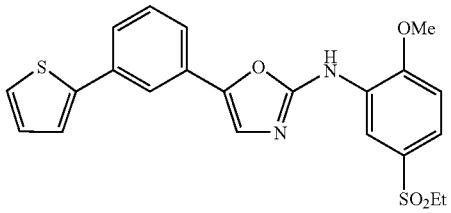

$^1$H NMR (400 MHz, $d_6$-DMSO): δ 9.76 (s, $_1$H), 8.74 (d, J=2.2, 1H), 7.82 (s, 1H), 7.60 (s, 1H), 7.50–7.56 (m, 4H), 7.41–7.46 (m, 2H), 7.22 (d, J=8.5, 1H), 7.13 (t, J=3.8, 1H), 3.94 (s, 3H), 3.16 (q, J=7.4, 2H), 1.07 (t, J=7.3, 3H). MS (ES+, m/z)=441 (m+H)$^+$.

Example 173

N-[5-(ethylsulfonyl)-2-methoxyphenyl]-5-(3-thien-3-ylphenyl)-1,3-oxazol-2-amine

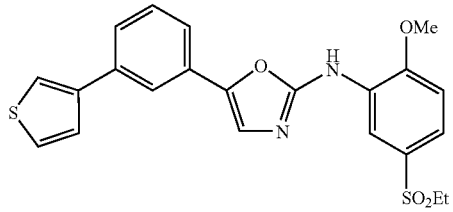

$^1$H NMR (400 MHz, d$_6$-DMSO): δ 9.80 (bs, 1H), 8.81 (s, 1H), 7.98 (s, 2H), 7.60–7.75 (m, 4H), 7.46–7.60 (m, 3H), 7.31 (d, J=8.6, 1H), 4.01 (s, 3H), 3.24 (q, J=7.4, 2H), 1.15 (t, J=7.3, 3H). MS (ES+, m/z)=441 (m+H)$^+$.

Example 174

N-[5-(ethylsulfonyl)-2-methoxyphenyl]-5-(3-pyridin-3-ylphenyl)-1,3-oxazol-2-amine

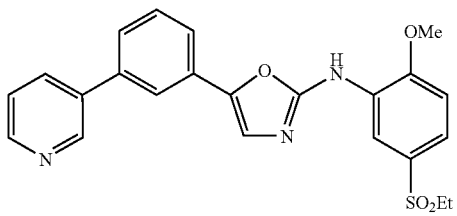

$^1$H NMR (400 MHz, d$_6$-DMSO): δ 9.74 (s, 1H), 9.08 (s, 1H), 8.72 (s, 2H), 8.44–8.52 (m, 1H), 7.98 (s, 1H), 7.70–7.84 (m, 1H), 7.64–7.68 (m, 3H), 7.58 (d, J=7.5, 1H), 7.46 (d, J=8.2, 1H), 7.22 (d, J=8.6, 1H), 3.93 (s, 3H), 3.16 (q, J=7.3, 2H), 1.06 (t, J=7.3, 3H). MS (ES+, m/z)=436 (m+H)$^+$.

Example 175

N-[5-(ethylsulfonyl)-2-methoxyphenyl]-5-(3-vinylphenyl)-1,3-oxazol-2-amine

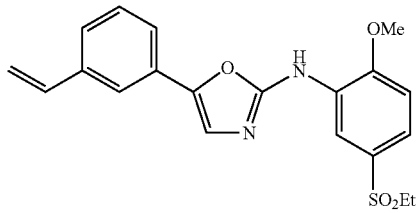

$^1$H NMR (400 MHz, d$_6$-DMSO): δ 9.69 (s, 1H), 8.72 (d, J=2.2, 1H), 7.66 (s, 1H), 7.36–7.55 (m, 5H), 7.22 (d, J=8.6, 1H), 6.72 (dd, J$_1$=11.2, J$_2$=17.5, 1H), 5.86 (d, J=17.6, 1H), 5.29 (d, J=11.2, 1H), 3.93 (s, 3H), 3.15 (q, J=7.3, 2H), 1.06 (t, J=7.3, 3H). MS (ES+, m/z)=385 (m+H)$^+$.

Example 176

5-(3-ethylphenyl)-N-[5-(ethylsulfonyl)-2-methoxyphenyl]-1,3-oxazol-2-amine

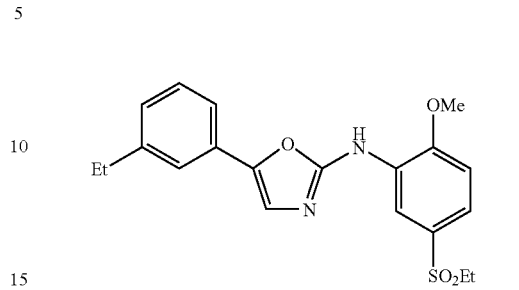

The title compound was obtained by the reduction of the title compound of Example 175. $^1$H NMR (400 MHz, d$_6$-DMSO): δ 9.68 (s, 1H), 8.73 (d, J=2.0, 1H), 7.44–7.48 (m, 3H), 7.40 (d, J=7.7, 1H), 7.32 (t, J=7.5, 1H), 7.23 (d, J=7.6, 1H), 7.10 (d, J=7.5, 1H), 3.94 (s, 3H), 3.18 (q, J=7.3, 2H), 2.60 (q, J=7.6, 2H), 1.18 (t, J=7.6, 3H), 1.08 (t, J=7.3, 3H), MS (ES+, m/z)=387 (m+H)$^+$.

Example 177

N-[5-(ethylsulfonyl)-2-methoxyphenyl]-5-(3-pyridin-4-ylphenyl)-1,3-oxazol-2-amine

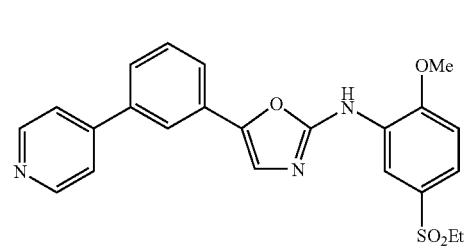

$^1$H NMR (400 MHz, d$_6$-DMSO): δ 9.73 (s, 1H), 8.74 (d, J=2.2, 1H), 8.63 (d, J=6.1, 2H) 7.97 (s, 1H), 7.71 (d, J=6.1, 2H), 7.64–7.68 (m, 3H), 7.55 (t, J=7.7, 1H), 7.44 (dd, J$_1$=2.2, J$_2$=8.5, 1H), 7.23 (d, J=8.6, 1H), 3.93 (s, 3H), 3.17 (q, J=7.3, 2H), 1.07 (t, J=7.3, 3H). MS (ES+, m/z)=436 (m+H)$^+$.

Example 178

N-[5-(ethylsulfonyl)-2-methoxyphenyl]-5-(3-pyridin-2-ylphenyl)-1,3-oxazol-2-amine

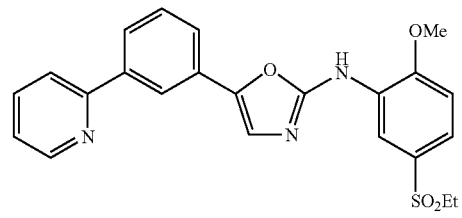

$^1$H NMR (400 MHz, d$_6$-DMSO): δ 9.79 (s, $_1$H), 8.76 (d, J=2.2, 1H), 8.65 (d, J=4., 1H) 8.32 (s, 1H), 7.98 (d, J=7.9, 1H), 7.94 (d, J=7.9, 1H), 7.88 (dt, J=1.6, 7.5, 1H), 7.65 (d,

J=7.9, 1H), 7.60 (s, 1H), 7.51 (t, J=7.9, 1H), 7.45 (dd, J=2.2, 8.6, 1H), 7.36 (dd, J=2.0, 7.1, 1H), 7.22 (d, J=8.6, 1H), 3.94 (s, 3H), 3.16 (q, J=7.3, 2H), 1.07 (t, J=7.3, 3H). MS (ES+, m/z)=436 (m+H)⁺.

Example 179

N-[5-(ethylsulfonyl)-2-methoxyphenyl]-5-[3-(1-methyl-1H-imidazol-5-yl)phenyl]-1,3-oxazol-2-amine

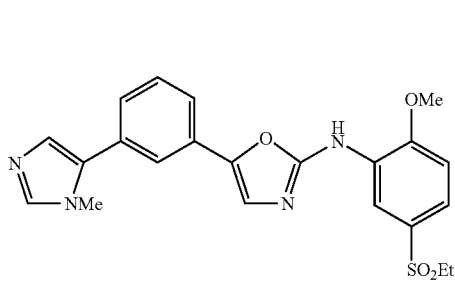

$^1$H NMR (400 MHz, d$_6$-DMSO): δ 9.71 (s, 1H), 8.73 (d, J=2.0, 1H), 7.68 (d, J=9.7, 2H), 7.59 (s, 1H), 7.55 (d, J=7.5, 1H), 7.45 (m, 2H), 7.35 (d, J=7.7, 1H), 7.22 (d, J=7.4, 1H), 7.07 (s, 1H), 3.93 (s, 3H), 3.67 (s, 3H), 3.15 (q, J=7.3, 2H), 1.06 (t, J=7.3, 3H). MS (ES+, m/z)=439 (m+H)⁺.

Example 180

5-(1,1'-biphenyl-3-yl)-N-[5-(ethylsulfonyl)-2-methoxyphenyl]-1,3-oxazol-2-amine

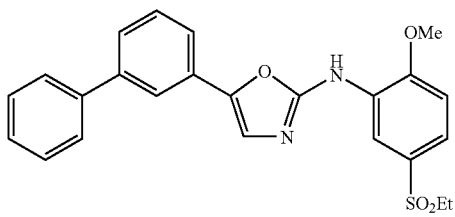

$^1$H NMR (400 MHz, d$_6$-DMSO): δ 9.72 (s, 1H), 8.74 (d, J=2.4, 1H), 7.85 (s, 1H), 7.67 (d, J=7.3, 2H), 7.61 (s, 1H), 7.44–7.58 (m, 6H), 7.37 (t, J=6.2, 1H), 7.22 (d, J=8.6, 1H), 3.93 (s, 3H), 3.15 (q, J=7.3, 2H), 1.06 (t, J=7.3, 3H). MS (ES+, m/z)=435 (m+H)⁺.

Example 181

N-[5-(ethylsulfonyl)-2-methoxyphenyl]-5-[3-(2-furyl)phenyl]-1,3-oxazol-2-amine

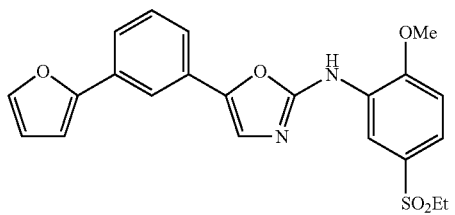

$^1$H NMR (400 MHz, d$_6$-DMSO): δ 9.85 (s, 1H), 8.83 (d, J=2.2, 1H), 7.97 (s, 1H), 7.83 (s, 1H), 7.62–7.68 (m, 2H), 7.50–7.60 (m, 3H), 7.30 (d, J=8.7, 1H), 7.05 (d, J=3.3, 1H), 6.67 (s, 1H), 4.02 (s, 3H), 3.25 (q, J=7.3, 2H), 1.15 (t, J=7.3, 3H). MS (ES+, m/z)=425 (m+H)⁺.

Example 182

N-[5-(ethylsulfonyl)-2-methoxyphenyl]-5-(3-pyrazin-2-ylphenyl)-1,3-oxazol-2-amine

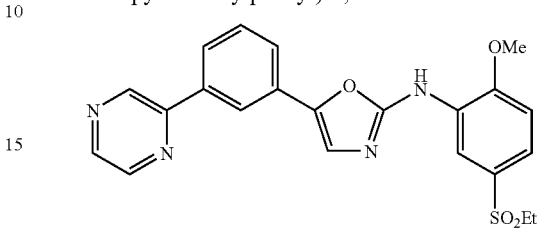

$^1$H NMR (400 MHz, d$_6$-DMSO): δ 9.80 (s, 1H), 9.28 (s, 1H), 8.76 (s, 1H), 8.71 (s, 1H), 8.62 (d, J=2.2, 1H), 8.36 (s, 1H), 8.01 (d, J=7.7, 1H), 7.71 (d, J=7.7, 1H), 7.64 (s, 1H), 7.57 (t, J=7.8, 1H), 7.45 (d, J=8.4, 1H), 7.23 (d, J=8.6, 1H), 3.94 (s, 3H), 3.16 (q, J=7.3, 2H), 1.07 (t, J=7.3, 3H). MS (ES+, m/z)=437 (m+H)⁺.

Example 183

N-[5-(ethylsulfonyl)-2-methoxyphenyl]-5-(4'-fluoro-1,1'-biphenyl-3-yl)-1,3-oxazol-2-amine

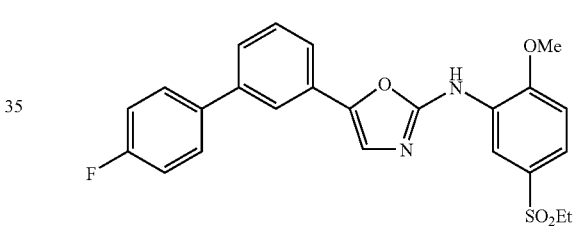

$^1$H NMR (400 MHz, d$_6$-DMSO): δ 9.73 (s, 1H), 8.74 (d, J=2.2, 1H), 7.83 (s, 1H), 7.67 (dd, J$_1$=5.5, J$_2$=8.8, 2H), 7.60 (s, 1H), 7.44–7.57 (m, 4H), 7.28 (t, J=8.8, 2H), 7.22 (d, J=8.6, 1H), 3.93 (s, 3H), 3.16 (q, J=7.3, 2H), 1.06 (t, J=7.3, 3H). MS (ES+, m/z)=453 (m+H)⁺.

Example 184

5-[3-(2,3-dihydro-1-benzofuran-5-yl)phenyl]-N-[5-(ethylsulfonyl)-2-methoxyphenyl]-1,3-oxazol-2-amine

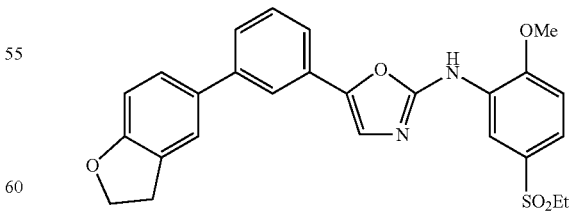

$^1$H NMR (400 MHz, d$_6$-DMSO): δ 9.72 (s, 1H), 8.74 (d, J=2.1, 1H), 7.78 (s, 1H), 7.35–7.62 (m, 7H), 7.22 (d, J=8.6, 1H), 6.82 (d, J=8.3, 1H), 4.53 (t, J=8.8, 2H), 3.93 (s, 3H), 3.14–3.22 (m, 4H), 1.04 (t, J=7.3, 3H). MS (ES+, m/z)=477 (m+H)⁺.

Example 185

N-[5-(ethylsulfonyl)-2-methoxyphenyl]-5-[3-(1,3-thiazol-2-yl)phenyl]-1,3-oxazol-2-amine

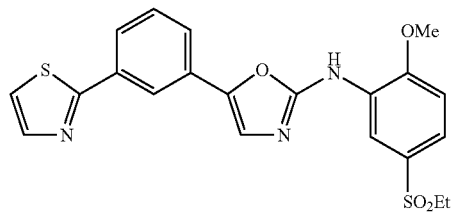

$^1$H NMR (400 MHz, d$_6$-DMSO): δ 9.77 (s, 1H), 9.09 (s, 1H), 8.73 (s, 1H), 8.34 (s, 1H), 7.83 (s, 1H), 7.41–7.65 (m, 5H), 7.23 (d, J=8.2, 1H), 3.93 (s, 3H), 3.16 (overlapping with water peak, 2H), 1.07 (t, J=7.3, 3H). MS (ES+, m/z)=442 (m+H)$^+$.

Example 186

4-methoxy-3-{[5-(3-pyridin-3-ylphenyl)-1,3-oxazol-2-yl]amino}benzenesulfonamide

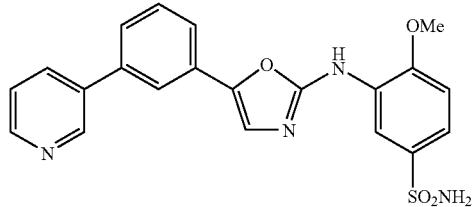

$^1$H NMR (400 MHz, d$_6$-DMSO): δ 9.62 (s, 1H), 8.73 (d, J=2.0, 1H), 8.66 (d, J=4.1, 1H), 8.32 (s, 1H), 7.99 (d, J=8.0, 1H), 7.93 (d, J=8.0, 1H), 7.90–7.86 (m, 1H), 7.65 (d, J=8.0, 1H), 7.58 (s, 1H), 7.53–7.49 (m, 1H), 7.41(d, J=8.6, 1H), 7.37–7.34 (m, 1H), 7.18 (s, 2H), 7.14 (d, J=8.6, 1H), 3.90 (s, 3H). MS (ES+, m/z)=423 (m+H)$^+$.

Example 187

3-{[5-(1,1'-biphenyl-3-yl)-1,3-oxazol-2-yl]amino}-4-methoxybenzenesulfonamide

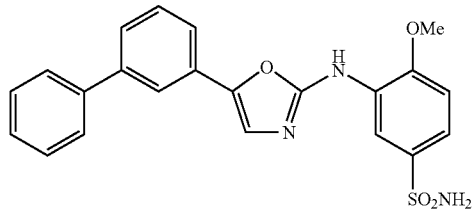

$^1$H NMR (400 MHz, d$_6$-DMSO): δ 9.56 (bs, 1H), 8.71 (d, J=2.2, 1H), 7.86 (s, 1H), 7.67 (d, J=7.5, 2H), 7.60–7.34 (m, 9H), 7.19–7.13 (m, 2H), 3.89 (s, 3H). MS (ES+, m/z)=422 (m+H)$^+$.

Example 188

4-methoxy-3-({5-[3-(1-methyl-1H-imidazol-5-yl)phenyl]-1,3-oxazol-2-yl}amino)benzenesulfonamide

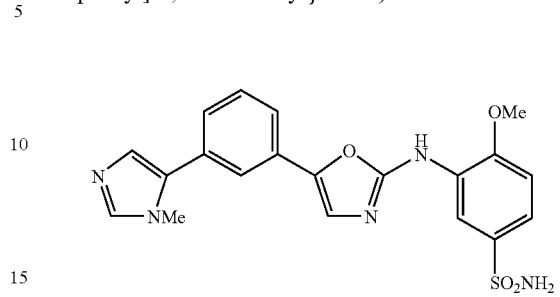

$^1$H NMR (400 MHz, d$_6$-DMSO): δ 9.35 (bs, 1H), 8.68 (s, 1H), 7.98 (s, 1H), 7.86 (s, 1H), 7.77 (s, 1H), 7.73–7.51 (m, 6H), 7.24 (m, 2H), 3.96 (s, 3H), 3.92 (s, 3H). MS (ES+, m/z)=427 (m+H)$^+$.

Example 189

3-{[5-(4-fluoro-1,1'-biphenyl-3-yl)-1,3-oxazol-2-yl]amino}-4-methoxy-N-methylbenzenesulfonamide

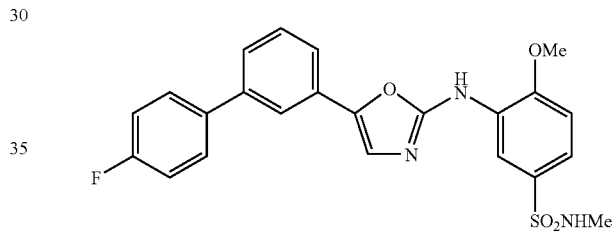

$^1$H NMR (400 MHz, d$_6$-DMSO): δ 9.61 (bs, 1H), 8.67 (d, J=2.2, 1H), 7.83 (s, 1H), 7.73–7.70 (m, 2H), 7.59 (s, 1H), 7.56 (d, J=7.0, 1H), 7.52–7.45 (m, 2H), 7.35 (dd, J$_1$=8.6, J$_2$=2.2, 1H), 7.30–7.25 (m, 3H), 7.17 (d, J=8.6, 1H), 3.91 (s, 3H), 2.36 (d, J=4.5, 3H). MS (ES+, m/z)=454 (m+H)$^+$.

Example 190 methyl 4-methoxy-3-{[5-(3-pyridin-2-ylphenyl)-1,3-oxazol-2-yl]amino}benzoate

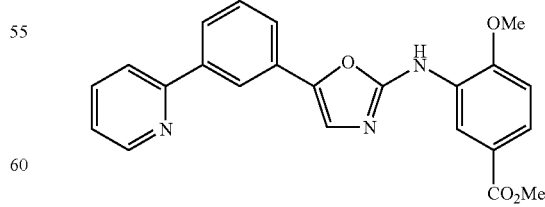

$^1$H NMR (300 MHz, d$_6$-DMSO): δ 9.62 (s, 1H), 8.83 (s, 1H), 8.74 (d, J=4.6, 1H), 8.40 (s, 1H), 8.08–7.94 (m, 3H), 7.74–7.57 (m, 4H), 7.46–7.42 (m, 1H), 7.19 (d, J=8.5, 1H), 3.99 (s, 3H), 3.87 (s, 3H). MS (ES+, m/z)=402, 403 (m+H)$^+$.

Example 191

3-{[5-(4'-fluoro-1,1'-biphenyl-3-yl)-1,3-oxazol-2-yl]amino}-4-methoxybenzenesulfonamide

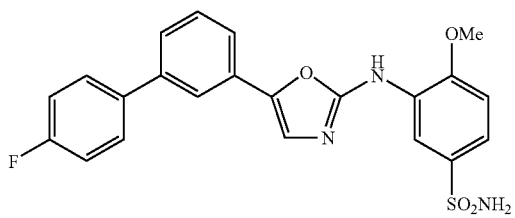

¹H NMR (400 MHz, d₆-DMSO): δ 9.64 (bs, 1H), 8.79 (s, 1H), 7.92 (s, 1H), 7.82–7.78 (m, 2H), 7.67–7.63 (m, 2H), 7.58–7.55 (m, 2H), 7.50 (d, J=8.8, 1H), 7.39–7.33 (m, 2H), 7.26–7.20 (m, 3H), 3.97 (s, 3H). MS (ES+, m/z)=440 (m+H)⁺.

Example 192

N-{5-[(1-ethylpropyl)sulfonyl]-2-methoxyphenyl}-5-(3-pyridin-2-ylphenyl)-1,3-oxazol-2-amine

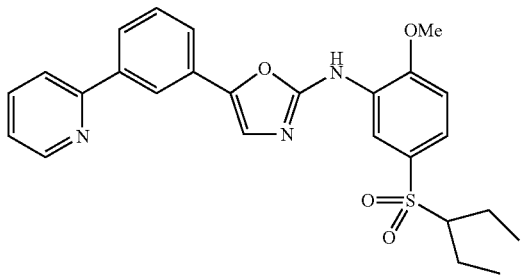

¹H NMR (300 MHz, d₆-DMSO): δ 9.87 (s, 1H), 8.82 (d, J=2.2, 1H), 8.73 (d, J=4.5, 1H), 8.40 (s, 1H), 8.08–7.93 (m, 3H), 7.74–7.68 (m, 2H), 7.62–7.41 (m, 3H), 7.30 (d, J=8.6, 1H), 4.02 (s, 3H), 2.99 (m, 1H), 1.80–1.73 (m, 2H), 1.66–1.56 (m, 2H), 0.75 (t, J=7.4, 6H), MS (ES+, m/z)=478 (m+H)⁺.

Example 193

N-[5-(isopropylsulfonyl)-2-methoxyphenyl]-5-(3-pyridin-2-ylphenyl)-1,3-oxazol-2-amine

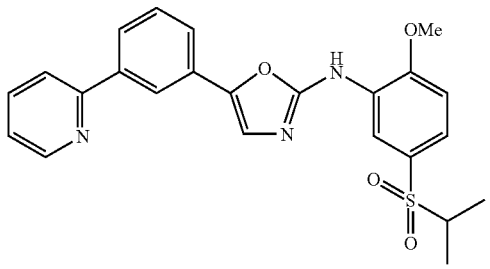

¹H NMR (400 MHz, d₆-DMSO): δ 9.91 (s, 1H), 8.76–8.73 (m, 2H), 8.32 (s, 1H), 8.16 (s, 2H), 7.93 (d, J=7.7, 1H), 7.72–7.42 (m, 5H), 7.24 (d, J=8.6, 1H), 3.94 (s, 3H), 3.29–3.22 (m, 1H), 1.20 (d, J=6.7, 6H). MS (ES+, m/z)=450 (m+H)⁺.

Example 194

N-[2-methoxy-5-(tetrahydrofuran-3-ylsulfonyl)phenyl]-5-(3-pyridin-2-ylphenyl)-1,3-oxazol-2-amine

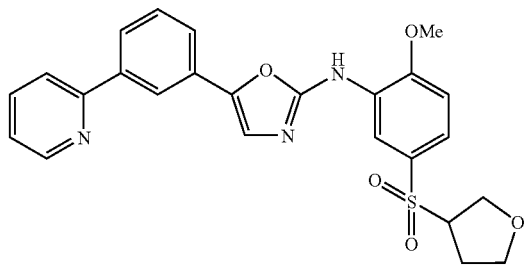

¹H NMR (300 MHz, d₆-DMSO): δ 9.92 (s, 1H), 8.88 (d, J=2.3, 1H), 8.73 (d, J=3.9, 1H), 8.41 (s, 1H), 8.08–7.93 (m, 3H), 7.75–7.69 (m, 2H), 7.62–7.54 (m, 2H), 7.46–7.41 (m, 1H), 7.31 (d, J=8.7, 1H), 4.12–3.42 (m, 2H), 2.20–2.12 (m, 2H). MS (ES+, m/z)=478 (m+H)⁺.

Example 195

N-[5-(isobutylsulfonyl)-2-methoxyphenyl]-5-(3-pyridin-2-ylphenyl)-1,3-oxazol-2-amine

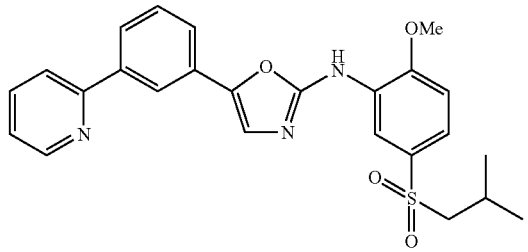

¹H NMR (400 MHz, d₆-DMSO): δ 9.79 (s, 1H), 8.77 (d, J=2.2, 1H), 8.65 (d, J=4.4, 1H), 8.32 (s, 1H), 7.99–7.85 (m, 3H), 7.65 (d, J=7.7, 1H), 7.61 (s, 1H), 7.53–7.46 (m, 2H), 7.37–7.33 (m, 1H), 7.21 (d, J=8.6, 1H), 3.27 (s, 3H), 3.07 (d, J=6.4, 2H), 2.01–1.93 (m, 1H), 0.92 (d, J=6.7, 6H). MS (ES+, m/z)=464 (m+H)⁺.

Example 196

5-(1,1'-biphenyl-3-yl)-N-{2-methoxy-5-[(1-pyridin-4-ylethyl)sulfonyl]phenyl}-1,3-oxazol-2-amine

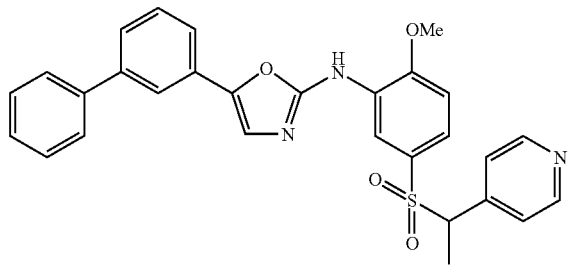

$^1$H NMR (400 MHz, d$_6$-DMSO): δ 9.68 (s, 1H), 8.56 (d, J=2.2, 1H), 8.43 (d, J=6.0, 2H), 7.85 (s, 1H), 7.69–7.67 (m, 2H), 7.59–7.43 (m, 6H), 7.36 (t, J=7.3, 1H), 7.20–7.12 (m, 4H), 4.62 (q, J=7.1, 1H), 3.91 (s, 3H), 1.53 (d, J=7.1, 3H). MS (ES+, m/z)=512 (m+H)$^+$.

Example 197

N-{2-methoxy-5-[(tetrahydrofuran-2-ylmethyl)sulfonyl]phenyl}-5-(3-pyridin-2-ylphenyl)-1,3-oxazol-2-amine

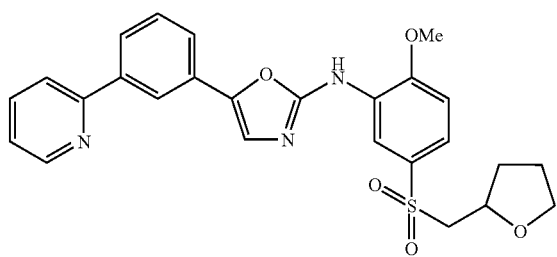

$^1$H NMR (300 MHz, d$_6$-DMSO): δ 9.85 (s, 1H), 8.84 (d, J=2.2, 1H), 8.73 (d, J=3.9, 1H), 8.40 (t, J=1.7, 1H), 8.08–7.93 (m, 3H), 7.73 (d, J=8.0, 1H), 7.68 (s, 1H), 7.62–7.54 (m, 2H), 7.46–7.41 (m, 1H), 7.29 (d, J=8.7, 1H), 4.15–4.06 (m, 1H), 4.01 (s, 3H), 3.70–3.52 (m, 2H), 3.47 (d, J=6.1, 2H), 2.05–1.94 (m, 1H), 1.86–1.69 (m, 2H), 1.65–1.54 (m, 1H). MS (ES+, m/z)=492 (m+H)$^+$.

Example 198

N-(2-methoxy-5-{[2-(4-methyl-1,3-thiazol-5-yl)ethyl]sulfonyl}phenyl)-5-(3-pyridin-2-ylphenyl)-1,3-oxazol-2-amine

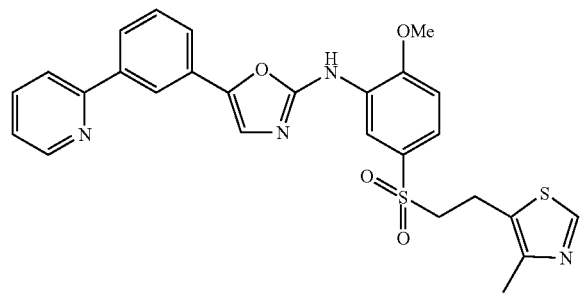

$^1$H NMR (400 MHz, d$_6$-DMSO): δ 9.80 (s, 1H), 8.78 (d, J=2.2, 1H), 8.72 (s, 1H), 8.65 (d, J=4.2, 1H), 8.33 (s, 1H), 7.98 (d, J=7.9, 1H), 7.93 (d, J=7.7, 1H), 7.87 (dt, J$_1$=7.7, J$_2$=1.7, 1H), 7.65 (d, J=7.9, 1H), 7.60 (s, 1H), 7.53–7.48 (m, 2H), 7.35 (dd, J$_1$=7.1, J$_2$=5.1, 1H), 7.21 (d, J=8.8, 1H), 3.93 (s, 3H), 3.49–3.46 (m, 2H), 3.06–3.03 (m, 2H), 2.18 (s, 3H). MS (ES+, m/z)=533 (m+H)$^+$.

Example 199

5-(1,1'-biphenyl-3-yl)-N-(3,4,5-trimethoxyphenyl)-1,3-oxazol-2-amine

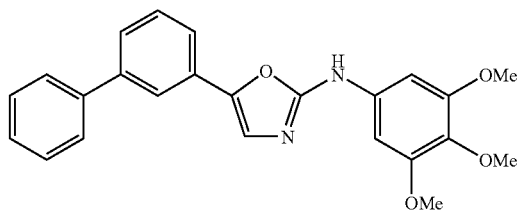

$^1$H NMR (400 MHz, d$_6$-DMSO): δ 10.21 (s, 1H), 7.78 (s, 1H), 7.65 (d, J=7.5, 2H), 7.54 (s, 1H), 7.52–7.42 (m, 6H), 7.32 (t, J=7.3, 1H), 6.97 (s, 2H), 3.72 (s, 6H), 3.56 (s, 3H), MS (ES+, m/z)=403 (m+H)$^+$.

Example 200

1-[3-(2-{[5-(ethylsulfonyl)-2-methoxyphenyl]amino}-1,3-oxazol-5-yl)phenyl]ethanone

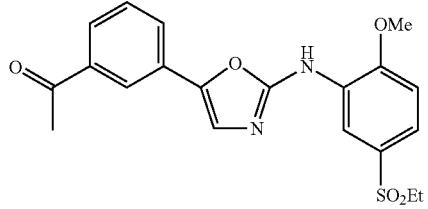

The title compound was obtained using 1-ethoxyvinyl-tributyltin as the Stille reagent. The resulting ethyl-vinyl ether was hydrolyzed by stirring with 1N HCl for 30 min. The title compound was isolated by dichloromethane extraction. $^1$H NMR (400 MHz, d$_6$-DMSO): δ 9.90 (s, 1H), 8.81 (d, J=2.3, 1H), 8.18 (s, 1H), 7.90 (d, J=9.2, 2H), 7.72 (s, 1H), 7.63 (t, J=8.0, 1H), 7.52 (dd, J$_1$=2.3, J$_2$=6.3, 1H), 7.31 (d, J=8.5, 1H), 4.01 (s, 3H), 3.24 (q, J=7.3, 2H), 2.66 (s, 3H), 1.15 (t, J=7.3, 3H). MS (ES+, m/z)=401 (m+H)$^+$.

Example 201

1-[4-(2-{[5-(ethylsulfonyl)-2-methoxyphenyl]amino}-1,3-oxazol-5-yl)phenyl]ethanone

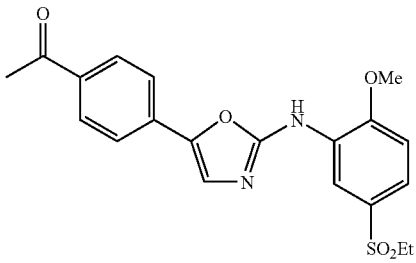

The title compound was obtained treating the title compound of Example 135 with 1-ethoxyvinyltributyltin as the Stille reagent. The resulting ethyl-vinyl ether was hydrolyzed by stirring with 1N HCl for 30 min. The title compound was isolated by dichloromethane extraction. $^1$H NMR (400 MHz, d$_6$-DMSO): δ 9.87 (s, 1H), 8.71 (d, J=2.2, 1H), 7.98 (d, J=8.5, 2H), 7.71–7.69 (m, 3H), 7.47 (dd, J$_1$=8.5, J$_2$=2.2, 1H), 7.23 (d, J=8.5, 1H), 3.93 (s, 3H), 3.16 (q, J=7.3, 2H), 2.53 (s, 3H), 1.07 (t, J=7.3, 3H). MS (ES+, m/z)=401 (m+H)$^+$.

Example 202

4-methoxy-3-{[5-(3-pyridin-3-ylphenyl)-1,3-oxazol-2-yl]amino}benzenesulfonyl fluoride

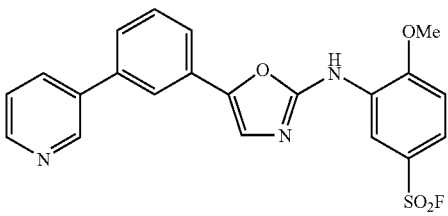

$^1$H NMR (400 MHz, d$_6$-DMSO): δ 10.05 (s, 1H), 9.02 (d, J=2.4, 1H), 8.91 (d, J=2.4, 1H), 8.57 (d, J=4.5, 1H), 8.08 (d, J=8.1, 1H); 7.93 (s, 1H), 7.72 (dd, J$_1$=8.8, J$_2$=2.4, 1H), 7.67 (s, 1H), 7.60–7.60 (m, 2H), 7.56–7.46 (m, 2H), 7.33 (d, J=8.8, 1H), 3.99 (s, 3H). MS (ES+, m/z)=426 (m+H)$^+$.

Example 203

4-methoxy-3-{[5-(3-pyridin-2-ylphenyl)-1,3-oxazol-2-yl]amino}benzenesulfonyl fluoride

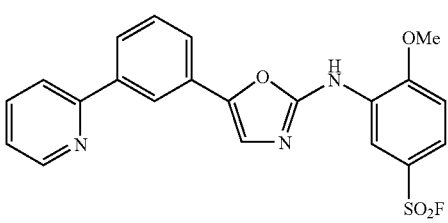

$^1$H NMR (400 MHz, d$_6$-DMSO): δ 10.20 (s, 1H), 9.12 (d, J=2.2, 1H), 8.74 (d, J=4.6, 1H), 8.42 (s, 1H), 8.07–7.94 (m, 3H), 7.82–7.72 (m, 3H), 7.60 (t, J=7.7, 1H), 7.46–7.39 (m, 2H), 4.07 (s, 3H). MS (ES+, m/z)=426 (m+H)$^+$.

Example 204

3'-(2-{[5-(ethylsulfonyl)-2-methoxyphenyl]amino}-1,3-oxazol-5-yl)-1,1'-biphenyl-4-carbonitrile

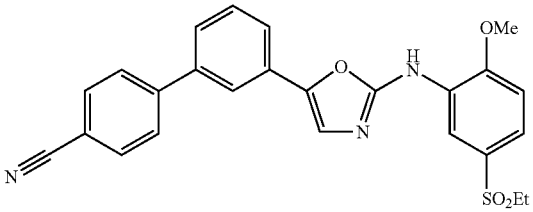

A mixture of the title compound of Example 100 (250 mg, 0.57 mmol), 4-cyanophenyl boronic acid (108 mg, 0.74 mmol), 2M aqueous sodium carbonate solution (0.5 mL, 1.0 mmol), and (bistriphenylphosphine)palladium(II) chloride (50 mg, 0.071 mmol) was suspended in DMF (2 mL) and stirred at 100° C. After 20 min, the reaction was determined to be complete by TLC analysis. After cooling to RT, the DMF was evaporated under reduced pressure. The crude product was partitioned between dichloromethane (50 mL) and water (50 mL). The organic layer was separated, dried over anhydrous magnesium sulfate, filtered, and concentrated under reduced pressure. The crude product was purified by column chromatography on silica gel eluting with hexane:ethyl acetate (1:1) to afford the title compound (152 mg, 58%) as a solid white powder. $^1$H NMR (400 MHz, d$_6$-DMSO): δ 9.82 (s, 1H), 8.81 (d, J=2.2, 1H), 7.95–8.05 (m, 5H), 7.68–7.74 (m, 3H), 7.63 (d, J=7.8, 1H), 7.53 (dd, J$_1$=2.2, J$_2$=8.7, 1H), 7.31 (d, J=8.5, 1H), 4.01 (s, 3H), 3.24 (q, J=7.3, 2H), 1.14 (t, J=7.3, 3H). MS (ES+, m/z)=459 (m+H)$^+$.

Unless otherwise indicated, the compounds of Examples 205–37 were prepared according to the general procedures set forth in the synthesis of the title compound of Example 204. It will be readily apparent to those skilled in the art that the syntheses of these examples is illustrated in Scheme 11 described above. The NMR data characterizing these examples describe either the salt form or the free base form.

Example 205

3'-(2-{[5-(ethylsulfonyl)-2-methoxyphenyl]amino}-1,3-oxazol-5-yl)-1,1'-biphenyl-3-carboxylic acid

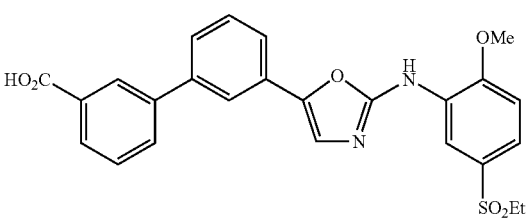

$^1$H NMR (400 MHz, d$_6$-DMSO): δ 9.83 (s, 1H), J=2.1, 1H), 8,21 (s, 1H), 7.90–7.98 (m, 3H), 7.66 (s, 1H), 7.52–7.65 (m, 4H), 7.49 (dd, J$_1$=2.3, J$_2$=8.5, 1H), 7.25 (d,

J=8.7, 1H), 3.97 (s, 3H), 3.19 (q, J=7.3, 2H), 1.10 (t, J=7.3, 3H). MS (ES+, m/z)=478 (m+H)⁺.

Example 206

3-(2-{[5-(ethylsulfonyl)-2-methoxyphenyl]amino}-1,3-oxazol-5-yl)-1,1'-biphenyl-3-carbonitrile

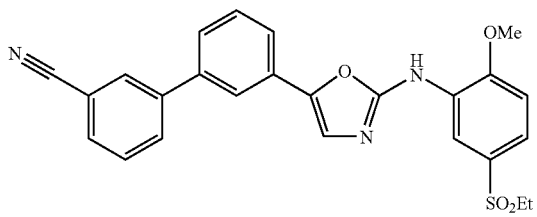

$^1$H NMR (400 MHz, d₆-DMSO): δ 9.76 (s, 1H), 8.77 (d, J=2.2, 1H), 8.21 (s, 1H), 8.07 (d, J=8.0, 1H) 7.96 (s, 1H), 7.86 (d, J=7.8, 1H), 7.71 (d, J=7.9, 1H), 7.62–7.68 (m, 3H), 7.57 (d, J=7.7, 1H), 7.49 (dd, J₁=2.3, J₂=8.5, 1H), 7.26 (d, J=8.6, 1H), 3.97 (s, 3H), 3.20 (q, J=7.3, 2H), 1.10 (t, J=7.3, 3H). MS (ES+, m/z)=459 (m+H)⁺.

Example 207

N-[5-(ethylsulfonyl)-2-methoxyphenyl]-5-(3'-fluoro-1,1'-biphenyl-3-yl)-1,3-oxazol-2-amine

$^1$H NMR (400 MHz, d₆-DMSO): δ 9.72 (s, 1H), 8.74 (d, J=2.2, 1H), 7.88 (s, 1H), 7.62 (s, 1H), 7.36–7.60 (m, 7H), 7.16–7.26 (m, 2H), 3.93 (s, 3H), 3.16 (q, J=7.3, 2H), 1.07 (t, J=7.3, 3H). MS (ES+, m/z)=453 (m+H)⁺.

Example 208

N-[5-(ethylsulfonyl)-2-methoxyphenyl]-5-(3-quinolin-3-ylphenyl)-1,3-oxazol-2-amine

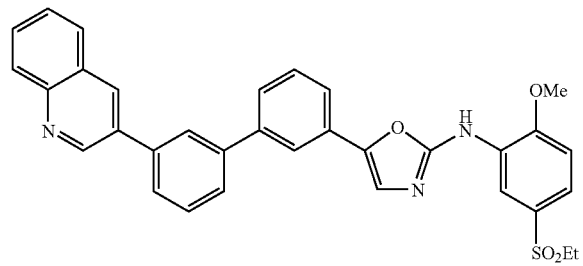

$^1$H NMR (400 MHz, d₆-DMSO): δ 9.75 (s, 1H), 9.26 (d, J=2.2, 1H), 8.75 (d, J=2.2, 1H), 8.68 (d, J=2.2, 1H), 8.02–8.07 (m, 3H), 7.73–7.77 (m, 2H), 7.56–7.66 (m, 4H), 7.46 (dd, J₁=2.1, J₂=8.4, 1H), 7.23 (d, J=8.6, 1H), 3.94 (s, 3H), 3.16 (q, J=7.3, 2H), 1.07 (t, J=7.3, 3H). MS (ES+, m/z)=486 (m+H)⁺.

Example 209

N-[5-(ethylsulfonyl)-2-methoxyphenyl]-5-[3-(5-methylthien-2-yl)phenyl]-1,3-oxazol-2-amine

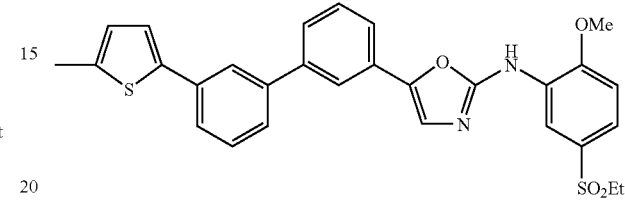

$^1$H NMR (400 MHz, d₆-DMSO): δ 9.75 (s, 1H), 8.74 (s, 1H), 7.74 (s, 1H), 7.52–7.61 (m, 1H), 7.33–7.50 (m, 4H), 7.32 (s, 1H), 7.22 (d, J=8.4, 1H), 6.81 (s, 1H), 3.93 (s, 3H), 3.17 (q, J=7.4, 2H), 1.07 (t, J=7.2, 3H) (note: 3H of methylthiazole not observed—overlaps with solvent water peak). MS (ES–, m/z)=453 (m–H)⁺.

Example 210

N-[5-(ethylsulfonyl)-2-methoxyphenyl]-5-[3-(1H-indol-5-yl)phenyl]-1,3-oxazol-2-amine

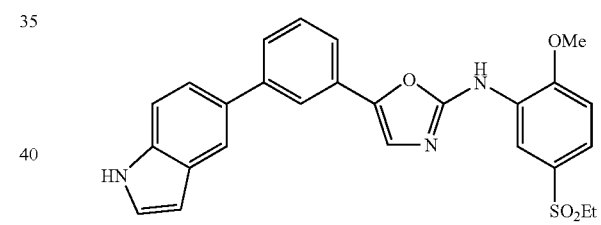

$^1$H NMR (400 MHz, d₆-DMSO): δ 11.13 (s, 1H), 9.74 (s, 1H), 8.76 (d, J=1.9, 1H), 7.87 (s, 1H), 7.83 (s, 1H), 7.39–7.59 (m, 7H), 7.35 (s, 1 H), 7.22 (d, J=8.4, 1H), 6.46 (s, 1H), 3.94 (s, 3H), 3.16 (q, J=7.3, 2H), 1.07 (t, J=7.3, 3H). MS (ES–, m/z)=472 (m–H)⁺.

Example 211 methyl 3'-(2-{[5-(ethylsulfonyl)-2-methoxyphenyl]amino}-1,3-oxazol-5-yl)-1,1'-biphenyl-4-carboxylate

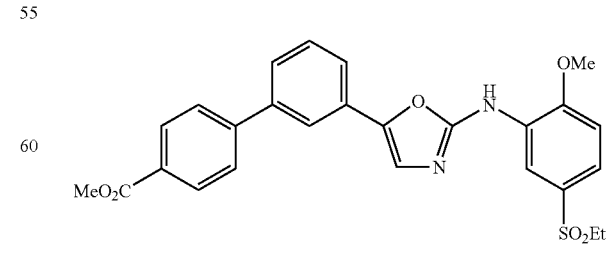

$^1$H NMR (400 MHz, d₆-DMSO): δ 9.77 (s, 1H), 8.77 (d, J=2.1, 1H), 8.06 (d, J=8.3, 2H), 7.96 (s, 1H), 7.88 (d, J=8.3,

2H), 7.62–7.69 (m, 3H), 7.58 (d, J=7.6, 1H), 7.49 (dd, $J_1$=2.2, $J_2$=8.4, 1H), 7.26 (d, J=8.6, 1H), 3,97 (s, 3H), 3.88 (s, 3H), 3.22 (q, J=7.3, 2H), 1.10 (t, J=7.3, 3H). MS (ES, m/z)=491 (m–H)⁺.

Example 212

3-{[5-(3'-fluoro-1,1'-biphenyl-3-yl)-1,3-oxazol-2-yl]amino}-4-methoxy-N-methylbenzenesulfonamide

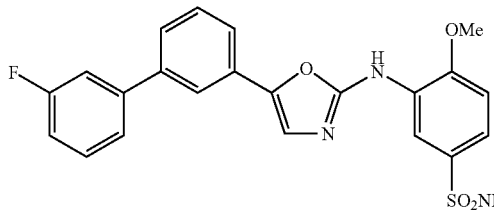

¹H NMR (400 MHz, d₆-DMSO): δ 9.62 (bs, 1H), 8.68 (s, 1H), 7.88 (s, 1H), 7.61–7.46 (m, 7H), 7.36 (d, J=8.4, 1H), 7.25–7.16 (m, 3H), 3.91 (s, 3H), 2.35 (s, 3H). MS (ES+, m/z)=454 (m+H)⁺.

Example 213

3-{[5-(1,1'-biphenyl-3-yl)-1,3-oxazol-2-yl]amino}-4-methoxybenzenesulfonyl fluoride

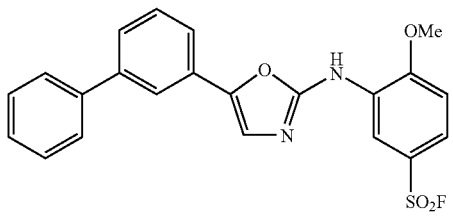

¹H NMR (400 MHz, d₆-DMSO): δ 10.05 (s, 1H), 9.03 (d, J=2.3, 1H), 7.86 (s, 1H), 7.72 (dd, $J_1$=8.7, $J_2$=2.3, 1H), 7.68–7.64 (m, 2H), 7.61–7.44 (m, 6H), 7.38–7.31 (m, 6H), 7.38–7.31 (m, 2H), 3.99 (s, 3H). MS (ES+, m/z)=425 (m+H)⁺.

Example 214

3-{[5-(3'-fluoro-1,1'-biphenyl-3-yl)-1,3-oxazol-2-yl]amino}-4-methoxybenzenesulfonamide

¹H NMR (400 MHz, d₆-DMSO): δ 9.56 (bs, 1H), 8.71 (d, J=2.2, 1H), 7.89 (s, 1H), 7.61–7.46 (m, 7H), 7.41 (dd, $J_1$=8.4, $J_2$=2.2, 1H), 7.21–7.13 (m, 4H), 3.89 (s, 3H). MS (ES+, m/z)=440 (m+H)⁺.

Example 215

N-[5-(ethylsulfonyl)-2-methoxyphenyl]-5-(2'-fluoro-1,1'-biphenyl-3-yl)-1,3-oxazol-2-amine

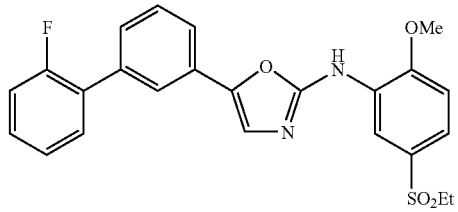

¹H NMR (400 MHz, d₆-DMSO): δ 9.82 (s, 1H), 8.82 (d, J=2.1, 1H), 7.82 (s, 1H), 7.70–7.34 (m, 9H), 7.30 (d, J=8.6, 1H), 4.00 (s, 3H), 3.23 (q, J=7.3, 2H), 1.14 (t, J=7.3, 3H). MS (ES+, m/z)=453 (m+H)⁺.

Example 216

5-(2'-chloro-1,1'-biphenyl-3-yl)-N-[5-(ethylsulfonyl)-2-methoxyphenyl]-1,3-oxazol-2-amine

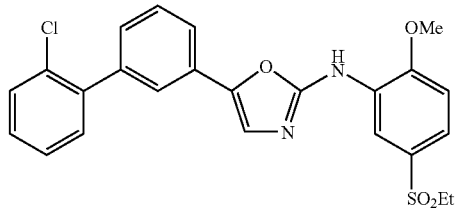

¹H NMR (400 MHz, d₆-DMSO): δ 9.80 (bs, 1H), 8.81 (s, 1H), 7.69–7.49 (m, 9H), 7.37 (d, J=7.9, 1H), 7.30 (d, J=8.7, 1H), 4.00 (s, 3H), 3.22 (q, J=7.2, 2H), 1.13 (t, J=7.2, 3H). MS (ES+, m/z)=469 (m+H)⁺, 471 (m+H)

Example 217

4-methoxy-N-methyl-3-{[5-(3-pyridin-2-ylphenyl)-1,3-oxazol-2-yl]amino}benzenesulfonamide

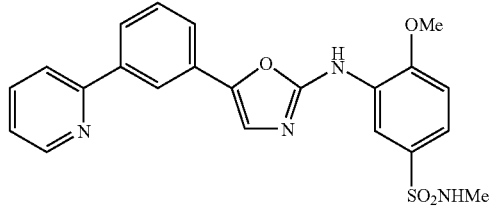

The title compound of Example 203 (100 mg, 0.24 μmol) was treated with methylamine (2 mL, 40% aq. soln.) in a sealed tube. After stirring at 100° C. overnight, the mixture

Example 218

N-ethyl-4-methoxy-3-{[5-(3-pyridin-2-ylphenyl)-1,3-oxazol-2-yl]amino}benzenesulfonamide

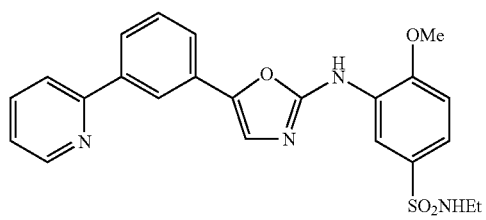

$^1$H NMR (400 MHz, d$_6$-DMSO): δ 9.48 (bs, 1H), 8.70 (s, 1H), 8.66 (d, J=3.8, 1H), 8.32 (s, 1H), 7.98 (d, J=7.9, 1H), 7.93 (d, J=7.7, 1H), 7.90–7.86 (m, 1H), 7.66–7.64 (m, 1H), 7.59 (s, 1H), 7.51 (t, J=7.7, 1H), 7.36 (m, 3H), 7.16 (d, J=8.6, 1H), 3.91 (s, 3H), 2.73 (m, 2H), 0.92 (t, J=7.2, 3H). MS (ES+, m/z)=451 (m+H)$^+$.

Example 219

4-methoxy-3-{[5-(3-pyridin-2-ylphenyl)-1,3-oxazol-2-yl]amino}benzenesulfonamide

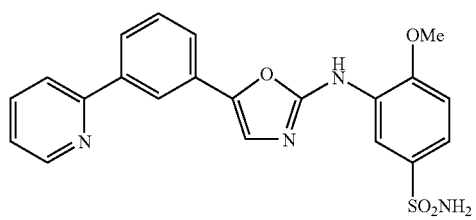

$^1$H NMR (400 MHz, d$_6$-DMSO): δ 9.62 (s, 1H), 8.73 (d, J=2.0, 1H), 8.66 (d, J=4.1, 1H), 8.32 (s, 1H), 7.99 (d, J=8.0, 1H), 7.93 (d, J=8.0, 1H), 7.90–7.86 (m, 1H), 7.65 (d, J=7.9, 1H), 7.58 (s, 1H), 7.59 (t, J=7.9, 1H), 7.41 (d, J=8.6, 1H), 7.37–7.34 (m, 1H), 7.18 (s, 2H), 7.14 (d, J=8.6, 1H), 3.90 (s, 3H). MS (ES+, m/z)=423 (m+H)$^+$.

Example 220

N-isopropyl-4-methoxy-3-{[5-(3-pyridin-2-ylphenyl)-1,3-oxazol-2-yl]amino}benzenesulfonamide

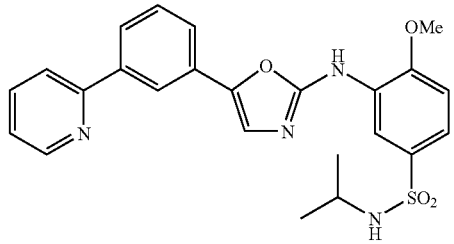

$^1$H NMR (300 MHz, d$_6$-DMSO): δ 8.80 (d, J=1.9, 1H), 8.74 (d, J=4.1, 1H), 8.40 (s, 1H), 8.09–7.93 (m, 3H), 7.73 (d, J=7.7, 1H), 7.67 (s, 1H), 7.59 (t, J=7.7, 1H), 7.48–7.41 (m, 3H), 7.23 (d, J=8.5, 1H), 3.98 (s, 3H), 3.26 (m, 1H), 0.98 (d, J=6.5, 6H). MS (ES+, m/z)=465 (m+H)$^+$.

Example 221

N-(cyclopropylmethyl)-4-methoxy-3-{[5-(3-pyridin-2-ylphenyl)-1,3-oxazol-2-yl]amino}benzenesulfonamide

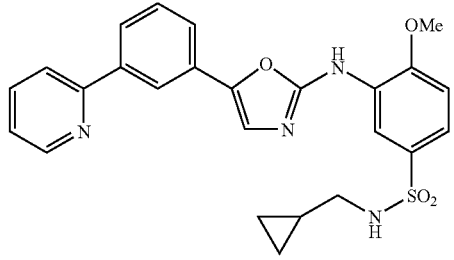

$^1$H NMR (400 MHz, d$_6$-DMSO): δ 9.64 (bs, 1H), 8.69 (s, 1H), 8.66 (d, J=4.1, 1H), 8.32 (s, 1H), 7.98 (d, J=7.9, 1H), 7.93 (d, J=7.7, 1H), 7.89–7.86 (m, 1H), 7.65 (d, J=7.7, 1H), 7.59 (s, 1H), 7.54–7.49 (m, 2H), 7.38–7.34 (m, 2H), 7.14 (d, J=8.5, 1H), 3.90 (s, 3H), 2.60 (t, J=6.0, 2H), 0.76 (m, 1H), 0.29 (d, J=7.5, 2H), 0.03 (d, J=4.6, 2H). MS (ES+, m/z)=477 (m+H)$^+$.

Example 222

N,N-diethyl-4-methoxy-3-{[5-(3-pyridin-2-ylphenyl)-1,3-oxazol-2-yl]amino}benzenesulfonamide

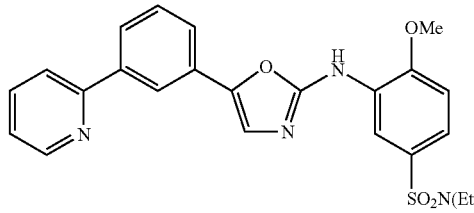

¹H NMR (400 MHz, d₆-DMSO): δ 9.76 (s, 1H), 8.74 (d, J=2.2, 1H), 8.77 (d, J=4.4, 1H), 8.35 (s, 1H), 8.07–7.89 (m, 3H), 7.68 (d, J=7.8, 1H), 7.63 (s, 1H), 7.55 (t, J=7.8, 1H), 7.41–7.39 (m, 2H), 7.19 (d, J=8.6, 1H), 3.95 (s, 3H), 3.14 (q, J=7.1, 4H), 1.04 (t, J=7.1, 4H), 1.04 (t, J=7.1, 6H). MS (ES+, m/z)=478 (m+H)⁺.

Example 223

N-isopropyl-4-methoxy-3-{[5-(3-pyridin-3-ylphenyl)-1,3-oxazol-2-yl]amino}benzenesulfonamide

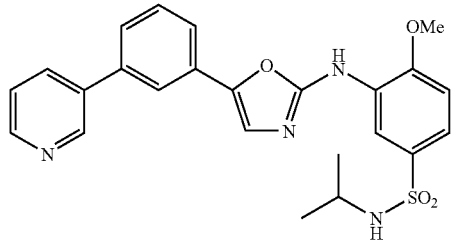

¹H NMR (400 MHz, d₆-DMSO): δ 9.59 (bs, 1H), 8.91 (s, 1H), 8.69 (d, J=2.0, 1H), 8.57 (d, J=4.6, 1H), 8.09 (d, J=8.1, 1H), 7.92 (s, 1H), 7.62–7.58 (m, 3H), 7.53 (d, J=7.7, 1H), 7.49–7.46 (m, 1H), 7.41–7.37 (m, 2H), 7.15 (d, J=8.6, 1H), 3.90 (s, 3H), 3.18 (m, 1H), 0.090 (d, J=6.6, 6H). MS (ES+, m/z)=465 (m+H)⁺.

Example 224

3-{[5-(1,1'-biphenyl-3-yl)-1,3-oxazol-2-yl]amino}-N-isopropyl-4-methoxybenzenesulfonamide

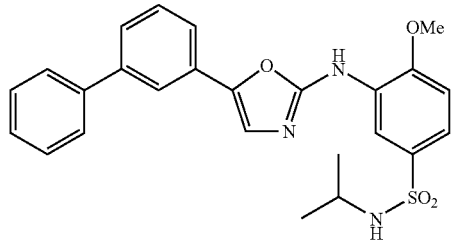

¹H NMR (400 MHz, d₆-DMSO): δ 9.56 (bs, 1H), 8.69 (s, 1H), 7.85 (s, 1H), 7.67 (d, J=7.1, 2H), 7.59 (s, 1H), 7.57–7.36 (m, 7H), 7.14 (d, J=8.6, 1H), 3.90 (s, 3H), 3.19 (m, 1H), 0.90 (d, J=6.4, 6H). MS (ES+, m/z)=464 (m+H)⁺.

Example 225

3-{[5-(1,1'-biphenyl-3-yl)-1,3-oxazol-2-yl]amino}-4-methoxy-N,N-dimethylbenzenesulfonamide

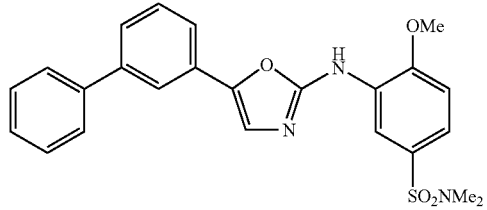

¹H NMR (400 MHz, d₆-DMSO): δ 9.70 (bs, 1H), 8.66 (d, J=2.0, 1H), 7.84 (s, 1H), 7.67 (d, J=7.5, 2H), 7.59 (s, 1H), 7.57–7.43 (m, 5H), 7.37 (d, J=7.3, 1H), 7.32 (dd, J₁=8.6, J₂=2.2, 1H), 7.20 (d, J=8.4, 1H), 3.93 (s, 3H), 2.55 (s, 6H). MS (ES+, m/z)=450 (m+H)⁺.

Example 226

3-{[5-(1,1'-biphenyl-3-yl)-1,3-oxazol-2-yl]amino-}-N-cyclopropyl-4-methoxybenzenesulfonamide

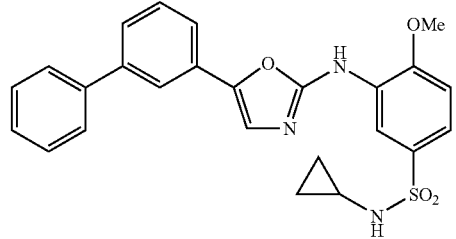

¹H NMR (400 MHz, d₆-DMSO): δ 9.61 (bs, 1H), 8.71 (d, J=2.2, 1H), 7.85 (s, 1H), 7.73 (s, 1H), 7.67 (d, J=7.3, 2H), 7.59 (s, 1H), 7.58–7.34 (m, 7H), 7.17 (d, J=8.6, 1H), 3.91 (s, 3H), 2.06 (m, 1H), 0.42–0.33 (m, 4H). MS (ES+, m/z)=462 (m+H)⁺.

Example 227

3-{[5-(1,1'-biphenyl-3-yl)-1,3-oxazol-2-yl]amino}-N-butyl-4-methoxybenzenesulfonamide

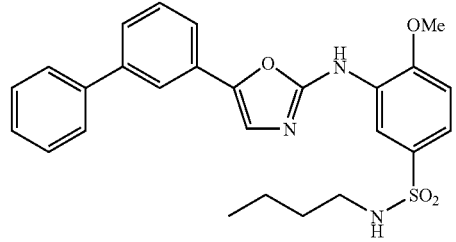

¹H NMR (300 MHz, d₆-DMSO): δ 8.76 (s, 1H), 7.94 (s, 1H), 7.74–7.43 (m, 10H), 7.35 (m, 1H), 3.98 (s, 3H), 2.75 (m, 2H), 1.37 (m, 2H), 1.26 (m, 2H), 0.81 (m, 3H). MS (ES+, m/z)=428 (m+H)⁺.

Example 228

3-{[5-(1,1'-biphenyl-3-yl)-1,3-oxazol-2-yl]amino}-N,N-diethyl-4-methoxybenzenesulfonamide

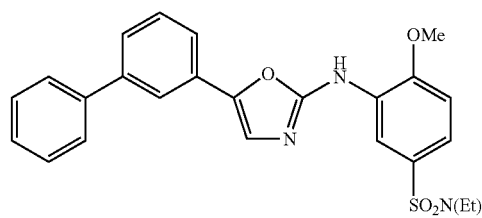

$^1$H NMR (400 MHz, d$_6$-DMSO): δ 9.69 (s, 1H), 8.74 (d, J=2.0, 1H), 7.89 (s, 1H), 7.70 (d, J=7.3, 2H), 7.64 (s, 1H), 7.61–7.39 (m, 6H), 7.19 (d, J=8.4, 1H), 3.94 (s, 3H), 3.14 (q, J=7.0, 4H), 1.03 (t, J=7.0, 6H). MS (ES+, m/z)=478 (m+H)$^+$.

Example 229

3-{[5-(1,1'-biphenyl-3-yl)-1,3-oxazol-2-yl]amino}-4-methoxy-N-(tetrahydrofuran-2-ylmethyl)benzenesulfonamide

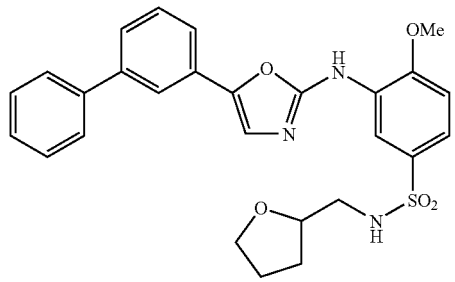

$^1$H NMR (400 MHz, d$_6$-DMSO): δ 9.68 (s, 1H), 8.76 (d, J=2.2, 1H), 7.94 (s, 1H), 7.76 (d, J=7.6, 2H), 7.53 (s, 1H), 7.51–7.41 (m, 7H), 7.23 (d, J=8.5, 1H), 3.98 (s, 3H), 3.85–3.81 (m, 1H), 3.71–7.66 (m, 1H), 3.62–3.57 (m, 1H), 2.82–2.76 (m, 2H), 1.90–1.75 (m, 3H), 1.58–1.52 (m, 1H). MS (ES+, m/z)=506 (m+H)$^+$.

Intermediate 230a (2E)-3-(dimethylamino)-1-[3-(2-{[5-(ethylsulfonyl)-2-methoxyphenyl]amino}-1,3-oxazol-5-yl)phenyl]prop-2-en-1-one

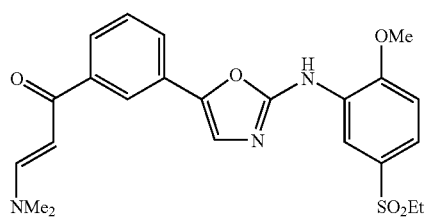

The title compound (3.0 g, 7.5 mmol) from Example 200 was combined with dimethylformamide ditertbutylacetal (10.0 g, 4.9 mmol) in DMF (ca. 4 mL). After the reaction was stirred at 130° C. for 2 h, the excess solvent was evaporated under reduced pressure. The crude product was coated onto silica gel and chromatographed on silica gel using dichloromethane (98%) and methanol (20%) as eluent affording the title compound (1.6 g, 3.9 mmol) as a yellow solid.

Example 230

4-[3-(2-{[5-(ethylsulfonyl)-2-methoxyphenyl]amino}-1,3-oxazol-5-yl)phenyl]-N-isopropylpyrimidin-2-amine

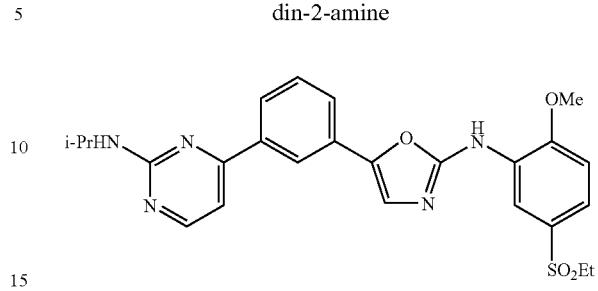

Intermediate 230a (100 mg, 0.22 mmol) was combined with n-isopropyl guanidine sulfate (100 mg, 0.5 mmol) and sodium methoxide (50 mg, 1 mmol) in absolute ethanol (35 mL) under an atmosphere of nitrogen. After refluxing for 18 h, an additional amount of guanidine (44 mg, 0.2 mmol) and sodium methoxide (20 mg, 0.4 mmol) was added and was refluxed for an additional 6 h. The reaction was cooled to RT and evaporated under reduced pressure. The crude product was diluted with dichloromethane (50 mL) and washed with water (50 mL). The organic layer was separated, dried with anhydrous magnesium sulfate, filtered, and evaporated under reduced pressure. The crude product was coated onto silica gel and chromatographed on silica gel using hexanes: ethyl acetate (1:1) as eluent affording the title compound (38 mg, 35%) as a white solid. $^1$H NMR (400 MHz, d$_6$-DMSO): δ 9.75 (s, 1H), 8.73 (d, J=2.0, 1H), 8.33 (d, J=5.0, 1H), 8.21 (s, 1H), 7.88–7.97 (m, 1H), 7.69 (d, J=5.8, 1H), 7.59 (s, 1H), 7.52 (t, J=7.9, 1H), 7.46 (dd, J$_1$=2.1, J$_2$=8.4, 1H), 7.23 (d, J=8.5, 1H), 7.09 (d, J=5.2, 1H), 7.04 (d, J=7.8, 1H), 4.02–4.20 (m, 1H), 3.93 (s, 3H), 3.17 (q, J=7.3, 2H), 1.15 (d, J=6.4, 6H), 1.06 (t, J=7.3, 3H). MS (ES+, m/z)=494 (m+H)$^+$.

The compounds of Examples 231–235, wherein Intermediate 230a is employed, were prepared according to the general procedures set forth in the synthesis of the title compound from Example 230. It will be readily apparent to those skilled in the art that the syntheses of these examples is illustrated in Scheme 12 described above. The NMR data characterizing these examples describe either the salt form or the free base form.

Example 231

N-benzyl-4-[3-(2-{[5-(ethylsulfonyl)-2-methoxyphenyl]amino}-1,3-oxazol-5-yl)phenyl]pyrimidin-2-amine

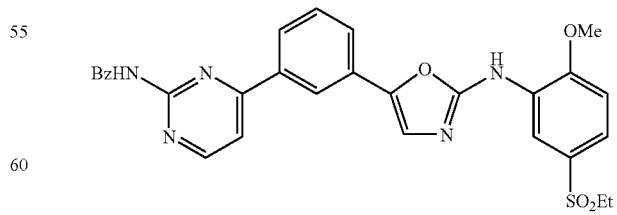

$^1$H NMR (400 MHz, d$_6$-DMSO): δ 9.71 (s, 1H), 8.72 (d, J=2.0, 1H), 8.34 (d, J=5.1, 1H), 8.21 (s, 1H), 7.92 (d, J=7.9, 1H), 7.75–7.85 (m, 1H), 7.69 (d, J=6.6, 1H), 7.57 (s, 1H), 7.51 (t, J=7.5, 1H), 7.45 (dd, J=2.3, 8.6, 1H), 7.12–7.38 (m,

7H), 4.55 (s, 2H), 3.93 (s, 3H), 3.15 (q, J=7.3, 2H), 1.06 (t, J=7.3, 3H). MS (ES+, m/z)=542 (m+H)+.

Example 232

N¹-{4-[3-(2-{[5-(ethylsulfonyl)-2-methoxyphenyl]amino}-1,3-oxazol-5-yl)phenyl]pyrimidin-2-yl}-N³,N³-dimethylpropane-1,3-diamine

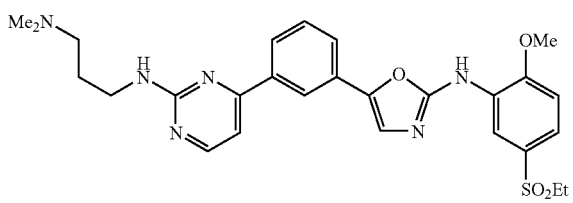

¹H NMR (400 MHz, d₆-DMSO): δ 9.76 (s, 1H), 8.77 (d, J=2.1, 1H), 8.37 (d, J=5.0, 1H), 8.26 (s, 1H), 7.92–8.02 (m, 1H), 7.73 (d, J=8.0, 1H), 7.63 (s, 1H), 7.57 (d, J=7.7, 1H), 7.50 (dd, J₁=2.2, J₂=8.3, 1H), 7.26 (d, J=8.7, 2H), 7.14 (d, J=5.3, 1H), 3.93 (s, 3H), 3.30 (s, 6H), 3.19 (q, J=7.3, 2H), 2.22–2.40 (m, 4H), 1.62–1.80 (m, 2H), 1.11 (t, J=7.3, 3H). MS (ES+, m/z)=537 (m+H)+.

Example 233

N-[5-(ethylsulfonyl)-2-methoxyphenyl]-5-[3-(2-phenylpyrimidin-4-yl)phenyl]-1,3-oxazol-2-amine

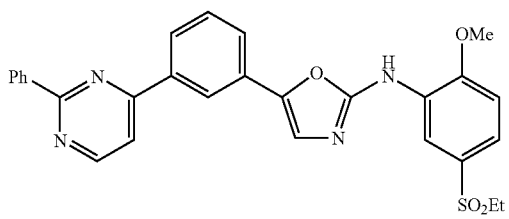

Intermediate 230a (63 mg, 0.14 mmol) was combined with benzamidine (22 mg, 0.18 mmol) in absolute ethanol (5 mL). After stirring at reflux for 3 h, an additional equivalent of benzamidine (22 mg) was added and allowed to reflux overnight, afterward an additional equivalent of benzamidine (22 mg) was added and allowed to reflux for an additional 4 h. After cooling to RT, a white precipitate was filtered and washed with ethanol (10 mL), affording the title compound (48 mg, 67%) as a white solid. ¹H NMR (400 MHz, d₆-DMSO): δ 9.80 (s, 1H), 8.98 (d, J=5.3, 1H), 8.76 (d, J=2.2, 1H), 7.46–8.54 (m, 3H), 8.20 (d, J=7.8, 1H), 8.03 (d, J=5.3, 1H), 7.78 (d, J=7.8, 1H), 7.70 (s, 1H), 7.63 (t, J=7.9, 1H), 7.50–7.58 (m, 3H), 7.46 (dd, J₁=2.2, J₂=8.7, 1H), 7.23 (d, J=8.5, 1H), 3.94 (s, 3H), 3.16 (q, J=7.3, 2H), 1.07 (t, J=7.3, 3H). MS (ES+, m/z)=513 (m+H)+.

Example 234

N-[5-(ethylsulfonyl-2-methoxyphenyl]-5-[3-(2-isopropylpyrimidin-4-ylphenyl]-1,3-oxazol-2-amine

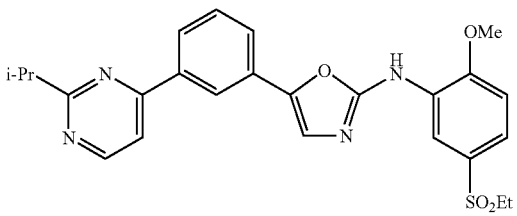

¹H NMR (400 MHz, d₆-DMSO): δ 9.79 (s, 1H), 8.80 (d, J=5.2, 1H), 8.74 (d, J=2.2, 1H), 8.34 (s, 1H), 8.06 (d, J=7.8, 1H), 7.88 (d, J=5.2, 1H), 7.74 (d, J=7.9, 1H), 7.63 (s, 1H), 7.59 (t, J=7.8, 1H), 7.45 (dd, J=2.3, 8.6, 1H), 7.23 (d, J=8.6, 1H), 3.94 (s, 3H), 3.13–3.22 (m, 3H), 1.30 (s, 6H), 1.07 (t, J=7.3, 3H). MS (ES+, m/z)=479 (m+H)+.

Example 235

5-[3-(2-tert-butylpyrimidin-4-yl)phenyl]-N-[5-(ethylsulfonyl)-2-methoxyphenyl]-1,3-oxazol-2-amine

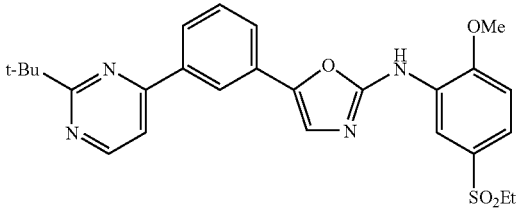

¹H NMR (400 MHz, d₆-DMSO): δ 9.75 (s, 1H), 8.80 (d, J=5.3, 1H), 8.72 (d, J=2.2, 1H), 8.28 (s, 1H), 8.02 (d, J=7.8, 1H), 7.87 (d, J=5.3, 1H), 7.68 (d, J=7.8, 1H), 7.52–7.59 (m, 2H), 7.30 (bs, 1H), 7.11 (d, J=8.6, 1H), 3.88 (s, 3H), 3.13 (q, J=7.3, 2H), 1.39 (s, 9H), 1.06 (t, J=7.3, 3H). MS (ES+, m/z)=493 (m+H)+.

Example 236

3'-(2-{[5-(ethylsulfonyl)-2-methoxyphenyl]amino}-1,3-oxazol-5-yl)-1,1'-biphenyl-4-carboxylic acid

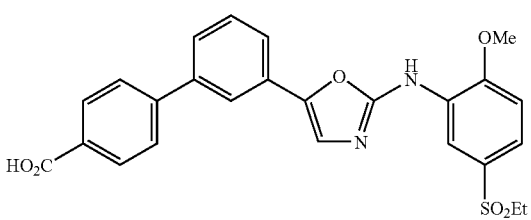

Lithium hydroxide hydrate (0.25 g, 6.0 mmol) was added to a partial suspension of the title compound from Example 211 (0.67 g, 1.4 mmol) in methanol (35 mL) and water (12 mL). After the reaction was stirred at reflux for 4 h, the methanol was evaporated under reduced pressure. The resulting aqueous suspension was neutralized with dilute HCl and filtered. The filtered solid was washed sequentially with water and dichloromethane to afford the title compound (0.47 g, 70%) as a tan solid. $^1$H NMR (400 MHz, d$_6$-DMSO): δ 11.2 (s, 1H), 9.75 (s, 1H), 8.75 (d, J=2.2, 1H), 7.97 (d, J=7.1, 2H), 7.88 (s, 1H), 7.66 (d, J=7.7, 2H), 7.61 (s, 1H), 7.57 (t, J=7.1, 2H), 7.50 (d, J=7.7, 1H), 7.44 (dd, J$_1$=2.2, J$_2$=8.6, 1H), 7.22 (d, J=8.6, 1H), 3.9 (s, 3H), 3.15 (q, J=7.3, 2H), 1.06 (t, J=7.3, 3H). MS (E−, m/z)=477 (M−H)$^+$.

Example 237

3'-(2-{[5-(ethylsulfonyl)-2-methoxyphenyl]amino}-1,3-oxazol-5-yl)-N-(2-morpholin-4-ylethyl)-1,1'-biphenyl-4-carboxamide

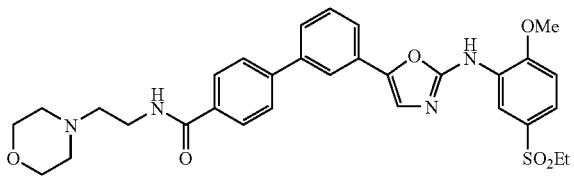

In succession, diethylcyanophosphonate (50.0 mg, 0.27 mmol) and triethylamine (65 mg, 0.65 mmol) were added to a solution of the title compound from Example 236 (104.0 mg, 0.22 mmol) and 2-(4-morpholino)ethylamine (54.0 mg, 0.42 mmol) in DMF (2 mL). After the reaction was allowed to stir for 1 h at RT, the reaction was quenched with water (10 mL). The resulting precipitate was filtered, washed with water (10 mL) and dried to afford the title compound (85 mg, 66%) as a tan solid. (In the event that a clean precipitate was not formed on quench, the aqueous solution was washed with 3:1 chloroform/i-propanol (3×20 mL). The combined organic layers were separated, dried by anhydrous magnesium sulfate, filtered, and evaporated under reduced pressure. The crude product purified by chromatography on silica gel using dichloromethane:methanol (up to 20% methanol gradient) as eluent to afford the title compound.) $^1$H NMR (400 MHz, d$_6$-DMSO): δ 9.71 (bs, 1H), 8.74 (d, J=2.1, 1H), 8.45 (t, J=5.5, 1H), 7.88–7.93 (m, 3H), 7.78 (d, J=8.2, 2H), 7.58–7.64 (m, 3H), 7.52 (t, J=7.7, 1H), 7.44 (dd, J$_1$=2.1, J$_1$=8.5, 1H), 7.23 (d, J=8.6, 1H), 3.93 (s, 3H), 3.52 (t, J=4.5, 4H), 3.36 (q, J=6.4, 2H), 3.25 (s, 2H), 3.15 (q, J=7.3, 2H), 2.33–2.40 (m, 4H), 1.10 (t, J=7.3, 3H). MS (ES+, m/z)=591 (m+H)$^+$.

Example 238

3'-(2-{[5-(ethylsulfonyl)-2-methoxyphenyl]amino}-1,3-oxazol-5-yl)-N-[3-(4-methylpiperazin-1-yl)propyl]-1,1'-biphenyl-4-carboxamide

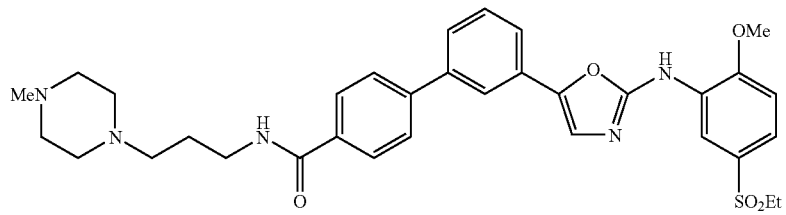

The title compound was prepared according to the general procedures set forth above in Example 237. $^1$H NMR (400 MHz, d$_6$-DMSO): δ 9.74 (bs, 1H), 8.74 (d, J=2.2, 1H). 8.53 (t, J=5.3, 1H), 7.88–7.92 (m, 3H), 7.77 (d, J=8.2, 2H). 7.58–7.64 (m, 3H), 7.51 (t, J=7.7, 1H), 7.45 (dd, J$_1$=2.2. J$_2$=8.6, 1H), 7.23 (d, J=8.6, 1H), 3.93 (s, 3H), 3.79–3.89 (m, 2H), 3.25 (s, 2H), 3.16 (q, J=7.3, 2H), 2.20–2.40 (m, 3H), 2.11 (s, 3H), 1.60–1.70 (m, 2H), 1.38–1.50 (m, 2H), 1.15 (t, J=7.1, 3H), 1.06 (t, J=7.3, 3H). MS (ES+, m/z)=618 (m+H)$^+$.

Biological Data

The compounds of the present invention have valuable pharmacologic properties. Different compounds from this class are particularly effective at inhibiting CDK2 and/or CDK4 enzymes at concentrations, which range from 0.0001 to 1 μM and additionally show specificity relative to other kinases. Representative data is shown in Table 1 following. Substrate phosphorylation assays were carried out as follows:

CDK4

Cyclin D1 and cyclin-dependent kinase 4 were expressed utilizing a baculovirus expression system. The catalytic activity of CDK4 protein was assayed by measuring the phosphorylation of Rb protein. A truncated Rb protein (residues 773–928 of the native retinoblastoma protein, fused to glutathione S-transferase to facilitate purification) was used as the phosphoryl acceptor. The assay conditions were 100 mM HEPES (N-[2-hydroxyethyl]piperzine-N'-[2-ethanesulfonic acid]), pH 7.5, 0.5 μM GST-Rb protein, 1 μCi/mL [$^{33}$P]-ATP (1 nM–20 μM), 5–20 mM MgCl$_2$, 2.5 mM EDTA, 1 mM dithiotheitol, 0.2 mg/mL bovine serum albumin, 2% (v/v) dimethyl sulfoxide (DMSO), CDK4 enzyme (5–50 nM) in a final volume of 50 μL. Reactions were incubated for time periods of 10–60 min at 30° C. and terminated by the addition of 50 μL quench (1 mM ATP/100 mM EDTA, pH 7.0). Detection of protein phosphorylation was accomplished by scintillation counting following collection of protein in 96 well plates coated with Glutathione or trapping of protein onto phosphocellulose filters. Counts detected by these methodologies minus the appropriate background were assumed to be proportional to the reaction initial rates. IC$_{50}$ values were determined by measuring enzyme activity in the presence of different inhibitor concentrations (0.1 nM to 50 μM). IC$_{50S}$ were determined by a least squares fit to the equation CPM=Vmax*(1−([I]/(K+[I])))+nsb, or pIC50s were determined by a fit to the equation CPM=nsb+(Vmax−nsb)/(1+(x/10$^x$−pIC50)), where nsb are the background counts.

CDK2

Cyclin dependent protein kinase 2 assays utilized the peptide Biotin-aminohexyl-ARRPMSPKKKA-NH$_2$ as phosphoryl group acceptor. CDK2 was expressed utilizing a baculovirus expression system and was partially purified to comprise 20–80% of total protein, with no detectable competing reactions present. Typically, assays were performed by incubating enzyme (0.2–10 nM), with and without inhibitor, peptide substrate (1–10 nM), [g-$^{32}$P]ATP (1–20 nM), and 10–20 mM Mg$^{2+}$ for periods of time generally within the range 10–120 minutes. Reactions were terminated with 0.2–2 volumes of either 20% acetic acid or 50–100 mM EDTA buffered to pH 7 (substrate consumption<20%). The buffer employed in enzyme assay was 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=Vmax*(1−([I]/(K+[I])))+nsb, or −pIC50s were determined by a fit to the equation CPM=nsb+(Vmax−nsb)/(1+(x/10$^x$−pIC50)), where nsb are the background counts. Filters are washed four times with 75 mM phosphoric acid. Radioactivity was determined by liquid scintillation counting.

The compounds of the present invention elicit important and measurable pharmacological responses. Different compounds from this class are particularly effective at inhibiting VEGFR2 enzymes, as described by the VEGFR2 HTRF assay below, at concentrations, which range from 0.0001 to 1 μM. Some exemplified compounds of the present invention also measurably and significantly inhibit the proliferation of endothelial cells that are stimulated for growth by activation with VEGF. Data for inhibition of cell proliferation are provided in Table 2 below.

VEGFR2HTRF Assay

The assays were performed in 96-well black plates. 10 nM hVEGFR2 was used to phosphorylate 0.36 μM peptide (Biotin-Ahx-EEEEYFELVAKKKK) in the presence of 75 μM ATP, 5 mM MgCl$_2$, 0.3 mM DTT, 0.1 mg/ml BSA, and 0.1 M HEPES (pH 7.5). 10 μl 0.5 M EDTA was added to reactions as negative controls. The 50 μl kinase reaction with or without inhibitors in 5% DMSO was carried out at room temperature for 45 minutes, then stopped by 40 μl of 125 mM EDTA. 2.4 μg/ml Streptavidin-APC and 0.15 μg/ml Eu-α-pY, in the presence of 0.1 mg/ml BSA, 0.1 M HEPES (pH7.5), were added to a final volume of 140 μl. The plate was incubated for 10 min at room temperature (22° C.) and read on the Victor with the time resolved fluorescence mode by exciting at 340 nm and reading the emission at 665 nm.

Reagent resources:

Peptide from Synpep (Dublin, Calif.)

ATP, MgCl$_2$, DUT, BSA, HEPES, EDTA, DMSO from Sigma

Streptavidin-APC from Molecular Probes (Eugene, Oreg.)

Eu-α-pY from EGetG Wallac (Gaithersburg, Md.)

Abbreviations:

| | |
|---|---|
| ATP | Adenosine Triphosphate |
| Streptavidin-APC | Streptavidin, allophycocyanine, crosslinked conjugate |
| DMSO | Dimethyl Sulfoxide |
| DTT | Dithiothreitol |
| BSA | Bovine Serum Albumin |
| HTRF | Homogenous Time Resolved Fluorescence |
| EDTA | Ethylenedinitrilo Tetraacetic Acid |
| HEPES | N-2-Hydroxyethyl Piperazine N-Ethane Sulfonic Acid |
| Eu-α-pY | Europium labeled anti-phosphotyrosine antibody |

Human Umbilical Vein Endothelial Cell (HUVEC) Proliferation Assay (BrdU Incorporation)

Materials

HUVEC cells and EGM-MV (Endothelial cell growth medium—microvascular) were purchased from Clonetics (San Diego, Calif.). VEGF and bFGF were purchased from RetD Systems (Minneapolis, Minn.). Anti-BrdU antibody was obtained from Chemicon International (Temecula, Calif.).

Methods

HUVECs were routinely maintained in EGM-MV medium and were used within passage 7. HUVECs were plated at a density of 2500 cells/well in M199 medium containing 5% FBS (Hyclone) in type I collagen coated plate (Becton Dickinson). The plate was incubated at 37° C. overnight. The medium was removed by aspiration, and test compounds were added to each well in a volume of 0.1 ml/well in serum-free M199 medium. Compound concentrations ranged from 1.5 nM to 30 micromolar. The plate was incubated for 30 min at 37° C. Another 0.1 ml of serum-free M199 medium containing BSA and VEGF (or bFGF) was added to give a final concentration of 0.1% BSA and 10 ng/ml VEGF (0.3 ng/ml bFGF). The plate was incubated at 37° C. for 72 hrs. BrdU was added to each well after the first 48 hrs to give a concentration of 10 micromolar. The calorimetric ELISA assay was performed according to manufacturer's (Roche Molecular Sciences) instructions, with detection by absorbance reading at 450 nm. Results were plotted as concentration of test compound vs. absorbance to give an IC$_{50}$ value for inhibition of BrdU incorporation.

TABLE 1

Inhibition of CDK4, CDK2 and VEGFR2
(+++ = <0.1 μM, ++ = <1 μM, + = <10 μM).

| Example | CDK4 IC$_{50}$ | CDK2 IC$_{50}$ | VEGFR2 IC$_{50}$ |
|---|---|---|---|
| 1 | ++ | ++ | + |
| 2 | ++ | ++ | ++ |
| 3 | ++ | + | ++ |
| 4 | +++ | ++ | ++ |
| 5 | +++ | ++ | ++ |
| 6 | +++ | ++ | ++ |
| 7 | ++ | + | ++ |
| 8 | ++ | + | ++ |
| 9 | ++ | ++ | ++ |
| 10 | + | | ++ |
| 11 | ++ | ++ | ++ |
| 12 | +++ | +++ | ++ |
| 13 | +++ | +++ | +++ |
| 14 | +++ | ++ | ++ |
| 15 | +++ | ++ | ++ |
| 16 | +++ | +++ | ++ |

TABLE 1-continued

Inhibition of CDK4, CDK2 and VEGFR2
(+++ = <0.1 μM, ++ = <1 μM, + = <10 μM).

| Example | CDK4 IC$_{50}$ | CDK2 IC$_{50}$ | VEGFR2 IC$_{50}$ |
|---|---|---|---|
| 17 | +++ | ++ | +++ |
| 18 | +++ | +++ | ++ |
| 19 | +++ | ++ | ++ |
| 20 | +++ | ++ | ++ |
| 21 | +++ | ++ | ++ |
| 22 | +++ | ++ | +++ |
| 23 | ++ | +++ | ++ |
| 24 | ++ | + | ++ |
| 25 | +++ | +++ | ++ |
| 26 | +++ | +++ | ++ |
| 27 | +++ | +++ | +++ |
| 28 | +++ | +++ | +++ |
| 29 | +++ | + | ++ |
| 30 | ++ | + | ++ |
| 31 | ++ | ++ | ++ |
| 32 | + | | |
| 33 | + | | |
| 34 | +++ | +++ | ++ |
| 35 | + | + | + |
| 36 | ++ | ++ | + |
| 37 | +++ | ++ | ++ |
| 38 | ++ | ++ | ++ |
| 39 | ++ | ++ | ++ |
| 40 | +++ | ++ | ++ |
| 41 | +++ | +++ | ++ |
| 42 | +++ | ++ | ++ |
| 43 | +++ | ++ | ++ |
| 44 | +++ | ++ | +++ |
| 45 | +++ | ++ | ++ |
| 46 | ++ | ++ | ++ |
| 47 | ++ | ++ | ++ |
| 48 | +++ | ++ | ++ |
| 49 | ++ | | |

TABLE 2

Inhibition of HUVEC proliferation (++ = <0.5 μM, + = <1 μM).

| Example | IC$_{50}$ |
|---|---|
| 51 | + |
| 56 | ++ |
| 70 | ++ |
| 74 | ++ |
| 82 | + |
| 86 | ++ |
| 89 | + |
| 90 | + |
| 93 | + |
| 94 | + |
| 95 | + |
| 97 | ++ |
| 100 | + |
| 109 | ++ |
| 110 | + |
| 116 | + |
| 122 | + |
| 123 | + |
| 124 | + |
| 129 | + |
| 130 | + |
| 132 | + |
| 133 | ++ |
| 134 | ++ |
| 137 | + |
| 141 | ++ |
| 148 | + |
| 153 | + |
| 158 | + |
| 165 | + |

TABLE 2-continued

Inhibition of HUVEC proliferation (++ = <0.5 μM, + = <1 μM).

| Example | IC$_{50}$ |
|---|---|
| 166 | + |
| 167 | + |
| 172 | ++ |
| 173 | ++ |
| 174 | + |
| 175 | + |
| 178 | ++ |
| 179 | ++ |
| 180 | ++ |
| 181 | ++ |
| 183 | ++ |
| 184 | ++ |
| 187 | ++ |
| 189 | ++ |
| 192 | + |
| 193 | + |
| 196 | ++ |
| 199 | ++ |
| 207 | ++ |
| 209 | ++ |
| 214 | + |
| 215 | ++ |
| 216 | ++ |
| 218 | ++ |
| 221 | + |
| 223 | ++ |
| 224 | ++ |
| 225 | ++ |
| 226 | ++ |
| 227 | + |
| 228 | ++ |
| 229 | + |

The application of which this description and claim(s) forms part may be used as a basis for priority in respect of any subsequent application. The claims of such subsequent application may be directed to any feature or combination of features described herein. They may take the form of product, composition, process or use claims and may include, by way of example and without limitation, one or more of the following claim(s):

What is claimed is:

1. A compound of Formula (II):

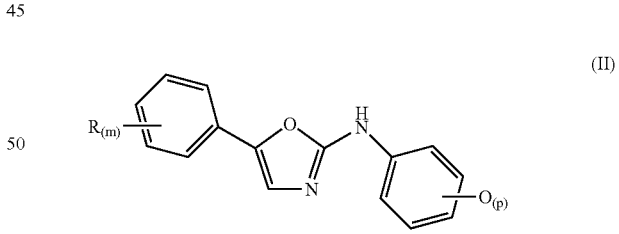

(II)

or a salt, solvate, or physiologically functional derivative thereof; wherein:

m is 1, 2, 3, or 4;

p is 0, 1, 2, 3, 4, or 5;

R is independently selected from the group consisting of halo, $C_1$–$C_6$ alkyl, $C_2$–$C_6$ alkynyl, $C_1$–$C_6$ alkoxy, —$NR^1R^2$, $C_1$–$C_4$ haloalkyl, hydroxy, —C(O)$R^1$, —OC(O)$R^1$, —C(O)$NR^1R^2$, —S(O)$_2R^1$, $C_1$–$C_6$ alkylsulfanyl, cyano, $C_1$–$C_2$ halalkoxy, and the group defined by —(Y)$_o$—(Y$^1$)$_r$—(Y$^2$); wherein:

Y is O and o is 0 or 1;

Y$^1$ is C(H)(R'), and r is 0, 1, 2, 3, or 4; and

147

Y² is aryl, heteroaryl, heterocyclic, C₃–C₇ cycloalkyl, or C₂–C₆ alkenyl;

Q is independently selected from the group consisting of halo, C₁–C₄ haloalkyl, C₁–C₆ alkyl, C₁–C₆ alkoxy, C₁–C₄ haloalkoxy, hydroxy, aralkoxy, C₁–C₆ alkenyl, alkynyl, C₁–C₄ hydroxyalkyl, cyano, aryloxy, C₁–C₂ halalkoxy, —NO₂, —C(O)OR¹, and the group defined by -(Z)_q-(Z¹)_r-(Z²), wherein:

Z is NH and q is 0 or 1; or

Z is CH₂ and q is 0, 1, 2, or 3; or

Z is O(CH₂)_n where n is 1, 2, 3, or 4 and q is 0 or 1;

Z¹ is S(O)₂ or C(O); and r is 0 or 1; and

Z² is C₁–C₆ alkyl, aryl, heteroaryl, heterocyclic, hydroxy, halo, aralkyl, C₁–C₂ haloalkyl, C(H)(R')R³, NH(CH₂)_nNR¹R², NH(CH₂)_nR³, NH(CH₂)_nOR¹ or NR¹R², where n is 1, 2, 3, or 4;

wherein when p is 2, each Q is independently selected from the group consisting of C₁–C₆ alkoxy, hydroxyl, and the group defined by -(Z)_q-(Z¹)_r-(Z²), wherein at least one Q is the group -(Z)_q-(Z¹)_r-(Z²) and:

Z is CH₂ and q is 0, 1, 2, or 3; or

Z is O(CH₂)_n where n is 1, 2, 3, or 4 and q is 0 or 1;

Z¹ is S(O)₂; and r is 1; and

Z² is C₁–C₆ alkyl, aryl, heteroaryl, heterocyclic, halo, aralkyl, C₁–C₂ haloalkyl, C(H)(R')R³, NH(CH₂)_nNR¹R², NH(CH₂)_nR³, NH(CH₂)_nOR¹ or NR¹R², where n is 1, 2, 3, or 4;

R¹ is hydrogen, C₁–C₄ alkyl, C₂–C₆ alkenyl, C₂–C₆ alkynyl, aryl, heteroaryl, C₃–C₇ cycloalkyl, heterocyclic, or aralkyl;

R² is hydrogen, C₁–C₄ alkyl, C₂–C₆ alkenyl, C₂–C₆ alkynyl, aryl, heteroaryl, C₃–C₇ cycloalkyl, heterocyclic, or aralkyl;

R³ is heteroaryl or heterocyclic, and

R' is hydrogen or C₁–C₃ alkyl.

2. A compound as claimed in claim 1, selected from the group consisting of:

5-(3-methoxyphenyl)-N-phenyl-1,3-oxazol-2-amine;
3-(2-anilino-1,3-oxazol-5-yl)phenol;
5-(3-methoxyphenyl)-N-[4-(4-methylpiperazin-1-yl)phenyl]-1,3-oxazol-2-amine;
N-[4-(4-ethylpiperazin-1-yl)phenyl]-5-(3-methoxyphenyl)-1,3-oxazol-2-amine;
5-(3-methoxyphenyl)-N-(4-morpholin-4-ylphenyl)-1,3-oxazol-2-amine;
5-(3-methoxyphenyl)-N-(4-piperidin-1-ylphenyl)-1,3-oxazol-2-amine;
5-(3-methoxyphenyl)-N-[4-(morpholin-4-ylmethyl)phenyl]-1,3-oxazol-2-amine;
5-(3-ethoxyphenyl)-N-[4-(4-methylpiperazin-1-yl)phenyl]-1,3-oxazol-2-amine;
5-(3-isopropoxyphenyl)-N-[4-(4-methylpiperazin-1-yl)phenyl]-1,3-oxazol-2-amine;
5-[3-(cyclopentyloxy)phenyl]-N-[4-(4-methylpiperazin-1-yl)phenyl]-1,3-oxazol-2-amine;
5-(3-isobutoxyphenyl)-N-[4-(4-methylpiperazin-1-yl)phenyl]-1,3-oxazol-2-amine;
5-[3-(benzyloxy)phenyl]-N-[4-(4-methylpiperazin-1-yl)phenyl]-1,3-oxazol-2-amine;
N-[4-(4-methylpiperazin-1-yl)phenyl]-5-{3-[(2-methylprop-2-enyl)oxy]phenyl}-1,3-oxazol-2-amine;
N-[4-(4-methylpiperazin-1-yl)phenyl]-5-(3-propoxyphenyl)-1,3-oxazol-2-amine;
5-[3-(cyclohexyloxy)phenyl]-N-[4-(4-methylpiperazin-1-yl)phenyl]-1,3-oxazol-2-amine;

148

N-[4-(3,5-dimethylpiperazin-1-yl)phenyl]-5-(3-methoxyphenyl)-1,3-oxazol-2-amine;
3-(2-{[4-(4-methylpiperazin-1-yl)phenyl]amino}-1,3-oxazol-5-yl)phenol;
5-[3-(cyclopentyloxy)phenyl]-N-(4-thiomorpholin-4-ylphenyl)-1,3-oxazol-2-amine;
5-(3-methoxyphenyl)-N-{4-[(4-methylpiperazin-1-yl)methyl]phenyl}-1,3-oxazol-2-amine;
N-{4-[(dimethylamino)methyl]phenyl}-5-(3-methoxyphenyl)-1,3-oxazol-2-amine;
5-[3-(cyclopentyloxy)phenyl]-N-{4-[(dimethylamino)methyl]phenyl}-1,3-oxazol-2-amine;
N-{4-[2-(dimethylamino)ethyl]phenyl}-5-(3-methoxyphenyl)-1,3-oxazol-2-amine;
5-(3-methoxyphenyl)-N-[4-(piperidin-1-ylmethyl)phenyl]-1,3-oxazol-2-amine;
5-(3-methoxyphenyl)-N-[4-(pyrrolidin-1-ylmethyl)phenyl]-1,3-oxazol-2-amine;
N-{4-[(diethylamino)methyl]phenyl}-5-(3-methoxyphenyl)-1,3-oxazol-2-amine;
N-[2-(diethylamino)ethyl]-4-{[5-(3-methoxyphenyl)-1,3-oxazol-2-yl]amino}benzamide;
5-(3-methoxyphenyl)-N-{4-[(4-methylpiperazin-1-yl)carbonyl]phenyl}-1,3-oxazol-2-amine;
4-({5-[3-(cyclopentyloxy)phenyl]-1,3-oxazol-2-yl}amino)-N-[2-(diethylamino)ethyl]benzamide;
N-[5-(ethylsulfonyl)-2-methoxyphenyl]-5-(3-methoxyphenyl)-1,3-oxazol-2-amine;
4-(2-{[5-(ethylsulfonyl)-2-methoxyphenyl]amino}-1,3-oxazol-5-yl)phenol;
3-{[5-(4-fluorophenyl)-1,3-oxazol-2-yl]amino}-4-methoxy-N,N-dimethylbenzenesulfonamide;
5-(4-fluorophenyl)-N-{2-methoxy-5-[(methylsulfonyl)methyl]phenyl}-1,3-oxazol-2-amine;
3-{[5-(4-fluorophenyl)-1,3-oxazol-2-yl]amino}-N,N-dimethylbenzenesulfonamide;
N-[3-(ethylsulfonyl)phenyl]-5-(4-fluorophenyl)-1,3-oxazol-2-amine;
3-{[5-(4-fluorophenyl)-1,3-oxazol-2-yl]amino}-4-methoxy-N-(pyridin-2-ylmethyl)benzenesulfonamide;
5-(4-fluorophenyl)-N-[2-methoxy-5-(methylsulfonyl)phenyl]-1,3-oxazol-2-amine;
3-{[5-(4-fluorophenyl)-1,3-oxazol-2-yl]amino}-4-methoxybenzenesulfonamide;
N-{5-[(1-ethylpropyl)sulfonyl]-2-methoxyphenyl}-5-(4-fluorophenyl)-1,3-oxazol-2-amine;
5-(4-fluorophenyl)-N-(2-methoxy-5-{[(5-methylisoxazol-3-yl)methyl]sulfonyl}phenyl)-1,3-oxazol-2-amine;
3-{[5-(3-bromophenyl)-1,3-oxazol-2-yl]amino}-4-methoxybenzenesulfonamide;
5-(4-fluorophenyl)-N-[5-(isobutylsulfonyl)-2-methoxyphenyl]-1,3-oxazol-2-amine;
5-(4-fluorophenyl)-N-{2-methoxy-5-[(tetrahydrofuran-2-ylmethyl)sulfonyl]phenyl}-1,3-oxazol-2-amine;
5-(4-fluorophenyl)-N-[2-methoxy-5-(tetrahydrofuran-3-ylsulfonyl)phenyl]-1,3-oxazol-2-amine;
5-(4-fluorophenyl)-N-(2-methoxy-5-{[2-(4-methyl-1,3-thiazol-5-yl)ethyl]sulfonyl}phenyl)-1,3-oxazol-2-amine;
5-(4-fluorophenyl)-N-[5-(isopropylsulfonyl)-2-methoxyphenyl]-1,3-oxazol-2-amine;
5-(3-bromophenyl)-N-[5-(isopropylsulfonyl)-2-methoxyphenyl]-1,3-oxazol-2-amine;
5-(4-fluorophenyl)-N-(5-{[2-(1H-imidazol-1-yl)ethyl]sulfonyl}-2-methoxyphenyl)-1,3-oxazol-2-amine;

5-(3-bromophenyl)-N-(2-methoxy-5-{[2-(4-methyl-1,3-thiazol-5-yl)ethyl]sulfonyl}phenyl)-1,3-oxazol-2-amine;
N-(2-ethoxyphenyl)-5-(3-methoxyphenyl)-1,3-oxazol-2-amine;
N-[5-(ethylsulfonyl)-2-methoxyphenyl]-5-(4-fluorophenyl)-1,3-oxazol-2-amine;
5-(3,4-difluorophenyl)-N-[5-(ethylsulfonyl)-2-methoxyphenyl]-1,3-oxazol-2-amine;
5-(4-fluorophenyl)-N-[3-(methylsulfonyl)phenyl]-1,3-oxazol-2-amine;
5-(4-fluorophenyl)-N-(3,4,5-trimethoxyphenyl)-1,3-oxazol-2-amine;
5-(3-bromophenyl)-N-(3,4,5-trimethoxyphenyl)-1,3-oxazol-2-amine;
5-(1,1'-biphenyl-3-yl)-N-(3,4,5-trimethoxyphenyl)-1,3-oxazol-2-amine;
3-{[5-(4-fluorophenyl)-1,3-oxazol-2-yl]amino{-4-methoxy-N-(3-pyrrolidin-1-ylpropyl)benzenesulfonamide;
3-{[5-(4-fluorophenyl)-1,3-oxazol-2-yl]amino}-N-[3-(1H-imidazol-1-yl)propyl]-4-methoxybenzenesulfonamide;
3-{[5-(4-fluorophenyl)-1,3-oxazol-2-yl]amino}-4-methoxy-N-(pyridin-3-ylmethyl)benzenesulfonamide;
3-{[5-(4-fluorophenyl)-1,3-oxazol-2-yl]amino}-4-methoxy-N-(pyridin-4-ylmethyl)benzenesulfonamide;
3-{[5-(4-fluorophenyl)-1,3-oxazol-2-yl]amino}-N-isopropyl-4-methoxybenzenesulfonamide;
3-{[5-(4-fluorophenyl)-1,3-oxazol-2-yl]amino}-4-methoxy-N-(tetrahydrofuran-2-ylmethyl)benzenesulfonamide;
5-(4-fluorophenyl)-N-[2-methoxy-5-(morpholin-4-ylsulfonyl)phenyl]-1,3-oxazol-2-amine;
5-(4-fluorophenyl)-N-{2-methoxy-5-[(4-methylpiperazin-1-yl)sulfonyl]phenyl}-1,3-oxazol-
N-(cyclopropylmethyl)-3-{[5-(4-fluorophenyl)-1,3-oxazol-2-yl]amino}-4-methoxybenzenesulfonamide;
3-{[5-(4-fluorophenyl)-1,3-oxazol-2-yl]amino}-4-methoxy-N-(3-methoxypropyl)benzenesulfonamide;
3-{[5-(4-fluorophenyl)-1,3-oxazol-2-yl]amino}-4-methoxy-N-methylbenzenesulfonamide;
N-(2-ethoxyethyl)-3-{[5-(4-fluorophenyl)-1,3-oxazol-2-yl]amino}-4-methoxybenzenesulfonamide;
N-[5-(isopropylsulfonyl)-2-methoxyphenyl]-5-(3-pyridin-2-ylphenyl)-1,3-oxazol-2-amine;
N-[2-methoxy-5-(tetrahydrofuran-3-ylsulfonyl)phenyl]-5-(3-pyridin-2-ylphenyl)-1,3-oxazol-2-amine;
N-[5-(isobutylsulfonyl)-2-methoxyphenyl]-5-(3-pyridin-2-ylphenyl)-1,3-oxazol-2-amine;
5-(1,1'-biphenyl-3-yl)-N-{2-methoxy-5-[(1-pyridin-4-ylethyl)sulfonyl]phenyl}-1,3-oxazol-2-amine;
N-{2-methoxy-5-[(tetrahydrofuran-2-ylmethyl)sulfonyl]phenyl}-5-(3-pyridin-2-ylphenyl)-1,3-oxazol-2-amine;
N-(2-methoxy-5-{[2-(4-methyl-1,3-thiazol-5-yl)ethyl]sulfonyl}phenyl)-5-(3-pyridin-2-ylphenyl)-1,3-oxazol-2-amine;
5-(4-chlorophenyl)-N-[5-(ethylsulfonyl)-2-methoxyphenyl]-1,3-oxazol-2-amine;
4-(2-{[5-(ethylsulfonyl)-2-methoxyphenyl]amino}-1,3-oxazol-5-yl)benzonitrile;
4-(2-{[5-(ethylsulfonyl)-2-methoxyphenyl]amino}-1,3-oxazol-5-yl)benzamide;
5-(4-bromophenyl)-N-[5-(ethylsulfonyl)-2-methoxyphenyl]-1,3-oxazol-2-amine;
5-(3-bromophenyl)-N-[5-(ethylsulfonyl)-2-methoxyphenyl]-1,3-oxazol-2-amine;
5-(3-chlorophenyl)-N-[5-(ethylsulfonyl)-2-methoxyphenyl]-1,3-oxazol-2-amine;
3-(2-{[5-(ethylsulfonyl)-2-methoxyphenyl]amino}-1,3-oxazol-5-yl)benzonitrile;
3-(2-{[5-(ethylsulfonyl)-2-methoxyphenyl]amino}-1,3-oxazol-5-yl)benzamide;
N-[5-(ethylsulfonyl)-2-methoxyphenyl]-5-(3-fluorophenyl)-1,3-oxazol-2-amine;
N-[5-(ethylsulfonyl)-2-methoxyphenyl]-5-[4-(trifluoromethyl)phenyl]-1,3-oxazol-2-amine;
5-(3,4-dichlorophenyl)-N-[5-(ethylsulfonyl)-2-methoxyphenyl]-1,3-oxazol-2-amine;
5-(4-chloro-3-methylphenyl)-N-[5-(ethylsulfonyl)-2-methoxyphenyl]-1,3-oxazol-2-amine;
5-(3,5-difluorophenyl)-N-[5-(ethylsulfonyl)-2-methoxyphenyl]-1,3-oxazol-2-amine;
N-[5-(ethylsulfonyl)-2-methoxyphenyl]-5-(3-trifluoromethylphenyl)-1,3-oxazol-2-amine;
N-[5-(ethylsulfonyl)-2-methoxyphenyl]-5-[4-(methylsulfonyl)phenyl]-1,3-oxazol-2-amine;
5-(3,4-dimethoxyphenyl)-N-[5-(ethylsulfonyl)-2-methoxyphenyl]-1,3-oxazol-2-amine;
3-{[5-(3-bromophenyl)-1,3-oxazol-2-yl]amino}-4-methoxybenzenesulfonyl fluoride;
3-(2-{[5-(ethylsulfonyl)-2-methoxyphenyl]amino}-1,3-oxazol-5-yl)phenyl benzoate;
3-(2-{[5-(ethylsulfonyl)-2-methylphenyl]amino}-1,3-oxazol-5-yl)phenol;
5-[3-(cyclopropylmethoxy)phenyl]-N-[5-(ethylsulfonyl)-2-methoxyphenyl]-1,3-oxazol-2-amine;
5-(3-butoxyphenyl)-N-[5-(ethylsulfonyl)-2-methoxyphenyl]-1,3-oxazol-2-amine;
N-[5-(ethylsulfonyl)-2-methoxyphenyl]-5-[3-(pyridin-2-ylmethoxy)phenyl]-1,3-oxazol-2-amine;
5-(3-benzyloxyphenyl)-N-[5-(ethylsulfonyl)-2-methoxyphenyl]-1,3-oxazol-2-amine;
N-[5-(ethylsulfonyl)-2-methoxyphenyl]-5-[3-(tetrahydro-2H-pyran-4-yloxy)phenyl]-1,3-oxazol-2-amine;
N-[5-(ethylsulfonyl)-2-methoxyphenyl]-5-[3-(2-pyridin-2-ylethoxy)phenyl]-1,3-oxazol-2-amine;
5-{3-[(2,3-dimethoxybenzyl)oxy]phenyl}-N-[5-(ethylsulfonyl)-2-methoxyphenyl]-1,3-oxazol-2-amine;
N-[5-(ethylsulfonyl)-2-methoxyphenyl]-5-[3-(1-pyridin-4-ylethoxy)phenyl]-1,3-oxazol-2-amine;
N-[5-(ethylsulfonyl)-2-methoxyphenyl]-5-[3-(tetrahydrofuran-3-yloxy)phenyl]-1,3-oxazol-2-amine;
5-{3-[(2-chloropyrimidin-4-yl)oxy]phenyl}-N-[5-(ethylsulfonyl)-2-methoxyphenyl]-1,3-oxazol-2-amine;
4-[3-(2-{[5-(ethylsulfonyl)-2-methoxyphenyl]amino}-1,3-oxazol-5-yl)phenoxy]-N-isopropylpyrimidin-2-amine;
N-[5-(ethylsulfonyl)-2-methoxyphenyl]-5-(3-phenoxyphenyl)-1,3-oxazol-2-amine;
5-(3',5'-difluoro-1,1'-biphenyl-3-yl)-N-[5-(ethylsulfonyl)-2-methoxyphenyl]-1,3-oxazol-2-amine;
N-[5-(ethylsulfonyl)-2-methoxyphenyl]-5-(3-thien-2-ylphenyl)-1,3-oxazol-2-amine;
N-[5-(ethylsulfonyl)-2-methoxyphenyl]-5-(3-thien-3-ylphenyl)-1,3-oxazol-2-amine;
N-[5-(ethylsulfonyl)-2-methoxyphenyl]-5-(3-pyridin-3-ylphenyl)-1,3-oxazol-2-amine;
N-[5-(ethylsulfonyl)-2-methoxyphenyl]-5-(3-vinylphenyl)-1,3-oxazol-2-amine;
5-(3-ethylphenyl)-N-[5-(ethylsulfonyl)-2-methoxyphenyl]-1,3-oxazol-2-amine;
N-[5-(ethylsulfonyl)-2-methoxyphenyl]-5-(3-pyridin-4-ylphenyl)-1,3-oxazol-2-amine;

N-[5-(ethylsulfonyl)-2-methoxyphenyl]-5-(3-pyridin-2-ylphenyl)-1,3-oxazol-2-amine;
N-[5-(ethylsulfonyl)-2-methoxyphenyl]-5-[3-(1-methyl-1H-imidazol-5-yl)phenyl]-1,3-oxazol-2-amine;
5-(1,1'-biphenyl-3-yl)-N-[5-(ethylsulfonyl)-2-methoxyphenyl]-1,3-oxazol-2-amine;
N-[5-(ethylsulfonyl)-2-methoxyphenyl]-5-[3-(2-furyl)phenyl]-1,3-oxazol-2-amine;
N-[5-(ethylsulfonyl)-2-methoxyphenyl]-5-(3-pyrazin-2-ylphenyl)-1,3-oxazol-2-amine;
N-[5-(ethylsulfonyl)-2-methoxyphenyl]-5-(4'-fluoro-1,1'-biphenyl-3-yl)-1,3-oxazol-2-amine;
5-[3-(2,3-dihydro-1-benzofuran-5-yl)phenyl]-N-[5-(ethylsulfonyl)-2-methoxyphenyl]-1,3-oxazol-2-amine;
N-[5-(ethylsulfonyl)-2-methoxyphenyl]-5-[3-(1,3-thiazol-2-yl)phenyl]-1,3-oxazol-2-amine;
4-methoxy-3-{[5-(3-pyridin-3-ylphenyl)-1,3-oxazol-2-yl]amino}benzenesulfonamide;
3-{[5-(1,1'-biphenyl-3-yl)-1,3-oxazol-2-yl]amino}-4-methoxybenzenesulfonamide;
4-methoxy-3-({5-[3-(1-methyl-1H-imidazol-5-yl)phenyl]-1,3-oxazol-2-yl}amino)benzenesulfonamide;
3-{[5-(4'-fluoro-1,1'-biphenyl-3-yl)-1,3-oxazol-2-yl]amino}-4-methoxy-N-methylbenzenesulfonamide;
methyl 4-methoxy-3-{[5-(3-pyridin-2-ylphenyl)-1,3-oxazol-2-yl]amino}benzoate;
3-{[5-(4'-fluoro-1,1'-biphenyl-3-yl)-1,3-oxazol-2-yl]amino}-4-methoxybenzenesulfonamide;
N-{5-[(1-ethylpropyl)sulfonyl]-2-methoxyphenyl}-5-(3-pyridin-2-ylphenyl)-1,3-oxazol-2-amine;
1-[3-(2-{[5-(ethylsulfonyl)-2-methoxyphenyl]amino}-1,3-oxazol-5-yl)phenyl]ethanone;
1-[4-(2-{[5-(ethylsulfonyl)-2-methoxyphenyl]amino}-1,3-oxazol-5-yl)phenyl]ethanone;
4-methoxy-3-{[5-(3-pyridin-3-ylphenyl)-1,3-oxazol-2-yl]amino}benzenesulfonyl fluoride;
4-methoxy-3-{[5-(3-pyridin-2-ylphenyl)-1,3-oxazol-2-yl]amino}benzenesulfonyl fluoride;
3'-(2-{[5-(ethylsulfonyl)-2-methoxyphenyl]amino}-1,3-oxazol-5-yl)-1,1'-biphenyl-4-carbonitrile;
3'-(2-{[5-(ethylsulfonyl)-2-methoxyphenyl]amino}-1,3-oxazol-5-yl)-1,1'-biphenyl-3-carboxylic acid;
3'-(2-{[5-(ethylsulfonyl)-2-methoxyphenyl]amino}-1,3-oxazol-5-yl)-1,1'-biphenyl-3-carbonitrile;
N-[5-(ethylsulfonyl)-2-methoxyphenyl]-5-(3'-fluoro-1,1'-biphenyl-3-yl)-1,3-oxazol-2-amine;
N-[5-(ethylsulfonyl)-2-methoxyphenyl]-5-(3-quinolin-3-ylphenyl)-1,3-oxazol-2-amine;
N-[5-(ethylsulfonyl)-2-methoxyphenyl]-5-[3-(5-methylthien-2-yl)phenyl]-1,3-oxazol-2-amine;
N-[5-(ethylsulfonyl)-2-methoxyphenyl]-5-[3-(1H-indol-5-yl)phenyl]-1,3-oxazol-2-amine;
methyl 3'-(2-{[5-(ethylsulfonyl)-2-methoxyphenyl]amino}-1,3-oxazol-5-yl)-1,1'-biphenyl-4-carboxylate;
3-{[5-(3'-fluoro-1,1'-biphenyl-3-yl)-1,3-oxazol-2-yl]amino}-4-methoxy-N-methylbenzenesulfonamide;
3-[5-(1,1'-biphenyl-3-yl)-1,3-oxazol-2-yl]amino}-4-methoxybenzenesulfonyl fluoride;
3-{[5-(3'-fluoro-1,1'-biphenyl-3-yl)-1,3-oxazol-2-yl]amino}-4-methoxybenzenesulfonamide;
N-[5-(ethylsulfonyl)-2-methoxyphenyl]-5-(2'-fluoro-1,1'-biphenyl-3-yl)-1,3-oxazol-2-amine;
5-(2'-chloro-1,1'-biphenyl-3-yl)-N-[5-(ethylsulfonyl)-2-methoxyphenyl]-1,3-oxazol-2-amine;
4-methoxy-N-methyl-3-{[5-(3-pyridin-2-ylphenyl)-1,3-oxazol-2-yl]amino}benzenesulfonamide;
N-ethyl-4-methoxy-3-{[5-(3-pyridin-2-ylphenyl)-1,3-oxazol-2-yl]amino}benzenesulfonamide;
4-methoxy-3-{[5-(3-pyridin-2-ylphenyl)-1,3-oxazol-2-yl]amino}benzenesulfonamide;
N-isopropyl-4-methoxy-3-{[5-(3-pyridin-2-ylphenyl)-1,3-oxazol-2-yl]amino}benzenesulfonamide;
N-(cyclopropylmethyl)-4-methoxy-3-{[5-(3-pyridin-2-ylphenyl)-1,3-oxazol-2-yl]amino}benzenesulfonamide;
N,N-diethyl-4-methoxy-3-{[5-(3-pyridin-2-ylphenyl)-1,3-oxazol-2-yl]amino}benzenesulfonamide;
N-isopropyl-4-methoxy-3-{[5-(3-pyridin-3-ylphenyl)-1,3-oxazol-2-yl]amino}benzenesulfonamide;
3-{[5-(1,1'-biphenyl-3-yl)-1,3-oxazol-2-yl]amino}-N-isopropyl-4-methoxybenzenesulfonamide;
3-{[5-(1,1'-biphenyl-3-yl)-1,3-oxazol-2-yl]amino}-4-methoxy-N,N-dimethylbenzenesulfonamide;
3-{[5-(1,1'-biphenyl-3-yl)-1,3-oxazol-2-yl]amino}-N-cyclopropyl-4-methoxybenzenesulfonamide;
3-{[5-(1,1'-biphenyl-3-yl)-1,3-oxazol-2-yl]amino}-N-butyl-4-methoxybenzenesulfonamide;
3-{[5-(1,1'-biphenyl-3-yl)-1,3-oxazol-2-yl]amino}-N,N-diethyl-4-methoxybenzenesulfonamide;
3-{[5-(1,1'-biphenyl-3-yl)-1,3-oxazol-2-yl]amino}-4-methoxy-N-(tetrahydrofuran-2-ylmethyl)benzenesulfonamide;
4-[3-(2-{[5-(ethylsulfonyl)-2-methoxyphenyl]amino}-1,3-oxazol-5-yl)phenyl]-N-isopropylpyrimidin-2-amine;
N-benzyl-4-[3-(2-{[5-(ethylsulfonyl)-2-methoxyphenyl]amino}-1,3-oxazol-5-yl)phenyl]pyrimidin-2-amine;
$N^1$-{4-[3-(2-{[5-(ethylsulfonyl)-2-methoxyphenyl]amino}-1,3-oxazol-5-yl)phenyl]pyrimidin-2-yl}-$N^3$,$N^3$-dimethylpropane-1,3-diamine;
N-[5-(ethylsulfonyl)-2-methoxyphenyl]-5-[3-(2-phenylpyrimidin-4-yl)phenyl]-1,3-oxazol-2-amine;
N-[5-(ethylsulfonyl)-2-methoxyphenyl]-5-[3-(2-isopropylpyrimidin-4-yl)phenyl]-1,3-oxazol-2-amine;
5-[3-(2-tert-butylpyrimidin-4-yl)phenyl]-N-[5-(ethylsulfonyl)-2-methoxyphenyl]-1,3-oxazol-2-amine;
3'-(2-{[5-(ethylsulfonyl)-2-methoxyphenyl]amino}-1,3-oxazol-5-yl)-1,1'-biphenyl-4-carboxylic acid;
3'-(2-{[5-(ethylsulfonyl)-2-methoxyphenyl]amino}-1,3-oxazol-5-yl)-N-(2-morpholin-4-ylethyl)-1,1'-biphenyl-4-carboxamide; and
3'-(2-{[5-(ethylsulfonyl)-2-methoxyphenyl]amino}-1,3-oxazol-5-yl)-N-[3-(4-methylpiperazin-1-yl)propyl]-1,1'-biphenyl-4-carboxamide;

or a salt, solvate, or physiologically functional derivative thereof.

3. A pharmaceutical composition, comprising: a therapeutically effective amount of a compound as claimed in 1, or a salt, solvate, or a physiologically functional derivative thereof and one or more of pharmaceutically acceptable carriers, diluents and excipients.

4. The pharmaceutical composition of claim 3, further comprising at least one additional anti-neoplastic agent.

5. The pharmaceutical composition of claim 4, further comprising an additional agent which inhibits angiogenesis.

* * * * *

UNITED STATES PATENT AND TRADEMARK OFFICE
CERTIFICATE OF CORRECTION

PATENT NO. : 7,189,712 B2
APPLICATION NO. : 10/530810
DATED : March 13, 2007
INVENTOR(S) : Brown et al.

It is certified that error appears in the above-identified patent and that said Letters Patent is hereby corrected as shown below:

Col. 3, line 39, delete "$C_1$-$C_2$-halalkoxy," and insert therefor --$C_1$-$C_2$-haloalkoxy--.

Col. 3, line 52, delete "$C_1$-$C_2$-halalkoxy,".

Col. 4, line 66, delete "$C_1$-$C_2$-halalkoxy," and insert therefor --$C_1$-$C_2$-haloalkoxy--.

Col. 5, lines 23-24, delete "$C_1$-$C_2$-halalkoxy,".

Col. 5, line 66, delete "$C_1$-$C_2$-halalkoxy," and insert therefor --$C_1$-$C_2$-haloalkoxy--.

Col. 6, line 10, delete "$C_1$-$C_2$-halalkoxy,".

Col. 12, line 23, delete "$C_1$-$C_2$".

Col. 25, line 38, delete "he" and insert therefor --the--.

Claim 1, Col. 146, line 64, delete "$C_1$-$C_2$-halalkoxy," and insert therefor --$C_1$-$C_2$-haloalkoxy--.

Claim 1, Col. 147, line 7, delete "$C_1$-$C_2$-halalkoxy,".

Claim 1, Col. 147, line 19, delete "-$(Z)_g$" and insert therefor --$(Z)_q$--.

Claim 1, Col. 147, line 20, delete "-$(Z)_g$" and insert therefor --$(Z)_q$--.

Claim 2, Col. 149, line 35, delete "1,3-oxazol-" and insert therefor --1,3-oxazol-2-amine--.

UNITED STATES PATENT AND TRADEMARK OFFICE
CERTIFICATE OF CORRECTION

PATENT NO. : 7,189,712 B2
APPLICATION NO. : 10/530810
DATED : March 13, 2007
INVENTOR(S) : Brown et al.

It is certified that error appears in the above-identified patent and that said Letters Patent is hereby corrected as shown below:

Claim 2, Col. 149, after line 35 and before line 36, the term "5-(4-fluorophenyl)-*N*-[2-methoxy-5-(thiomorpholin-4-ylsulfonyl)phenyl]-1,3-oxazol-2-amine".

Signed and Sealed this

Third Day of June, 2008

JON W. DUDAS
*Director of the United States Patent and Trademark Office*